(12) United States Patent
Bentley et al.

(10) Patent No.: US 7,020,563 B1
(45) Date of Patent: Mar. 28, 2006

(54) METHOD OF DESIGNING AGONISTS AND ANTAGONISTS TO IGF RECEPTOR

(75) Inventors: John David Bentley, Macedon (AU); Peter Archibald Tulloch, deceased, late of Parkville (AU); by Paul Alexander Tulloch, legal representative, Denmark (AU); Leah Jane Cosgrove, Somerton Park (AU); Maurice John Frenkel, South Caulfield (AU); Thomas Peter John Garrett, Brunswick (AU); Lynne Jean Lawrence, Brunswick (AU); Melzhen Lou, Scoresby (AU); George Oscar Lovrecz, North Balwyn (AU); Colin Wesley Ward, Carlton (AU)

(73) Assignee: Commonwealth Scientific and Industrial Research Organisation, Australian Capital Territory (AU)

( * ) Notice: Subject to any disclaimer, the term of this patent is extended or adjusted under 35 U.S.C. 154(b) by 0 days.

(21) Appl. No.: 09/555,275

(22) PCT Filed: Nov. 27, 1998

(86) PCT No.: PCT/AU98/00998

§ 371 (c)(1),
(2), (4) Date: Aug. 30, 2001

(87) PCT Pub. No.: WO99/28347

PCT Pub. Date: Jun. 10, 1999

(30) Foreign Application Priority Data

Nov. 27, 1997 (AU) ..................................... PP 0585
Mar. 25, 1998 (AU) ..................................... PP 2598

(51) Int. Cl.
*G01N 33/48* (2006.01)
*G01N 33/50* (2006.01)
*G01N 33/53* (2006.01)
*G06F 19/00* (2006.01)

(52) U.S. Cl. ............................. 702/27; 702/19; 702/20; 435/7.2

(58) Field of Classification Search .................. 702/19; 703/1; 530/350; 435/7.1
See application file for complete search history.

(56) References Cited

U.S. PATENT DOCUMENTS 5,705,335 A * 1/1998 Hendry

FOREIGN PATENT DOCUMENTS

WO    WO 90/00562    1/1990

OTHER PUBLICATIONS

"Crystallization of the first three domains of the human insulin-like growth factor-1 receptor", N. McKern et al., Protein Science (1997), No. 6, pp. 2663-2666.
"Crystal structure of the first three domains of the type-1 insulin-like growth factor receptor", T. Garrett et al., Nature, vol. 394, Jul. 23, 1998, pp. 395-399.
Baserga, Renato, et al. "The IGF-I receptor in cell growth, transformation and apoptosis" Biochemica et Biophysica Acta, vol. 1332, Jun. 1997, pp. F105-F126.

* cited by examiner

*Primary Examiner*—Marianne P. Allen
(74) *Attorney, Agent, or Firm*—McDermott Will & Emery LLP

(57) ABSTRACT

Identification of the human insulin receptor binding site sequence of certain spatial molecular structures conforming to such binding site and of certain insulinomimetic sequences including the binding site sequence are disclosed.

10 Claims, 62 Drawing Sheets

| ATOM | 1 | CB | GLU | 1 | 55.907 | 11.986 | 66.300 | 1.00 | 59.11 | AAAA | C |
|---|---|---|---|---|---|---|---|---|---|---|---|
| ATOM | 2 | CG | GLU | 1 | 56.138 | 11.019 | 65.162 | 1.00 | 78.17 | AAAA | C |
| ATOM | 3 | CD | GLU | 1 | 57.382 | 11.319 | 64.321 | 1.00 | 85.10 | AAAA | C |
| ATOM | 4 | OE1 | GLU | 1 | 58.404 | 10.754 | 64.796 | 1.00 | 86.18 | AAAA | O |
| ATOM | 5 | OE2 | GLU | 1 | 57.424 | 12.013 | 63.270 | 1.00 | 78.70 | AAAA | O |
| ATOM | 6 | C | GLU | 1 | 53.508 | 12.557 | 66.350 | 1.00 | 48.46 | AAAA | C |
| ATOM | 7 | O | GLU | 1 | 52.685 | 11.863 | 65.784 | 1.00 | 51.27 | AAAA | O |
| ATOM | 10 | N | GLU | 1 | 54.256 | 10.338 | 67.159 | 1.00 | 61.64 | AAAA | N |
| ATOM | 12 | CA | GLU | 1 | 54.602 | 11.778 | 67.081 | 1.00 | 54.77 | AAAA | C |
| ATOM | 13 | N | ILE | 2 | 53.608 | 13.860 | 66.375 | 1.00 | 37.66 | AAAA | N |
| ATOM | 15 | CA | ILE | 2 | 52.768 | 14.699 | 65.604 | 1.00 | 40.87 | AAAA | C |
| ATOM | 16 | CB | ILE | 2 | 52.925 | 16.122 | 66.160 | 1.00 | 41.97 | AAAA | C |
| ATOM | 17 | CG2 | ILE | 2 | 52.036 | 17.122 | 65.484 | 1.00 | 38.50 | AAAA | C |
| ATOM | 18 | CG1 | ILE | 2 | 52.560 | 16.006 | 67.663 | 1.00 | 46.58 | AAAA | C |
| ATOM | 19 | CD1 | ILE | 2 | 53.150 | 17.176 | 68.498 | 1.00 | 32.29 | AAAA | C |
| ATOM | 20 | C | ILE | 2 | 53.122 | 14.711 | 64.139 | 1.00 | 46.47 | AAAA | C |
| ATOM | 21 | O | ILE | 2 | 54.258 | 15.029 | 63.852 | 1.00 | 51.66 | AAAA | O |
| ATOM | 22 | N | CYS | 3 | 52.235 | 14.409 | 63.196 | 1.00 | 49.61 | AAAA | N |
| ATOM | 24 | CA | CYS | 3 | 52.435 | 14.677 | 61.773 | 1.00 | 38.93 | AAAA | C |
| ATOM | 25 | C | CYS | 3 | 51.429 | 15.708 | 61.302 | 1.00 | 42.06 | AAAA | C |
| ATOM | 26 | O | CYS | 3 | 50.290 | 15.521 | 61.690 | 1.00 | 42.37 | AAAA | O |
| ATOM | 27 | CB | CYS | 3 | 52.159 | 13.415 | 60.999 | 1.00 | 35.66 | AAAA | C |
| ATOM | 28 | SG | CYS | 3 | 53.019 | 12.004 | 61.674 | 1.00 | 36.98 | AAAA | S |
| ATOM | 29 | N | GLY | 4 | 51.851 | 16.709 | 60.580 | 1.00 | 42.39 | AAAA | N |
| ATOM | 31 | CA | GLY | 4 | 50.973 | 17.718 | 60.003 | 1.00 | 47.71 | AAAA | C |
| ATOM | 32 | C | GLY | 4 | 51.703 | 18.407 | 58.869 | 1.00 | 48.23 | AAAA | C |
| ATOM | 33 | O | GLY | 4 | 52.916 | 18.345 | 58.884 | 1.00 | 55.36 | AAAA | O |
| ATOM | 34 | N | PRO | 5 | 51.056 | 19.212 | 58.048 | 1.00 | 49.63 | AAAA | N |
| ATOM | 35 | CD | PRO | 5 | 51.637 | 19.947 | 56.860 | 1.00 | 45.28 | AAAA | C |
| ATOM | 36 | CA | PRO | 5 | 49.605 | 19.341 | 58.083 | 1.00 | 41.57 | AAAA | C |
| ATOM | 37 | CB | PRO | 5 | 49.397 | 20.703 | 57.474 | 1.00 | 44.30 | AAAA | C |
| ATOM | 38 | CG | PRO | 5 | 50.632 | 21.036 | 56.683 | 1.00 | 46.43 | AAAA | C |
| ATOM | 39 | C | PRO | 5 | 48.932 | 18.217 | 57.354 | 1.00 | 36.40 | AAAA | C |
| ATOM | 40 | O | PRO | 5 | 49.403 | 17.094 | 57.396 | 1.00 | 43.35 | AAAA | O |
| ATOM | 41 | N | GLY | 6 | 47.787 | 18.438 | 56.795 | 1.00 | 39.15 | AAAA | N |
| ATOM | 43 | CA | GLY | 6 | 46.896 | 17.336 | 56.350 | 1.00 | 39.24 | AAAA | C |
| ATOM | 44 | C | GLY | 6 | 47.710 | 16.365 | 55.529 | 1.00 | 33.68 | AAAA | C |
| ATOM | 45 | O | GLY | 6 | 48.510 | 16.863 | 54.753 | 1.00 | 36.00 | AAAA | O |
| ATOM | 46 | N | ILE | 7 | 47.586 | 15.111 | 55.788 | 1.00 | 35.70 | AAAA | N |
| ATOM | 48 | CA | ILE | 7 | 48.307 | 14.053 | 55.141 | 1.00 | 37.65 | AAAA | C |
| ATOM | 49 | CB | ILE | 7 | 48.556 | 12.797 | 55.933 | 1.00 | 36.31 | AAAA | C |
| ATOM | 50 | CG2 | ILE | 7 | 49.043 | 11.700 | 54.988 | 1.00 | 34.67 | AAAA | C |
| ATOM | 51 | CG1 | ILE | 7 | 49.561 | 12.857 | 57.067 | 1.00 | 39.34 | AAAA | C |
| ATOM | 52 | CD1 | ILE | 7 | 49.678 | 14.249 | 57.668 | 1.00 | 40.22 | AAAA | C |
| ATOM | 53 | C | ILE | 7 | 47.338 | 13.762 | 53.977 | 1.00 | 45.00 | AAAA | C |
| ATOM | 54 | O | ILE | 7 | 46.150 | 13.843 | 54.195 | 1.00 | 51.52 | AAAA | O |
| ATOM | 55 | N | ASP | 8 | 47.767 | 13.631 | 52.751 | 1.00 | 45.60 | AAAA | N |
| ATOM | 57 | CA | ASP | 8 | 46.938 | 13.283 | 51.631 | 1.00 | 44.05 | AAAA | C |
| ATOM | 58 | CB | ASP | 8 | 47.003 | 14.469 | 50.651 | 1.00 | 44.21 | AAAA | C |
| ATOM | 59 | CG | ASP | 8 | 45.909 | 14.379 | 49.600 | 1.00 | 43.48 | AAAA | C |
| ATOM | 60 | OD1 | ASP | 8 | 45.660 | 13.262 | 49.096 | 1.00 | 51.77 | AAAA | O |
| ATOM | 61 | OD2 | ASP | 8 | 45.253 | 15.374 | 49.251 | 1.00 | 46.84 | AAAA | O |
| ATOM | 62 | C | ASP | 8 | 47.428 | 12.000 | 50.992 | 1.00 | 42.16 | AAAA | C |
| ATOM | 63 | O | ASP | 8 | 48.423 | 12.143 | 50.330 | 1.00 | 48.50 | AAAA | O |
| ATOM | 64 | N | ILE | 9 | 47.096 | 10.817 | 51.321 | 1.00 | 42.76 | AAAA | N |
| ATOM | 66 | CA | ILE | 9 | 47.441 | 9.505 | 50.939 | 1.00 | 44.05 | AAAA | C |
| ATOM | 67 | CB | ILE | 9 | 47.212 | 8.483 | 52.077 | 1.00 | 40.82 | AAAA | C |
| ATOM | 68 | CG2 | ILE | 9 | 47.669 | 7.085 | 51.653 | 1.00 | 36.35 | AAAA | C |
| ATOM | 69 | CG1 | ILE | 9 | 47.888 | 8.917 | 53.364 | 1.00 | 41.17 | AAAA | C |
| ATOM | 70 | CD1 | ILE | 9 | 49.376 | 8.947 | 53.286 | 1.00 | 43.78 | AAAA | C |
| ATOM | 71 | C | ILE | 9 | 46.530 | 9.137 | 49.794 | 1.00 | 51.48 | AAAA | C |
| ATOM | 72 | O | ILE | 9 | 45.338 | 9.420 | 49.832 | 1.00 | 63.05 | AAAA | O |
| ATOM | 73 | N | ARG | 10 | 47.004 | 8.417 | 48.812 | 1.00 | 54.87 | AAAA | N |
| ATOM | 75 | CA | ARG | 10 | 46.283 | 8.089 | 47.600 | 1.00 | 54.17 | AAAA | C |
| ATOM | 76 | CB | ARG | 10 | 45.703 | 9.358 | 47.023 | 1.00 | 48.54 | AAAA | C |
| ATOM | 77 | CG | ARG | 10 | 46.361 | 10.169 | 45.952 | 1.00 | 46.55 | AAAA | C |
| ATOM | 78 | CD | ARG | 10 | 46.002 | 11.635 | 46.264 | 1.00 | 52.63 | AAAA | C |
| ATOM | 79 | NE | ARG | 10 | 45.082 | 12.226 | 45.284 | 1.00 | 59.27 | AAAA | N |
| ATOM | 81 | CZ | ARG | 10 | 44.269 | 13.262 | 45.498 | 1.00 | 56.22 | AAAA | C |
| ATOM | 82 | NH1 | ARG | 10 | 44.153 | 13.891 | 46.666 | 1.00 | 55.14 | AAAA | N |
| ATOM | 85 | NH2 | ARG | 10 | 43.455 | 13.803 | 44.602 | 1.00 | 52.29 | AAAA | N |
| ATOM | 88 | C | ARG | 10 | 47.019 | 7.373 | 46.492 | 1.00 | 57.23 | AAAA | C |
| ATOM | 89 | O | ARG | 10 | 48.240 | 7.288 | 46.281 | 1.00 | 56.32 | AAAA | O |
| ATOM | 90 | N | ASN | 11 | 46.248 | 6.654 | 45.629 | 1.00 | 57.23 | AAAA | N |
| ATOM | 92 | CA | ASN | 11 | 46.800 | 5.917 | 44.494 | 1.00 | 50.73 | AAAA | C |
| ATOM | 93 | CB | ASN | 11 | 47.704 | 6.798 | 43.671 | 1.00 | 44.65 | AAAA | C |
| ATOM | 94 | CG | ASN | 11 | 46.878 | 7.732 | 42.829 | 1.00 | 50.72 | AAAA | C |
| ATOM | 95 | OD1 | ASN | 11 | 45.749 | 7.451 | 42.403 | 1.00 | 72.59 | AAAA | O |
| ATOM | 96 | ND2 | ASN | 11 | 47.499 | 8.869 | 42.587 | 1.00 | 54.38 | AAAA | N |

Figure 1

| ATOM | 99  | C   | ASN | 11 | 47.635 | 4.736  | 44.915 | 1.00 53.07 | AAAA C |
| ATOM | 100 | O   | ASN | 11 | 47.303 | 3.701  | 44.347 | 1.00 51.95 | AAAA O |
| ATOM | 101 | N   | ASP | 12 | 48.566 | 4.822  | 45.878 | 1.00 50.96 | AAAA N |
| ATOM | 103 | CA  | ASP | 12 | 49.204 | 3.570  | 46.263 | 1.00 55.44 | AAAA C |
| ATOM | 104 | CB  | ASP | 12 | 50.668 | 3.568  | 45.758 | 1.00 66.47 | AAAA C |
| ATOM | 105 | CG  | ASP | 12 | 50.879 | 4.026  | 44.314 | 1.00 68.25 | AAAA C |
| ATOM | 106 | OD1 | ASP | 12 | 50.441 | 3.185  | 43.457 | 1.00 58.31 | AAAA O |
| ATOM | 107 | OD2 | ASP | 12 | 51.391 | 5.120  | 43.989 | 1.00 70.56 | AAAA O |
| ATOM | 108 | C   | ASP | 12 | 49.061 | 3.322  | 47.758 | 1.00 59.23 | AAAA C |
| ATOM | 109 | O   | ASP | 12 | 49.687 | 3.849  | 48.711 | 1.00 59.65 | AAAA O |
| ATOM | 110 | N   | TYR | 13 | 48.411 | 2.187  | 48.036 | 1.00 59.64 | AAAA N |
| ATOM | 112 | CA  | TYR | 13 | 48.328 | 1.672  | 49.397 | 1.00 64.06 | AAAA C |
| ATOM | 113 | CB  | TYR | 13 | 47.968 | 0.196  | 49.409 | 1.00 64.56 | AAAA C |
| ATOM | 114 | CG  | TYR | 13 | 47.467 | -0.357 | 50.721 | 1.00 69.18 | AAAA C |
| ATOM | 115 | CD1 | TYR | 13 | 46.216 | -0.024 | 51.248 | 1.00 72.71 | AAAA C |
| ATOM | 116 | CE1 | TYR | 13 | 45.746 | -0.541 | 52.450 | 1.00 71.51 | AAAA C |
| ATOM | 117 | CD2 | TYR | 13 | 48.233 | -1.247 | 51.457 | 1.00 70.36 | AAAA C |
| ATOM | 118 | CE2 | TYR | 13 | 47.788 | -1.778 | 52.661 | 1.00 71.64 | AAAA C |
| ATOM | 119 | CZ  | TYR | 13 | 46.542 | -1.420 | 53.160 | 1.00 71.31 | AAAA C |
| ATOM | 120 | OH  | TYR | 13 | 46.144 | -1.977 | 54.358 | 1.00 63.25 | AAAA O |
| ATOM | 122 | C   | TYR | 13 | 49.622 | 1.839  | 50.198 | 1.00 65.99 | AAAA C |
| ATOM | 123 | O   | TYR | 13 | 49.621 | 2.321  | 51.354 | 1.00 65.01 | AAAA O |
| ATOM | 124 | N   | GLN | 14 | 50.786 | 1.541  | 49.594 | 1.00 63.51 | AAAA N |
| ATOM | 126 | CA  | GLN | 14 | 52.078 | 1.681  | 50.218 | 1.00 63.51 | AAAA C |
| ATOM | 127 | CB  | GLN | 14 | 53.174 | 1.318  | 49.219 | 1.00 68.37 | AAAA C |
| ATOM | 128 | CG  | GLN | 14 | 52.863 | -0.078 | 48.686 | 1.00 84.62 | AAAA C |
| ATOM | 129 | CD  | GLN | 14 | 53.990 | -0.515 | 47.754 | 1.00 92.28 | AAAA C |
| ATOM | 130 | OE1 | GLN | 14 | 53.945 | -0.161 | 46.573 | 1.00 94.82 | AAAA O |
| ATOM | 131 | NE2 | GLN | 14 | 54.920 | -1.254 | 48.361 | 1.00 98.03 | AAAA N |
| ATOM | 134 | C   | GLN | 14 | 52.434 | 3.058  | 50.753 | 1.00 61.62 | AAAA C |
| ATOM | 135 | O   | GLN | 14 | 53.266 | 3.292  | 51.644 | 1.00 62.09 | AAAA O |
| ATOM | 136 | N   | GLN | 15 | 51.628 | 4.038  | 50.349 | 1.00 57.02 | AAAA N |
| ATOM | 138 | CA  | GLN | 15 | 51.724 | 5.399  | 50.834 | 1.00 51.71 | AAAA C |
| ATOM | 139 | CB  | GLN | 15 | 50.861 | 6.220  | 49.911 | 1.00 43.75 | AAAA C |
| ATOM | 140 | CG  | GLN | 15 | 51.566 | 6.605  | 48.648 | 1.00 59.65 | AAAA C |
| ATOM | 141 | CD  | GLN | 15 | 51.554 | 8.105  | 48.428 | 1.00 72.96 | AAAA C |
| ATOM | 142 | OE1 | GLN | 15 | 51.168 | 9.005  | 49.184 | 1.00 80.58 | AAAA O |
| ATOM | 143 | NE2 | GLN | 15 | 52.016 | 8.378  | 47.211 | 1.00 74.17 | AAAA N |
| ATOM | 146 | C   | GLN | 15 | 51.219 | 5.530  | 52.258 | 1.00 50.15 | AAAA C |
| ATOM | 147 | O   | GLN | 15 | 51.576 | 6.500  | 52.940 | 1.00 48.04 | AAAA O |
| ATOM | 148 | N   | LEU | 16 | 50.440 | 4.535  | 52.688 | 1.00 46.22 | AAAA N |
| ATOM | 150 | CA  | LEU | 16 | 49.913 | 4.449  | 54.019 | 1.00 45.52 | AAAA C |
| ATOM | 151 | CB  | LEU | 16 | 48.950 | 3.295  | 54.159 | 1.00 37.73 | AAAA C |
| ATOM | 152 | CG  | LEU | 16 | 47.502 | 3.425  | 53.707 | 1.00 41.40 | AAAA C |
| ATOM | 153 | CD1 | LEU | 16 | 46.837 | 2.063  | 53.790 | 1.00 42.43 | AAAA C |
| ATOM | 154 | CD2 | LEU | 16 | 46.687 | 4.424  | 54.545 | 1.00 35.93 | AAAA C |
| ATOM | 155 | C   | LEU | 16 | 51.042 | 4.280  | 55.039 | 1.00 51.52 | AAAA C |
| ATOM | 156 | O   | LEU | 16 | 50.913 | 4.601  | 56.235 | 1.00 52.53 | AAAA O |
| ATOM | 157 | N   | LYS | 17 | 52.252 | 3.936  | 54.560 | 1.00 51.01 | AAAA N |
| ATOM | 159 | CA  | LYS | 17 | 53.422 | 3.914  | 55.404 | 1.00 50.73 | AAAA C |
| ATOM | 160 | CB  | LYS | 17 | 54.609 | 3.252  | 54.737 | 1.00 56.10 | AAAA C |
| ATOM | 161 | CG  | LYS | 17 | 54.539 | 1.733  | 54.831 | 1.00 62.40 | AAAA C |
| ATOM | 162 | CD  | LYS | 17 | 54.768 | 1.278  | 53.387 | 1.00 63.85 | AAAA C |
| ATOM | 163 | CE  | LYS | 17 | 55.316 | -0.141 | 53.426 | 1.00 68.40 | AAAA C |
| ATOM | 164 | NZ  | LYS | 17 | 56.537 | -0.225 | 52.554 | 1.00 73.83 | AAAA N |
| ATOM | 168 | C   | LYS | 17 | 53.944 | 5.270  | 55.852 | 1.00 44.78 | AAAA C |
| ATOM | 169 | O   | LYS | 17 | 54.492 | 5.262  | 56.933 | 1.00 39.39 | AAAA O |
| ATOM | 170 | N   | ARG | 18 | 53.524 | 6.344  | 55.201 | 1.00 41.15 | AAAA N |
| ATOM | 172 | CA  | ARG | 18 | 53.827 | 7.673  | 55.676 | 1.00 43.01 | AAAA C |
| ATOM | 173 | CB  | ARG | 18 | 53.250 | 8.702  | 54.704 | 1.00 43.97 | AAAA C |
| ATOM | 174 | CG  | ARG | 18 | 53.888 | 8.764  | 53.333 | 1.00 53.60 | AAAA C |
| ATOM | 175 | CD  | ARG | 18 | 52.964 | 9.362  | 52.269 | 1.00 60.34 | AAAA C |
| ATOM | 176 | NE  | ARG | 18 | 52.528 | 10.703 | 52.650 | 1.00 50.00 | AAAA N |
| ATOM | 178 | CZ  | ARG | 18 | 51.628 | 11.444 | 52.021 | 1.00 48.86 | AAAA C |
| ATOM | 179 | NH1 | ARG | 18 | 51.068 | 10.941 | 50.943 | 1.00 47.96 | AAAA N |
| ATOM | 182 | NH2 | ARG | 18 | 51.377 | 12.656 | 52.555 | 1.00 43.72 | AAAA N |
| ATOM | 185 | C   | ARG | 18 | 53.268 | 7.924  | 57.077 | 1.00 44.03 | AAAA C |
| ATOM | 186 | O   | ARG | 18 | 53.402 | 9.010  | 57.644 | 1.00 45.53 | AAAA O |
| ATOM | 187 | N   | LEU | 19 | 52.445 | 7.069  | 57.632 | 1.00 46.36 | AAAA N |
| ATOM | 189 | CA  | LEU | 19 | 51.653 | 7.282  | 58.794 | 1.00 50.25 | AAAA C |
| ATOM | 190 | CB  | LEU | 19 | 50.186 | 6.924  | 58.674 | 1.00 50.83 | AAAA C |
| ATOM | 191 | CG  | LEU | 19 | 49.202 | 7.371  | 57.608 | 1.00 46.43 | AAAA C |
| ATOM | 192 | CD1 | LEU | 19 | 47.846 | 6.743  | 57.852 | 1.00 22.57 | AAAA C |
| ATOM | 193 | CD2 | LEU | 19 | 49.018 | 8.866  | 57.495 | 1.00 45.88 | AAAA C |
| ATOM | 194 | C   | LEU | 19 | 52.210 | 6.428  | 59.912 | 1.00 49.87 | AAAA C |
| ATOM | 195 | O   | LEU | 19 | 51.870 | 6.810  | 61.030 | 1.00 51.54 | AAAA O |
| ATOM | 196 | N   | GLU | 20 | 53.270 | 5.708  | 59.652 | 1.00 49.35 | AAAA N |
| ATOM | 198 | CA  | GLU | 20 | 53.819 | 4.833  | 60.679 | 1.00 49.60 | AAAA C |
| ATOM | 199 | CB  | GLU | 20 | 54.876 | 3.960  | 59.982 | 1.00 57.91 | AAAA C |

Figure 1A-1

| ATOM | 200 | CG | GLU | 20 | 55.893 | 4.840 | 59.272 | 1.00 | 70.16 | AAAA | C |
| --- | --- | --- | --- | --- | --- | --- | --- | --- | --- | --- | --- |
| ATOM | 201 | CD | GLU | 20 | 57.095 | 4.077 | 58.757 | 1.00 | 69.35 | AAAA | C |
| ATOM | 202 | OE1 | GLU | 20 | 58.123 | 4.795 | 58.722 | 1.00 | 71.38 | AAAA | O |
| ATOM | 203 | OE2 | GLU | 20 | 56.993 | 2.885 | 58.420 | 1.00 | 72.84 | AAAA | O |
| ATOM | 204 | C | GLU | 20 | 54.310 | 5.417 | 61.989 | 1.00 | 43.55 | AAAA | C |
| ATOM | 205 | O | GLU | 20 | 54.301 | 4.652 | 62.937 | 1.00 | 40.01 | AAAA | O |
| ATOM | 206 | N | ASN | 21 | 54.633 | 6.659 | 62.207 | 1.00 | 41.06 | AAAA | N |
| ATOM | 208 | CA | ASN | 21 | 55.054 | 7.204 | 63.454 | 1.00 | 47.17 | AAAA | C |
| ATOM | 209 | C | ASN | 21 | 54.066 | 8.141 | 64.108 | 1.00 | 49.76 | AAAA | C |
| ATOM | 210 | O | ASN | 21 | 54.228 | 8.456 | 65.303 | 1.00 | 48.10 | AAAA | O |
| ATOM | 211 | CB | ASN | 21 | 56.379 | 8.003 | 63.290 | 1.00 | 59.11 | AAAA | C |
| ATOM | 212 | CG | ASN | 21 | 57.413 | 7.051 | 62.796 | 1.00 | 68.38 | AAAA | C |
| ATOM | 213 | OD1 | ASN | 21 | 57.499 | 5.855 | 63.122 | 1.00 | 58.51 | AAAA | O |
| ATOM | 214 | ND2 | ASN | 21 | 58.348 | 7.469 | 61.890 | 1.00 | 77.90 | AAAA | N |
| ATOM | 216 | N | CYS | 22 | 53.129 | 8.711 | 63.351 | 1.00 | 47.44 | AAAA | N |
| ATOM | 218 | CA | CYS | 22 | 52.107 | 9.614 | 63.879 | 1.00 | 42.99 | AAAA | C |
| ATOM | 219 | C | CYS | 22 | 51.215 | 9.089 | 65.021 | 1.00 | 40.43 | AAAA | C |
| ATOM | 220 | O | CYS | 22 | 50.750 | 7.923 | 65.069 | 1.00 | 36.07 | AAAA | O |
| ATOM | 221 | CB | CYS | 22 | 51.182 | 9.921 | 62.690 | 1.00 | 44.82 | AAAA | C |
| ATOM | 222 | SG | CYS | 22 | 52.076 | 10.328 | 61.148 | 1.00 | 39.51 | AAAA | S |
| ATOM | 223 | N | THR | 23 | 51.287 | 9.801 | 66.137 | 1.00 | 36.24 | AAAA | N |
| ATOM | 225 | CA | THR | 23 | 50.339 | 9.482 | 67.204 | 1.00 | 43.51 | AAAA | C |
| ATOM | 226 | CB | THR | 23 | 50.944 | 9.481 | 68.593 | 1.00 | 41.38 | AAAA | C |
| ATOM | 227 | OG1 | THR | 23 | 51.410 | 10.843 | 68.822 | 1.00 | 51.21 | AAAA | O |
| ATOM | 229 | CG2 | THR | 23 | 52.110 | 8.571 | 68.838 | 1.00 | 33.83 | AAAA | C |
| ATOM | 230 | C | THR | 23 | 49.250 | 10.599 | 67.116 | 1.00 | 44.55 | AAAA | C |
| ATOM | 231 | O | THR | 23 | 48.085 | 10.414 | 67.481 | 1.00 | 45.95 | AAAA | O |
| ATOM | 232 | N | VAL | 24 | 49.646 | 11.797 | 66.689 | 1.00 | 33.03 | AAAA | N |
| ATOM | 234 | CA | VAL | 24 | 48.732 | 12.855 | 66.442 | 1.00 | 35.29 | AAAA | C |
| ATOM | 235 | CB | VAL | 24 | 48.925 | 13.979 | 67.456 | 1.00 | 30.60 | AAAA | C |
| ATOM | 236 | CG1 | VAL | 24 | 48.056 | 15.157 | 67.082 | 1.00 | 27.21 | AAAA | C |
| ATOM | 237 | CG2 | VAL | 24 | 48.656 | 13.566 | 68.886 | 1.00 | 25.37 | AAAA | C |
| ATOM | 238 | C | VAL | 24 | 48.895 | 13.447 | 65.043 | 1.00 | 41.52 | AAAA | C |
| ATOM | 239 | O | VAL | 24 | 49.987 | 13.963 | 64.791 | 1.00 | 44.40 | AAAA | O |
| ATOM | 240 | N | ILE | 25 | 47.855 | 13.450 | 64.203 | 1.00 | 40.13 | AAAA | N |
| ATOM | 242 | CA | ILE | 25 | 47.908 | 14.094 | 62.882 | 1.00 | 32.05 | AAAA | C |
| ATOM | 243 | CB | ILE | 25 | 47.113 | 13.299 | 61.853 | 1.00 | 25.85 | AAAA | C |
| ATOM | 244 | CG2 | ILE | 25 | 47.027 | 14.039 | 60.542 | 1.00 | 18.73 | AAAA | C |
| ATOM | 245 | CG1 | ILE | 25 | 47.677 | 11.896 | 61.705 | 1.00 | 29.80 | AAAA | C |
| ATOM | 246 | CD1 | ILE | 25 | 47.169 | 11.155 | 60.471 | 1.00 | 27.41 | AAAA | C |
| ATOM | 247 | C | ILE | 25 | 47.397 | 15.490 | 62.941 | 1.00 | 32.92 | AAAA | C |
| ATOM | 248 | O | ILE | 25 | 46.223 | 15.776 | 63.213 | 1.00 | 40.91 | AAAA | O |
| ATOM | 249 | N | GLU | 26 | 48.264 | 16.472 | 63.042 | 1.00 | 36.60 | AAAA | N |
| ATOM | 251 | CA | GLU | 26 | 47.832 | 17.847 | 63.226 | 1.00 | 29.24 | AAAA | C |
| ATOM | 252 | CB | GLU | 26 | 48.875 | 18.703 | 63.856 | 1.00 | 29.92 | AAAA | C |
| ATOM | 253 | CG | GLU | 26 | 48.490 | 20.144 | 64.116 | 1.00 | 38.06 | AAAA | C |
| ATOM | 254 | CD | GLU | 26 | 49.561 | 20.762 | 65.013 | 1.00 | 37.39 | AAAA | C |
| ATOM | 255 | OE1 | GLU | 26 | 50.654 | 20.937 | 64.489 | 1.00 | 41.56 | AAAA | O |
| ATOM | 256 | OE2 | GLU | 26 | 49.571 | 21.175 | 66.182 | 1.00 | 49.16 | AAAA | O |
| ATOM | 257 | C | GLU | 26 | 47.413 | 18.376 | 61.869 | 1.00 | 37.79 | AAAA | C |
| ATOM | 258 | O | GLU | 26 | 48.161 | 19.069 | 61.181 | 1.00 | 39.68 | AAAA | O |
| ATOM | 259 | N | GLY | 27 | 46.117 | 18.104 | 61.582 | 1.00 | 37.28 | AAAA | N |
| ATOM | 261 | CA | GLY | 27 | 45.498 | 18.503 | 60.320 | 1.00 | 31.17 | AAAA | C |
| ATOM | 262 | C | GLY | 27 | 44.531 | 17.400 | 59.893 | 1.00 | 33.72 | AAAA | C |
| ATOM | 263 | O | GLY | 27 | 43.988 | 16.715 | 60.775 | 1.00 | 33.29 | AAAA | O |
| ATOM | 264 | N | TYR | 28 | 44.304 | 17.209 | 58.604 | 1.00 | 29.24 | AAAA | N |
| ATOM | 266 | CA | TYR | 28 | 43.318 | 16.189 | 58.253 | 1.00 | 28.93 | AAAA | C |
| ATOM | 267 | CB | TYR | 28 | 42.403 | 16.794 | 57.217 | 1.00 | 31.53 | AAAA | C |
| ATOM | 268 | CG | TYR | 28 | 43.058 | 17.256 | 55.962 | 1.00 | 31.78 | AAAA | C |
| ATOM | 269 | CD1 | TYR | 28 | 43.704 | 16.355 | 55.116 | 1.00 | 36.07 | AAAA | C |
| ATOM | 270 | CE1 | TYR | 28 | 44.361 | 16.706 | 53.967 | 1.00 | 28.91 | AAAA | C |
| ATOM | 271 | CD2 | TYR | 28 | 43.130 | 18.572 | 55.606 | 1.00 | 30.98 | AAAA | C |
| ATOM | 272 | CE2 | TYR | 28 | 43.769 | 18.972 | 54.428 | 1.00 | 28.77 | AAAA | C |
| ATOM | 273 | CZ | TYR | 28 | 44.367 | 18.021 | 53.652 | 1.00 | 31.53 | AAAA | C |
| ATOM | 274 | OH | TYR | 28 | 44.971 | 18.425 | 52.464 | 1.00 | 44.74 | AAAA | O |
| ATOM | 276 | C | TYR | 28 | 43.953 | 14.946 | 57.697 | 1.00 | 29.23 | AAAA | C |
| ATOM | 277 | O | TYR | 28 | 45.119 | 15.147 | 57.383 | 1.00 | 35.58 | AAAA | O |
| ATOM | 278 | N | LEU | 29 | 43.250 | 13.900 | 57.445 | 1.00 | 26.63 | AAAA | N |
| ATOM | 280 | CA | LEU | 29 | 43.764 | 12.730 | 56.803 | 1.00 | 29.83 | AAAA | C |
| ATOM | 281 | CB | LEU | 29 | 43.830 | 11.611 | 57.856 | 1.00 | 27.09 | AAAA | C |
| ATOM | 282 | CG | LEU | 29 | 44.212 | 10.258 | 57.242 | 1.00 | 31.90 | AAAA | C |
| ATOM | 283 | CD1 | LEU | 29 | 45.538 | 10.396 | 56.469 | 1.00 | 35.03 | AAAA | C |
| ATOM | 284 | CD2 | LEU | 29 | 44.551 | 9.203 | 58.290 | 1.00 | 25.05 | AAAA | C |
| ATOM | 285 | C | LEU | 29 | 42.897 | 12.342 | 55.616 | 1.00 | 33.84 | AAAA | C |
| ATOM | 286 | O | LEU | 29 | 41.689 | 12.165 | 55.806 | 1.00 | 43.29 | AAAA | O |
| ATOM | 287 | N | HIS | 30 | 43.389 | 12.285 | 54.395 | 1.00 | 35.95 | AAAA | N |
| ATOM | 289 | CA | HIS | 30 | 42.681 | 11.891 | 53.197 | 1.00 | 34.92 | AAAA | C |
| ATOM | 290 | CB | HIS | 30 | 42.893 | 12.801 | 52.027 | 1.00 | 32.85 | AAAA | C |

Figure 1A-2

```
ATOM    291  CG   HIS    30      42.372   14.155   52.046  1.00 25.08      AAAA C
ATOM    292  CD2  HIS    30      41.519   14.753   52.907  1.00 40.88      AAAA C
ATOM    293  ND1  HIS    30      42.717   15.120   51.128  1.00 33.66      AAAA N
ATOM    295  CE1  HIS    30      42.080   16.281   51.444  1.00 31.33      AAAA C
ATOM    296  NE2  HIS    30      41.329   16.093   52.539  1.00 37.27      AAAA N
ATOM    298  C    HIS    30      43.173   10.538   52.714  1.00 37.68      AAAA C
ATOM    299  O    HIS    30      44.357   10.388   52.541  1.00 38.70      AAAA O
ATOM    300  N    ILE    31      42.308    9.542   52.584  1.00 40.02      AAAA N
ATOM    302  CA   ILE    31      42.750    8.271   51.992  1.00 39.47      AAAA C
ATOM    303  CB   ILE    31      42.668    7.204   53.063  1.00 37.95      AAAA C
ATOM    304  CG2  ILE    31      43.161    5.830   52.651  1.00 23.86      AAAA C
ATOM    305  CG1  ILE    31      43.481    7.555   54.335  1.00 41.66      AAAA C
ATOM    306  CD1  ILE    31      43.170    6.575   55.473  1.00 28.22      AAAA C
ATOM    307  C    ILE    31      41.884    8.044   50.755  1.00 46.52      AAAA C
ATOM    308  O    ILE    31      40.753    7.589   50.827  1.00 43.56      AAAA O
ATOM    309  N    LEU    32      42.314    8.489   49.556  1.00 49.89      AAAA N
ATOM    311  CA   LEU    32      41.484    8.235   48.380  1.00 49.77      AAAA C
ATOM    312  CB   LEU    32      41.127    9.515   47.603  1.00 47.48      AAAA C
ATOM    313  CG   LEU    32      42.091   10.688   47.562  1.00 45.33      AAAA C
ATOM    314  CD1  LEU    32      41.517   11.812   46.673  1.00 35.77      AAAA C
ATOM    315  CD2  LEU    32      42.371   11.229   48.960  1.00 49.18      AAAA C
ATOM    316  C    LEU    32      42.136    7.296   47.353  1.00 51.00      AAAA C
ATOM    317  O    LEU    32      43.338    7.370   47.186  1.00 41.36      AAAA O
ATOM    318  N    LEU    33      41.270    6.722   46.497  1.00 50.74      AAAA N
ATOM    320  CA   LEU    33      41.602    6.175   45.197  1.00 49.92      AAAA C
ATOM    321  CB   LEU    33      42.091    7.262   44.182  1.00 34.83      AAAA C
ATOM    322  CG   LEU    33      41.233    8.537   44.164  1.00 33.92      AAAA C
ATOM    323  CD1  LEU    33      41.892    9.587   43.298  1.00 37.49      AAAA C
ATOM    324  CD2  LEU    33      39.823    8.313   43.644  1.00 33.01      AAAA C
ATOM    325  C    LEU    33      42.618    5.073   45.287  1.00 48.35      AAAA C
ATOM    326  O    LEU    33      43.580    5.077   44.538  1.00 54.14      AAAA O
ATOM    327  N    ILE    34      42.543    4.212   46.254  1.00 47.61      AAAA N
ATOM    329  CA   ILE    34      43.523    3.184   46.540  1.00 51.70      AAAA C
ATOM    330  CB   ILE    34      44.101    3.346   47.963  1.00 57.98      AAAA C
ATOM    331  CG2  ILE    34      44.538    2.043   48.600  1.00 48.98      AAAA C
ATOM    332  CG1  ILE    34      45.267    4.371   47.967  1.00 46.70      AAAA C
ATOM    333  CD1  ILE    34      45.561    4.704   49.439  1.00 66.47      AAAA C
ATOM    334  C    ILE    34      42.829    1.844   46.408  1.00 59.85      AAAA C
ATOM    335  O    ILE    34      41.726    1.531   46.856  1.00 60.11      AAAA O
ATOM    336  N    SER    35      43.622    0.833   46.013  1.00 67.79      AAAA N
ATOM    338  CA   SER    35      43.048   -0.511   45.922  1.00 68.80      AAAA C
ATOM    339  CB   SER    35      42.767   -0.882   44.469  1.00 64.16      AAAA C
ATOM    340  OG   SER    35      41.731   -1.846   44.498  1.00 75.76      AAAA O
ATOM    342  C    SER    35      43.928   -1.564   46.537  1.00 70.73      AAAA C
ATOM    343  O    SER    35      44.885   -1.954   45.909  1.00 73.65      AAAA O
ATOM    344  N    LYS    36      43.687   -2.017   47.740  1.00 74.75      AAAA N
ATOM    346  CA   LYS    36      44.465   -3.014   48.421  1.00 76.09      AAAA C
ATOM    347  CB   LYS    36      44.046   -3.131   49.885  1.00 81.22      AAAA C
ATOM    348  CG   LYS    36      45.147   -3.654   50.775  1.00 78.87      AAAA C
ATOM    349  CD   LYS    36      44.693   -4.575   51.887  1.00 81.39      AAAA C
ATOM    350  CE   LYS    36      44.890   -6.025   51.492  1.00 89.38      AAAA C
ATOM    351  NZ   LYS    36      44.371   -6.989   52.506  1.00 91.63      AAAA N
ATOM    355  C    LYS    36      44.252   -4.362   47.753  1.00 81.41      AAAA C
ATOM    356  O    LYS    36      43.145   -4.772   47.451  1.00 78.20      AAAA O
ATOM    357  N    ALA    37      45.371   -5.080   47.615  1.00 88.27      AAAA N
ATOM    359  CA   ALA    37      45.361   -6.396   46.986  1.00 90.10      AAAA C
ATOM    360  CB   ALA    37      46.700   -6.655   46.327  1.00 95.49      AAAA C
ATOM    361  C    ALA    37      45.011   -7.473   47.995  1.00 92.36      AAAA C
ATOM    362  O    ALA    37      45.668   -7.627   49.012  1.00 92.35      AAAA O
ATOM    363  N    SER    38      44.031   -8.301   47.622  1.00 94.31      AAAA N
ATOM    365  CA   SER    38      43.528   -9.352   48.484  1.00 95.70      AAAA C
ATOM    366  CB   SER    38      42.405  -10.164   47.858  1.00 97.44      AAAA C
ATOM    367  OG   SER    38      42.061  -11.176   48.814  1.00103.48      AAAA O
ATOM    369  C    SER    38      44.702  -10.263   48.821  1.00 96.87      AAAA C
ATOM    370  O    SER    38      44.761  -10.778   49.924  1.00 98.06      AAAA O
ATOM    371  N    ASP    39      45.584  -10.415   47.852  1.00 97.99      AAAA N
ATOM    373  CA   ASP    39      46.821  -11.148   47.980  1.00 99.19      AAAA C
ATOM    374  CB   ASP    39      47.579  -11.050   46.652  1.00102.13      AAAA C
ATOM    375  CG   ASP    39      47.696  -12.387   45.948  0.01101.22      AAAA C
ATOM    376  OD1  ASP    39      46.644  -12.978   45.623  0.01101.42      AAAA O
ATOM    377  OD2  ASP    39      48.833  -12.848   45.718  0.01101.41      AAAA O
ATOM    378  C    ASP    39      47.660  -10.564   49.105  1.00 99.40      AAAA C
ATOM    379  O    ASP    39      47.692  -11.056   50.224  1.00 99.15      AAAA O
ATOM    380  N    TYR    40      48.354   -9.479   48.818  1.00100.96      AAAA N
ATOM    382  CA   TYR    40      49.120   -8.706   49.802  1.00101.16      AAAA C
ATOM    383  CB   TYR    40      49.511   -7.393   49.130  1.00103.67      AAAA C
ATOM    384  CG   TYR    40      50.159   -6.281   49.887  1.00107.81      AAAA C
ATOM    385  CD1  TYR    40      50.931   -5.325   49.228  1.00109.56      AAAA C
```

Figure 1A-3

| | | | | | | | | | | |
|---|---|---|---|---|---|---|---|---|---|---|
| ATOM | 386 | CE1 | TYR | 40 | 51.540 | -4.280 | 49.910 | 1.00 | 109.67 | AAAA C |
| ATOM | 387 | CD2 | TYR | 40 | 50.044 | -6.115 | 51.254 | 1.00 | 109.28 | AAAA C |
| ATOM | 388 | CE2 | TYR | 40 | 50.618 | -5.102 | 51.976 | 1.00 | 109.83 | AAAA C |
| ATOM | 389 | CZ | TYR | 40 | 51.372 | -4.181 | 51.276 | 1.00 | 110.16 | AAAA C |
| ATOM | 390 | OH | TYR | 40 | 51.999 | -3.127 | 51.893 | 1.00 | 109.84 | AAAA O |
| ATOM | 392 | C | TYR | 40 | 48.343 | -8.529 | 51.100 | 1.00 | 99.10 | AAAA C |
| ATOM | 393 | O | TYR | 40 | 47.168 | -8.182 | 51.183 | 1.00 | 99.05 | AAAA O |
| ATOM | 394 | N | LYS | 41 | 49.041 | -8.653 | 52.218 | 1.00 | 98.62 | AAAA N |
| ATOM | 396 | CA | LYS | 41 | 48.443 | -8.549 | 53.546 | 1.00 | 100.30 | AAAA C |
| ATOM | 397 | CB | LYS | 41 | 49.385 | -9.160 | 54.599 | 1.00 | 104.42 | AAAA C |
| ATOM | 398 | CG | LYS | 41 | 49.218 | -10.649 | 54.814 | 0.01 | 101.06 | AAAA C |
| ATOM | 399 | CD | LYS | 41 | 47.776 | -11.107 | 54.919 | 0.01 | 100.66 | AAAA C |
| ATOM | 400 | CE | LYS | 41 | 47.205 | -10.880 | 56.308 | 0.01 | 99.86 | AAAA C |
| ATOM | 401 | NZ | LYS | 41 | 47.882 | -11.728 | 57.328 | 0.01 | 99.62 | AAAA N |
| ATOM | 405 | C | LYS | 41 | 48.035 | -7.136 | 53.947 | 1.00 | 98.99 | AAAA C |
| ATOM | 406 | O | LYS | 41 | 47.615 | -6.371 | 53.057 | 1.00 | 103.33 | AAAA O |
| ATOM | 407 | N | SER | 42 | 48.198 | -6.754 | 55.221 | 1.00 | 91.75 | AAAA N |
| ATOM | 409 | CA | SER | 42 | 47.825 | -5.412 | 55.604 | 1.00 | 85.06 | AAAA C |
| ATOM | 410 | CB | SER | 42 | 46.385 | -5.520 | 56.147 | 1.00 | 95.33 | AAAA C |
| ATOM | 411 | OG | SER | 42 | 46.547 | -6.140 | 57.426 | 1.00 | 104.63 | AAAA O |
| ATOM | 413 | C | SER | 42 | 48.628 | -4.715 | 56.687 | 1.00 | 80.78 | AAAA C |
| ATOM | 414 | O | SER | 42 | 49.326 | -5.259 | 57.538 | 1.00 | 81.03 | AAAA O |
| ATOM | 415 | N | TYR | 43 | 48.495 | -3.395 | 56.676 | 1.00 | 73.03 | AAAA N |
| ATOM | 417 | CA | TYR | 43 | 49.069 | -2.488 | 57.635 | 1.00 | 67.25 | AAAA C |
| ATOM | 418 | CB | TYR | 43 | 49.086 | -1.119 | 56.965 | 1.00 | 65.37 | AAAA C |
| ATOM | 419 | CG | TYR | 43 | 49.953 | -1.021 | 55.727 | 1.00 | 63.92 | AAAA C |
| ATOM | 420 | CD1 | TYR | 43 | 50.931 | -1.935 | 55.406 | 1.00 | 63.87 | AAAA C |
| ATOM | 421 | CE1 | TYR | 43 | 51.698 | -1.781 | 54.274 | 1.00 | 66.09 | AAAA C |
| ATOM | 422 | CD2 | TYR | 43 | 49.770 | 0.050 | 54.870 | 1.00 | 63.30 | AAAA C |
| ATOM | 423 | CE2 | TYR | 43 | 50.536 | 0.214 | 53.728 | 1.00 | 67.62 | AAAA C |
| ATOM | 424 | CZ | TYR | 43 | 51.508 | -0.712 | 53.432 | 1.00 | 66.94 | AAAA C |
| ATOM | 425 | OH | TYR | 43 | 52.262 | -0.563 | 52.305 | 1.00 | 65.23 | AAAA O |
| ATOM | 427 | C | TYR | 43 | 48.248 | -2.381 | 58.925 | 1.00 | 64.88 | AAAA C |
| ATOM | 428 | O | TYR | 43 | 47.088 | -2.851 | 59.030 | 1.00 | 62.90 | AAAA O |
| ATOM | 429 | N | ARG | 44 | 48.782 | -1.567 | 59.825 | 1.00 | 57.88 | AAAA N |
| ATOM | 431 | CA | ARG | 44 | 48.019 | -1.285 | 61.039 | 1.00 | 56.45 | AAAA C |
| ATOM | 432 | CB | ARG | 44 | 47.842 | -2.611 | 61.760 | 1.00 | 46.51 | AAAA C |
| ATOM | 433 | CG | ARG | 44 | 47.815 | -2.375 | 63.244 | 1.00 | 54.66 | AAAA C |
| ATOM | 434 | CD | ARG | 44 | 46.885 | -3.327 | 63.986 | 1.00 | 58.54 | AAAA C |
| ATOM | 435 | NE | ARG | 44 | 47.090 | -2.927 | 65.403 | 1.00 | 68.56 | AAAA N |
| ATOM | 437 | CZ | ARG | 44 | 46.464 | -3.536 | 66.395 | 1.00 | 64.82 | AAAA C |
| ATOM | 438 | NH1 | ARG | 44 | 45.644 | -4.529 | 66.132 | 1.00 | 61.63 | AAAA N |
| ATOM | 441 | NH2 | ARG | 44 | 46.674 | -3.139 | 67.628 | 1.00 | 66.03 | AAAA N |
| ATOM | 444 | C | ARG | 44 | 48.811 | -0.285 | 61.845 | 1.00 | 55.59 | AAAA C |
| ATOM | 445 | O | ARG | 44 | 49.916 | -0.552 | 62.320 | 1.00 | 58.43 | AAAA O |
| ATOM | 446 | N | PHE | 45 | 48.276 | 0.866 | 62.139 | 1.00 | 51.13 | AAAA N |
| ATOM | 448 | CA | PHE | 45 | 48.865 | 1.944 | 62.863 | 1.00 | 45.94 | AAAA C |
| ATOM | 449 | CB | PHE | 45 | 48.774 | 3.249 | 61.978 | 1.00 | 35.89 | AAAA C |
| ATOM | 450 | CG | PHE | 45 | 49.106 | 2.937 | 60.554 | 1.00 | 30.29 | AAAA C |
| ATOM | 451 | CD1 | PHE | 45 | 50.373 | 3.051 | 59.998 | 1.00 | 45.72 | AAAA C |
| ATOM | 452 | CD2 | PHE | 45 | 48.127 | 2.428 | 59.728 | 1.00 | 35.95 | AAAA C |
| ATOM | 453 | CE1 | PHE | 45 | 50.653 | 2.715 | 58.672 | 1.00 | 47.76 | AAAA C |
| ATOM | 454 | CE2 | PHE | 45 | 48.358 | 2.096 | 58.406 | 1.00 | 39.92 | AAAA C |
| ATOM | 455 | CZ | PHE | 45 | 49.612 | 2.244 | 57.867 | 1.00 | 46.44 | AAAA C |
| ATOM | 456 | C | PHE | 45 | 48.181 | 2.123 | 64.203 | 1.00 | 41.65 | AAAA C |
| ATOM | 457 | O | PHE | 45 | 47.708 | 3.223 | 64.475 | 1.00 | 40.99 | AAAA O |
| ATOM | 458 | N | PRO | 46 | 48.494 | 1.338 | 65.212 | 1.00 | 43.20 | AAAA N |
| ATOM | 459 | CD | PRO | 46 | 49.300 | 0.097 | 65.132 | 1.00 | 47.74 | AAAA C |
| ATOM | 460 | CA | PRO | 46 | 48.032 | 1.530 | 66.560 | 1.00 | 43.34 | AAAA C |
| ATOM | 461 | CB | PRO | 46 | 48.514 | 0.319 | 67.380 | 1.00 | 44.92 | AAAA C |
| ATOM | 462 | CG | PRO | 46 | 49.404 | -0.464 | 66.514 | 1.00 | 45.48 | AAAA C |
| ATOM | 463 | C | PRO | 46 | 48.558 | 2.768 | 67.233 | 1.00 | 41.30 | AAAA C |
| ATOM | 464 | O | PRO | 46 | 48.329 | 2.830 | 68.443 | 1.00 | 44.57 | AAAA O |
| ATOM | 465 | N | LYS | 47 | 49.450 | 3.533 | 66.676 | 1.00 | 39.33 | AAAA N |
| ATOM | 467 | CA | LYS | 47 | 49.991 | 4.679 | 67.362 | 1.00 | 38.10 | AAAA C |
| ATOM | 468 | CB | LYS | 47 | 51.378 | 4.981 | 66.852 | 1.00 | 48.07 | AAAA C |
| ATOM | 469 | CG | LYS | 47 | 52.032 | 3.995 | 65.902 | 1.00 | 67.95 | AAAA C |
| ATOM | 470 | CD | LYS | 47 | 53.563 | 3.976 | 65.891 | 1.00 | 61.33 | AAAA C |
| ATOM | 471 | CE | LYS | 47 | 54.115 | 4.648 | 67.147 | 1.00 | 72.19 | AAAA C |
| ATOM | 472 | NZ | LYS | 47 | 54.024 | 6.132 | 66.874 | 1.00 | 79.29 | AAAA N |
| ATOM | 476 | C | LYS | 47 | 49.014 | 5.848 | 67.195 | 1.00 | 39.76 | AAAA C |
| ATOM | 477 | O | LYS | 47 | 49.189 | 6.827 | 67.952 | 1.00 | 35.45 | AAAA O |
| ATOM | 478 | N | LEU | 48 | 48.300 | 5.886 | 66.053 | 1.00 | 36.45 | AAAA N |
| ATOM | 480 | CA | LEU | 48 | 47.370 | 7.004 | 65.800 | 1.00 | 40.40 | AAAA C |
| ATOM | 481 | CB | LEU | 48 | 46.823 | 6.919 | 64.389 | 1.00 | 28.59 | AAAA C |
| ATOM | 482 | CG | LEU | 48 | 45.947 | 7.967 | 63.787 | 1.00 | 31.04 | AAAA C |
| ATOM | 483 | CD1 | LEU | 48 | 46.637 | 9.310 | 63.878 | 1.00 | 36.86 | AAAA C |

Figure 1A-4

```
ATOM    484  CD2 LEU    48      45.591    7.738   62.294  1.00 34.49      AAAA C
ATOM    485  C   LEU    48      46.186    7.022   66.807  1.00 42.21      AAAA C
ATOM    486  O   LEU    48      45.271    6.187   66.863  1.00 36.48      AAAA O
ATOM    487  N   THR    49      46.138    8.041   67.673  1.00 38.95      AAAA N
ATOM    489  CA  THR    49      45.045    8.151   68.574  1.00 37.96      AAAA C
ATOM    490  CB  THR    49      45.548    8.207   70.034  1.00 48.69      AAAA C
ATOM    491  OG1 THR    49      46.396    9.340   70.225  1.00 35.90      AAAA O
ATOM    493  CG2 THR    49      46.230    6.957   70.529  1.00 31.99      AAAA C
ATOM    494  C   THR    49      44.230    9.425   68.321  1.00 39.48      AAAA C
ATOM    495  O   THR    49      43.111    9.451   68.837  1.00 34.49      AAAA O
ATOM    496  N   VAL    50      44.735   10.415   67.605  1.00 37.32      AAAA N
ATOM    498  CA  VAL    50      43.995   11.664   67.418  1.00 38.72      AAAA C
ATOM    499  CB  VAL    50      44.293   12.708   68.503  1.00 37.24      AAAA C
ATOM    500  CG1 VAL    50      43.630   14.066   68.208  1.00 29.96      AAAA C
ATOM    501  CG2 VAL    50      43.884   12.311   69.913  1.00 32.52      AAAA C
ATOM    502  C   VAL    50      44.271   12.305   66.048  1.00 37.03      AAAA C
ATOM    503  O   VAL    50      45.195   11.863   65.431  1.00 37.96      AAAA O
ATOM    504  N   ILE    51      43.319   12.939   65.415  1.00 37.49      AAAA N
ATOM    506  CA  ILE    51      43.301   13.575   64.133  1.00 32.48      AAAA C
ATOM    507  CB  ILE    51      42.346   12.864   63.152  1.00 34.51      AAAA C
ATOM    508  CG2 ILE    51      41.995   13.802   61.978  1.00 32.31      AAAA C
ATOM    509  CG1 ILE    51      43.026   11.611   62.671  1.00 30.78      AAAA C
ATOM    510  CD1 ILE    51      42.358   10.559   61.815  1.00 19.69      AAAA C
ATOM    511  C   ILE    51      42.659   14.939   64.431  1.00 34.14      AAAA C
ATOM    512  O   ILE    51      41.546   14.830   64.923  1.00 29.08      AAAA O
ATOM    513  N   THR    52      43.342   16.058   64.238  1.00 33.93      AAAA N
ATOM    515  CA  THR    52      42.806   17.305   64.719  1.00 33.83      AAAA C
ATOM    516  CB  THR    52      43.961   18.338   64.939  1.00 35.39      AAAA C
ATOM    517  OG1 THR    52      44.726   18.567   63.781  1.00 41.28      AAAA O
ATOM    519  CG2 THR    52      44.775   17.926   66.134  1.00 22.01      AAAA C
ATOM    520  C   THR    52      41.741   17.961   63.863  1.00 39.02      AAAA C
ATOM    521  O   THR    52      41.202   19.030   64.243  1.00 38.88      AAAA O
ATOM    522  N   GLU    53      41.524   17.477   62.639  1.00 36.93      AAAA N
ATOM    524  CA  GLU    53      40.434   17.953   61.785  1.00 38.38      AAAA C
ATOM    525  CB  GLU    53      41.064   18.512   60.483  1.00 29.76      AAAA C
ATOM    526  CG  GLU    53      42.061   19.552   60.834  1.00 30.48      AAAA C
ATOM    527  CD  GLU    53      42.517   20.396   59.697  1.00 40.82      AAAA C
ATOM    528  OE1 GLU    53      42.638   19.908   58.556  1.00 57.56      AAAA O
ATOM    529  OE2 GLU    53      42.799   21.559   59.931  1.00 35.74      AAAA O
ATOM    530  C   GLU    53      39.506   16.789   61.388  1.00 39.19      AAAA C
ATOM    531  O   GLU    53      38.922   16.311   62.386  1.00 38.95      AAAA O
ATOM    532  N   TYR    54      39.639   16.353   60.102  1.00 30.60      AAAA N
ATOM    534  CA  TYR    54      38.666   15.342   59.713  1.00 35.96      AAAA C
ATOM    535  CB  TYR    54      37.654   15.802   58.636  1.00 30.71      AAAA C
ATOM    536  CG  TYR    54      38.247   16.476   57.388  1.00 21.18      AAAA C
ATOM    537  CD1 TYR    54      38.487   15.733   56.305  1.00 20.22      AAAA C
ATOM    538  CE1 TYR    54      38.980   16.243   55.086  1.00 21.04      AAAA C
ATOM    539  CD2 TYR    54      38.577   17.844   57.307  1.00 23.97      AAAA C
ATOM    540  CE2 TYR    54      39.049   18.384   56.124  1.00 24.69      AAAA C
ATOM    541  CZ  TYR    54      39.263   17.569   55.032  1.00 26.72      AAAA C
ATOM    542  OH  TYR    54      39.763   18.047   53.847  1.00 37.55      AAAA O
ATOM    544  C   TYR    54      39.405   14.115   59.142  1.00 33.87      AAAA C
ATOM    545  O   TYR    54      40.513   14.360   58.678  1.00 30.40      AAAA O
ATOM    546  N   LEU    55      38.683   13.021   59.004  1.00 23.24      AAAA N
ATOM    548  CA  LEU    55      39.111   11.812   58.454  1.00 30.08      AAAA C
ATOM    549  CB  LEU    55      39.011   10.663   59.510  1.00 14.78      AAAA C
ATOM    550  CG  LEU    55      39.349    9.314   58.818  1.00 26.98      AAAA C
ATOM    551  CD1 LEU    55      40.668    9.477   58.040  1.00 26.66      AAAA C
ATOM    552  CD2 LEU    55      39.496    8.093   59.705  1.00 14.45      AAAA C
ATOM    553  C   LEU    55      38.201   11.548   57.238  1.00 37.43      AAAA C
ATOM    554  O   LEU    55      36.995   11.632   57.427  1.00 39.55      AAAA O
ATOM    555  N   LEU    56      38.700   11.348   56.035  1.00 41.83      AAAA N
ATOM    557  CA  LEU    56      37.955   11.201   54.799  1.00 36.98      AAAA C
ATOM    558  CB  LEU    56      37.998   12.446   53.949  1.00 33.29      AAAA C
ATOM    559  CG  LEU    56      37.984   12.514   52.416  1.00 30.35      AAAA C
ATOM    560  CD1 LEU    56      37.076   11.460   51.821  1.00 47.95      AAAA C
ATOM    561  CD2 LEU    56      37.286   13.807   51.985  1.00 33.47      AAAA C
ATOM    562  C   LEU    56      38.595   10.047   54.008  1.00 39.75      AAAA C
ATOM    563  O   LEU    56      39.714   10.205   53.547  1.00 44.38      AAAA O
ATOM    564  N   LEU    57      37.846    9.008   53.800  1.00 36.68      AAAA N
ATOM    566  CA  LEU    57      38.133    7.832   53.034  1.00 41.53      AAAA C
ATOM    567  CB  LEU    57      37.944    6.588   53.916  1.00 37.00      AAAA C
ATOM    568  CG  LEU    57      39.064    6.534   55.026  1.00 36.13      AAAA C
ATOM    569  CD1 LEU    57      38.513    6.890   56.417  1.00 33.26      AAAA C
ATOM    570  CD2 LEU    57      39.630    5.162   55.039  1.00 24.11      AAAA C
ATOM    571  C   LEU    57      37.203    7.825   51.838  1.00 46.03      AAAA C
ATOM    572  O   LEU    57      35.985    7.993   51.969  1.00 44.78      AAAA O
```

Figure 1A-5

```
ATOM    573  N    PHE    58      37.792    7.898   50.642  1.00 47.07      AAAA N
ATOM    575  CA   PHE    58      36.895    8.002   49.467  1.00 48.75      AAAA C
ATOM    576  CB   PHE    58      36.704    9.448   49.102  1.00 46.67      AAAA C
ATOM    577  CG   PHE    58      36.447    9.815   47.692  1.00 54.66      AAAA C
ATOM    578  CD1  PHE    58      37.413    9.706   46.697  1.00 55.19      AAAA C
ATOM    579  CD2  PHE    58      35.200   10.301   47.326  1.00 53.86      AAAA C
ATOM    580  CE1  PHE    58      37.124   10.063   45.396  1.00 50.36      AAAA C
ATOM    581  CE2  PHE    58      34.885   10.655   46.011  1.00 41.84      AAAA C
ATOM    582  CZ   PHE    58      35.877   10.521   45.037  1.00 46.50      AAAA C
ATOM    583  C    PHE    58      37.351    7.052   48.379  1.00 49.71      AAAA C
ATOM    584  O    PHE    58      38.487    7.073   47.934  1.00 52.16      AAAA O
ATOM    585  N    ARG    59      36.471    6.118   47.944  1.00 44.26      AAAA N
ATOM    587  CA   ARG    59      36.753    5.281   46.815  1.00 40.80      AAAA C
ATOM    588  CB   ARG    59      36.911    5.993   45.427  1.00 23.79      AAAA C
ATOM    589  CG   ARG    59      35.869    7.020   45.121  1.00 46.53      AAAA C
ATOM    590  CD   ARG    59      35.921    7.562   43.706  1.00 37.64      AAAA C
ATOM    591  NE   ARG    59      35.822    6.422   42.806  1.00 49.23      AAAA N
ATOM    593  CZ   ARG    59      34.950    5.832   42.036  1.00 41.36      AAAA C
ATOM    594  NH1  ARG    59      33.702    6.277   41.931  1.00 47.00      AAAA N
ATOM    597  NH2  ARG    59      35.237    4.729   41.327  1.00 42.58      AAAA N
ATOM    600  C    ARG    59      38.037    4.494   47.049  1.00 42.25      AAAA C
ATOM    601  O    ARG    59      38.981    4.513   46.232  1.00 44.11      AAAA O
ATOM    602  N    VAL    60      38.001    3.625   48.023  1.00 40.84      AAAA N
ATOM    604  CA   VAL    60      39.101    2.743   48.341  1.00 39.14      AAAA C
ATOM    605  CB   VAL    60      39.624    3.066   49.751  1.00 40.12      AAAA C
ATOM    606  CG1  VAL    60      40.407    1.872   50.296  1.00 35.05      AAAA C
ATOM    607  CG2  VAL    60      40.425    4.352   49.893  1.00 28.86      AAAA C
ATOM    608  C    VAL    60      38.539    1.337   48.368  1.00 43.56      AAAA C
ATOM    609  O    VAL    60      37.535    1.224   49.072  1.00 47.66      AAAA O
ATOM    610  N    ALA    61      39.094    0.371   47.659  1.00 41.92      AAAA N
ATOM    612  CA   ALA    61      38.617   -0.992   47.749  1.00 42.05      AAAA C
ATOM    613  CB   ALA    61      38.302   -1.483   46.364  1.00 52.40      AAAA C
ATOM    614  C    ALA    61      39.613   -1.934   48.386  1.00 43.08      AAAA C
ATOM    615  O    ALA    61      40.757   -1.602   48.670  1.00 50.59      AAAA O
ATOM    616  N    GLY    62      39.200   -3.105   48.849  1.00 45.71      AAAA N
ATOM    618  CA   GLY    62      40.136   -4.079   49.385  1.00 45.39      AAAA C
ATOM    619  C    GLY    62      40.262   -3.902   50.872  1.00 48.04      AAAA C
ATOM    620  O    GLY    62      40.587   -4.835   51.604  1.00 52.34      AAAA O
ATOM    621  N    LEU    63      39.985   -2.734   51.383  1.00 46.90      AAAA N
ATOM    623  CA   LEU    63      40.003   -2.443   52.805  1.00 49.11      AAAA C
ATOM    624  CB   LEU    63      40.274   -0.953   53.027  1.00 41.41      AAAA C
ATOM    625  CG   LEU    63      40.265   -0.423   54.443  1.00 53.41      AAAA C
ATOM    626  CD1  LEU    63      41.172   -1.164   55.416  1.00 48.27      AAAA C
ATOM    627  CD2  LEU    63      40.637    1.047   54.246  1.00 50.51      AAAA C
ATOM    628  C    LEU    63      38.643   -2.881   53.323  1.00 54.20      AAAA C
ATOM    629  O    LEU    63      37.587   -2.430   52.837  1.00 57.73      AAAA O
ATOM    630  N    GLU    64      38.658   -3.862   54.190  1.00 53.97      AAAA N
ATOM    632  CA   GLU    64      37.462   -4.448   54.749  1.00 56.96      AAAA C
ATOM    633  CB   GLU    64      37.689   -5.956   54.734  1.00 65.33      AAAA C
ATOM    634  CG   GLU    64      37.832   -6.484   53.293  1.00 75.14      AAAA C
ATOM    635  CD   GLU    64      37.404   -7.940   53.128  1.00 78.10      AAAA C
ATOM    636  OE1  GLU    64      37.424   -8.698   54.132  1.00 63.93      AAAA O
ATOM    637  OE2  GLU    64      37.036   -8.320   51.978  1.00 88.77      AAAA O
ATOM    638  C    GLU    64      37.096   -4.007   56.163  1.00 57.12      AAAA C
ATOM    639  O    GLU    64      35.986   -4.332   56.600  1.00 59.82      AAAA O
ATOM    640  N    SER    65      37.766   -3.042   56.761  1.00 50.64      AAAA N
ATOM    642  CA   SER    65      37.539   -2.523   58.060  1.00 47.19      AAAA C
ATOM    643  CB   SER    65      37.743   -3.596   59.139  1.00 49.24      AAAA C
ATOM    644  OG   SER    65      37.501   -2.971   60.429  1.00 50.90      AAAA O
ATOM    646  C    SER    65      38.516   -1.405   58.432  1.00 48.35      AAAA C
ATOM    647  O    SER    65      39.716   -1.692   58.374  1.00 52.75      AAAA O
ATOM    648  N    LEU    66      38.054   -0.289   58.984  1.00 41.03      AAAA N
ATOM    650  CA   LEU    66      38.956    0.758   59.405  1.00 41.94      AAAA C
ATOM    651  CB   LEU    66      38.247    2.083   59.498  1.00 25.25      AAAA C
ATOM    652  CG   LEU    66      37.283    2.476   58.402  1.00 34.49      AAAA C
ATOM    653  CD1  LEU    66      36.974    3.951   58.512  1.00 30.81      AAAA C
ATOM    654  CD2  LEU    66      37.767    2.200   56.994  1.00 34.34      AAAA C
ATOM    655  C    LEU    66      39.646    0.462   60.734  1.00 45.39      AAAA C
ATOM    656  O    LEU    66      40.762    0.947   60.927  1.00 41.05      AAAA O
ATOM    657  N    GLY    67      39.000   -0.346   61.583  1.00 45.21      AAAA N
ATOM    659  CA   GLY    67      39.773   -0.672   62.799  1.00 48.14      AAAA C
ATOM    660  C    GLY    67      40.998   -1.508   62.445  1.00 44.51      AAAA C
ATOM    661  O    GLY    67      41.855   -1.724   63.287  1.00 45.42      AAAA O
ATOM    662  N    ASP    68      41.013   -2.189   61.309  1.00 47.60      AAAA N
ATOM    664  CA   ASP    68      42.194   -2.834   60.738  1.00 50.99      AAAA C
ATOM    665  CB   ASP    68      42.012   -3.417   59.361  1.00 39.42      AAAA C
ATOM    666  CG   ASP    68      41.205   -4.678   59.311  1.00 45.82      AAAA C
ATOM    667  OD1  ASP    68      40.912   -5.341   60.320  1.00 44.69      AAAA O
ATOM    668  OD2  ASP    68      40.819   -5.065   58.187  1.00 47.23      AAAA O
```

Figure 1A-6

| | | | | | | | | | | |
|---|---|---|---|---|---|---|---|---|---|---|
| ATOM | 669 | C | ASP | 68 | 43.363 | -1.837 | 60.596 | 1.00 | 45.89 | AAAA C |
| ATOM | 670 | O | ASP | 68 | 44.436 | -2.269 | 60.903 | 1.00 | 44.84 | AAAA O |
| ATOM | 671 | N | LEU | 69 | 43.145 | -0.609 | 60.247 | 1.00 | 42.49 | AAAA N |
| ATOM | 673 | CA | LEU | 69 | 44.175 | 0.352 | 60.048 | 1.00 | 45.80 | AAAA C |
| ATOM | 674 | CB | LEU | 69 | 43.920 | 1.393 | 58.945 | 1.00 | 45.25 | AAAA C |
| ATOM | 675 | CG | LEU | 69 | 43.902 | 0.882 | 57.494 | 1.00 | 54.25 | AAAA C |
| ATOM | 676 | CD1 | LEU | 69 | 43.541 | 2.037 | 56.565 | 1.00 | 47.26 | AAAA C |
| ATOM | 677 | CD2 | LEU | 69 | 45.211 | 0.200 | 57.113 | 1.00 | 50.76 | AAAA C |
| ATOM | 678 | C | LEU | 69 | 44.347 | 1.107 | 61.350 | 1.00 | 49.50 | AAAA C |
| ATOM | 679 | O | LEU | 69 | 45.470 | 1.210 | 61.851 | 1.00 | 54.51 | AAAA O |
| ATOM | 680 | N | PHE | 70 | 43.296 | 1.737 | 61.869 | 1.00 | 44.60 | AAAA N |
| ATOM | 682 | CA | PHE | 70 | 43.423 | 2.564 | 63.046 | 1.00 | 39.67 | AAAA C |
| ATOM | 683 | CB | PHE | 70 | 42.987 | 3.973 | 62.700 | 1.00 | 26.08 | AAAA C |
| ATOM | 684 | CG | PHE | 70 | 43.465 | 4.501 | 61.390 | 1.00 | 45.32 | AAAA C |
| ATOM | 685 | CD1 | PHE | 70 | 42.532 | 4.748 | 60.384 | 1.00 | 47.41 | AAAA C |
| ATOM | 686 | CD2 | PHE | 70 | 44.815 | 4.767 | 61.130 | 1.00 | 48.77 | AAAA C |
| ATOM | 687 | CE1 | PHE | 70 | 42.945 | 5.263 | 59.159 | 1.00 | 56.16 | AAAA C |
| ATOM | 688 | CE2 | PHE | 70 | 45.229 | 5.256 | 59.895 | 1.00 | 47.24 | AAAA C |
| ATOM | 689 | CZ | PHE | 70 | 44.293 | 5.506 | 58.896 | 1.00 | 49.54 | AAAA C |
| ATOM | 690 | C | PHE | 70 | 42.655 | 1.999 | 64.219 | 1.00 | 40.09 | AAAA C |
| ATOM | 691 | O | PHE | 70 | 41.874 | 2.734 | 64.838 | 1.00 | 35.74 | AAAA O |
| ATOM | 692 | N | PRO | 71 | 43.053 | 0.852 | 64.768 | 1.00 | 39.19 | AAAA N |
| ATOM | 693 | CD | PRO | 71 | 44.269 | 0.058 | 64.411 | 1.00 | 39.94 | AAAA C |
| ATOM | 694 | CA | PRO | 71 | 42.444 | 0.237 | 65.899 | 1.00 | 35.30 | AAAA C |
| ATOM | 695 | CB | PRO | 71 | 43.308 | -0.983 | 66.246 | 1.00 | 38.03 | AAAA C |
| ATOM | 696 | CG | PRO | 71 | 44.669 | -0.564 | 65.717 | 1.00 | 38.36 | AAAA C |
| ATOM | 697 | C | PRO | 71 | 42.453 | 1.089 | 67.126 | 1.00 | 33.72 | AAAA C |
| ATOM | 698 | O | PRO | 71 | 42.005 | 0.630 | 68.159 | 1.00 | 39.32 | AAAA O |
| ATOM | 699 | N | ASN | 72 | 43.058 | 2.220 | 67.231 | 1.00 | 36.55 | AAAA N |
| ATOM | 701 | CA | ASN | 72 | 43.204 | 3.032 | 68.401 | 1.00 | 32.60 | AAAA C |
| ATOM | 702 | CB | ASN | 72 | 44.637 | 2.916 | 68.962 | 1.00 | 36.89 | AAAA C |
| ATOM | 703 | CG | ASN | 72 | 44.735 | 1.638 | 69.761 | 1.00 | 47.03 | AAAA C |
| ATOM | 704 | OD1 | ASN | 72 | 44.644 | 1.619 | 70.979 | 1.00 | 64.42 | AAAA O |
| ATOM | 705 | ND2 | ASN | 72 | 44.880 | 0.475 | 69.169 | 1.00 | 63.17 | AAAA N |
| ATOM | 708 | C | ASN | 72 | 42.875 | 4.477 | 68.135 | 1.00 | 30.11 | AAAA C |
| ATOM | 709 | O | ASN | 72 | 43.099 | 5.201 | 69.104 | 1.00 | 36.53 | AAAA O |
| ATOM | 710 | N | LEU | 73 | 42.309 | 4.809 | 66.978 | 1.00 | 27.62 | AAAA N |
| ATOM | 712 | CA | LEU | 73 | 41.940 | 6.207 | 66.730 | 1.00 | 34.07 | AAAA C |
| ATOM | 713 | CB | LEU | 73 | 41.476 | 6.373 | 65.292 | 1.00 | 28.37 | AAAA C |
| ATOM | 714 | CG | LEU | 73 | 40.819 | 7.713 | 64.882 | 1.00 | 29.33 | AAAA C |
| ATOM | 715 | CD1 | LEU | 73 | 41.918 | 8.721 | 64.963 | 1.00 | 31.86 | AAAA C |
| ATOM | 716 | CD2 | LEU | 73 | 40.202 | 7.518 | 63.478 | 1.00 | 32.07 | AAAA C |
| ATOM | 717 | C | LEU | 73 | 40.929 | 6.569 | 67.817 | 1.00 | 32.14 | AAAA C |
| ATOM | 718 | O | LEU | 73 | 40.073 | 5.737 | 68.081 | 1.00 | 35.02 | AAAA O |
| ATOM | 719 | N | THR | 74 | 41.081 | 7.585 | 68.582 | 1.00 | 29.47 | AAAA N |
| ATOM | 721 | CA | THR | 74 | 40.150 | 7.826 | 69.683 | 1.00 | 34.80 | AAAA C |
| ATOM | 722 | CB | THR | 74 | 41.028 | 7.744 | 70.952 | 1.00 | 46.09 | AAAA C |
| ATOM | 723 | OG1 | THR | 74 | 41.729 | 6.485 | 70.880 | 1.00 | 46.30 | AAAA O |
| ATOM | 725 | CG2 | THR | 74 | 40.262 | 7.831 | 72.253 | 1.00 | 39.45 | AAAA C |
| ATOM | 726 | C | THR | 74 | 39.424 | 9.155 | 69.602 | 1.00 | 35.48 | AAAA C |
| ATOM | 727 | O | THR | 74 | 38.270 | 9.322 | 70.077 | 1.00 | 35.32 | AAAA O |
| ATOM | 728 | N | VAL | 75 | 40.047 | 10.198 | 69.073 | 1.00 | 29.80 | AAAA N |
| ATOM | 730 | CA | VAL | 75 | 39.351 | 11.474 | 68.892 | 1.00 | 34.91 | AAAA C |
| ATOM | 731 | CB | VAL | 75 | 39.856 | 12.445 | 69.955 | 1.00 | 26.03 | AAAA C |
| ATOM | 732 | CG1 | VAL | 75 | 39.173 | 13.801 | 69.934 | 1.00 | 24.51 | AAAA C |
| ATOM | 733 | CG2 | VAL | 75 | 39.675 | 11.910 | 71.366 | 1.00 | 19.87 | AAAA C |
| ATOM | 734 | C | VAL | 75 | 39.613 | 12.045 | 67.494 | 1.00 | 37.57 | AAAA C |
| ATOM | 735 | O | VAL | 75 | 40.724 | 11.808 | 67.022 | 1.00 | 35.99 | AAAA O |
| ATOM | 736 | N | ILE | 76 | 38.600 | 12.555 | 66.796 | 1.00 | 35.91 | AAAA N |
| ATOM | 738 | CA | ILE | 76 | 38.696 | 13.340 | 65.592 | 1.00 | 31.48 | AAAA C |
| ATOM | 739 | CB | ILE | 76 | 37.831 | 12.769 | 64.492 | 1.00 | 29.60 | AAAA C |
| ATOM | 740 | CG2 | ILE | 76 | 37.856 | 13.630 | 63.208 | 1.00 | 19.54 | AAAA C |
| ATOM | 741 | CG1 | ILE | 76 | 38.222 | 11.314 | 64.277 | 1.00 | 28.52 | AAAA C |
| ATOM | 742 | CD1 | ILE | 76 | 37.149 | 10.556 | 63.478 | 1.00 | 28.85 | AAAA C |
| ATOM | 743 | C | ILE | 76 | 38.157 | 14.718 | 66.000 | 1.00 | 33.84 | AAAA C |
| ATOM | 744 | O | ILE | 76 | 36.987 | 14.777 | 66.274 | 1.00 | 38.84 | AAAA O |
| ATOM | 745 | N | ARG | 77 | 38.906 | 15.733 | 66.230 | 1.00 | 30.32 | AAAA N |
| ATOM | 747 | CA | ARG | 77 | 38.605 | 16.901 | 67.021 | 1.00 | 30.82 | AAAA C |
| ATOM | 748 | CB | ARG | 77 | 39.961 | 17.475 | 67.461 | 1.00 | 26.62 | AAAA C |
| ATOM | 749 | CG | ARG | 77 | 39.993 | 18.836 | 68.058 | 1.00 | 52.42 | AAAA C |
| ATOM | 750 | CD | ARG | 77 | 41.290 | 18.957 | 68.908 | 1.00 | 49.10 | AAAA C |
| ATOM | 751 | NE | ARG | 77 | 41.411 | 17.817 | 69.773 | 1.00 | 39.23 | AAAA N |
| ATOM | 753 | CZ | ARG | 77 | 40.977 | 18.016 | 71.064 | 1.00 | 48.79 | AAAA C |
| ATOM | 754 | NH1 | ARG | 77 | 40.440 | 19.104 | 71.610 | 1.00 | 30.34 | AAAA N |
| ATOM | 757 | NH2 | ARG | 77 | 41.061 | 17.012 | 71.941 | 1.00 | 40.38 | AAAA N |
| ATOM | 760 | C | ARG | 77 | 37.643 | 17.733 | 66.225 | 1.00 | 31.75 | AAAA C |
| ATOM | 761 | O | ARG | 77 | 36.944 | 18.637 | 66.664 | 1.00 | 31.40 | AAAA O |
| ATOM | 762 | N | GLY | 78 | 37.688 | 17.661 | 64.884 | 1.00 | 32.87 | AAAA N |
| ATOM | 764 | CA | GLY | 78 | 36.982 | 18.409 | 63.950 | 1.00 | 16.23 | AAAA C |

Figure 1A-7

```
ATOM    765  C   GLY    78      37.199  19.880  64.063  1.00 31.58      AAAA C
ATOM    766  O   GLY    78      36.363  20.775  63.674  1.00 34.03      AAAA O
ATOM    767  N   TRP    79      38.439  20.321  64.304  1.00 31.21      AAAA N
ATOM    769  CA  TRP    79      38.757  21.740  64.337  1.00 30.80      AAAA C
ATOM    770  CB  TRP    79      40.177  21.943  64.845  1.00 39.07      AAAA C
ATOM    771  CG  TRP    79      40.626  23.343  65.164  1.00 36.64      AAAA C
ATOM    772  CD2 TRP    79      41.691  24.001  64.433  1.00 28.52      AAAA C
ATOM    773  CE2 TRP    79      41.826  25.288  65.002  1.00 36.49      AAAA C
ATOM    774  CE3 TRP    79      42.473  23.625  63.370  1.00 37.96      AAAA C
ATOM    775  CD1 TRP    79      40.199  24.235  66.113  1.00 29.59      AAAA C
ATOM    776  NE1 TRP    79      40.917  25.413  66.054  1.00 27.67      AAAA N
ATOM    778  CZ2 TRP    79      42.770  26.213  64.543  1.00 31.83      AAAA C
ATOM    779  CZ3 TRP    79      43.389  24.548  62.876  1.00 46.14      AAAA C
ATOM    780  CH2 TRP    79      43.525  25.794  63.470  1.00 35.31      AAAA C
ATOM    781  C   TRP    79      38.606  22.418  62.986  1.00 28.75      AAAA C
ATOM    782  O   TRP    79      38.585  23.624  62.961  1.00 23.61      AAAA O
ATOM    783  N   LYS    80      38.659  21.684  61.895  1.00 31.84      AAAA N
ATOM    785  CA  LYS    80      38.305  22.153  60.573  1.00 32.78      AAAA C
ATOM    786  CB  LYS    80      39.453  22.498  59.689  1.00 41.17      AAAA C
ATOM    787  CG  LYS    80      39.838  23.911  59.470  1.00 34.68      AAAA C
ATOM    788  CD  LYS    80      41.025  24.350  60.306  1.00 44.77      AAAA C
ATOM    789  CE  LYS    80      41.276  25.811  59.898  1.00 50.41      AAAA C
ATOM    790  NZ  LYS    80      42.530  25.752  59.092  1.00 67.26      AAAA N
ATOM    791  C   LYS    80      37.585  20.960  59.917  1.00 34.52      AAAA C
ATOM    792  O   LYS    80      37.950  19.843  60.237  1.00 37.62      AAAA O
ATOM    793  N   LEU    81      36.477  21.267  59.207  1.00 31.77      AAAA N
ATOM    795  CA  LEU    81      35.742  20.157  58.600  1.00 31.02      AAAA C
ATOM    796  CB  LEU    81      34.290  20.315  59.092  1.00 31.20      AAAA C
ATOM    797  CG  LEU    81      34.115  20.319  60.632  1.00 36.97      AAAA C
ATOM    798  CD1 LEU    81      32.832  21.080  60.954  1.00 27.98      AAAA C
ATOM    799  CD2 LEU    81      34.089  18.955  61.297  1.00 28.77      AAAA C
ATOM    800  C   LEU    81      35.733  20.023  57.104  1.00 29.86      AAAA C
ATOM    801  O   LEU    81      36.082  20.947  56.368  1.00 29.34      AAAA O
ATOM    802  N   PHE    82      35.430  18.813  56.594  1.00 27.78      AAAA N
ATOM    804  CA  PHE    82      35.176  18.653  55.182  1.00 28.68      AAAA C
ATOM    805  CB  PHE    82      35.513  17.226  54.795  1.00 32.78      AAAA C
ATOM    806  CG  PHE    82      35.348  16.901  53.357  1.00 30.48      AAAA C
ATOM    807  CD1 PHE    82      36.378  17.130  52.447  1.00 32.86      'AAAA C
ATOM    808  CD2 PHE    82      34.142  16.361  52.914  1.00 30.93      AAAA C
ATOM    809  CE1 PHE    82      36.217  16.769  51.104  1.00 43.27      AAAA C
ATOM    810  CE2 PHE    82      33.963  16.061  51.538  1.00 26.30      AAAA C
ATOM    811  CZ  PHE    82      35.005  16.238  50.672  1.00 37.73      AAAA C
ATOM.   812  C   PHE    82      33.670  18.911  54.993  1.00 30.06      AAAA C
ATOM    813  O   PHE    82      32.830  18.045  55.278  1.00 27.36      AAAA O
ATOM    814  N   TYR    83      33.301  20.148  54.770  1.00 31.68      AAAA N
ATOM    815  CA  TYR    83      31.911  20.605  54.633  1.00 40.76      AAAA C
ATOM    816  C   TYR    83      31.043  19.977  55.726  1.00 44.00      AAAA C
ATOM    817  O   TYR    83      30.075  19.210  55.487  1.00 50.47      AAAA O
ATOM    818  CB  TYR    83      31.359  20.199  53.269  1.00 31.55      AAAA C
ATOM    819  CG  TYR    83      32.196  20.742  52.117  0.01 20.00      AAAA C
ATOM    820  CD1 TYR    83      33.254  19.982  51.609  0.01 20.00      AAAA C
ATOM    821  CD2 TYR    83      31.906  21.998  51.575  0.01 20.00      AAAA C
ATOM    822  CE1 TYR    83      34.027  20.480  50.556  0.01 20.00      AAAA C
ATOM    823  CE2 TYR    83      32.679  22.496  50.521  0.01 20.00      AAAA C
ATOM    824  CZ  TYR    83      33.740  21.737  50.012  0.01 20.00      AAAA C
ATOM    825  OH  TYR    83      34.492  22.222  48.989  0.01 20.00      AAAA O
ATOM    826  N   ASN    84      31.043  20.461  56.924  1.00 40.91      AAAA N
ATOM    827  CA  ASN    84      30.250  20.057  58.056  1.00 36.54      AAAA C
ATOM    828  CB  ASN    84      28.763  20.046  57.700  1.00 47.84      AAAA C
ATOM    829  CG  ASN    84      28.274  21.164  56.797  1.00 60.75      AAAA C
ATOM    830  OD1 ASN    84      28.319  22.343  57.119  1.00 45.55      AAAA O
ATOM    831  ND2 ASN    84      27.839  20.876  55.552  1.00 65.98      AAAA N
ATOM    832  C   ASN    84      30.686  18.679  58.556  1.00 36.33      AAAA C
ATOM    833  O   ASN    84      30.137  18.206  59.580  1.00 38.24      AAAA O
ATOM    834  N   TYR    85      31.455  17.900  57.800  1.00 32.78      AAAA N
ATOM    836  CA  TYR    85      31.617  16.504  58.222  1.00 35.45      AAAA C
ATOM    837  CB  TYR    85      31.473  15.579  57.000  1.00 35.54      AAAA C
ATOM    838  CG  TYR    85      30.078  15.733  56.453  1.00 41.35      AAAA C
ATOM    839  CD1 TYR    85      29.868  16.291  55.199  1.00 38.22      AAAA C
ATOM    840  CE1 TYR    85      28.611  16.445  54.704  1.00 40.83      AAAA C
ATOM    841  CD2 TYR    85      28.954  15.371  57.200  1.00 47.42      AAAA C
ATOM    842  CE2 TYR    85      27.661  15.533  56.705  1.00 45.91      AAAA C
ATOM    843  CZ  TYR    85      27.497  16.072  55.445  1.00 46.06      AAAA C
ATOM    844  OH  TYR    85      26.258  16.315  54.886  1.00 46.05      AAAA O
ATOM    846  C   TYR    85      32.977  16.367  58.891  1.00 32.08      AAAA C
ATOM    847  O   TYR    85      33.943  16.977  58.495  1.00 37.44      AAAA O
ATOM    848  N   ALA    86      33.027  15.691  59.979  1.00 30.21      AAAA N
ATOM    850  CA  ALA    86      34.257  15.325  60.670  1.00 34.10      AAAA C
ATOM    851  CB  ALA    86      33.999  15.370  62.157  1.00 25.48      AAAA C
```

Figure 1A-8

```
ATOM    852  C    ALA    86      34.729   13.962   60.216  1.00 32.67      AAAA C
ATOM    853  O    ALA    86      35.795   13.481   60.577  1.00 35.10      AAAA O
ATOM    854  N    LEU    87      33.832   13.173   59.597  1.00 28.56      AAAA N
ATOM    856  CA   LEU    87      34.188   11.805   59.323  1.00 29.26      AAAA C
ATOM    857  CB   LEU    87      33.798   10.860   60.471  1.00 13.64      AAAA C
ATOM    858  CG   LEU    87      33.801    9.363   60.188  1.00 25.77      AAAA C
ATOM    859  CD1  LEU    87      35.140    8.915   59.571  1.00 27.21      AAAA C
ATOM    860  CD2  LEU    87      33.637    8.432   61.393  1.00 23.52      AAAA C
ATOM    861  C    LEU    87      33.530   11.429   58.021  1.00 35.60      AAAA C
ATOM    862  O    LEU    87      32.320   11.421   58.001  1.00 38.97      AAAA O
ATOM    863  N    VAL    88      34.174   11.300   56.875  1.00 37.86      AAAA N
ATOM    865  CA   VAL    88      33.438   11.032   55.628  1.00 33.32      AAAA C
ATOM    866  CB   VAL    88      33.666   12.085   54.553  1.00 22.38      AAAA C
ATOM    867  CG1  VAL    88      32.974   11.675   53.261  1.00 19.24      AAAA C
ATOM    868  CG2  VAL    88      33.165   13.402   55.042  1.00 13.27      AAAA C
ATOM    869  C    VAL    88      33.898    9.684   55.114  1.00 31.79      AAAA C
ATOM    870  O    VAL    88      35.069    9.407   55.117  1.00 33.57      AAAA O
ATOM    871  N    ILE    89      33.078    8.728   54.822  1.00 31.08      AAAA N
ATOM    873  CA   ILE    89      33.361    7.433   54.280  1.00 30.45      AAAA C
ATOM    874  CB   ILE    89      32.941    6.384   55.296  1.00 30.17      AAAA C
ATOM    875  CG2  ILE    89      32.898    4.954   54.821  1.00 37.24      AAAA C
ATOM    876  CG1  ILE    89      33.893    6.420   56.500  1.00 24.92      AAAA C
ATOM    877  CD1  ILE    89      33.424    5.613   57.675  1.00 23.96      AAAA C
ATOM    878  C    ILE    89      32.509    7.206   53.027  1.00 40.64      AAAA C
ATOM    879  O    ILE    89      31.330    6.881   53.205  1.00 38.69      AAAA O
ATOM    880  N    PHE    90      33.082    7.464   51.845  1.00 41.45      AAAA N
ATOM    882  CA   PHE    90      32.346    7.371   50.591  1.00 37.67      AAAA C
ATOM    883  CB   PHE    90      32.347    8.776   50.110  1.00 32.17      AAAA C
ATOM    884  CG   PHE    90      31.581    9.081   48.865  1.00 39.77      AAAA C
ATOM    885  CD1  PHE    90      30.387    9.772   49.025  1.00 32.02      AAAA C
ATOM    886  CD2  PHE    90      32.052    8.721   47.620  1.00 29.28      AAAA C
ATOM    887  CE1  PHE    90      29.611   10.111   47.938  1.00 33.30      AAAA C
ATOM    888  CE2  PHE    90      31.290    9.086   46.534  1.00 43.09      AAAA C
ATOM    889  CZ   PHE    90      30.083    9.764   46.687  1.00 50.24      AAAA C
ATOM    890  C    PHE    90      32.856    6.384   49.557  1.00 40.72      AAAA C
ATOM    891  O    PHE    90      34.027    6.296   49.203  1.00 46.15      AAAA O
ATOM    892  N    GLU    91      32.024    5.519   49.001  1.00 39.16      AAAA N
ATOM    894  CA   GLU    91      32.248    4.601   47.954  1.00 42.45      AAAA C
ATOM    895  CB   GLU    91      32.479    5.231   46.583  1.00 38.08      AAAA C
ATOM    896  CG   GLU    91      31.136    5.865   46.250  1.00 58.86      AAAA C
ATOM    897  CD   GLU    91      30.855    5.776   44.757  1.00 63.55      AAAA C
ATOM    898  OE1  GLU    91      31.473    6.651   44.082  1.00 64.10      AAAA O
ATOM    899  OE2  GLU    91      30.058    4.813   44.573  1.00 63.64      AAAA O
ATOM    900  C    GLU    91      33.422    3.734   48.313  1.00 42.06      AAAA C
ATOM    901  O    GLU    91      34.298    3.411   47.587  1.00 44.71      AAAA O
ATOM    902  N    MET    92      33.352    3.209   49.482  1.00 46.52      AAAA N
ATOM    904  CA   MET    92      34.409    2.401   50.088  1.00 42.26      AAAA C
ATOM    905  CB   MET    92      34.299    2.659   51.584  1.00 38.37      AAAA C
ATOM    906  CG   MET    92      35.412    2.156   52.420  1.00 59.29      AAAA C
ATOM    907  SD   MET    92      36.802    3.306   52.401  1.00 57.67      AAAA S
ATOM    908  CE   MET    92      36.340    4.405   51.108  1.00 38.36      AAAA C
ATOM    909  C    MET    92      34.012    1.005   49.745  1.00 43.37      AAAA C
ATOM    910  O    MET    92      33.335    0.298   50.523  1.00 45.58      AAAA O
ATOM    911  N    THR    93      34.449    0.518   48.602  1.00 47.09      AAAA N
ATOM    913  CA   THR    93      34.175   -0.900   48.273  1.00 47.32      AAAA C
ATOM    914  CB   THR    93      34.666   -1.281   46.868  1.00 55.28      AAAA C
ATOM    915  OG1  THR    93      34.013   -0.488   45.892  1.00 57.81      AAAA O
ATOM    917  CG2  THR    93      34.332   -2.715   46.516  1.00 44.71      AAAA C
ATOM    918  C    THR    93      34.885   -1.874   49.186  1.00 51.83      AAAA C
ATOM    919  O    THR    93      36.115   -1.777   49.361  1.00 57.91      AAAA O
ATOM    920  N    ASN    94      34.237   -2.983   49.493  1.00 49.85      AAAA N
ATOM    922  CA   ASN    94      34.747   -4.069   50.285  1.00 45.64      AAAA C
ATOM    923  CB   ASN    94      36.241   -4.315   50.001  1.00 59.01      AAAA C
ATOM    924  CG   ASN    94      36.494   -4.849   48.599  1.00 75.44      AAAA C
ATOM    925  OD1  ASN    94      36.847   -4.081   47.688  1.00 77.49      AAAA O
ATOM    926  ND2  ASN    94      36.308   -6.153   48.408  1.00 79.63      AAAA N
ATOM    929  C    ASN    94      34.522   -3.838   51.763  1.00 42.58      AAAA C
ATOM    930  O    ASN    94      34.752   -4.814   52.501  1.00 46.36      AAAA O
ATOM    931  N    LEU    95      34.308   -2.609   52.182  1.00 37.28      AAAA N
ATOM    933  CA   LEU    95      34.324   -2.277   53.621  1.00 39.96      AAAA C
ATOM    934  CB   LEU    95      34.185   -0.786   53.851  1.00 34.05      AAAA C
ATOM    935  CG   LEU    95      34.323   -0.296   55.269  1.00 35.81      AAAA C
ATOM    936  CD1  LEU    95      35.785   -0.537   55.598  1.00 35.48      AAAA C
ATOM    937  CD2  LEU    95      33.847    1.177   55.344  1.00 25.46      AAAA C
ATOM    938  C    LEU    95      33.163   -2.986   54.275  1.00 43.75      AAAA C
ATOM    939  O    LEU    95      32.048   -2.936   53.772  1.00 44.04      AAAA O
ATOM    940  N    LYS    96      33.451   -3.863   55.213  1.00 46.50      AAAA N
ATOM    942  CA   LYS    96      32.364   -4.648   55.779  1.00 42.76      AAAA C
ATOM    943  CB   LYS    96      32.801   -6.075   55.995  1.00 41.41      AAAA C
```

Figure 1A-9

```
ATOM    944  CG  LYS    96      32.760  -6.976  54.788  1.00 49.78      AAAA C
ATOM    945  CD  LYS    96      32.984  -8.446  55.127  1.00 58.09      AAAA C
ATOM    946  CE  LYS    96      33.772  -9.160  54.027  1.00 73.43      AAAA C
ATOM    947  NZ  LYS    96      34.098 -10.556  54.489  1.00 79.13      AAAA N
ATOM    951  C   LYS    96      31.970  -4.055  57.122  1.00 45.29      AAAA C
ATOM    952  O   LYS    96      30.978  -4.502  57.691  1.00 46.23      AAAA O
ATOM    953  N   ASP    97      32.685  -3.071  57.645  1.00 45.15      AAAA N
ATOM    955  CA  ASP    97      32.299  -2.384  58.861  1.00 42.15      AAAA C
ATOM    956  CB  ASP    97      32.294  -3.292  60.059  1.00 45.39      AAAA C
ATOM    957  CG  ASP    97      33.662  -3.562  60.624  1.00 56.95      AAAA C
ATOM    958  OD1 ASP    97      34.579  -2.825  61.012  1.00 59.88      AAAA O
ATOM    959  OD2 ASP    97      33.931  -4.782  60.714  1.00 56.01      AAAA O
ATOM    960  C   ASP    97      33.209  -1.224  59.201  1.00 41.25      AAAA C
ATOM    961  O   ASP    97      34.160  -1.074  58.437  1.00 47.03      AAAA O
ATOM    962  N   ILE    98      32.822  -0.366  60.129  1.00 40.41      AAAA N
ATOM    964  CA  ILE    98      33.675   0.820  60.340  1.00 37.83      AAAA C
ATOM    965  CB  ILE    98      32.983   2.006  61.006  1.00 38.99      AAAA C
ATOM    966  CG2 ILE    98      34.007   3.133  61.207  1.00 38.95      AAAA C
ATOM    967  CG1 ILE    98      31.835   2.488  60.092  1.00 34.84      AAAA C
ATOM    968  CD1 ILE    98      31.629   3.958  59.948  1.00 39.29      AAAA C
ATOM    969  C   ILE    98      34.854   0.322  61.114  1.00 35.11      AAAA C
ATOM    970  O   ILE    98      35.970   0.669  60.841  1.00 43.05      AAAA O
ATOM    971  N   GLY    99      34.618  -0.393  62.192  1.00 34.22      AAAA N
ATOM    973  CA  GLY    99      35.477  -0.972  63.121  1.00 33.74      AAAA C
ATOM    974  C   GLY    99      36.279  -0.084  64.024  1.00 35.90      AAAA C
ATOM    975  O   GLY    99      37.023  -0.572  64.899  1.00 38.21      AAAA O
ATOM    976  N   LEU   100      36.190   1.221  63.913  1.00 33.35      AAAA N
ATOM    978  CA  LEU   100      36.763   2.215  64.771  1.00 31.65      AAAA C
ATOM    979  CB  LEU   100      36.496   3.636  64.294  1.00 29.87      AAAA C
ATOM    980  CG  LEU   100      36.943   3.980  62.835  1.00 32.13      AAAA C
ATOM    981  CD1 LEU   100      36.710   5.479  62.610  1.00 21.38      AAAA C
ATOM    982  CD2 LEU   100      38.412   3.599  62.644  1.00 37.68      AAAA C
ATOM    983  C   LEU   100      36.312   1.976  66.194  1.00 31.94      AAAA C
ATOM    984  O   LEU   100      35.950   2.863  66.979  1.00 31.95      AAAA O
ATOM    985  N   TYR   101      36.704   0.851  66.779  1.00 31.87      AAAA N
ATOM    987  CA  TYR   101      36.329   0.395  68.071  1.00 33.33      AAAA C
ATOM    988  CB  TYR   101      36.491  -1.104  68.264  1.00 41.03      AAAA C
ATOM    989  CG  TYR   101      37.919  -1.559  68.369  1.00 46.66      AAAA C
ATOM    990  CD1 TYR   101      38.571  -1.380  69.587  1.00 51.20      AAAA C
ATOM    991  CE1 TYR   101      39.901  -1.743  69.749  1.00 49.44      AAAA C
ATOM    992  CD2 TYR   101      38.615  -2.112  67.322  1.00 45.15      AAAA C
ATOM    993  CE2 TYR   101      39.927  -2.505  67.479  1.00 47.08      AAAA C
ATOM    994  CZ  TYR   101      40.548  -2.321  68.688  1.00 49.43      AAAA C
ATOM    995  OH  TYR   101      41.834  -2.662  68.997  1.00 55.82      AAAA O
ATOM    997  C   TYR   101      36.989   1.059  69.214  1.00 33.46      AAAA C
ATOM    998  O   TYR   101      36.630   0.813  70.375  1.00 43.00      AAAA O
ATOM    999  N   ASN   102      37.752   2.091  69.068  1.00 38.12      AAAA N
ATOM   1001  CA  ASN   102      38.093   2.979  70.223  1.00 30.78      AAAA C
ATOM   1002  CB  ASN   102      39.603   2.911  70.363  1.00 48.63      AAAA C
ATOM   1003  CG  ASN   102      40.112   1.804  71.268  1.00 54.01      AAAA C
ATOM   1004  OD1 ASN   102      39.738   1.864  72.454  1.00 47.22      AAAA O
ATOM   1005  ND2 ASN   102      40.864   0.845  70.767  1.00 43.08      AAAA N
ATOM   1008  C   ASN   102      37.673   4.385  69.947  1.00 33.82      AAAA C
ATOM   1009  O   ASN   102      38.047   5.364  70.592  1.00 39.84      AAAA O
ATOM   1010  N   LEU   103      36.845   4.640  68.882  1.00 35.28      AAAA N
ATOM   1012  CA  LEU   103      36.473   6.040  68.621  1.00 36.57      AAAA C
ATOM   1013  CB  LEU   103      35.948   6.140  67.213  1.00 34.77      AAAA C
ATOM   1014  CG  LEU   103      35.525   7.482  66.612  1.00 30.32      AAAA C
ATOM   1015  CD1 LEU   103      36.606   8.513  66.646  1.00 23.20      AAAA C
ATOM   1016  CD2 LEU   103      35.198   7.169  65.146  1.00 37.10      AAAA C
ATOM   1017  C   LEU   103      35.484   6.508  69.691  1.00 37.31      AAAA C
ATOM   1018  O   LEU   103      34.449   5.874  69.837  1.00 34.24      AAAA O
ATOM   1019  N   ARG   104      35.810   7.456  70.563  1.00 33.31      AAAA N
ATOM   1021  CA  ARG   104      34.920   7.841  71.605  1.00 29.86      AAAA C
ATOM   1022  CB  ARG   104      35.568   7.657  73.018  1.00 38.17      AAAA C
ATOM   1023  CG  ARG   104      36.356   6.375  73.165  1.00 48.37      AAAA C
ATOM   1024  CD  ARG   104      35.425   5.183  73.248  1.00 50.71      AAAA C
ATOM   1025  NE  ARG   104      34.582   5.320  74.413  1.00 52.38      AAAA N
ATOM   1027  CZ  ARG   104      34.900   4.847  75.621  1.00 72.73      AAAA C
ATOM   1028  NH1 ARG   104      36.047   4.214  75.800  1.00 81.87      AAAA N
ATOM   1031  NH2 ARG   104      33.990   5.070  76.577  1.00 78.12      AAAA N
ATOM   1034  C   ARG   104      34.466   9.273  71.540  1.00 32.58      AAAA C
ATOM   1035  O   ARG   104      33.553   9.743  72.223  1.00 39.89      AAAA O
ATOM   1036  N   ASN   105      34.992  10.065  70.637  1.00 33.47      AAAA N
ATOM   1038  CA  ASN   105      34.549  11.450  70.590  1.00 30.97      AAAA C
ATOM   1044  C   ASN   105      34.907  12.149  69.310  1.00 31.00      AAAA C
ATOM   1045  O   ASN   105      36.086  12.067  69.050  1.00 37.79      AAAA O
ATOM   1039  CB  ASN   105      35.203  12.199  71.721  1.00 12.28      AAAA C
```

Figure 1A-10

| | | | | | | | | | |
|---|---|---|---|---|---|---|---|---|---|
| ATOM | 1040 | CG | ASN | 105 | 34.786 | 13.568 | 71.756 | 1.00 24.93 | AAAA C |
| ATOM | 1041 | OD1 | ASN | 105 | 35.125 | 14.549 | 71.127 | 1.00 38.14 | AAAA O |
| ATOM | 1042 | ND2 | ASN | 105 | 33.828 | 13.985 | 72.649 | 1.00 35.96 | AAAA N |
| ATOM | 1046 | N | ILE | 106 | 33.969 | 12.669 | 68.576 | 1.00 31.90 | AAAA N |
| ATOM | 1048 | CA | ILE | 106 | 34.129 | 13.551 | 67.469 | 1.00 23.39 | AAAA C |
| ATOM | 1049 | CB | ILE | 106 | 33.239 | 13.185 | 66.307 | 1.00 16.54 | AAAA C |
| ATOM | 1050 | CG2 | ILE | 106 | 33.132 | 14.408 | 65.374 | 1.00 20.38 | AAAA C |
| ATOM | 1051 | CG1 | ILE | 106 | 33.928 | 12.034 | 65.558 | 1.00 18.30 | AAAA C |
| ATOM | 1052 | CD1 | ILE | 106 | 33.055 | 11.293 | 64.643 | 1.00 25.48 | AAAA C |
| ATOM | 1053 | C | ILE | 106 | 33.803 | 14.909 | 68.009 | 1.00 27.40 | AAAA C |
| ATOM | 1054 | O | ILE | 106 | 32.628 | 15.106 | 68.243 | 1.00 32.86 | AAAA O |
| ATOM | 1055 | N | THR | 107 | 34.719 | 15.789 | 68.350 | 1.00 30.43 | AAAA N |
| ATOM | 1057 | CA | THR | 107 | 34.532 | 16.983 | 69.145 | 1.00 28.27 | AAAA C |
| ATOM | 1058 | CB | THR | 107 | 35.902 | 17.607 | 69.579 | 1.00 35.78 | AAAA C |
| ATOM | 1059 | OG1 | THR | 107 | 36.819 | 16.503 | 69.738 | 1.00 40.26 | AAAA O |
| ATOM | 1061 | CG2 | THR | 107 | 35.954 | 18.411 | 70.855 | 1.00 28.13 | AAAA C |
| ATOM | 1062 | C | THR | 107 | 33.728 | 17.950 | 68.332 | 1.00 27.95 | AAAA C |
| ATOM | 1063 | O | THR | 107 | 33.392 | 19.060 | 68.831 | 1.00 32.99 | AAAA O |
| ATOM | 1064 | N | ARG | 108 | 33.669 | 17.777 | 67.019 | 1.00 30.28 | AAAA N |
| ATOM | 1066 | CA | ARG | 108 | 33.046 | 18.809 | 66.180 | 1.00 31.25 | AAAA C |
| ATOM | 1067 | CB | ARG | 108 | 33.965 | 20.011 | 65.951 | 1.00 25.13 | AAAA C |
| ATOM | 1068 | CG | ARG | 108 | 33.105 | 21.174 | 65.543 | 1.00 30.68 | AAAA C |
| ATOM | 1069 | CD | ARG | 108 | 33.917 | 22.444 | 65.529 | 1.00 17.12 | AAAA C |
| ATOM | 1070 | NE | ARG | 108 | 33.511 | 23.376 | 64.451 | 1.00 33.40 | AAAA N |
| ATOM | 1072 | CZ | ARG | 108 | 34.045 | 23.608 | 63.266 | 1.00 46.41 | AAAA C |
| ATOM | 1073 | NH1 | ARG | 108 | 35.162 | 22.929 | 62.868 | 1.00 40.30 | AAAA N |
| ATOM | 1076 | NH2 | ARG | 108 | 33.454 | 24.543 | 62.494 | 1.00 39.82 | AAAA N |
| ATOM | 1079 | C | ARG | 108 | 32.701 | 18.328 | 64.784 | 1.00 31.50 | AAAA C |
| ATOM | 1080 | O | ARG | 108 | 33.379 | 17.381 | 64.430 | 1.00 32.67 | AAAA O |
| ATOM | 1081 | N | GLY | 109 | 31.567 | 18.809 | 64.284 | 1.00 32.60 | AAAA N |
| ATOM | 1083 | CA | GLY | 109 | 31.082 | 18.385 | 62.983 | 1.00 28.87 | AAAA C |
| ATOM | 1084 | C | GLY | 109 | 30.470 | 17.008 | 63.001 | 1.00 32.32 | AAAA C |
| ATOM | 1085 | O | GLY | 109 | 30.471 | 16.306 | 64.006 | 1.00 38.03 | AAAA O |
| ATOM | 1086 | N | ALA | 110 | 29.920 | 16.560 | 61.894 | 1.00 34.11 | AAAA N |
| ATOM | 1088 | CA | ALA | 110 | 29.086 | 15.371 | 61.833 | 1.00 36.77 | AAAA C |
| ATOM | 1089 | CB | ALA | 110 | 27.708 | 15.721 | 61.223 | 1.00 15.32 | AAAA C |
| ATOM | 1090 | C | ALA | 110 | 29.745 | 14.335 | 60.957 | 1.00 32.12 | AAAA C |
| ATOM | 1091 | O | ALA | 110 | 30.921 | 14.332 | 60.687 | 1.00 34.11 | AAAA O |
| ATOM | 1092 | N | ILE | 111 | 29.030 | 13.337 | 60.557 | 1.00 26.55 | AAAA N |
| ATOM | 1094 | CA | ILE | 111 | 29.569 | 12.273 | 59.771 | 1.00 32.90 | AAAA C |
| ATOM | 1095 | CB | ILE | 111 | 29.669 | 10.967 | 60.591 | 1.00 38.07 | AAAA C |
| ATOM | 1096 | CG2 | ILE | 111 | 30.091 | 11.140 | 62.036 | 1.00 34.05 | AAAA C |
| ATOM | 1097 | CG1 | ILE | 111 | 28.345 | 10.237 | 60.684 | 1.00 26.54 | AAAA C |
| ATOM | 1098 | CD1 | ILE | 111 | 28.437 | 8.872 | 61.407 | 1.00 27.11 | AAAA C |
| ATOM | 1099 | C | ILE | 111 | 28.738 | 11.928 | 58.521 | 1.00 33.98 | AAAA C |
| ATOM | 1100 | O | ILE | 111 | 27.533 | 12.179 | 58.532 | 1.00 32.15 | AAAA O |
| ATOM | 1101 | N | ARG | 112 | 29.432 | 11.423 | 57.501 | 1.00 30.54 | AAAA N |
| ATOM | 1103 | CA | ARG | 112 | 28.773 | 11.107 | 56.247 | 1.00 27.48 | AAAA C |
| ATOM | 1104 | CB | ARG | 112 | 29.186 | 12.085 | 55.169 | 1.00 26.35 | AAAA C |
| ATOM | 1105 | CG | ARG | 112 | 28.548 | 11.653 | 53.816 | 1.00 25.83 | AAAA C |
| ATOM | 1106 | CD | ARG | 112 | 28.659 | 12.912 | 52.992 | 1.00 32.92 | AAAA C |
| ATOM | 1107 | NE | ARG | 112 | 27.950 | 12.726 | 51.770 | 1.00 50.34 | AAAA N |
| ATOM | 1109 | CZ | ARG | 112 | 27.778 | 13.503 | 50.720 | 1.00 47.61 | AAAA C |
| ATOM | 1110 | NH1 | ARG | 112 | 28.334 | 14.695 | 50.696 | 1.00 44.92 | AAAA N |
| ATOM | 1113 | NH2 | ARG | 112 | 27.012 | 12.925 | 49.789 | 1.00 46.00 | AAAA N |
| ATOM | 1116 | C | ARG | 112 | 29.200 | 9.738 | 55.791 | 1.00 29.74 | AAAA C |
| ATOM | 1117 | O | ARG | 112 | 30.343 | 9.611 | 55.406 | 1.00 36.52 | AAAA O |
| ATOM | 1118 | N | ILE | 113 | 28.326 | 8.754 | 55.886 | 1.00 33.99 | AAAA N |
| ATOM | 1120 | CA | ILE | 113 | 28.612 | 7.376 | 55.555 | 1.00 36.26 | AAAA C |
| ATOM | 1121 | CB | ILE | 113 | 28.457 | 6.461 | 56.760 | 1.00 33.27 | AAAA C |
| ATOM | 1122 | CG2 | ILE | 113 | 28.850 | 5.021 | 56.449 | 1.00 15.85 | AAAA C |
| ATOM | 1123 | CG1 | ILE | 113 | 29.374 | 7.012 | 57.874 | 1.00 31.92 | AAAA C |
| ATOM | 1124 | CD1 | ILE | 113 | 29.324 | 6.250 | 59.176 | 1.00 42.34 | AAAA C |
| ATOM | 1125 | C | ILE | 113 | 27.729 | 6.959 | 54.398 | 1.00 39.26 | AAAA C |
| ATOM | 1126 | O | ILE | 113 | 26.637 | 6.482 | 54.664 | 1.00 50.72 | AAAA O |
| ATOM | 1127 | N | GLU | 114 | 28.175 | 7.199 | 53.190 | 1.00 35.86 | AAAA N |
| ATOM | 1129 | CA | GLU | 114 | 27.491 | 7.103 | 51.935 | 1.00 38.76 | AAAA C |
| ATOM | 1130 | CB | GLU | 114 | 27.471 | 8.443 | 51.216 | 1.00 25.58 | AAAA C |
| ATOM | 1131 | CG | GLU | 114 | 26.567 | 8.402 | 49.969 | 1.00 27.97 | AAAA C |
| ATOM | 1132 | CD | GLU | 114 | 26.349 | 9.840 | 49.578 | 1.00 36.85 | AAAA C |
| ATOM | 1133 | OE1 | GLU | 114 | 26.763 | 10.662 | 50.414 | 1.00 45.57 | AAAA O |
| ATOM | 1134 | OE2 | GLU | 114 | 25.787 | 10.106 | 48.488 | 1.00 35.53 | AAAA O |
| ATOM | 1135 | C | GLU | 114 | 28.039 | 6.072 | 50.944 | 1.00 44.17 | AAAA C |
| ATOM | 1136 | O | GLU | 114 | 29.120 | 5.538 | 51.090 | 1.00 49.97 | AAAA O |
| ATOM | 1137 | N | LYS | 115 | 27.191 | 5.556 | 50.096 | 1.00 40.55 | AAAA N |
| ATOM | 1139 | CA | LYS | 115 | 27.219 | 4.440 | 49.242 | 1.00 41.16 | AAAA C |
| ATOM | 1140 | CB | LYS | 115 | 27.275 | 4.764 | 47.718 | 1.00 23.62 | AAAA C |
| ATOM | 1141 | CG | LYS | 115 | 27.019 | 6.194 | 47.411 | 1.00 18.39 | AAAA C |

Figure 1A-11

| | | | | | | | | | | |
|---|---|---|---|---|---|---|---|---|---|---|
| ATOM | 1142 | CD | LYS | 115 | 26.537 | 6.355 | 45.982 | 1.00 | 24.74 | AAAA C |
| ATOM | 1143 | CE | LYS | 115 | 26.751 | 7.804 | 45.622 | 1.00 | 41.86 | AAAA C |
| ATOM | 1144 | NZ | LYS | 115 | 27.165 | 8.045 | 44.196 | 1.00 | 60.91 | AAAA N |
| ATOM | 1148 | C | LYS | 115 | 28.287 | 3.421 | 49.611 | 1.00 | 42.39 | AAAA C |
| ATOM | 1149 | O | LYS | 115 | 29.102 | 3.103 | 48.749 | 1.00 | 46.68 | AAAA O |
| ATOM | 1150 | N | ASN | 116 | 28.137 | 2.677 | 50.665 | 1.00 | 40.99 | AAAA N |
| ATOM | 1152 | CA | ASN | 116 | 29.022 | 1.570 | 50.976 | 1.00 | 37.33 | AAAA C |
| ATOM | 1153 | CB | ASN | 116 | 29.534 | 1.868 | 52.381 | 1.00 | 46.12 | AAAA C |
| ATOM | 1154 | CG | ASN | 116 | 30.372 | 3.153 | 52.345 | 1.00 | 48.92 | AAAA C |
| ATOM | 1155 | OD1 | ASN | 116 | 31.337 | 3.016 | 51.583 | 1.00 | 38.59 | AAAA O |
| ATOM | 1156 | ND2 | ASN | 116 | 29.927 | 4.174 | 53.056 | 1.00 | 37.35 | AAAA N |
| ATOM | 1159 | C | ASN | 116 | 28.275 | 0.277 | 50.974 | 1.00 | 42.52 | AAAA C |
| ATOM | 1160 | O | ASN | 116 | 28.067 | -0.361 | 52.033 | 1.00 | 48.24 | AAAA O |
| ATOM | 1161 | N | ALA | 117 | 27.989 | -0.188 | 49.772 | 1.00 | 40.94 | AAAA N |
| ATOM | 1163 | CA | ALA | 117 | 27.195 | -1.376 | 49.542 | 1.00 | 43.35 | AAAA C |
| ATOM | 1164 | CB | ALA | 117 | 27.494 | -1.884 | 48.156 | 1.00 | 47.63 | AAAA C |
| ATOM | 1165 | C | ALA | 117 | 27.294 | -2.504 | 50.529 | 1.00 | 46.55 | AAAA C |
| ATOM | 1166 | O | ALA | 117 | 26.211 | -2.998 | 50.890 | 1.00 | 51.24 | AAAA O |
| ATOM | 1167 | N | ASP | 118 | 28.484 | -2.823 | 51.005 | 1.00 | 47.43 | AAAA N |
| ATOM | 1169 | CA | ASP | 118 | 28.559 | -3.980 | 51.920 | 1.00 | 45.74 | AAAA C |
| ATOM | 1170 | CB | ASP | 118 | 29.659 | -4.945 | 51.477 | 1.00 | 55.39 | AAAA C |
| ATOM | 1171 | CG | ASP | 118 | 29.684 | -5.119 | 49.958 | 1.00 | 59.40 | AAAA C |
| ATOM | 1172 | OD1 | ASP | 118 | 28.870 | -5.976 | 49.608 | 1.00 | 64.40 | AAAA O |
| ATOM | 1173 | OD2 | ASP | 118 | 30.448 | -4.447 | 49.207 | 1.00 | 66.73 | AAAA O |
| ATOM | 1174 | C | ASP | 118 | 28.818 | -3.586 | 53.353 | 1.00 | 37.29 | AAAA C |
| ATOM | 1175 | O | ASP | 118 | 29.127 | -4.536 | 54.026 | 1.00 | 42.89 | AAAA O |
| ATOM | 1176 | N | LEU | 119 | 28.670 | -2.327 | 53.685 | 1.00 | 36.46 | AAAA N |
| ATOM | 1178 | CA | LEU | 119 | 28.986 | -1.885 | 55.047 | 1.00 | 40.58 | AAAA C |
| ATOM | 1179 | CB | LEU | 119 | 29.159 | -0.389 | 55.145 | 1.00 | 34.31 | AAAA C |
| ATOM | 1180 | CG | LEU | 119 | 29.640 | 0.331 | 56.378 | 1.00 | 36.58 | AAAA C |
| ATOM | 1181 | CD1 | LEU | 119 | 30.950 | -0.101 | 56.948 | 1.00 | 35.77 | AAAA C |
| ATOM | 1182 | CD2 | LEU | 119 | 29.791 | 1.830 | 56.104 | 1.00 | 29.68 | AAAA C |
| ATOM | 1183 | C | LEU | 119 | 27.937 | -2.376 | 56.007 | 1.00 | 43.67 | AAAA C |
| ATOM | 1184 | O | LEU | 119 | 26.748 | -2.248 | 55.743 | 1.00 | 45.32 | AAAA O |
| ATOM | 1185 | N | CYS | 120 | 28.361 | -2.967 | 57.110 | 1.00 | 43.53 | AAAA N |
| ATOM | 1187 | CA | CYS | 120 | 27.378 | -3.407 | 58.089 | 1.00 | 38.93 | AAAA C |
| ATOM | 1188 | C | CYS | 120 | 27.881 | -2.921 | 59.426 | 1.00 | 41.91 | AAAA C |
| ATOM | 1189 | O | CYS | 120 | 28.660 | -1.960 | 59.446 | 1.00 | 43.66 | AAAA O |
| ATOM | 1190 | CB | CYS | 120 | 27.285 | -4.907 | 58.100 | 1.00 | 37.59 | AAAA C |
| ATOM | 1191 | SG | CYS | 120 | 26.568 | -5.622 | 56.639 | 1.00 | 58.32 | AAAA S |
| ATOM | 1192 | N | TYR | 121 | 27.328 | -3.456 | 60.509 | 1.00 | 38.05 | AAAA N |
| ATOM | 1194 | CA | TYR | 121 | 27.795 | -3.010 | 61.827 | 1.00 | 38.68 | AAAA C |
| ATOM | 1195 | CB | TYR | 121 | 29.189 | -3.572 | 62.130 | 1.00 | 34.61 | AAAA C |
| ATOM | 1196 | CG | TYR | 121 | 28.950 | -5.032 | 62.519 | 1.00 | 36.52 | AAAA C |
| ATOM | 1197 | CD1 | TYR | 121 | 29.087 | -6.045 | 61.582 | 1.00 | 33.58 | AAAA C |
| ATOM | 1198 | CE1 | TYR | 121 | 28.852 | -7.350 | 61.980 | 1.00 | 41.21 | AAAA C |
| ATOM | 1199 | CD2 | TYR | 121 | 28.560 | -5.337 | 63.817 | 1.00 | 36.31 | AAAA C |
| ATOM | 1200 | CE2 | TYR | 121 | 28.287 | -6.630 | 64.201 | 1.00 | 39.48 | AAAA C |
| ATOM | 1201 | CZ | TYR | 121 | 28.432 | -7.641 | 63.270 | 1.00 | 46.07 | AAAA C |
| ATOM | 1202 | OH | TYR | 121 | 28.161 | -8.924 | 63.730 | 1.00 | 49.20 | AAAA O |
| ATOM | 1204 | C | TYR | 121 | 27.674 | -1.523 | 61.789 | 1.00 | 38.83 | AAAA C |
| ATOM | 1205 | O | TYR | 121 | 28.445 | -0.778 | 62.369 | 1.00 | 43.22 | AAAA O |
| ATOM | 1206 | N | LEU | 122 | 26.587 | -1.045 | 61.180 | 1.00 | 39.58 | AAAA N |
| ATOM | 1208 | CA | LEU | 122 | 26.361 | 0.405 | 61.090 | 1.00 | 44.82 | AAAA C |
| ATOM | 1209 | CB | LEU | 122 | 25.990 | 0.715 | 59.634 | 1.00 | 46.48 | AAAA C |
| ATOM | 1210 | CG | LEU | 122 | 26.497 | 2.014 | 59.108 | 1.00 | 44.44 | AAAA C |
| ATOM | 1211 | CD1 | LEU | 122 | 25.778 | 2.448 | 57.859 | 1.00 | 32.19 | AAAA C |
| ATOM | 1212 | CD2 | LEU | 122 | 26.136 | 3.057 | 60.170 | 1.00 | 47.76 | AAAA C |
| ATOM | 1213 | C | LEU | 122 | 25.212 | 0.910 | 61.935 | 1.00 | 44.85 | AAAA C |
| ATOM | 1214 | O | LEU | 122 | 25.269 | 1.759 | 62.839 | 1.00 | 47.66 | AAAA O |
| ATOM | 1215 | N | SER | 123 | 24.104 | 0.137 | 61.843 | 1.00 | 40.12 | AAAA N |
| ATOM | 1217 | CA | SER | 123 | 22.949 | 0.435 | 62.703 | 1.00 | 33.88 | AAAA C |
| ATOM | 1218 | CB | SER | 123 | 21.754 | -0.330 | 62.239 | 1.00 | 19.26 | AAAA C |
| ATOM | 1219 | OG | SER | 123 | 21.964 | -1.762 | 62.402 | 1.00 | 34.35 | AAAA O |
| ATOM | 1221 | C | SER | 123 | 23.165 | 0.060 | 64.159 | 1.00 | 37.43 | AAAA C |
| ATOM | 1222 | O | SER | 123 | 22.326 | 0.280 | 65.025 | 1.00 | 35.33 | AAAA O |
| ATOM | 1223 | N | THR | 124 | 24.242 | -0.698 | 64.432 | 1.00 | 39.03 | AAAA N |
| ATOM | 1225 | CA | THR | 124 | 24.554 | -1.165 | 65.753 | 1.00 | 37.78 | AAAA C |
| ATOM | 1226 | CB | THR | 124 | 25.368 | -2.461 | 65.719 | 1.00 | 42.39 | AAAA C |
| ATOM | 1227 | OG1 | THR | 124 | 26.502 | -2.020 | 64.924 | 1.00 | 47.70 | AAAA O |
| ATOM | 1229 | CG2 | THR | 124 | 24.677 | -3.622 | 65.006 | 1.00 | 40.93 | AAAA C |
| ATOM | 1230 | C | THR | 124 | 25.522 | -0.206 | 66.445 | 1.00 | 39.29 | AAAA C |
| ATOM | 1231 | O | THR | 124 | 25.948 | -0.642 | 67.499 | 1.00 | 41.41 | AAAA O |
| ATOM | 1232 | N | VAL | 125 | 25.737 | 1.001 | 65.985 | 1.00 | 37.80 | AAAA N |
| ATOM | 1234 | CA | VAL | 125 | 26.594 | 1.964 | 66.661 | 1.00 | 41.06 | AAAA C |
| ATOM | 1235 | CB | VAL | 125 | 27.683 | 2.542 | 65.714 | 1.00 | 39.50 | AAAA C |
| ATOM | 1236 | CG1 | VAL | 125 | 28.570 | 3.599 | 66.352 | 1.00 | 28.36 | AAAA C |
| ATOM | 1237 | CG2 | VAL | 125 | 28.693 | 1.565 | 65.110 | 1.00 | 33.07 | AAAA C |

Figure 1A-12

```
ATOM   1238  C    VAL  125    25.759   3.127  67.179  1.00 41.17      AAAA C
ATOM   1239  O    VAL  125    24.941   3.750  66.531  1.00 41.22      AAAA O
ATOM   1240  N    ASP  126    26.072   3.636  68.367  1.00 44.54      AAAA N
ATOM   1242  CA   ASP  126    25.310   4.734  68.967  1.00 37.44      AAAA C
ATOM   1243  CB   ASP  126    24.862   4.335  70.342  1.00 34.73      AAAA C
ATOM   1244  CG   ASP  126    23.879   5.303  70.983  1.00 45.53      AAAA C
ATOM   1245  OD1  ASP  126    23.699   6.520  70.685  1.00 27.71      AAAA O
ATOM   1246  OD2  ASP  126    23.220   4.865  71.964  1.00 52.32      AAAA O
ATOM   1247  C    ASP  126    26.146   5.985  68.872  1.00 40.83      AAAA C
ATOM   1248  O    ASP  126    26.740   6.400  69.888  1.00 42.78      AAAA O
ATOM   1249  N    TRP  127    26.029   6.649  67.704  1.00 35.42      AAAA N
ATOM   1251  CA   TRP  127    26.777   7.856  67.410  1.00 33.02      AAAA C
ATOM   1252  CB   TRP  127    26.568   8.296  65.930  1.00 24.89      AAAA C
ATOM   1253  CG   TRP  127    27.195   7.372  64.907  1.00 34.36      AAAA C
ATOM   1254  CD2  TRP  127    28.587   7.208  64.518  1.00 28.60      AAAA C
ATOM   1255  CE2  TRP  127    28.631   6.186  63.579  1.00 29.06      AAAA C
ATOM   1256  CE3  TRP  127    29.778   7.845  64.873  1.00 35.51      AAAA C
ATOM   1257  CD1  TRP  127    26.465   6.450  64.188  1.00 18.67      AAAA C
ATOM   1258  NE1  TRP  127    27.311   5.712  63.394  1.00 42.87      AAAA N
ATOM   1260  CZ2  TRP  127    29.792   5.783  62.954  1.00 32.53      AAAA C
ATOM   1261  CZ3  TRP  127    30.972   7.445  64.285  1.00 31.51      AAAA C
ATOM   1262  CH2  TRP  127    30.937   6.405  63.336  1.00 37.86      AAAA C
ATOM   1263  C    TRP  127    26.558   9.010  68.367  1.00 36.09      AAAA C
ATOM   1264  O    TRP  127    27.382   9.977  68.497  1.00 40.87      AAAA O
ATOM   1265  N    SER  128    25.493   8.931  69.171  1.00 31.24      AAAA N
ATOM   1267  CA   SER  128    25.201  10.041  70.081  1.00 34.04      AAAA C
ATOM   1268  CB   SER  128    23.757  10.042  70.603  1.00 36.87      AAAA C
ATOM   1269  OG   SER  128    23.433   8.917  71.424  1.00 28.96      AAAA O
ATOM   1271  C    SER  128    26.133   9.975  71.292  1.00 32.39      AAAA C
ATOM   1272  O    SER  128    26.212  10.857  72.134  1.00 30.91      AAAA O
ATOM   1273  N    LEU  129    26.662   8.792  71.549  1.00 27.18      AAAA N
ATOM   1275  CA   LEU  129    27.701   8.607  72.526  1.00 36.73      AAAA C
ATOM   1276  CB   LEU  129    27.920   7.132  72.741  1.00 32.53      AAAA C
ATOM   1277  CG   LEU  129    26.795   6.324  73.371  1.00 39.28      AAAA C
ATOM   1278  CD1  LEU  129    27.292   5.024  73.975  1.00 32.54      AAAA C
ATOM   1279  CD2  LEU  129    26.237   7.117  74.560  1.00 32.12      AAAA C
ATOM   1280  C    LEU  129    29.054   9.226  72.113  1.00 38.04      AAAA C
ATOM   1281  O    LEU  129    29.645  10.001  72.874  1.00 34.50      AAAA O
ATOM   1282  N    ILE  130    29.316   9.217  70.807  1.00 42.09      AAAA N
ATOM   1284  CA   ILE  130    30.480   9.743  70.144  1.00 41.35      AAAA C
ATOM   1285  CB   ILE  130    30.793   8.886  68.901  1.00 41.73      AAAA C
ATOM   1286  CG2  ILE  130    31.992   9.434  68.176  1.00 31.95      AAAA C
ATOM   1287  CG1  ILE  130    30.969   7.413  69.347  1.00 26.64      AAAA C
ATOM   1288  CD1  ILE  130    31.053   6.457  68.165  1.00 42.65      AAAA C
ATOM   1289  C    ILE  130    30.305  11.178  69.679  1.00 46.48      AAAA C
ATOM   1290  O    ILE  130    31.224  11.985  69.966  1.00 38.46      AAAA O
ATOM   1291  N    LEU  131    29.089  11.495  69.193  1.00 45.14      AAAA N
ATOM   1293  CA   LEU  131    28.895  12.865  68.651  1.00 41.45      AAAA C
ATOM   1294  CB   LEU  131    28.499  12.616  67.259  1.00 46.81      AAAA C
ATOM   1295  CG   LEU  131    28.823  12.805  65.878  1.00 36.79      AAAA C
ATOM   1296  CD1  LEU  131    29.128  11.405  65.324  1.00 30.15      AAAA C
ATOM   1297  CD2  LEU  131    27.625  13.581  65.334  1.00 19.92      AAAA C
ATOM   1298  C    LEU  131    27.661  13.525  69.285  1.00 39.28      AAAA C
ATOM   1299  O    LEU  131    26.599  12.867  69.311  1.00 37.75      AAAA O
ATOM   1300  N    ASP  132    27.742  14.811  69.518  1.00 33.73      AAAA N
ATOM   1302  CA   ASP  132    26.610  15.542  70.003  1.00 38.20      AAAA C
ATOM   1303  CB   ASP  132    27.017  16.944  70.381  1.00 43.17      AAAA C
ATOM   1304  CG   ASP  132    27.349  17.137  71.834  1.00 43.29      AAAA C
ATOM   1305  OD1  ASP  132    27.536  16.122  72.521  1.00 47.12      AAAA O
ATOM   1306  OD2  ASP  132    27.413  18.331  72.208  1.00 60.58      AAAA O
ATOM   1307  C    ASP  132    25.520  15.659  68.946  1.00 43.46      AAAA C
ATOM   1308  O    ASP  132    24.481  15.032  68.939  1.00 49.32      AAAA O
ATOM   1309  N    ALA  133    25.754  16.398  67.900  1.00 45.03      AAAA N
ATOM   1311  CA   ALA  133    24.947  16.776  66.773  1.00 38.62      AAAA C
ATOM   1312  CB   ALA  133    25.628  17.987  66.092  1.00 33.82      AAAA C
ATOM   1313  C    ALA  133    24.694  15.669  65.775  1.00 33.33      AAAA C
ATOM   1314  O    ALA  133    24.777  15.791  64.517  1.00 33.71      AAAA O
ATOM   1315  N    VAL  134    24.115  14.565  66.219  1.00 27.88      AAAA N
ATOM   1317  CA   VAL  134    23.813  13.440  65.377  1.00 29.90      AAAA C
ATOM   1318  CB   VAL  134    23.202  12.241  66.120  1.00 40.63      AAAA C
ATOM   1319  CG1  VAL  134    24.265  11.441  66.855  1.00 35.20      AAAA C
ATOM   1320  CG2  VAL  134    22.095  12.701  67.068  1.00 30.84      AAAA C
ATOM   1321  C    VAL  134    22.735  13.732  64.353  1.00 36.98      AAAA C
ATOM   1322  O    VAL  134    22.616  13.106  63.292  1.00 32.95      AAAA O
ATOM   1323  N    SER  135    21.920  14.777  64.626  1.00 39.65      AAAA N
ATOM   1325  CA   SER  135    20.886  15.139  63.692  1.00 43.12      AAAA C
ATOM   1326  CB   SER  135    20.093  16.277  64.305  1.00 45.19      AAAA C
ATOM   1327  OG   SER  135    20.882  17.369  64.684  1.00 39.25      AAAA O
```

Figure 1A-13

```
ATOM   1329  C    SER   135      21.396  15.516  62.309  1.00 41.15      AAAA C
ATOM   1330  O    SER   135      20.615  15.642  61.359  1.00 43.81      AAAA O
ATOM   1331  N    ASN   136      22.615  15.911  62.165  1.00 41.11      AAAA N
ATOM   1333  CA   ASN   136      23.298  16.353  60.978  1.00 37.21      AAAA C
ATOM   1334  CB   ASN   136      24.324  17.372  61.399  1.00 39.66      AAAA C
ATOM   1335  CG   ASN   136      23.724  18.709  61.717  1.00 36.59      AAAA C
ATOM   1336  OD1  ASN   136      22.695  19.079  61.149  1.00 50.81      AAAA O
ATOM   1337  ND2  ASN   136      24.379  19.441  62.585  1.00 47.85      AAAA N
ATOM   1340  C    ASN   136      24.031  15.230  60.259  1.00 35.31      AAAA C
ATOM   1341  O    ASN   136      24.535  15.484  59.194  1.00 38.70      AAAA O
ATOM   1342  N    ASN   137      24.057  14.035  60.793  1.00 29.11      AAAA N
ATOM   1344  CA   ASN   137      24.721  12.959  60.126  1.00 32.98      AAAA C
ATOM   1345  CB   ASN   137      24.737  11.703  61.033  1.00 24.45      AAAA C
ATOM   1346  CG   ASN   137      25.631  11.965  62.217  1.00 26.63      AAAA C
ATOM   1347  OD1  ASN   137      26.070  13.121  62.369  1.00 30.22      AAAA O
ATOM   1348  ND2  ASN   137      25.830  10.923  63.000  1.00 18.90      AAAA N
ATOM   1351  C    ASN   137      23.950  12.749  58.817  1.00 35.89      AAAA C
ATOM   1352  O    ASN   137      22.716  12.755  58.855  1.00 38.57      AAAA O
ATOM   1353  N    TYR   138      24.592  12.251  57.785  1.00 32.86      AAAA N
ATOM   1355  CA   TYR   138      24.093  11.983  56.489  1.00 30.25      AAAA C
ATOM   1356  CB   TYR   138      24.682  12.861  55.421  1.00 27.10      AAAA C
ATOM   1357  CG   TYR   138      24.018  12.741  54.078  1.00 37.89      AAAA C
ATOM   1358  CD1  TYR   138      23.083  13.671  53.648  1.00 39.22      AAAA C
ATOM   1359  CE1  TYR   138      22.510  13.579  52.392  1.00 37.65      AAAA C
ATOM   1360  CD2  TYR   138      24.357  11.717  53.195  1.00 44.28      AAAA C
ATOM   1361  CE2  TYR   138      23.801  11.615  51.951  1.00 41.97      AAAA C
ATOM   1362  CZ   TYR   138      22.868  12.562  51.564  1.00 39.42      AAAA C
ATOM   1363  OH   TYR   138      22.296  12.504  50.318  1.00 45.48      AAAA O
ATOM   1365  C    TYR   138      24.373  10.578  56.051  1.00 31.33      AAAA C
ATOM   1366  O    TYR   138      25.505  10.317  55.797  1.00 37.76      AAAA O
ATOM   1367  N    ILE   139      23.461   9.660  56.116  1.00 35.40      AAAA N
ATOM   1369  CA   ILE   139      23.637   8.249  55.935  1.00 34.04      AAAA C
ATOM   1370  CB   ILE   139      23.234   7.450  57.171  1.00 28.66      AAAA C
ATOM   1371  CG2  ILE   139      23.640   5.984  57.093  1.00 21.99      AAAA C
ATOM   1372  CG1  ILE   139      23.711   8.057  58.469  1.00 42.81      AAAA C
ATOM   1373  CD1  ILE   139      24.455   7.100  59.389  1.00 52.23      AAAA C
ATOM   1374  C    ILE   139      22.729   7.708  54.830  1.00 35.73      AAAA C
ATOM   1375  O    ILE   139      21.538   7.890  54.757  1.00 42.61      AAAA O
ATOM   1376  N    VAL   140      23.286   6.997  53.873  1.00 35.29      AAAA N
ATOM   1378  CA   VAL   140      22.533   6.481  52.755  1.00 32.39      AAAA C
ATOM   1379  CB   VAL   140      21.967   7.627  51.881  1.00 36.05      AAAA C
ATOM   1380  CG1  VAL   140      22.800   8.375  50.881  1.00 25.88      AAAA C
ATOM   1381  CG2  VAL   140      20.807   7.034  51.047  1.00 34.96      AAAA C
ATOM   1382  C    VAL   140      23.422   5.670  51.874  1.00 41.96      AAAA C
ATOM   1383  O    VAL   140      24.537   6.172  51.637  1.00 44.03      AAAA O
ATOM   1384  N    GLY   141      22.899   4.562  51.402  1.00 42.66      AAAA N
ATOM   1386  CA   GLY   141      23.381   3.805  50.278  1.00 30.94      AAAA C
ATOM   1387  C    GLY   141      24.265   2.696  50.835  1.00 38.98      AAAA C
ATOM   1388  O    GLY   141      25.132   2.003  50.176  1.00 35.87      AAAA O
ATOM   1389  N    ASN   142      23.985   2.418  52.116  1.00 38.92      AAAA N
ATOM   1391  CA   ASN   142      24.858   1.390  52.746  1.00 44.32      AAAA C
ATOM   1392  CB   ASN   142      25.257   1.774  54.187  1.00 43.12      AAAA C
ATOM   1393  CG   ASN   142      26.131   3.022  54.152  1.00 42.00      AAAA C
ATOM   1394  OD1  ASN   142      26.984   3.077  53.269  1.00 40.47      AAAA O
ATOM   1395  ND2  ASN   142      25.945   4.022  55.019  1.00 41.98      AAAA N
ATOM   1398  C    ASN   142      24.153   0.066  52.687  1.00 45.84      AAAA C
ATOM   1399  O    ASN   142      23.113  -0.015  52.055  1.00 49.65      AAAA O
ATOM   1400  N    LYS   143      24.674  -0.990  53.272  1.00 45.23      AAAA N
ATOM   1402  CA   LYS   143      24.073  -2.299  53.195  1.00 49.14      AAAA C
ATOM   1403  CB   LYS   143      25.166  -3.328  53.433  1.00 41.49      AAAA C
ATOM   1404  CG   LYS   143      24.750  -4.686  53.832  1.00 44.96      AAAA C
ATOM   1405  CD   LYS   143      25.512  -5.743  53.100  1.00 48.66      AAAA C
ATOM   1406  CE   LYS   143      25.043  -7.131  53.558  1.00 38.35      AAAA C
ATOM   1407  NZ   LYS   143      26.080  -8.093  53.040  1.00 53.83      AAAA N
ATOM   1411  C    LYS   143      22.902  -2.431  54.169  1.00 52.85      AAAA C
ATOM   1412  O    LYS   143      22.960  -2.099  55.360  1.00 55.21      AAAA O
ATOM   1413  N    PRO   144      21.806  -3.047  53.731  1.00 52.39      AAAA N
ATOM   1414  CD   PRO   144      21.617  -3.469  52.315  1.00 52.58      AAAA C
ATOM   1415  CA   PRO   144      20.559  -3.118  54.489  1.00 48.30      AAAA C
ATOM   1416  CB   PRO   144      19.549  -3.602  53.455  1.00 51.41      AAAA C
ATOM   1417  CG   PRO   144      20.134  -3.299  52.099  1.00 50.41      AAAA C
ATOM   1418  C    PRO   144      20.621  -4.050  55.659  1.00 44.65      AAAA C
ATOM   1419  O    PRO   144      20.904  -5.236  55.501  1.00 36.84      AAAA O
ATOM   1420  N    PRO   145      20.318  -3.533  56.859  1.00 45.12      AAAA N
ATOM   1421  CD   PRO   145      20.123  -2.054  57.094  1.00 38.17      AAAA C
ATOM   1422  CA   PRO   145      20.448  -4.233  58.128  1.00 40.19      AAAA C
ATOM   1423  CB   PRO   145      19.704  -3.288  59.099  1.00 37.08      AAAA C
ATOM   1424  CG   PRO   145      20.040  -1.910  58.602  1.00 33.65      AAAA C
```

Figure 1A-14

| | | | | | | | | | | |
|---|---|---|---|---|---|---|---|---|---|---|
|ATOM|1425|C|PRO|145|19.993|-5.655|58.155|1.00 47.17|AAAA|C|
|ATOM|1426|O|PRO|145|20.556|-6.592|58.768|1.00 48.05|AAAA|O|
|ATOM|1427|N|LYS|146|18.879|-5.924|57.489|1.00 53.72|AAAA|N|
|ATOM|1429|CA|LYS|146|18.268|-7.229|57.295|1.00 56.94|AAAA|C|
|ATOM|1430|CB|LYS|146|16.894|-7.050|56.647|1.00 65.44|AAAA|C|
|ATOM|1431|CG|LYS|146|16.220|-8.232|55.982|1.00 64.32|AAAA|C|
|ATOM|1432|CD|LYS|146|14.797|-8.422|56.451|0.01 62.75|AAAA|C|
|ATOM|1433|CE|LYS|146|14.194|-9.717|55.934|0.01 62.14|AAAA|C|
|ATOM|1434|NZ|LYS|146|12.720|-9.610|55.753|0.01 61.38|AAAA|N|
|ATOM|1438|C|LYS|146|19.138|-8.138|56.446|1.00 61.40|AAAA|C|
|ATOM|1439|O|LYS|146|19.237|-9.346|56.732|1.00 66.22|AAAA|O|
|ATOM|1440|N|GLU|147|19.779|-7.649|55.389|1.00 62.92|AAAA|N|
|ATOM|1442|CA|GLU|147|20.827|-8.446|54.742|1.00 67.00|AAAA|C|
|ATOM|1443|CB|GLU|147|21.101|-8.070|53.294|1.00 62.32|AAAA|C|
|ATOM|1444|CG|GLU|147|19.867|-7.579|52.567|1.00 73.15|AAAA|C|
|ATOM|1445|CD|GLU|147|20.164|-7.413|51.093|1.00 85.90|AAAA|C|
|ATOM|1446|OE1|GLU|147|21.339|-7.636|50.701|1.00 95.25|AAAA|O|
|ATOM|1447|OE2|GLU|147|19.201|-7.053|50.376|1.00 87.47|AAAA|O|
|ATOM|1448|C|GLU|147|22.136|-8.470|55.541|1.00 69.40|AAAA|C|
|ATOM|1449|O|GLU|147|22.883|-9.437|55.361|1.00 72.86|AAAA|O|
|ATOM|1450|N|CYS|148|22.506|-7.484|56.355|1.00 66.76|AAAA|N|
|ATOM|1452|CA|CYS|148|23.693|-7.588|57.183|1.00 64.65|AAAA|C|
|ATOM|1453|C|CYS|148|23.598|-8.702|58.196|1.00 65.56|AAAA|C|
|ATOM|1454|O|CYS|148|24.473|-9.524|58.414|1.00 65.89|AAAA|O|
|ATOM|1455|CB|CYS|148|23.952|-6.301|58.001|1.00 57.29|AAAA|C|
|ATOM|1456|SG|CYS|148|24.565|-5.091|56.808|1.00 59.22|AAAA|S|
|ATOM|1457|N|GLY|149|22.514|-8.743|58.977|1.00 67.88|AAAA|N|
|ATOM|1459|CA|GLY|149|22.387|-9.744|60.029|1.00 62.15|AAAA|C|
|ATOM|1460|C|GLY|149|23.443|-9.627|61.120|1.00 59.18|AAAA|C|
|ATOM|1461|O|GLY|149|23.925|-10.603|61.699|1.00 61.11|AAAA|O|
|ATOM|1462|N|ASP|150|23.717|-8.426|61.596|1.00 54.88|AAAA|N|
|ATOM|1464|CA|ASP|150|24.794|-8.198|62.533|1.00 55.78|AAAA|C|
|ATOM|1465|CB|ASP|150|25.041|-6.703|62.750|1.00 49.10|AAAA|C|
|ATOM|1466|CG|ASP|150|25.320|-6.034|61.410|1.00 58.50|AAAA|C|
|ATOM|1467|OD1|ASP|150|25.726|-6.796|60.480|1.00 57.73|AAAA|O|
|ATOM|1468|OD2|ASP|150|25.102|-4.819|61.363|1.00 49.69|AAAA|O|
|ATOM|1469|C|ASP|150|24.519|-8.854|63.855|1.00 59.36|AAAA|C|
|ATOM|1470|O|ASP|150|23.392|-8.820|64.377|1.00 67.48|AAAA|O|
|ATOM|1471|N|LEU|151|25.532|-9.369|64.524|1.00 54.39|AAAA|N|
|ATOM|1473|CA|LEU|151|25.314|-9.908|65.853|1.00 52.79|AAAA|C|
|ATOM|1474|CB|LEU|151|25.208|-11.409|65.806|1.00 58.55|AAAA|C|
|ATOM|1475|CG|LEU|151|24.063|-12.101|65.092|1.00 69.45|AAAA|C|
|ATOM|1476|CD1|LEU|151|24.515|-13.421|64.489|1.00 65.26|AAAA|C|
|ATOM|1477|CD2|LEU|151|22.837|-12.372|65.951|1.00 65.43|AAAA|C|
|ATOM|1478|C|LEU|151|26.409|-9.454|66.805|1.00 51.93|AAAA|C|
|ATOM|1479|O|LEU|151|27.598|-9.734|66.634|1.00 55.59|AAAA|O|
|ATOM|1480|N|CYS|152|26.024|-8.773|67.849|1.00 48.62|AAAA|N|
|ATOM|1482|CA|CYS|152|26.992|-8.189|68.740|1.00 56.73|AAAA|C|
|ATOM|1483|C|CYS|152|27.650|-9.325|69.493|1.00 63.58|AAAA|C|
|ATOM|1484|O|CYS|152|27.074|-10.405|69.575|1.00 62.40|AAAA|O|
|ATOM|1485|CB|CYS|152|26.358|-7.144|69.657|1.00 41.99|AAAA|C|
|ATOM|1486|SG|CYS|152|25.985|-5.635|68.703|1.00 55.83|AAAA|S|
|ATOM|1487|N|PRO|153|28.826|-9.072|70.059|1.00 68.05|AAAA|N|
|ATOM|1488|CD|PRO|153|29.618|-7.838|69.903|1.00 66.66|AAAA|C|
|ATOM|1489|CA|PRO|153|29.497|-10.094|70.851|1.00 70.60|AAAA|C|
|ATOM|1490|CB|PRO|153|30.601|-9.323|71.557|1.00 69.98|AAAA|C|
|ATOM|1491|CG|PRO|153|30.861|-8.159|70.690|1.00 70.58|AAAA|C|
|ATOM|1492|C|PRO|153|28.543|-10.734|71.850|1.00 69.64|AAAA|C|
|ATOM|1493|O|PRO|153|27.859|-10.075|72.615|1.00 69.58|AAAA|O|
|ATOM|1494|N|GLY|154|28.444|-12.049|71.843|1.00 71.23|AAAA|N|
|ATOM|1496|CA|GLY|154|27.610|-12.804|72.745|1.00 78.07|AAAA|C|
|ATOM|1497|C|GLY|154|26.245|-13.230|72.223|1.00 81.75|AAAA|C|
|ATOM|1498|O|GLY|154|25.786|-14.318|72.547|1.00 80.26|AAAA|O|
|ATOM|1499|N|THR|155|25.649|-12.468|71.314|1.00 84.54|AAAA|N|
|ATOM|1501|CA|THR|155|24.314|-12.683|70.828|1.00 89.38|AAAA|C|
|ATOM|1502|CB|THR|155|24.016|-11.661|69.705|1.00 85.07|AAAA|C|
|ATOM|1503|OG1|THR|155|24.063|-10.417|70.420|1.00 84.51|AAAA|O|
|ATOM|1505|CG2|THR|155|22.686|-11.995|69.092|1.00 82.27|AAAA|C|
|ATOM|1506|C|THR|155|24.060|-14.094|70.353|1.00 93.69|AAAA|C|
|ATOM|1507|O|THR|155|23.005|-14.664|70.617|1.00 95.92|AAAA|O|
|ATOM|1508|N|MET|156|25.003|-14.655|69.617|1.00 97.23|AAAA|N|
|ATOM|1510|CA|MET|156|24.884|-15.973|69.024|1.00 99.05|AAAA|C|
|ATOM|1511|CB|MET|156|25.907|-16.190|67.896|1.00100.40|AAAA|C|
|ATOM|1512|CG|MET|156|25.456|-15.675|66.542|0.01 99.75|AAAA|C|
|ATOM|1513|SD|MET|156|23.687|-15.857|66.255|0.01 99.72|AAAA|S|
|ATOM|1514|CE|MET|156|23.664|-17.214|65.087|0.01 99.59|AAAA|C|
|ATOM|1515|C|MET|156|25.027|-17.106|70.032|1.00100.57|AAAA|C|
|ATOM|1516|O|MET|156|24.353|-18.122|69.835|1.00101.64|AAAA|O|

Figure 1A-15

```
ATOM   1517  N    ALA   157      25.974  -17.057   70.967  1.00100.53      AAAA N
ATOM   1519  CA   ALA   157      26.022  -18.102   71.986  1.00101.00      AAAA C
ATOM   1520  CB   ALA   157      27.317  -18.158   72.766  1.00103.42      AAAA C
ATOM   1521  C    ALA   157      24.856  -17.890   72.959  1.00101.10      AAAA C
ATOM   1522  O    ALA   157      23.893  -18.654   72.921  1.00104.59      AAAA O
ATOM   1523  N    GLU   158      24.984  -16.906   73.841  1.00 98.39      AAAA N
ATOM   1525  CA   GLU   158      23.935  -16.629   74.781  1.00 97.43      AAAA C
ATOM   1526  CB   GLU   158      23.128  -17.865   75.208  1.00105.93      AAAA C
ATOM   1527  CG   GLU   158      21.687  -17.546   75.560  1.00113.87      AAAA C
ATOM   1528  CD   GLU   158      21.347  -16.081   75.302  1.00119.34      AAAA C
ATOM   1529  OE1  GLU   158      21.284  -15.733   74.096  1.00126.27      AAAA O
ATOM   1530  OE2  GLU   158      21.199  -15.317   76.282  1.00117.79      AAAA O
ATOM   1531  C    GLU   158      24.434  -15.915   76.025  1.00 95.00      AAAA C
ATOM   1532  O    GLU   158      23.988  -16.117   77.145  1.00 95.89      AAAA O
ATOM   1533  N    SER   159      25.276  -14.942   75.769  1.00 93.30      AAAA N
ATOM   1535  CA   SER   159      25.810  -14.119   76.848  1.00 92.28      AAAA C
ATOM   1536  CB   SER   159      26.989  -14.805   77.517  1.00 97.37      AAAA C
ATOM   1537  OG   SER   159      26.972  -14.427   78.886  1.00 98.08      AAAA O
ATOM   1539  C    SER   159      26.228  -12.793   76.226  1.00 91.47      AAAA C
ATOM   1540  O    SER   159      27.368  -12.592   75.810  1.00 92.75      AAAA O
ATOM   1541  N    PRO   160      25.196  -12.007   75.932  1.00 88.65      AAAA N
ATOM   1542  CD   PRO   160      23.789  -12.122   76.395  1.00 86.67      AAAA C
ATOM   1543  CA   PRO   160      25.463  -10.701   75.361  1.00 84.74      AAAA C
ATOM   1544  CB   PRO   160      24.125   -9.978   75.456  1.00 84.79      AAAA C
ATOM   1545  CG   PRO   160      23.370  -10.671   76.515  1.00 84.62      AAAA C
ATOM   1546  C    PRO   160      26.503  -10.025   76.236  1.00 79.60      AAAA C
ATOM   1547  O    PRO   160      26.319   -9.934   77.456  1.00 79.70      AAAA O
ATOM   1548  N    MET   161      27.563   -9.522   75.596  1.00 74.45      AAAA N
ATOM   1550  CA   MET   161      28.530   -8.735   76.378  1.00 67.04      AAAA C
ATOM   1551  CB   MET   161      29.924   -9.178   76.038  1.00 69.93      AAAA C
ATOM   1552  CG   MET   161      30.118  -10.630   75.706  1.00 71.43      AAAA C
ATOM   1553  SD   MET   161      30.716  -11.621   77.094  1.00 85.25      AAAA S
ATOM   1554  CE   MET   161      29.841  -10.905   78.471  1.00 69.31      AAAA C
ATOM   1555  C    MET   161      28.358   -7.234   76.189  1.00 61.76      AAAA C
ATOM   1556  O    MET   161      28.788   -6.443   77.034  1.00 58.60      AAAA O
ATOM   1557  N    CYS   162      27.681   -6.819   75.095  1.00 54.81      AAAA N
ATOM   1559  CA   CYS   162      27.493   -5.384   74.938  1.00 49.76      AAAA C
ATOM   1560  C    CYS   162      26.306   -4.777   75.670  1.00 51.52      AAAA C
ATOM   1561  O    CYS   162      25.224   -5.324   75.928  1.00 53.89      AAAA O
ATOM   1562  CB   CYS   162      27.422   -5.099   73.459  1.00 48.31      AAAA C
ATOM   1563  SG   CYS   162      28.533   -6.064   72.432  1.00 54.02      AAAA S
ATOM   1564  N    GLU   163      26.409   -3.522   76.031  1.00 46.31      AAAA N
ATOM   1566  CA   GLU   163      25.355   -2.675   76.538  1.00 47.19      AAAA C
ATOM   1567  CB   GLU   163      26.051   -1.412   77.027  1.00 49.95      AAAA C
ATOM   1568  CG   GLU   163      26.476   -1.364   78.465  1.00 62.30      AAAA C
ATOM   1569  CD   GLU   163      25.817   -0.135   79.116  1.00 81.67      AAAA C
ATOM   1570  OE1  GLU   163      26.470    0.473   80.016  1.00 73.22      AAAA O
ATOM   1571  OE2  GLU   163      24.646    0.208   78.721  1.00 80.93      AAAA O
ATOM   1572  C    GLU   163      24.299   -2.340   75.472  1.00 49.05      AAAA C
ATOM   1573  O    GLU   163      24.488   -2.423   74.234  1.00 45.90      AAAA O
ATOM   1574  N    LYS   164      23.142   -1.815   75.880  1.00 47.43      AAAA N
ATOM   1576  CA   LYS   164      22.011   -1.499   75.081  1.00 43.92      AAAA C
ATOM   1577  CB   LYS   164      20.714   -2.244   75.450  1.00 44.48      AAAA C
ATOM   1578  CG   LYS   164      20.560   -3.639   74.870  1.00 48.65      AAAA C
ATOM   1579  CD   LYS   164      19.480   -4.432   75.622  1.00 49.04      AAAA C
ATOM   1580  CE   LYS   164      18.409   -5.012   74.720  1.00 49.21      AAAA C
ATOM   1581  NZ   LYS   164      17.951   -6.372   75.134  1.00 37.67      AAAA N
ATOM   1585  C    LYS   164      21.615   -0.040   75.204  1.00 45.01      AAAA C
ATOM   1586  O    LYS   164      21.466    0.484   76.282  1.00 45.69      AAAA O
ATOM   1587  N    THR   165      21.333    0.570   74.034  1.00 44.94      AAAA N
ATOM   1589  CA   THR   165      20.775    1.943   74.077  1.00 43.13      AAAA C
ATOM   1590  CB   THR   165      21.831    2.952   73.553  1.00 47.81      AAAA C
ATOM   1591  OG1  THR   165      22.053    2.689   72.127  1.00 39.13      AAAA O
ATOM   1593  CG2  THR   165      23.119    2.842   74.362  1.00 40.40      AAAA C
ATOM   1594  C    THR   165      19.532    1.881   73.189  1.00 40.92      AAAA C
ATOM   1595  O    THR   165      19.346    0.897   72.414  1.00 35.91      AAAA O
ATOM   1596  N    THR   166      18.781    2.985   73.173  1.00 39.18      AAAA N
ATOM   1598  CA   THR   166      17.689    2.991   72.182  1.00 42.97      AAAA C
ATOM   1599  CB   THR   166      16.297    3.096   72.833  1.00 55.99      AAAA C
ATOM   1600  OG1  THR   166      15.662    4.385   72.819  1.00 41.42      AAAA O
ATOM   1602  CG2  THR   166      16.157    2.740   74.313  1.00 42.83      AAAA C
ATOM   1603  C    THR   166      17.983    4.051   71.137  1.00 40.17      AAAA C
ATOM   1604  O    THR   166      18.219    5.206   71.509  1.00 35.72      AAAA O
ATOM   1605  N    ILE   167      17.912    3.725   69.866  1.00 42.21      AAAA N
ATOM   1607  CA   ILE   167      18.182    4.672   68.777  1.00 41.05      AAAA C
ATOM   1608  CB   ILE   167      19.437    4.335   67.904  1.00 39.50      AAAA C
ATOM   1609  CG2  ILE   167      19.589    5.346   66.716  1.00 15.26      AAAA C
ATOM   1610  CG1  ILE   167      20.722    4.305   68.724  1.00 36.20      AAAA C
```

Figure 1A-16

| | | | | | | | | | | |
|---|---|---|---|---|---|---|---|---|---|---|
| ATOM | 1611 | CD1 | ILE | 167 | 21.899 | 3.665 | 67.966 | 1.00 | 35.70 | AAAA C |
| ATOM | 1612 | C | ILE | 167 | 16.937 | 4.524 | 67.882 | 1.00 | 40.94 | AAAA C |
| ATOM | 1613 | O | ILE | 167 | 16.655 | 3.435 | 67.394 | 1.00 | 35.51 | AAAA O |
| ATOM | 1614 | N | ASN | 168 | 16.318 | 5.635 | 67.537 | 1.00 | 42.29 | AAAA N |
| ATOM | 1616 | CA | ASN | 168 | 15.112 | 5.633 | 66.713 | 1.00 | 45.22 | AAAA C |
| ATOM | 1617 | CB | ASN | 168 | 15.526 | 5.253 | 65.292 | 1.00 | 45.69 | AAAA C |
| ATOM | 1618 | CG | ASN | 168 | 14.497 | 5.696 | 64.244 | 1.00 | 51.19 | AAAA C |
| ATOM | 1619 | OD1 | ASN | 168 | 14.344 | 5.112 | 63.150 | 1.00 | 41.75 | AAAA O |
| ATOM | 1620 | ND2 | ASN | 168 | 13.749 | 6.763 | 64.522 | 1.00 | 48.89 | AAAA N |
| ATOM | 1623 | C | ASN | 168 | 13.954 | 4.739 | 67.141 | 1.00 | 46.55 | AAAA C |
| ATOM | 1624 | O | ASN | 168 | 13.544 | 3.879 | 66.326 | 1.00 | 45.95 | AAAA O |
| ATOM | 1625 | N | ASN | 169 | 13.644 | 4.728 | 68.433 | 1.00 | 45.12 | AAAA N |
| ATOM | 1627 | CA | ASN | 169 | 12.717 | 3.759 | 69.007 | 1.00 | 43.67 | AAAA C |
| ATOM | 1628 | CB | ASN | 169 | 11.315 | 4.106 | 68.540 | 1.00 | 36.84 | AAAA C |
| ATOM | 1629 | CG | ASN | 169 | 10.943 | 5.487 | 69.093 | 1.00 | 42.75 | AAAA C |
| ATOM | 1630 | OD1 | ASN | 169 | 10.917 | 5.779 | 70.280 | 1.00 | 36.67 | AAAA O |
| ATOM | 1631 | ND2 | ASN | 169 | 10.658 | 6.448 | 68.213 | 1.00 | 40.74 | AAAA N |
| ATOM | 1634 | C | ASN | 169 | 13.003 | 2.306 | 68.719 | 1.00 | 44.69 | AAAA C |
| ATOM | 1635 | O | ASN | 169 | 12.100 | 1.544 | 68.383 | 1.00 | 45.72 | AAAA O |
| ATOM | 1636 | N | GLU | 170 | 14.226 | 1.907 | 68.862 | 1.00 | 41.64 | AAAA N |
| ATOM | 1638 | CA | GLU | 170 | 14.655 | 0.513 | 68.850 | 1.00 | 45.88 | AAAA C |
| ATOM | 1639 | CB | GLU | 170 | 15.283 | 0.278 | 67.524 | 1.00 | 55.92 | AAAA C |
| ATOM | 1640 | CG | GLU | 170 | 15.028 | -0.953 | 66.702 | 1.00 | 67.08 | AAAA C |
| ATOM | 1641 | CD | GLU | 170 | 14.517 | -0.605 | 65.294 | 1.00 | 74.56 | AAAA C |
| ATOM | 1642 | OE1 | GLU | 170 | 13.869 | 0.466 | 65.049 | 1.00 | 77.75 | AAAA O |
| ATOM | 1643 | OE2 | GLU | 170 | 14.763 | -1.437 | 64.389 | 1.00 | 70.71 | AAAA O |
| ATOM | 1644 | C | GLU | 170 | 15.647 | 0.379 | 70.010 | 1.00 | 47.10 | AAAA C |
| ATOM | 1645 | O | GLU | 170 | 16.582 | 1.172 | 70.213 | 1.00 | 49.92 | AAAA O |
| ATOM | 1646 | N | TYR | 171 | 15.344 | -0.462 | 70.952 | 1.00 | 49.10 | AAAA N |
| ATOM | 1648 | CA | TYR | 171 | 16.231 | -0.688 | 72.097 | 1.00 | 51.81 | AAAA C |
| ATOM | 1649 | CB | TYR | 171 | 15.434 | -0.861 | 73.359 | 1.00 | 49.94 | AAAA C |
| ATOM | 1650 | CG | TYR | 171 | 16.175 | -1.168 | 74.620 | 1.00 | 48.90 | AAAA C |
| ATOM | 1651 | CD1 | TYR | 171 | 16.980 | -0.210 | 75.237 | 1.00 | 46.46 | AAAA C |
| ATOM | 1652 | CE1 | TYR | 171 | 17.634 | -0.469 | 76.407 | 1.00 | 41.17 | AAAA C |
| ATOM | 1653 | CD2 | TYR | 171 | 16.065 | -2.429 | 75.194 | 1.00 | 43.62 | AAAA C |
| ATOM | 1654 | CE2 | TYR | 171 | 16.734 | -2.675 | 76.366 | 1.00 | 44.44 | AAAA C |
| ATOM | 1655 | CZ | TYR | 171 | 17.516 | -1.718 | 76.973 | 1.00 | 43.58 | AAAA C |
| ATOM | 1656 | OH | TYR | 171 | 18.174 | -2.017 | 78.146 | 1.00 | 40.16 | AAAA O |
| ATOM | 1658 | C | TYR | 171 | 17.058 | -1.938 | 71.832 | 1.00 | 51.41 | AAAA C |
| ATOM | 1659 | O | TYR | 171 | 16.519 | -3.024 | 71.889 | 1.00 | 52.59 | AAAA O |
| ATOM | 1660 | N | ASN | 172 | 18.331 | -1.752 | 71.493 | 1.00 | 53.70 | AAAA N |
| ATOM | 1662 | CA | ASN | 172 | 19.203 | -2.898 | 71.193 | 1.00 | 52.36 | AAAA C |
| ATOM | 1663 | CB | ASN | 172 | 19.085 | -3.278 | 69.709 | 1.00 | 55.43 | AAAA C |
| ATOM | 1664 | CG | ASN | 172 | 18.939 | -4.766 | 69.498 | 1.00 | 61.75 | AAAA C |
| ATOM | 1665 | OD1 | ASN | 172 | 19.233 | -5.646 | 70.304 | 1.00 | 61.61 | AAAA O |
| ATOM | 1666 | ND2 | ASN | 172 | 18.449 | -5.048 | 68.295 | 1.00 | 57.97 | AAAA N |
| ATOM | 1669 | C | ASN | 172 | 20.665 | -2.712 | 71.560 | 1.00 | 43.81 | AAAA C |
| ATOM | 1670 | O | ASN | 172 | 21.163 | -1.760 | 72.213 | 1.00 | 39.38 | AAAA O |
| ATOM | 1671 | N | TYR | 173 | 21.373 | -3.796 | 71.393 | 1.00 | 43.20 | AAAA N |
| ATOM | 1673 | CA | TYR | 173 | 22.794 | -3.929 | 71.698 | 1.00 | 44.76 | AAAA C |
| ATOM | 1674 | CB | TYR | 173 | 23.223 | -5.374 | 71.514 | 1.00 | 41.66 | AAAA C |
| ATOM | 1675 | CG | TYR | 173 | 22.759 | -6.274 | 72.630 | 1.00 | 45.18 | AAAA C |
| ATOM | 1676 | CD1 | TYR | 173 | 21.931 | -7.316 | 72.237 | 1.00 | 46.48 | AAAA C |
| ATOM | 1677 | CE1 | TYR | 173 | 21.438 | -8.181 | 73.193 | 1.00 | 51.36 | AAAA C |
| ATOM | 1678 | CD2 | TYR | 173 | 23.081 | -6.132 | 73.978 | 1.00 | 44.86 | AAAA C |
| ATOM | 1679 | CE2 | TYR | 173 | 22.583 | -7.016 | 74.916 | 1.00 | 46.92 | AAAA C |
| ATOM | 1680 | CZ | TYR | 173 | 21.757 | -8.038 | 74.535 | 1.00 | 50.33 | AAAA C |
| ATOM | 1681 | OH | TYR | 173 | 21.171 | -9.006 | 75.328 | 1.00 | 50.64 | AAAA O |
| ATOM | 1683 | C | TYR | 173 | 23.673 | -3.099 | 70.762 | 1.00 | 46.94 | AAAA C |
| ATOM | 1684 | O | TYR | 173 | 23.389 | -2.983 | 69.567 | 1.00 | 49.76 | AAAA O |
| ATOM | 1685 | N | ARG | 174 | 24.579 | -2.318 | 71.366 | 1.00 | 47.79 | AAAA N |
| ATOM | 1687 | CA | ARG | 174 | 25.517 | -1.496 | 70.577 | 1.00 | 49.13 | AAAA C |
| ATOM | 1688 | CB | ARG | 174 | 25.537 | -0.132 | 71.233 | 1.00 | 44.32 | AAAA C |
| ATOM | 1689 | CG | ARG | 174 | 24.210 | 0.623 | 71.234 | 1.00 | 48.14 | AAAA C |
| ATOM | 1690 | CD | ARG | 174 | 23.372 | 0.344 | 70.003 | 1.00 | 51.47 | AAAA C |
| ATOM | 1691 | NE | ARG | 174 | 21.974 | 0.760 | 70.039 | 1.00 | 48.35 | AAAA N |
| ATOM | 1693 | CZ | ARG | 174 | 21.144 | 0.570 | 69.017 | 1.00 | 48.23 | AAAA C |
| ATOM | 1694 | NH1 | ARG | 174 | 21.477 | 0.022 | 67.864 | 1.00 | 38.96 | AAAA N |
| ATOM | 1697 | NH2 | ARG | 174 | 19.909 | 1.022 | 69.197 | 1.00 | 54.65 | AAAA N |
| ATOM | 1700 | C | ARG | 174 | 26.921 | -2.094 | 70.461 | 1.00 | 45.98 | AAAA C |
| ATOM | 1701 | O | ARG | 174 | 27.548 | -2.557 | 71.406 | 1.00 | 44.97 | AAAA O |
| ATOM | 1702 | N | CYS | 175 | 27.493 | -2.183 | 69.294 | 1.00 | 46.21 | AAAA N |
| ATOM | 1704 | CA | CYS | 175 | 28.787 | -2.758 | 68.997 | 1.00 | 45.60 | AAAA C |
| ATOM | 1705 | C | CYS | 175 | 29.407 | -2.395 | 67.665 | 1.00 | 46.23 | AAAA C |
| ATOM | 1706 | O | CYS | 175 | 28.755 | -2.018 | 66.665 | 1.00 | 44.78 | AAAA O |
| ATOM | 1707 | CB | CYS | 175 | 28.576 | -4.253 | 69.167 | 1.00 | 35.62 | AAAA C |
| ATOM | 1708 | SG | CYS | 175 | 27.812 | -5.181 | 67.827 | 1.00 | 51.92 | AAAA S |
| ATOM | 1709 | N | TRP | 176 | 30.764 | -2.517 | 67.583 | 1.00 | 48.16 | AAAA N |

Figure 1A-17

```
ATOM   1711  CA   TRP   176      31.430   -2.091   66.325  1.00 42.48      AAAA C
ATOM   1712  CB   TRP   176      32.769   -1.409   66.564  1.00 36.38      AAAA C
ATOM   1713  CG   TRP   176      32.689   -0.069   67.203  1.00 25.56      AAAA C
ATOM   1714  CD2  TRP   176      32.588    1.186   66.480  1.00 23.71      AAAA C
ATOM   1715  CE2  TRP   176      32.558    2.217   67.422  1.00 32.40      AAAA C
ATOM   1716  CE3  TRP   176      32.535    1.520   65.141  1.00 24.31      AAAA C
ATOM   1717  CD1  TRP   176      32.730    0.257   68.525  1.00 28.37      AAAA C
ATOM   1718  NE1  TRP   176      32.636    1.636   68.678  1.00 37.21      AAAA N
ATOM   1720  CZ2  TRP   176      32.441    3.565   67.088  1.00 28.51      AAAA C
ATOM   1721  CZ3  TRP   176      32.447    2.822   64.789  1.00 22.23      AAAA C
ATOM   1722  CH2  TRP   176      32.406    3.817   65.745  1.00 29.51      AAAA C
ATOM   1723  C    TRP   176      31.631   -3.268   65.408  1.00 39.30      AAAA C
ATOM   1724  O    TRP   176      31.703   -3.121   64.199  1.00 39.15      AAAA O
ATOM   1725  N    THR   177      31.682   -4.460   66.005  1.00 41.33      AAAA N
ATOM   1727  CA   THR   177      31.964   -5.644   65.161  1.00 49.28      AAAA C
ATOM   1728  CB   THR   177      33.480   -6.062   65.162  1.00 43.66      AAAA C
ATOM   1729  OG1  THR   177      34.309   -5.025   64.613  1.00 47.85      AAAA O
ATOM   1731  CG2  THR   177      33.676   -7.271   64.283  1.00 58.51      AAAA C
ATOM   1732  C    THR   177      31.290   -6.814   65.858  1.00 48.76      AAAA C
ATOM   1733  O    THR   177      30.982   -6.539   67.001  1.00 51.53      AAAA O
ATOM   1734  N    THR   178      31.269   -8.000   65.331  1.00 51.96      AAAA N
ATOM   1736  CA   THR   178      30.924   -9.236   65.946  1.00 58.95      AAAA C
ATOM   1737  CB   THR   178      31.253  -10.500   65.082  1.00 66.55      AAAA C
ATOM   1738  OG1  THR   178      31.505  -10.066   63.734  1.00 75.70      AAAA O
ATOM   1740  CG2  THR   178      30.104  -11.489   65.148  1.00 74.23      AAAA C
ATOM   1741  C    THR   178      31.714   -9.539   67.213  1.00 60.25      AAAA C
ATOM   1742  O    THR   178      31.204  -10.202   68.135  1.00 66.05      AAAA O
ATOM   1743  N    ASN   179      32.977   -9.130   67.253  1.00 57.56      AAAA N
ATOM   1745  CA   ASN   179      33.793   -9.392   68.443  1.00 53.39      AAAA C
ATOM   1746  CB   ASN   179      35.130  -10.024   68.068  1.00 48.46      AAAA C
ATOM   1747  CG   ASN   179      34.897  -11.218   67.126  1.00 56.25      AAAA C
ATOM   1748  OD1  ASN   179      34.412  -12.294   67.553  1.00 51.38      AAAA O
ATOM   1749  ND2  ASN   179      35.229  -11.063   65.863  1.00 48.10      AAAA N
ATOM   1752  C    ASN   179      34.096   -8.190   69.285  1.00 50.78      AAAA C
ATOM   1753  O    ASN   179      34.556   -8.377   70.426  1.00 57.97      AAAA O
ATOM   1754  N    ARG   180      33.626   -7.022   68.913  1.00 47.06      AAAA N
ATOM   1756  CA   ARG   180      33.808   -5.820   69.691  1.00 48.25      AAAA C
ATOM   1757  CB   ARG   180      34.925   -4.962   69.074  1.00 49.72      AAAA C
ATOM   1758  CG   ARG   180      36.324   -5.501   69.285  1.00 60.92      AAAA C
ATOM   1759  CD   ARG   180      37.288   -4.948   68.279  1.00 70.83      AAAA C
ATOM   1760  NE   ARG   180      38.569   -5.605   68.203  1.00 76.18      AAAA N
ATOM   1762  CZ   ARG   180      39.298   -5.895   69.276  1.00 76.59      AAAA C
ATOM   1763  NH1  ARG   180      38.877   -5.608   70.498  1.00 80.82      AAAA N
ATOM   1766  NH2  ARG   180      40.474   -6.478   69.180  1.00 79.33      AAAA N
ATOM   1769  C    ARG   180      32.530   -4.977   69.821  1.00 48.10      AAAA C
ATOM   1770  O    ARG   180      31.862   -4.476   68.905  1.00 46.99      AAAA O
ATOM   1771  N    CYS   181      32.230   -4.728   71.063  1.00 44.80      AAAA N
ATOM   1773  CA   CYS   181      31.199   -3.924   71.619  1.00 45.20      AAAA C
ATOM   1774  C    CYS   181      31.646   -2.463   71.692  1.00 44.50      AAAA C
ATOM   1775  O    CYS   181      32.835   -2.227   71.724  1.00 47.09      AAAA O
ATOM   1776  CB   CYS   181      30.940   -4.282   73.110  1.00 43.88      AAAA C
ATOM   1777  SG   CYS   181      30.363   -5.944   73.346  1.00 56.08      AAAA S
ATOM   1778  N    GLN   182      30.659   -1.600   71.690  1.00 39.30      AAAA N
ATOM   1780  CA   GLN   182      30.948   -0.177   71.690  1.00 43.43      AAAA C
ATOM   1781  CB   GLN   182      29.749    0.619   71.196  1.00 23.99      AAAA C
ATOM   1782  CG   GLN   182      29.809    2.085   71.435  1.00 28.57      AAAA C
ATOM   1783  CD   GLN   182      28.757    2.867   70.733  1.00 29.35      AAAA C
ATOM   1784  OE1  GLN   182      27.898    2.304   70.033  1.00 38.55      AAAA O
ATOM   1785  NE2  GLN   182      28.857    4.164   70.912  1.00 28.14      AAAA N
ATOM   1788  C    GLN   182      31.218    0.089   73.162  1.00 46.07      AAAA C
ATOM   1789  O    GLN   182      30.458   -0.327   74.041  1.00 47.01      AAAA O
ATOM   1790  N    LYS   183      32.213    0.866   73.524  1.00 46.98      AAAA N
ATOM   1792  CA   LYS   183      32.479    1.064   74.934  1.00 45.26      AAAA C
ATOM   1793  CB   LYS   183      33.966    1.275   75.185  1.00 48.68      AAAA C
ATOM   1794  CG   LYS   183      34.865    0.267   74.482  1.00 47.95      AAAA C
ATOM   1795  CD   LYS   183      36.337    0.734   74.523  1.00 48.06      AAAA C
ATOM   1796  CE   LYS   183      37.178   -0.208   73.684  1.00 46.78      AAAA C
ATOM   1797  NZ   LYS   183      38.499   -0.654   74.158  1.00 44.00      AAAA N
ATOM   1801  C    LYS   183      31.659    2.205   75.477  1.00 48.13      AAAA C
ATOM   1802  O    LYS   183      31.679    3.305   74.946  1.00 48.84      AAAA O
ATOM   1803  N    MET   184      31.165    2.014   76.698  1.00 52.59      AAAA N
ATOM   1805  CA   MET   184      30.388    3.041   77.413  1.00 53.22      AAAA C
ATOM   1806  CB   MET   184      28.927    2.613   77.537  1.00 54.27      AAAA C
ATOM   1807  CG   MET   184      27.855    2.955   76.536  1.00 56.16      AAAA C
ATOM   1808  SD   MET   184      26.911    1.601   75.912  1.00 57.56      AAAA S
ATOM   1809  CE   MET   184      26.738    1.855   74.171  1.00 46.57      AAAA C
ATOM   1810  C    MET   184      31.051    3.200   78.770  1.00 50.55      AAAA C
ATOM   1811  O    MET   184      31.770    2.292   79.116  1.00 48.82      AAAA O
```

Figure 1A-18

```
ATOM   1812  N    CYS  185      30.796    4.195   79.565  1.00 53.97      AAAA N
ATOM   1814  CA   CYS  185      31.342    4.365   80.892  1.00 58.63      AAAA C
ATOM   1815  C    CYS  185      30.297    4.320   81.989  1.00 65.16      AAAA C
ATOM   1816  O    CYS  185      29.133    4.649   81.761  1.00 65.87      AAAA O
ATOM   1817  CB   CYS  185      31.965    5.772   81.000  1.00 60.37      AAAA C
ATOM   1818  SG   CYS  185      33.623    5.771   80.312  1.00 60.09      AAAA S
ATOM   1819  N    PRO  186      30.688    3.978   83.206  1.00 69.41      AAAA N
ATOM   1820  CD   PRO  186      32.066    3.777   83.702  1.00 71.11      AAAA C
ATOM   1821  CA   PRO  186      29.717    3.933   84.304  1.00 69.11      AAAA C
ATOM   1822  CB   PRO  186      30.523    3.487   85.503  1.00 68.03      AAAA C
ATOM   1823  CG   PRO  186      31.910    3.920   85.198  1.00 71.02      AAAA C
ATOM   1824  C    PRO  186      29.120    5.320   84.431  1.00 69.47      AAAA C
ATOM   1825  O    PRO  186      29.820    6.345   84.507  1.00 65.93      AAAA O
ATOM   1826  N    SER  187      27.801    5.367   84.546  1.00 68.78      AAAA N
ATOM   1828  CA   SER  187      27.050    6.592   84.750  1.00 69.29      AAAA C
ATOM   1829  CB   SER  187      25.594    6.287   85.129  1.00 78.29      AAAA C
ATOM   1830  OG   SER  187      25.474    4.935   85.566  1.00 91.78      AAAA O
ATOM   1832  C    SER  187      27.630    7.476   85.836  1.00 67.19      AAAA C
ATOM   1833  O    SER  187      27.606    8.708   85.803  1.00 63.98      AAAA O
ATOM   1834  N    THR  188      28.108    6.853   86.908  1.00 68.20      AAAA N
ATOM   1836  CA   THR  188      28.870    7.507   87.963  1.00 68.39      AAAA C
ATOM   1837  CB   THR  188      29.805    6.459   88.618  1.00 73.84      AAAA C
ATOM   1838  OG1  THR  188      28.943    5.365   89.016  1.00 89.33      AAAA O
ATOM   1840  CG2  THR  188      30.605    7.048   89.759  1.00 73.71      AAAA C
ATOM   1841  C    THR  188      29.802    8.583   87.429  1.00 67.52      AAAA C
ATOM   1842  O    THR  188      29.843    9.739   87.834  1.00 68.30      AAAA O
ATOM   1843  N    CYS  189      30.643    8.247   86.446  1.00 63.89      AAAA N
ATOM   1845  CA   CYS  189      31.583    9.116   85.817  1.00 57.29      AAAA C
ATOM   1846  C    CYS  189      30.951   10.331   85.195  1.00 57.70      AAAA C
ATOM   1847  O    CYS  189      31.648   11.327   85.017  1.00 57.56      AAAA O
ATOM   1848  CB   CYS  189      32.416    8.372   84.769  1.00 58.67      AAAA C
ATOM   1849  SG   CYS  189      33.347    7.001   85.535  1.00 53.46      AAAA S
ATOM   1850  N    GLY  190      29.689   10.322   84.806  1.00 56.91      AAAA N
ATOM   1852  CA   GLY  190      29.038   11.521   84.323  1.00 57.28      AAAA C
ATOM   1853  C    GLY  190      29.444   11.834   82.886  1.00 59.62      AAAA C
ATOM   1854  O    GLY  190      29.609   10.932   82.082  1.00 57.91      AAAA O
ATOM   1855  N    LYS  191      29.842   13.052   82.624  1.00 62.78      AAAA N
ATOM   1857  CA   LYS  191      30.359   13.520   81.364  1.00 67.72      AAAA C
ATOM   1858  CB   LYS  191      30.058   15.035   81.214  1.00 72.76      AAAA C
ATOM   1859  CG   LYS  191      28.568   15.288   81.002  1.00 84.69      AAAA C
ATOM   1860  CD   LYS  191      28.207   16.733   80.723  1.00 90.15      AAAA C
ATOM   1861  CE   LYS  191      26.713   16.806   80.471  1.00 91.83      AAAA C
ATOM   1862  NZ   LYS  191      26.368   16.182   79.152  1.00 97.62      AAAA N
ATOM   1866  C    LYS  191      31.868   13.299   81.270  1.00 70.13      AAAA C
ATOM   1867  O    LYS  191      32.486   13.935   80.415  1.00 71.76      AAAA O
ATOM   1868  N    ARG  192      32.488   12.441   82.079  1.00 66.29      AAAA N
ATOM   1870  CA   ARG  192      33.885   12.171   82.044  1.00 59.95      AAAA C
ATOM   1871  CB   ARG  192      34.505   12.070   83.432  1.00 66.58      AAAA C
ATOM   1872  CG   ARG  192      34.670   13.400   84.131  1.00 71.59      AAAA C
ATOM   1873  CD   ARG  192      34.386   13.330   85.625  1.00 73.91      AAAA C
ATOM   1874  NE   ARG  192      35.622   13.280   86.377  1.00 85.74      AAAA N
ATOM   1876  CZ   ARG  192      35.968   12.407   87.330  1.00 90.67      AAAA C
ATOM   1877  NH1  ARG  192      35.026   11.486   87.600  1.00 88.49      AAAA N
ATOM   1880  NH2  ARG  192      37.162   12.463   87.950  1.00 72.95      AAAA N
ATOM   1883  C    ARG  192      34.221   10.851   81.337  1.00 58.83      AAAA C
ATOM   1884  O    ARG  192      33.336   10.007   81.176  1.00 55.13      AAAA O
ATOM   1885  N    ALA  193      35.521   10.795   80.968  1.00 50.19      AAAA N
ATOM   1887  CA   ALA  193      35.962    9.557   80.355  1.00 46.24      AAAA C
ATOM   1888  CB   ALA  193      37.167    9.921   79.541  1.00 45.15      AAAA C
ATOM   1889  C    ALA  193      36.221    8.525   81.451  1.00 48.97      AAAA C
ATOM   1890  O    ALA  193      36.220    8.908   82.616  1.00 44.80      AAAA O
ATOM   1891  N    CYS  194      36.544    7.304   81.065  1.00 50.30      AAAA N
ATOM   1893  CA   CYS  194      36.836    6.302   82.043  1.00 57.50      AAAA C
ATOM   1894  C    CYS  194      37.834    5.304   81.448  1.00 61.25      AAAA C
ATOM   1895  O    CYS  194      37.952    5.291   80.216  1.00 61.52      AAAA O
ATOM   1896  CB   CYS  194      35.510    5.741   82.504  1.00 57.96      AAAA C
ATOM   1897  SG   CYS  194      34.785    4.524   81.402  1.00 54.49      AAAA S
ATOM   1898  N    THR  195      38.422    4.499   82.311  1.00 58.51      AAAA N
ATOM   1900  CA   THR  195      39.462    3.584   81.913  1.00 57.42      AAAA C
ATOM   1901  CB   THR  195      40.237    3.142   83.188  1.00 65.73      AAAA C
ATOM   1902  OG1  THR  195      40.288    4.248   84.091  1.00 70.15      AAAA O
ATOM   1904  CG2  THR  195      41.684    2.864   82.745  1.00 77.91      AAAA C
ATOM   1905  C    THR  195      38.857    2.404   81.226  1.00 54.59      AAAA C
ATOM   1906  O    THR  195      37.633    2.315   81.318  1.00 58.75      AAAA O
ATOM   1907  N    GLU  196      39.610    1.408   80.882  1.00 55.95      AAAA N
ATOM   1909  CA   GLU  196      39.139    0.145   80.364  1.00 60.07      AAAA C
ATOM   1910  CB   GLU  196      40.395   -0.612   79.914  1.00 68.06      AAAA C
ATOM   1911  CG   GLU  196      40.479   -1.146   78.526  1.00 73.96      AAAA C
```

Figure 1A-19

| | | | | | | | | | | |
|---|---|---|---|---|---|---|---|---|---|---|
| ATOM | 1912 | CD | GLU | 196 | 39.235 | -0.983 | 77.670 | 1.00 | 83.08 | AAAA C |
| ATOM | 1913 | OE1 | GLU | 196 | 38.356 | -1.884 | 77.687 | 1.00 | 81.19 | AAAA O |
| ATOM | 1914 | OE2 | GLU | 196 | 39.060 | 0.041 | 76.939 | 1.00 | 82.10 | AAAA O |
| ATOM | 1915 | C | GLU | 196 | 38.382 | -0.579 | 81.467 | 1.00 | 63.91 | AAAA C |
| ATOM | 1916 | O | GLU | 196 | 37.690 | -1.537 | 81.159 | 1.00 | 63.51 | AAAA O |
| ATOM | 1917 | N | ASN | 197 | 38.666 | -0.312 | 82.739 | 1.00 | 67.40 | AAAA N |
| ATOM | 1919 | CA | ASN | 197 | 38.025 | -0.947 | 83.886 | 1.00 | 69.21 | AAAA C |
| ATOM | 1920 | CB | ASN | 197 | 39.021 | -1.394 | 84.966 | 1.00 | 68.49 | AAAA C |
| ATOM | 1921 | CG | ASN | 197 | 39.722 | -2.692 | 84.672 | 0.01 | 69.09 | AAAA C |
| ATOM | 1922 | OD1 | ASN | 197 | 40.364 | -3.273 | 85.551 | 0.01 | 69.04 | AAAA O |
| ATOM | 1923 | ND2 | ASN | 197 | 39.622 | -3.183 | 83.443 | 0.01 | 68.97 | AAAA N |
| ATOM | 1926 | C | ASN | 197 | 37.033 | 0.043 | 84.486 | 1.00 | 69.01 | AAAA C |
| ATOM | 1927 | O | ASN | 197 | 36.845 | 0.281 | 85.664 | 1.00 | 68.24 | AAAA O |
| ATOM | 1928 | N | ASN | 198 | 36.384 | 0.795 | 83.607 | 1.00 | 69.91 | AAAA N |
| ATOM | 1930 | CA | ASN | 198 | 35.356 | 1.734 | 84.048 | 1.00 | 68.48 | AAAA C |
| ATOM | 1931 | CB | ASN | 198 | 34.120 | 0.880 | 84.373 | 1.00 | 60.12 | AAAA C |
| ATOM | 1932 | CG | ASN | 198 | 33.806 | 0.095 | 83.102 | 1.00 | 69.29 | AAAA C |
| ATOM | 1933 | OD1 | ASN | 198 | 33.475 | 0.654 | 82.054 | 1.00 | 73.20 | AAAA O |
| ATOM | 1934 | ND2 | ASN | 198 | 33.980 | -1.206 | 83.268 | 1.00 | 65.34 | AAAA N |
| ATOM | 1937 | C | ASN | 198 | 35.784 | 2.563 | 85.228 | 1.00 | 64.01 | AAAA C |
| ATOM | 1938 | O | ASN | 198 | 34.992 | 2.827 | 86.117 | 1.00 | 64.20 | AAAA O |
| ATOM | 1939 | N | GLU | 199 | 36.955 | 3.164 | 85.157 | 1.00 | 64.75 | AAAA N |
| ATOM | 1941 | CA | GLU | 199 | 37.342 | 4.054 | 86.255 | 1.00 | 64.64 | AAAA C |
| ATOM | 1942 | CB | GLU | 199 | 38.702 | 3.624 | 86.744 | 1.00 | 66.11 | AAAA C |
| ATOM | 1943 | CG | GLU | 199 | 38.846 | 3.717 | 88.233 | 1.00 | 77.15 | AAAA C |
| ATOM | 1944 | CD | GLU | 199 | 39.579 | 2.532 | 88.832 | 1.00 | 80.24 | AAAA C |
| ATOM | 1945 | OE1 | GLU | 199 | 39.385 | 2.406 | 90.066 | 1.00 | 81.65 | AAAA O |
| ATOM | 1946 | OE2 | GLU | 199 | 40.282 | 1.821 | 88.079 | 1.00 | 77.94 | AAAA O |
| ATOM | 1947 | C | GLU | 199 | 37.314 | 5.463 | 85.690 | 1.00 | 62.92 | AAAA C |
| ATOM | 1948 | O | GLU | 199 | 37.922 | 5.676 | 84.632 | 1.00 | 63.62 | AAAA O |
| ATOM | 1949 | N | CYS | 200 | 36.605 | 6.393 | 86.313 | 1.00 | 56.16 | AAAA N |
| ATOM | 1951 | CA | CYS | 200 | 36.600 | 7.721 | 85.740 | 1.00 | 55.11 | AAAA C |
| ATOM | 1952 | C | CYS | 200 | 37.978 | 8.315 | 85.521 | 1.00 | 57.77 | AAAA C |
| ATOM | 1953 | O | CYS | 200 | 38.884 | 8.058 | 86.300 | 1.00 | 63.79 | AAAA O |
| ATOM | 1954 | CB | CYS | 200 | 35.824 | 8.664 | 86.648 | 1.00 | 52.70 | AAAA C |
| ATOM | 1955 | SG | CYS | 200 | 34.196 | 8.100 | 87.098 | 1.00 | 55.85 | AAAA S |
| ATOM | 1956 | N | CYS | 201 | 38.124 | 9.192 | 84.540 | 1.00 | 54.50 | AAAA N |
| ATOM | 1958 | CA | CYS | 201 | 39.338 | 9.889 | 84.202 | 1.00 | 48.19 | AAAA C |
| ATOM | 1959 | C | CYS | 201 | 39.236 | 11.287 | 84.786 | 1.00 | 42.34 | AAAA C |
| ATOM | 1960 | O | CYS | 201 | 38.165 | 11.704 | 85.166 | 1.00 | 54.32 | AAAA O |
| ATOM | 1961 | CB | CYS | 201 | 39.590 | 10.070 | 82.695 | 1.00 | 40.90 | AAAA C |
| ATOM | 1962 | SG | CYS | 201 | 39.644 | 8.597 | 81.747 | 1.00 | 51.42 | AAAA S |
| ATOM | 1963 | N | HIS | 202 | 40.254 | 12.075 | 84.675 | 1.00 | 39.12 | AAAA N |
| ATOM | 1965 | CA | HIS | 202 | 40.290 | 13.461 | 85.128 | 1.00 | 41.55 | AAAA C |
| ATOM | 1966 | C | HIS | 202 | 39.284 | 14.184 | 84.289 | 1.00 | 46.59 | AAAA C |
| ATOM | 1967 | O | HIS | 202 | 39.176 | 13.851 | 83.103 | 1.00 | 51.64 | AAAA O |
| ATOM | 1968 | CB | HIS | 202 | 41.712 | 13.952 | 84.810 | 1.00 | 45.20 | AAAA C |
| ATOM | 1969 | CG | HIS | 202 | 41.996 | 15.330 | 85.267 | 1.00 | 38.71 | AAAA C |
| ATOM | 1970 | ND1 | HIS | 202 | 41.501 | 16.404 | 84.550 | 1.00 | 51.32 | AAAA N |
| ATOM | 1971 | CE1 | HIS | 202 | 41.887 | 17.528 | 85.178 | 1.00 | 47.62 | AAAA C |
| ATOM | 1972 | CD2 | HIS | 202 | 42.665 | 15.813 | 86.340 | 1.00 | 39.59 | AAAA C |
| ATOM | 1973 | NE2 | HIS | 202 | 42.563 | 17.207 | 86.258 | 1.00 | 43.48 | AAAA N |
| ATOM | 1975 | N | PRO | 203 | 38.738 | 15.293 | 84.711 | 1.00 | 47.74 | AAAA N |
| ATOM | 1976 | CD | PRO | 203 | 38.758 | 15.840 | 86.082 | 1.00 | 46.97 | AAAA C |
| ATOM | 1977 | CA | PRO | 203 | 37.780 | 15.987 | 83.879 | 1.00 | 46.44 | AAAA C |
| ATOM | 1978 | CB | PRO | 203 | 37.248 | 17.107 | 84.742 | 1.00 | 39.47 | AAAA C |
| ATOM | 1979 | CG | PRO | 203 | 38.131 | 17.210 | 85.910 | 1.00 | 43.37 | AAAA C |
| ATOM | 1980 | C | PRO | 203 | 38.440 | 16.519 | 82.607 | 1.00 | 53.27 | AAAA C |
| ATOM | 1981 | O | PRO | 203 | 37.698 | 17.045 | 81.731 | 1.00 | 53.16 | AAAA O |
| ATOM | 1982 | N | GLU | 204 | 39.792 | 16.535 | 82.561 | 1.00 | 50.34 | AAAA N |
| ATOM | 1984 | CA | GLU | 204 | 40.439 | 17.139 | 81.381 | 1.00 | 50.52 | AAAA C |
| ATOM | 1985 | CB | GLU | 204 | 41.727 | 17.891 | 81.804 | 1.00 | 48.58 | AAAA C |
| ATOM | 1986 | CG | GLU | 204 | 41.397 | 19.251 | 82.397 | 1.00 | 43.74 | AAAA C |
| ATOM | 1987 | CD | GLU | 204 | 40.778 | 20.282 | 81.501 | 1.00 | 55.26 | AAAA C |
| ATOM | 1988 | OE1 | GLU | 204 | 40.766 | 20.344 | 80.248 | 1.00 | 64.04 | AAAA O |
| ATOM | 1989 | OE2 | GLU | 204 | 40.226 | 21.198 | 82.141 | 1.00 | 57.66 | AAAA O |
| ATOM | 1990 | C | GLU | 204 | 40.718 | 16.084 | 80.319 | 1.00 | 45.71 | AAAA C |
| ATOM | 1991 | O | GLU | 204 | 41.238 | 16.405 | 79.251 | 1.00 | 46.56 | AAAA O |
| ATOM | 1992 | N | CYS | 205 | 40.612 | 14.830 | 80.735 | 1.00 | 42.05 | AAAA N |
| ATOM | 1994 | CA | CYS | 205 | 40.997 | 13.764 | 79.838 | 1.00 | 45.81 | AAAA C |
| ATOM | 1995 | C | CYS | 205 | 39.892 | 13.628 | 78.819 | 1.00 | 49.20 | AAAA C |
| ATOM | 1996 | O | CYS | 205 | 38.746 | 13.920 | 79.133 | 1.00 | 50.34 | AAAA O |
| ATOM | 1997 | CB | CYS | 205 | 41.288 | 12.491 | 80.572 | 1.00 | 51.55 | AAAA C |
| ATOM | 1998 | SG | CYS | 205 | 42.923 | 12.246 | 81.251 | 1.00 | 52.89 | AAAA S |
| ATOM | 1999 | N | LEU | 206 | 40.232 | 13.579 | 77.520 | 1.00 | 49.88 | AAAA N |
| ATOM | 2001 | CA | LEU | 206 | 39.169 | 13.446 | 76.533 | 1.00 | 41.49 | AAAA C |
| ATOM | 2002 | CB | LEU | 206 | 39.266 | 14.505 | 75.462 | 1.00 | 48.66 | AAAA C |
| ATOM | 2003 | CG | LEU | 206 | 38.274 | 14.365 | 74.305 | 1.00 | 47.45 | AAAA C |

Figure 1A-20

```
ATOM   2004  CD1 LEU  206    36.879  14.243  74.895  1.00 45.79      AAAA C
ATOM   2005  CD2 LEU  206    38.331  15.599  73.420  1.00 50.71      AAAA C
ATOM   2006  C   LEU  206    39.310  12.109  75.912  1.00 38.44      AAAA C
ATOM   2007  O   LEU  206    40.400  11.568  75.813  1.00 36.59      AAAA O
ATOM   2008  N   GLY  207    38.264  11.359  75.681  1.00 42.41      AAAA N
ATOM   2010  CA  GLY  207    38.403  10.098  74.978  1.00 40.57      AAAA C
ATOM   2011  C   GLY  207    38.466   9.061  76.058  1.00 47.15      AAAA C
ATOM   2012  O   GLY  207    37.668   8.102  76.057  1.00 45.04      AAAA O
ATOM   2013  N   SER  208    39.622   9.079  76.760  1.00 50.36      AAAA N
ATOM   2015  CA  SER  208    39.832   7.898  77.660  1.00 48.27      AAAA C
ATOM   2016  CB  SER  208    39.909   6.631  76.787  1.00 35.77      AAAA C
ATOM   2017  OG  SER  208    40.600   5.597  77.461  1.00 61.34      AAAA O
ATOM   2019  C   SER  208    41.144   8.068  78.377  1.00 49.17      AAAA C
ATOM   2020  O   SER  208    41.781   9.084  78.163  1.00 48.24      AAAA O
ATOM   2021  N   CYS  209    41.599   7.123  79.189  1.00 52.04      AAAA N
ATOM   2023  CA  CYS  209    42.824   7.307  79.964  1.00 55.98      AAAA C
ATOM   2024  C   CYS  209    43.453   6.035  80.484  1.00 57.41      AAAA C
ATOM   2025  O   CYS  209    42.862   4.963  80.423  1.00 58.33      AAAA O
ATOM   2026  CB  CYS  209    42.629   8.258  81.146  1.00 52.51      AAAA C
ATOM   2027  SG  CYS  209    41.380   7.602  82.261  1.00 58.22      AAAA S
ATOM   2028  N   SER  210    44.734   6.145  80.883  1.00 59.37      AAAA N
ATOM   2030  CA  SER  210    45.506   4.950  81.318  1.00 58.10      AAAA C
ATOM   2031  CB  SER  210    47.022   5.083  81.105  1.00 55.07      AAAA C
ATOM   2032  OG  SER  210    47.546   6.204  81.818  1.00 64.49      AAAA O
ATOM   2034  C   SER  210    45.331   4.713  82.826  1.00 56.34      AAAA C
ATOM   2035  O   SER  210    45.529   3.614  83.326  1.00 54.42      AAAA O
ATOM   2036  N   ALA  211    45.105   5.806  83.548  1.00 52.79      AAAA N
ATOM   2038  CA  ALA  211    44.980   5.684  85.004  1.00 56.60      AAAA C
ATOM   2039  CB  ALA  211    46.333   5.926  85.649  1.00 63.41      AAAA C
ATOM   2040  C   ALA  211    43.962   6.747  85.395  1.00 56.58      AAAA C
ATOM   2041  O   ALA  211    43.957   7.792  84.711  1.00 50.78      AAAA O
ATOM   2042  N   PRO  212    43.117   6.416  86.359  1.00 55.93      AAAA N
ATOM   2043  CD  PRO  212    43.042   5.166  87.115  1.00 55.86      AAAA C
ATOM   2044  CA  PRO  212    41.951   7.257  86.575  1.00 55.50      AAAA C
ATOM   2045  CB  PRO  212    41.104   6.470  87.556  1.00 59.65      AAAA C
ATOM   2046  CG  PRO  212    42.021   5.483  88.175  1.00 54.56      AAAA C
ATOM   2047  C   PRO  212    42.409   8.535  87.177  1.00 53.64      AAAA C
ATOM   2048  O   PRO  212    43.611   8.725  87.393  1.00 57.48      AAAA O
ATOM   2049  N   ALA  213    41.537   9.492  87.347  1.00 53.87      AAAA N
ATOM   2051  CA  ALA  213    41.912  10.710  88.057  1.00 59.41      AAAA C
ATOM   2052  CB  ALA  213    41.783  10.255  89.541  1.00 66.40      AAAA C
ATOM   2053  C   ALA  213    43.289  11.300  87.907  1.00 61.40      AAAA C
ATOM   2054  O   ALA  213    43.728  12.202  88.652  1.00 60.03      AAAA O
ATOM   2055  N   ASN  214    44.068  10.999  86.899  1.00 64.80      AAAA N
ATOM   2057  CA  ASN  214    45.366  11.551  86.596  1.00 63.36      AAAA C
ATOM   2063  C   ASN  214    45.300  12.284  85.251  1.00 61.56      AAAA C
ATOM   2064  O   ASN  214    45.198  11.794  84.117  1.00 58.38      AAAA O
ATOM   2058  CB  ASN  214    46.336  10.379  86.608  1.00 67.32      AAAA C
ATOM   2059  CG  ASN  214    47.697  10.896  86.362  1.00 75.48      AAAA C
ATOM   2060  OD1 ASN  214    48.254  11.105  85.302  1.00 83.64      AAAA O
ATOM   2061  ND2 ASN  214    48.513  11.170  87.427  1.00 90.05      AAAA N
ATOM   2065  N   ASP  215    45.666  13.565  85.305  1.00 59.78      AAAA N
ATOM   2067  CA  ASP  215    45.618  14.432  84.143  1.00 56.47      AAAA C
ATOM   2068  CB  ASP  215    45.430  15.926  84.446  1.00 40.19      AAAA C
ATOM   2069  CG  ASP  215    46.671  16.543  84.986  1.00 56.36      AAAA C
ATOM   2070  OD1 ASP  215    46.590  17.699  85.473  1.00 56.17      AAAA O
ATOM   2071  OD2 ASP  215    47.766  15.926  84.941  1.00 60.51      AAAA O
ATOM   2072  C   ASP  215    46.818  14.315  83.221  1.00 53.78      AAAA C
ATOM   2073  O   ASP  215    46.998  15.148  82.322  1.00 53.58      AAAA O
ATOM   2074  N   THR  216    47.719  13.425  83.511  1.00 50.87      AAAA N
ATOM   2076  CA  THR  216    48.883  13.114  82.734  1.00 45.76      AAAA C
ATOM   2077  CB  THR  216    50.201  13.176  83.529  1.00 53.46      AAAA C
ATOM   2078  OG1 THR  216    50.403  11.977  84.335  1.00 45.14      AAAA O
ATOM   2080  CG2 THR  216    50.436  14.314  84.518  1.00 41.38      AAAA C
ATOM   2081  C   THR  216    48.681  11.712  82.158  1.00 48.34      AAAA C
ATOM   2082  O   THR  216    49.596  11.282  81.444  1.00 47.49      AAAA O
ATOM   2083  N   ALA  217    47.559  11.057  82.476  1.00 49.65      AAAA N
ATOM   2085  CA  ALA  217    47.259   9.760  81.845  1.00 51.83      AAAA C
ATOM   2086  CB  ALA  217    46.908   8.775  82.943  1.00 52.62      AAAA C
ATOM   2087  C   ALA  217    46.207   9.747  80.709  1.00 50.60      AAAA C
ATOM   2088  O   ALA  217    45.775   8.632  80.335  1.00 49.13      AAAA O
ATOM   2089  N   CYS  218    45.744  10.905  80.226  1.00 43.56      AAAA N
ATOM   2091  CA  CYS  218    44.802  11.030  79.157  1.00 48.09      AAAA C
ATOM   2092  C   CYS  218    45.166  10.331  77.869  1.00 47.06      AAAA C
ATOM   2093  O   CYS  218    46.300   9.967  77.642  1.00 55.57      AAAA O
ATOM   2094  CB  CYS  218    44.536  12.501  78.775  1.00 51.54      AAAA C
ATOM   2095  SG  CYS  218    44.256  13.494  80.302  1.00 56.98      AAAA S
ATOM   2096  N   VAL  219    44.226  10.085  76.978  1.00 43.40      AAAA N
```

Figure 1A-21

```
ATOM   2098  CA   VAL  219     44.575    9.547   75.654  1.00 35.22      AAAA C
ATOM   2099  CB   VAL  219     43.693    8.427   75.242  1.00 32.26      AAAA C
ATOM   2100  CG1  VAL  219     43.952    7.873   73.886  1.00 36.19      AAAA C
ATOM   2101  CG2  VAL  219     43.811    7.144   76.071  1.00 45.51      AAAA C
ATOM   2102  C    VAL  219     44.453   10.750   74.735  1.00 32.06      AAAA C
ATOM   2103  O    VAL  219     45.303   10.897   73.874  1.00 42.27      AAAA O
ATOM   2104  N    ALA  220     43.728   11.759   75.187  1.00 24.24      AAAA N
ATOM   2106  CA   ALA  220     43.630   12.985   74.385  1.00 27.99      AAAA C
ATOM   2107  CB   ALA  220     42.536   12.919   73.331  1.00 28.42      AAAA C
ATOM   2108  C    ALA  220     43.292   14.071   75.390  1.00 29.21      AAAA C
ATOM   2109  O    ALA  220     42.846   13.604   76.455  1.00 37.88      AAAA O
ATOM   2110  N    CYS  221     43.285   15.334   75.058  1.00 30.27      AAAA N
ATOM   2112  CA   CYS  221     42.753   16.382   75.875  1.00 35.55      AAAA C
ATOM   2113  C    CYS  221     41.460   17.055   75.452  1.00 47.06      AAAA C
ATOM   2114  O    CYS  221     41.265   17.598   74.368  1.00 49.57      AAAA O
ATOM   2115  CB   CYS  221     43.804   17.478   76.063  1.00 47.45      AAAA C
ATOM   2116  SG   CYS  221     45.494   16.935   76.538  1.00 47.06      AAAA S
ATOM   2117  N    ARG  222     40.503   17.133   76.396  1.00 51.47      AAAA N
ATOM   2119  CA   ARG  222     39.281   17.906   76.338  1.00 51.86      AAAA C
ATOM   2120  CB   ARG  222     38.647   18.074   77.712  1.00 54.53      AAAA C
ATOM   2121  CG   ARG  222     37.314   18.687   77.854  1.00 45.56      AAAA C
ATOM   2122  CD   ARG  222     36.538   18.338   79.087  1.00 54.45      AAAA C
ATOM   2123  NE   ARG  222     36.272   16.947   79.269  1.00 65.53      AAAA N
ATOM   2125  CZ   ARG  222     35.534   16.080   78.617  1.00 67.60      AAAA C
ATOM   2126  NH1  ARG  222     34.925   16.599   77.533  1.00 70.26      AAAA N
ATOM   2129  NH2  ARG  222     35.342   14.780   78.901  1.00 54.11      AAAA N
ATOM   2132  C    ARG  222     39.562   19.286   75.740  1.00 50.66      AAAA C
ATOM   2133  O    ARG  222     38.737   19.845   75.009  1.00 58.34      AAAA O
ATOM   2134  N    HIS  223     40.556   19.981   76.190  1.00 45.65      AAAA N
ATOM   2136  CA   HIS  223     40.988   21.291   75.821  1.00 46.93      AAAA C
ATOM   2137  CB   HIS  223     41.057   22.251   77.011  1.00 49.51      AAAA C
ATOM   2138  CG   HIS  223     39.710   22.344   77.647  1.00 58.83      AAAA C
ATOM   2139  CD2  HIS  223     38.820   23.360   77.556  1.00 61.08      AAAA C
ATOM   2140  ND1  HIS  223     39.082   21.388   78.425  1.00 63.28      AAAA N
ATOM   2142  CE1  HIS  223     37.881   21.815   78.759  1.00 58.01      AAAA C
ATOM   2143  NE2  HIS  223     37.681   23.010   78.232  1.00 48.56      AAAA N
ATOM   2145  C    HIS  223     42.363   21.260   75.122  1.00 50.78      AAAA C
ATOM   2146  O    HIS  223     42.506   20.753   74.003  1.00 47.43      AAAA O
ATOM   2147  N    TYR  224     43.359   21.847   75.769  1.00 49.20      AAAA N
ATOM   2149  CA   TYR  224     44.712   21.992   75.259  1.00 48.17      AAAA C
ATOM   2150  CB   TYR  224     45.144   23.430   75.426  1.00 44.07      AAAA C
ATOM   2151  CG   TYR  224     44.318   24.234   74.417  1.00 51.77      AAAA C
ATOM   2152  CD1  TYR  224     43.193   24.869   74.904  1.00 48.94      AAAA C
ATOM   2153  CE1  TYR  224     42.401   25.633   74.089  1.00 48.41      AAAA C
ATOM   2154  CD2  TYR  224     44.623   24.358   73.065  1.00 54.82      AAAA C
ATOM   2155  CE2  TYR  224     43.847   25.131   72.233  1.00 56.09      AAAA C
ATOM   2156  CZ   TYR  224     42.739   25.745   72.766  1.00 54.23      AAAA C
ATOM   2157  OH   TYR  224     41.915   26.522   72.017  1.00 61.70      AAAA O
ATOM   2159  C    TYR  224     45.725   21.095   75.892  1.00 48.19      AAAA C
ATOM   2160  O    TYR  224     45.776   20.913   77.111  1.00 55.75      AAAA O
ATOM   2161  N    TYR  225     46.584   20.514   75.077  1.00 48.79      AAAA N
ATOM   2163  CA   TYR  225     47.655   19.653   75.555  1.00 43.02      AAAA C
ATOM   2164  CB   TYR  225     48.020   18.639   74.548  1.00 42.32      AAAA C
ATOM   2165  CG   TYR  225     49.286   17.926   74.954  1.00 46.95      AAAA C
ATOM   2166  CD1  TYR  225     49.299   16.858   75.817  1.00 43.57      AAAA C
ATOM   2167  CE1  TYR  225     50.450   16.221   76.173  1.00 47.26      AAAA C
ATOM   2168  CD2  TYR  225     50.487   18.407   74.421  1.00 52.82      AAAA C
ATOM   2169  CE2  TYR  225     51.656   17.791   74.781  1.00 53.94      AAAA C
ATOM   2170  CZ   TYR  225     51.639   16.707   75.644  1.00 52.31      AAAA C
ATOM   2171  OH   TYR  225     52.886   16.186   75.905  1.00 50.71      AAAA O
ATOM   2173  C    TYR  225     48.872   20.507   75.793  1.00 47.13      AAAA C
ATOM   2174  O    TYR  225     49.080   21.514   75.150  1.00 53.97      AAAA O
ATOM   2175  N    TYR  226     49.634   20.253   76.821  1.00 56.84      AAAA N
ATOM   2177  CA   TYR  226     50.814   21.001   77.172  1.00 56.83      AAAA C
ATOM   2178  CB   TYR  226     50.455   22.343   77.785  1.00 59.51      AAAA C
ATOM   2179  CG   TYR  226     51.741   23.126   77.941  1.00 65.45      AAAA C
ATOM   2180  CD1  TYR  226     52.121   23.557   79.197  1.00 69.12      AAAA C
ATOM   2181  CE1  TYR  226     53.289   24.275   79.400  1.00 70.77      AAAA C
ATOM   2182  CD2  TYR  226     52.580   23.409   76.864  1.00 69.38      AAAA C
ATOM   2183  CE2  TYR  226     53.758   24.118   77.020  1.00 70.94      AAAA C
ATOM   2184  CZ   TYR  226     54.099   24.549   78.301  1.00 72.96      AAAA C
ATOM   2185  OH   TYR  226     55.267   25.254   78.435  1.00 70.84      AAAA O
ATOM   2187  C    TYR  226     51.784   20.356   78.165  1.00 57.55      AAAA C
ATOM   2188  O    TYR  226     51.492   20.133   79.350  1.00 56.90      AAAA O
ATOM   2189  N    ALA  227     52.978   20.080   77.642  1.00 53.82      AAAA N
ATOM   2191  CA   ALA  227     54.061   19.557   78.440  1.00 51.82      AAAA C
ATOM   2192  CB   ALA  227     54.528   20.620   79.428  1.00 55.81      AAAA C
ATOM   2193  C    ALA  227     53.600   18.309   79.170  1.00 53.56      AAAA C
```

Figure 1A-22

```
ATOM   2194  O    ALA  227      53.663  18.218  80.413  1.00 49.63      AAAA O
ATOM   2195  N    GLY  228      53.076  17.360  78.393  1.00 50.68      AAAA N
ATOM   2197  CA   GLY  228      52.585  16.135  79.028  1.00 49.02      AAAA C
ATOM   2198  C    GLY  228      51.312  16.330  79.861  1.00 51.61      AAAA C
ATOM   2199  O    GLY  228      51.028  15.538  80.776  1.00 51.10      AAAA O
ATOM   2200  N    VAL  229      50.643  17.495  79.791  1.00 47.09      AAAA N
ATOM   2202  CA   VAL  229      49.489  17.671  80.635  1.00 51.11      AAAA C
ATOM   2203  CB   VAL  229      49.908  18.610  81.774  1.00 56.52      AAAA C
ATOM   2204  CG1  VAL  229      48.627  18.896  82.566  1.00 38.39      AAAA C
ATOM   2205  CG2  VAL  229      51.002  18.035  82.682  1.00 50.16      AAAA C
ATOM   2206  C    VAL  229      48.255  18.173  79.873  1.00 51.37      AAAA C
ATOM   2207  O    VAL  229      48.344  19.279  79.309  1.00 53.71      AAAA O
ATOM   2208  N    CYS  230      47.100  17.518  80.036  1.00 42.21      AAAA N
ATOM   2210  CA   CYS  230      45.881  18.117  79.471  1.00 40.32      AAAA C
ATOM   2211  C    CYS  230      45.456  19.350  80.228  1.00 38.42      AAAA C
ATOM   2212  O    CYS  230      44.964  19.248  81.321  1.00 41.62      AAAA O
ATOM   2213  CB   CYS  230      44.746  17.132  79.370  1.00 31.54      AAAA C
ATOM   2214  SG   CYS  230      45.149  15.753  78.266  1.00 43.61      AAAA S
ATOM   2215  N    VAL  231      45.637  20.534  79.731  1.00 39.83      AAAA N
ATOM   2217  CA   VAL  231      45.445  21.769  80.462  1.00 46.57      AAAA C
ATOM   2218  CB   VAL  231      46.618  22.736  80.088  1.00 50.99      AAAA C
ATOM   2219  CG1  VAL  231      46.798  23.878  81.053  1.00 50.41      AAAA C
ATOM   2220  CG2  VAL  231      47.838  21.913  80.506  1.00 44.95      AAAA C
ATOM   2221  C    VAL  231      44.111  22.321  80.057  1.00 52.59      AAAA C
ATOM   2222  O    VAL  231      43.599  22.183  78.936  1.00 55.30      AAAA O
ATOM   2223  N    PRO  232      43.482  23.105  80.913  1.00 54.28      AAAA N
ATOM   2224  CD   PRO  232      43.830  23.385  82.320  1.00 54.25      AAAA C
ATOM   2225  CA   PRO  232      42.153  23.625  80.575  1.00 54.39      AAAA C
ATOM   2226  CB   PRO  232      41.537  23.877  81.928  1.00 53.73      AAAA C
ATOM   2227  CG   PRO  232      42.683  24.287  82.765  1.00 55.00      AAAA C
ATOM   2228  C    PRO  232      42.361  24.913  79.795  1.00 56.37      AAAA C
ATOM   2229  O    PRO  232      41.498  25.482  79.137  1.00 55.79      AAAA O
ATOM   2230  N    ALA  233      43.615  25.400  79.901  1.00 54.76      AAAA N
ATOM   2232  CA   ALA  233      43.998  26.569  79.124  1.00 49.93      AAAA C
ATOM   2233  CB   ALA  233      43.440  27.807  79.746  1.00 35.43      AAAA C
ATOM   2234  C    ALA  233      45.502  26.662  78.974  1.00 49.79      AAAA C
ATOM   2235  O    ALA  233      46.195  25.879  79.616  1.00 51.41      AAAA O
ATOM   2236  N    CYS  234      45.984  27.508  78.072  1.00 45.07      AAAA N
ATOM   2238  CA   CYS  234      47.430  27.518  77.907  1.00 48.63      AAAA C
ATOM   2239  C    CYS  234      48.001  28.340  79.076  1.00 50.93      AAAA C
ATOM   2240  O    CYS  234      47.650  29.513  79.250  1.00 47.57      AAAA O
ATOM   2241  CB   CYS  234      47.816  28.034  76.511  1.00 43.10      AAAA C
ATOM   2242  SG   CYS  234      47.608  26.789  75.226  1.00 43.04      AAAA S
ATOM   2243  N    PRO  235      49.127  27.853  79.599  1.00 49.55      AAAA N
ATOM   2244  CD   PRO  235      49.692  26.557  79.207  1.00 48.75      AAAA C
ATOM   2245  CA   PRO  235      49.911  28.569  80.599  1.00 51.69      AAAA C
ATOM   2246  CB   PRO  235      50.984  27.581  80.975  1.00 50.80      AAAA C
ATOM   2247  CG   PRO  235      50.912  26.417  80.077  1.00 50.06      AAAA C
ATOM   2248  C    PRO  235      50.487  29.852  80.050  1.00 57.11      AAAA C
ATOM   2249  O    PRO  235      50.848  29.957  78.870  1.00 59.60      AAAA O
ATOM   2250  N    PRO  236      50.676  30.875  80.887  1.00 59.85      AAAA N
ATOM   2251  CD   PRO  236      50.405  30.822  82.363  1.00 55.85      AAAA C
ATOM   2252  CA   PRO  236      51.323  32.143  80.493  1.00 52.27      AAAA C
ATOM   2253  CB   PRO  236      51.695  32.814  81.826  1.00 53.62      AAAA C
ATOM   2254  CG   PRO  236      50.652  32.277  82.754  1.00 56.73      AAAA C
ATOM   2255  C    PRO  236      52.545  31.886  79.671  1.00 44.21      AAAA C
ATOM   2256  O    PRO  236      53.218  30.892  79.928  1.00 43.40      AAAA O
ATOM   2257  N    ASN  237      52.837  32.757  78.716  1.00 46.54      AAAA N
ATOM   2259  CA   ASN  237      53.895  32.623  77.716  1.00 45.94      AAAA C
ATOM   2260  CB   ASN  237      55.258  32.653  78.456  1.00 58.65      AAAA C
ATOM   2261  CG   ASN  237      55.357  33.855  79.371  1.00 58.51      AAAA C
ATOM   2262  OD1  ASN  237      56.044  33.762  80.379  1.00 72.25      AAAA O
ATOM   2263  ND2  ASN  237      54.631  34.910  79.051  1.00 62.99      AAAA N
ATOM   2266  C    ASN  237      53.897  31.425  76.788  1.00 46.87      AAAA C
ATOM   2267  O    ASN  237      54.962  30.935  76.326  1.00 54.50      AAAA O
ATOM   2268  N    THR  238      52.817  30.657  76.692  1.00 42.91      AAAA N
ATOM   2270  CA   THR  238      52.617  29.567  75.780  1.00 40.20      AAAA C
ATOM   2271  CB   THR  238      52.461  28.248  76.466  1.00 42.62      AAAA C
ATOM   2272  OG1  THR  238      51.227  28.343  77.237  1.00 50.88      AAAA O
ATOM   2274  CG2  THR  238      53.552  27.886  77.424  1.00 34.84      AAAA C
ATOM   2275  C    THR  238      51.279  29.875  75.078  1.00 42.59      AAAA C
ATOM   2276  O    THR  238      50.669  30.864  75.509  1.00 42.51      AAAA O
ATOM   2277  N    TYR  239      51.051  29.488  73.832  1.00 42.62      AAAA N
ATOM   2279  CA   TYR  239      49.949  29.959  73.024  1.00 41.87      AAAA C
ATOM   2280  CB   TYR  239      50.457  30.907  71.931  1.00 44.86      AAAA C
ATOM   2281  CG   TYR  239      51.099  32.125  72.564  1.00 42.05      AAAA C
ATOM   2282  CD1  TYR  239      52.467  32.086  72.815  1.00 39.41      AAAA C
ATOM   2283  CE1  TYR  239      53.092  33.152  73.415  1.00 43.27      AAAA C
```

| | | | | | | | | | |
|---|---|---|---|---|---|---|---|---|---|
| ATOM | 2284 | CD2 | TYR | 239 | 50.376 | 33.230 | 72.923 | 1.00 44.15 | AAAA C |
| ATOM | 2285 | CE2 | TYR | 239 | 50.972 | 34.310 | 73.536 | 1.00 46.22 | AAAA C |
| ATOM | 2286 | CZ | TYR | 239 | 52.339 | 34.243 | 73.779 | 1.00 50.49 | AAAA C |
| ATOM | 2287 | OH | TYR | 239 | 53.013 | 35.370 | 74.387 | 1.00 55.47 | AAAA O |
| ATOM | 2289 | C | TYR | 239 | 49.232 | 28.813 | 72.315 | 1.00 45.54 | AAAA C |
| ATOM | 2290 | O | TYR | 239 | 49.922 | 27.810 | 72.021 | 1.00 46.66 | AAAA O |
| ATOM | 2291 | N | ARG | 240 | 47.895 | 28.990 | 72.126 | 1.00 40.62 | AAAA N |
| ATOM | 2293 | CA | ARG | 240 | 47.177 | 27.892 | 71.426 | 1.00 38.78 | AAAA C |
| ATOM | 2294 | CB | ARG | 240 | 45.675 | 28.127 | 71.452 | 1.00 39.77 | AAAA C |
| ATOM | 2295 | CG | ARG | 240 | 45.116 | 28.944 | 72.588 | 1.00 43.37 | AAAA C |
| ATOM | 2296 | CD | ARG | 240 | 43.573 | 28.957 | 72.683 | 1.00 38.60 | AAAA C |
| ATOM | 2297 | NE | ARG | 240 | 43.114 | 29.683 | 71.455 | 1.00 53.98 | AAAA N |
| ATOM | 2299 | CZ | ARG | 240 | 43.123 | 31.015 | 71.530 | 1.00 48.07 | AAAA C |
| ATOM | 2300 | NH1 | ARG | 240 | 43.513 | 31.562 | 72.668 | 1.00 47.65 | AAAA N |
| ATOM | 2303 | NH2 | ARG | 240 | 42.788 | 31.778 | 70.533 | 1.00 51.03 | AAAA N |
| ATOM | 2306 | C | ARG | 240 | 47.627 | 27.737 | 69.979 | 1.00 31.72 | AAAA C |
| ATOM | 2307 | O | ARG | 240 | 47.937 | 28.730 | 69.302 | 1.00 32.37 | AAAA O |
| ATOM | 2308 | N | PHE | 241 | 47.779 | 26.542 | 69.549 | 1.00 27.95 | AAAA N |
| ATOM | 2310 | CA | PHE | 241 | 48.182 | 26.269 | 68.183 | 1.00 30.41 | AAAA C |
| ATOM | 2311 | CB | PHE | 241 | 49.678 | 25.940 | 68.151 | 1.00 34.83 | AAAA C |
| ATOM | 2312 | CG | PHE | 241 | 50.235 | 25.653 | 66.773 | 1.00 26.84 | AAAA C |
| ATOM | 2313 | CD1 | PHE | 241 | 50.165 | 26.567 | 65.753 | 1.00 25.31 | AAAA C |
| ATOM | 2314 | CD2 | PHE | 241 | 50.785 | 24.417 | 66.573 | 1.00 27.38 | AAAA C |
| ATOM | 2315 | CE1 | PHE | 241 | 50.676 | 26.232 | 64.509 | 1.00 37.24 | AAAA C |
| ATOM | 2316 | CE2 | PHE | 241 | 51.294 | 24.101 | 65.320 | 1.00 38.45 | AAAA C |
| ATOM | 2317 | CZ | PHE | 241 | 51.281 | 25.010 | 64.281 | 1.00 21.17 | AAAA C |
| ATOM | 2318 | C | PHE | 241 | 47.382 | 25.089 | 67.621 | 1.00 35.77 | AAAA C |
| ATOM | 2319 | O | PHE | 241 | 47.543 | 24.013 | 68.186 | 1.00 36.77 | AAAA O |
| ATOM | 2320 | N | GLU | 242 | 46.738 | 25.301 | 66.468 | 1.00 32.30 | AAAA N |
| ATOM | 2322 | CA | GLU | 242 | 45.964 | 24.269 | 65.805 | 1.00 35.43 | AAAA C |
| ATOM | 2323 | CB | GLU | 242 | 46.953 | 23.144 | 65.472 | 1.00 37.98 | AAAA C |
| ATOM | 2324 | CG | GLU | 242 | 47.867 | 23.415 | 64.314 | 1.00 38.63 | AAAA C |
| ATOM | 2325 | CD | GLU | 242 | 47.207 | 23.965 | 63.075 | 1.00 39.27 | AAAA C |
| ATOM | 2326 | OE1 | GLU | 242 | 46.380 | 23.205 | 62.517 | 1.00 42.79 | AAAA O |
| ATOM | 2327 | OE2 | GLU | 242 | 47.354 | 25.109 | 62.626 | 1.00 36.36 | AAAA O |
| ATOM | 2328 | C | GLU | 242 | 44.752 | 23.771 | 66.600 | 1.00 34.36 | AAAA C |
| ATOM | 2329 | O | GLU | 242 | 44.390 | 22.611 | 66.511 | 1.00 28.53 | AAAA O |
| ATOM | 2330 | N | GLY | 243 | 44.135 | 24.589 | 67.449 | 1.00 36.94 | AAAA N |
| ATOM | 2332 | CA | GLY | 243 | 43.048 | 24.154 | 68.303 | 1.00 34.57 | AAAA C |
| ATOM | 2333 | C | GLY | 243 | 43.428 | 23.107 | 69.319 | 1.00 37.76 | AAAA C |
| ATOM | 2334 | O | GLY | 243 | 42.474 | 22.473 | 69.746 | 1.00 43.00 | AAAA O |
| ATOM | 2335 | N | TRP | 244 | 44.637 | 22.636 | 69.611 | 1.00 39.53 | AAAA N |
| ATOM | 2337 | CA | TRP | 244 | 44.797 | 21.536 | 70.566 | 1.00 40.85 | AAAA C |
| ATOM | 2338 | CB | TRP | 244 | 44.774 | 20.271 | 69.764 | 1.00 26.76 | AAAA C |
| ATOM | 2339 | CG | TRP | 244 | 46.012 | 19.885 | 69.028 | 1.00 43.19 | AAAA C |
| ATOM | 2340 | CD2 | TRP | 244 | 47.019 | 18.983 | 69.498 | 1.00 39.55 | AAAA C |
| ATOM | 2341 | CE2 | TRP | 244 | 47.998 | 18.906 | 68.489 | 1.00 36.50 | AAAA C |
| ATOM | 2342 | CE3 | TRP | 244 | 47.186 | 18.254 | 70.692 | 1.00 32.18 | AAAA C |
| ATOM | 2343 | CD1 | TRP | 244 | 46.424 | 20.308 | 67.779 | 1.00 43.37 | AAAA C |
| ATOM | 2344 | NE1 | TRP | 244 | 47.595 | 19.727 | 67.469 | 1.00 38.89 | AAAA N |
| ATOM | 2346 | CZ2 | TRP | 244 | 49.150 | 18.128 | 68.620 | 1.00 39.01 | AAAA C |
| ATOM | 2347 | CZ3 | TRP | 244 | 48.336 | 17.478 | 70.815 | 1.00 43.98 | AAAA C |
| ATOM | 2348 | CH2 | TRP | 244 | 49.322 | 17.425 | 69.784 | 1.00 42.50 | AAAA C |
| ATOM | 2349 | C | TRP | 244 | 45.998 | 21.517 | 71.509 | 1.00 42.98 | AAAA C |
| ATOM | 2350 | O | TRP | 244 | 46.253 | 20.501 | 72.146 | 1.00 42.70 | AAAA O |
| ATOM | 2351 | N | ARG | 245 | 46.888 | 22.485 | 71.435 | 1.00 44.16 | AAAA N |
| ATOM | 2353 | CA | ARG | 245 | 48.168 | 22.472 | 72.095 | 1.00 46.47 | AAAA C |
| ATOM | 2354 | CB | ARG | 245 | 49.203 | 21.602 | 71.367 | 1.00 47.30 | AAAA C |
| ATOM | 2355 | CG | ARG | 245 | 49.885 | 22.309 | 70.203 | 1.00 48.97 | AAAA C |
| ATOM | 2356 | CD | ARG | 245 | 51.129 | 21.552 | 69.819 | 1.00 39.28 | AAAA C |
| ATOM | 2357 | NE | ARG | 245 | 51.586 | 21.665 | 68.444 | 1.00 50.86 | AAAA N |
| ATOM | 2359 | CZ | ARG | 245 | 52.629 | 21.044 | 67.895 | 1.00 46.73 | AAAA C |
| ATOM | 2360 | NH1 | ARG | 245 | 53.344 | 20.236 | 68.653 | 1.00 50.15 | AAAA N |
| ATOM | 2363 | NH2 | ARG | 245 | 53.072 | 21.126 | 66.638 | 1.00 41.69 | AAAA N |
| ATOM | 2366 | C | ARG | 245 | 48.771 | 23.863 | 72.271 | 1.00 46.01 | AAAA C |
| ATOM | 2367 | O | ARG | 245 | 48.394 | 24.793 | 71.541 | 1.00 47.44 | AAAA O |
| ATOM | 2368 | N | CYS | 246 | 49.625 | 23.881 | 73.317 | 1.00 42.08 | AAAA N |
| ATOM | 2370 | CA | CYS | 246 | 50.246 | 25.199 | 73.628 | 1.00 43.48 | AAAA C |
| ATOM | 2371 | C | CYS | 246 | 51.695 | 25.217 | 73.183 | 1.00 43.38 | AAAA C |
| ATOM | 2372 | O | CYS | 246 | 52.476 | 24.239 | 73.320 | 1.00 42.51 | AAAA O |
| ATOM | 2373 | CB | CYS | 246 | 50.102 | 25.392 | 75.138 | 1.00 48.91 | AAAA C |
| ATOM | 2374 | SG | CYS | 246 | 48.386 | 25.049 | 75.797 | 1.00 43.68 | AAAA S |
| ATOM | 2375 | N | VAL | 247 | 52.121 | 26.288 | 72.564 | 1.00 41.21 | AAAA N |
| ATOM | 2377 | CA | VAL | 247 | 53.417 | 26.468 | 71.982 | 1.00 36.51 | AAAA C |
| ATOM | 2378 | CB | VAL | 247 | 53.568 | 26.357 | 70.444 | 1.00 36.87 | AAAA C |
| ATOM | 2379 | CG1 | VAL | 247 | 53.089 | 24.988 | 70.024 | 1.00 32.71 | AAAA C |
| ATOM | 2380 | CG2 | VAL | 247 | 53.129 | 27.602 | 69.729 | 1.00 28.20 | AAAA C |
| ATOM | 2381 | C | VAL | 247 | 53.969 | 27.812 | 72.373 | 1.00 39.37 | AAAA C |

Figure 1A-24

```
ATOM   2382  O    VAL  247      53.230  28.770  72.540  1.00 38.80      AAAA O
ATOM   2383  N    ASP  248      55.291  27.820  72.711  1.00 45.21      AAAA N
ATOM   2385  CA   ASP  248      55.895  29.115  73.098  1.00 40.19      AAAA C
ATOM   2386  CB   ASP  248      57.091  28.946  73.953  1.00 42.63      AAAA C
ATOM   2387  CG   ASP  248      58.126  27.997  73.394  1.00 58.81      AAAA C
ATOM   2388  OD1  ASP  248      59.067  27.795  74.187  1.00 53.06      AAAA O
ATOM   2389  OD2  ASP  248      58.167  27.395  72.313  1.00 69.51      AAAA O
ATOM   2390  C    ASP  248      56.315  29.883  71.839  1.00 36.99      AAAA C
ATOM   2391  O    ASP  248      56.292  29.288  70.772  1.00 39.70      AAAA O
ATOM   2392  N    ARG  249      56.545  31.163  71.918  1.00 30.72      AAAA N
ATOM   2394  CA   ARG  249      56.950  32.057  70.906  1.00 36.17      AAAA C
ATOM   2395  CB   ARG  249      57.223  33.485  71.491  1.00 21.29      AAAA C
ATOM   2396  CG   ARG  249      57.594  34.424  70.326  1.00 24.96      AAAA C
ATOM   2397  CD   ARG  249      57.814  35.811  70.843  1.00 21.23      AAAA C
ATOM   2398  NE   ARG  249      56.658  36.150  71.689  1.00 39.75      AAAA N
ATOM   2400  CZ   ARG  249      55.632  36.823  71.101  1.00 39.35      AAAA C
ATOM   2401  NH1  ARG  249      55.642  37.118  69.801  1.00 25.41      AAAA N
ATOM   2404  NH2  ARG  249      54.641  37.118  71.946  1.00 44.04      AAAA N
ATOM   2407  C    ARG  249      58.134  31.685  70.010  1.00 40.63      AAAA C
ATOM   2408  O    ARG  249      58.086  31.923  68.797  1.00 44.79      AAAA O
ATOM   2409  N    ASP  250      59.149  30.974  70.468  1.00 41.87      AAAA N
ATOM   2411  CA   ASP  250      60.287  30.739  69.606  1.00 46.90      AAAA C
ATOM   2412  CB   ASP  250      61.740  30.726  70.154  1.00 53.11      AAAA C
ATOM   2413  CG   ASP  250      62.421  32.122  70.081  1.00 71.49      AAAA C
ATOM   2414  OD1  ASP  250      63.124  32.682  69.176  1.00 58.53      AAAA O
ATOM   2415  OD2  ASP  250      62.272  32.928  71.071  1.00 70.30      AAAA O
ATOM   2416  C    ASP  250      59.881  29.536  68.771  1.00 41.22      AAAA C
ATOM   2417  O    ASP  250      60.291  29.443  67.616  1.00 39.06      AAAA O
ATOM   2418  N    PHE  251      59.116  28.609  69.299  1.00 36.13      AAAA N
ATOM   2420  CA   PHE  251      58.457  27.601  68.489  1.00 34.88      AAAA C
ATOM   2421  CB   PHE  251      57.468  26.746  69.256  1.00 29.82      AAAA C
ATOM   2422  CG   PHE  251      56.701  25.801  68.385  1.00 41.50      AAAA C
ATOM   2423  CD1  PHE  251      57.101  24.479  68.263  1.00 30.66      AAAA C
ATOM   2424  CD2  PHE  251      55.559  26.213  67.686  1.00 37.78      AAAA C
ATOM   2425  CE1  PHE  251      56.414  23.597  67.424  1.00 29.30      AAAA C
ATOM   2426  CE2  PHE  251      54.847  25.372  66.856  1.00 36.09      AAAA C
ATOM   2427  CZ   PHE  251      55.294  24.070  66.715  1.00 36.21      AAAA C
ATOM   2428  C    PHE  251      57.624  28.290  67.338  1.00 39.28      AAAA C
ATOM   2429  O    PHE  251      57.811  28.010  66.144  1.00 30.27      AAAA O
ATOM   2430  N    CYS  252      56.734  29.225  67.713  1.00 35.13      AAAA N
ATOM   2432  CA   CYS  252      55.895  29.870  66.728  1.00 38.80      AAAA C
ATOM   2433  C    CYS  252      56.827  30.598  65.747  1.00 44.73      AAAA C
ATOM   2434  O    CYS  252      56.552  30.534  64.536  1.00 43.20      AAAA O
ATOM   2435  CB   CYS  252      54.903  30.778  67.379  1.00 35.65      AAAA C
ATOM   2436  SG   CYS  252      53.562  31.544  66.459  1.00 39.03      AAAA S
ATOM   2437  N    ALA  253      57.872  31.256  66.285  1.00 41.53      AAAA N
ATOM   2439  CA   ALA  253      58.687  32.071  65.415  1.00 40.39      AAAA C
ATOM   2440  CB   ALA  253      59.529  33.088  66.172  1.00 36.07      AAAA C
ATOM   2441  C    ALA  253      59.551  31.167  64.539  1.00 42.88      AAAA C
ATOM   2442  O    ALA  253      60.147  31.735  63.640  1.00 47.42      AAAA O
ATOM   2443  N    ASN  254      59.657  29.859  64.700  1.00 38.75      AAAA N
ATOM   2445  CA   ASN  254      60.546  29.073  63.928  1.00 42.94      AAAA C
ATOM   2446  CB   ASN  254      61.667  28.497  64.847  1.00 48.09      AAAA C
ATOM   2447  CG   ASN  254      62.696  29.635  65.031  1.00 49.54      AAAA C
ATOM   2448  OD1  ASN  254      63.468  29.840  64.081  1.00 61.38      AAAA O
ATOM   2449  ND2  ASN  254      62.607  30.321  66.144  1.00 48.38      AAAA N
ATOM   2452  C    ASN  254      59.907  27.959  63.135  1.00 53.72      AAAA C
ATOM   2453  O    ASN  254      60.552  26.965  62.804  1.00 51.19      AAAA O
ATOM   2454  N    ILE  255      58.612  28.136  62.766  1.00 57.77      AAAA N
ATOM   2456  CA   ILE  255      57.828  27.107  62.134  1.00 53.28      AAAA C
ATOM   2457  CB   ILE  255      56.329  27.322  62.304  1.00 50.41      AAAA C
ATOM   2458  CG2  ILE  255      55.477  26.595  61.246  1.00 51.95      AAAA C
ATOM   2459  CG1  ILE  255      55.778  26.675  63.553  1.00 40.59      AAAA C
ATOM   2460  CD1  ILE  255      54.479  27.317  64.006  1.00 38.97      AAAA C
ATOM   2461  C    ILE  255      58.127  26.886  60.651  1.00 52.62      AAAA C
ATOM   2462  O    ILE  255      58.196  25.709  60.252  1.00 53.96      AAAA O
ATOM   2463  N    LEU  256      58.290  27.960  59.918  1.00 49.96      AAAA N
ATOM   2465  CA   LEU  256      58.680  27.764  58.516  1.00 63.68      AAAA C
ATOM   2466  CB   LEU  256      58.175  29.012  57.799  1.00 56.80      AAAA C
ATOM   2467  CG   LEU  256      56.671  29.196  57.864  1.00 59.11      AAAA C
ATOM   2468  CD1  LEU  256      56.310  30.654  57.645  1.00 43.31      AAAA C
ATOM   2469  CD2  LEU  256      55.965  28.222  56.928  1.00 55.88      AAAA C
ATOM   2470  C    LEU  256      60.193  27.622  58.355  1.00 66.23      AAAA C
ATOM   2471  O    LEU  256      60.691  27.511  57.245  1.00 70.29      AAAA O
ATOM   2472  N    SER  257      60.942  27.559  59.430  1.00 64.61      AAAA N
ATOM   2474  CA   SER  257      62.352  27.529  59.534  1.00 69.23      AAAA C
ATOM   2475  CB   SER  257      62.924  27.318  60.955  1.00 62.45      AAAA C
ATOM   2476  OG   SER  257      63.381  25.980  61.074  1.00 56.18      AAAA O
```

Figure 1A-25

```
ATOM   2478  C    SER   257      62.973  26.497  58.610  1.00 70.77      AAAA C
ATOM   2479  O    SER   257      64.127  26.731  58.246  1.00 72.50      AAAA O
ATOM   2480  N    ALA   258      62.322  25.389  58.320  1.00 74.61      AAAA N
ATOM   2482  CA   ALA   258      62.933  24.488  57.343  1.00 76.34      AAAA C
ATOM   2483  CB   ALA   258      62.570  23.039  57.584  1.00 80.82      AAAA C
ATOM   2484  C    ALA   258      62.663  24.964  55.921  1.00 78.21      AAAA C
ATOM   2485  O    ALA   258      62.880  24.139  55.029  1.00 79.60      AAAA O
ATOM   2486  N    GLU   259      62.069  26.109  55.651  1.00 79.05      AAAA N
ATOM   2488  CA   GLU   259      61.742  26.621  54.349  1.00 83.84      AAAA C
ATOM   2489  CB   GLU   259      60.226  26.457  54.135  1.00 86.99      AAAA C
ATOM   2490  CG   GLU   259      59.687  25.049  54.314  1.00 89.38      AAAA C
ATOM   2491  CD   GLU   259      58.364  25.032  55.057  1.00 97.77      AAAA C
ATOM   2492  OE1  GLU   259      58.080  24.088  55.838  1.00101.45      AAAA O
ATOM   2493  OE2  GLU   259      57.598  26.002  54.837  1.00 94.58      AAAA O
ATOM   2494  C    GLU   259      62.117  28.078  54.083  1.00 85.43      AAAA C
ATOM   2495  O    GLU   259      62.059  29.009  54.903  1.00 88.01      AAAA O
ATOM   2496  N    SER   260      62.298  28.338  52.799  1.00 84.66      AAAA N
ATOM   2498  CA   SER   260      62.725  29.625  52.254  1.00 84.03      AAAA C
ATOM   2499  CB   SER   260      63.753  29.269  51.173  1.00 87.24      AAAA C
ATOM   2500  OG   SER   260      63.306  29.419  49.835  1.00 93.65      AAAA O
ATOM   2502  C    SER   260      61.558  30.466  51.789  1.00 80.84      AAAA C
ATOM   2503  O    SER   260      61.496  30.889  50.635  1.00 81.31      AAAA O
ATOM   2504  N    SER   261      60.617  30.785  52.685  1.00 78.56      AAAA N
ATOM   2506  CA   SER   261      59.423  31.540  52.308  1.00 72.13      AAAA C
ATOM   2507  CB   SER   261      58.179  31.297  53.170  1.00 67.30      AAAA C
ATOM   2508  OG   SER   261      57.436  30.334  52.451  1.00 74.74      AAAA O
ATOM   2510  C    SER   261      59.683  33.032  52.318  1.00 66.90      AAAA C
ATOM   2511  O    SER   261      60.048  33.588  53.334  1.00 63.24      AAAA O
ATOM   2512  N    ASP   262      59.364  33.659  51.204  1.00 65.30      AAAA N
ATOM   2514  CA   ASP   262      59.358  35.071  50.915  1.00 58.55      AAAA C
ATOM   2515  CB   ASP   262      59.268  35.285  49.400  1.00 64.85      AAAA C
ATOM   2516  CG   ASP   262      59.389  36.713  48.931  1.00 76.42      AAAA C
ATOM   2517  OD1  ASP   262      59.473  37.708  49.701  1.00 79.81      AAAA O
ATOM   2518  OD2  ASP   262      59.404  36.873  47.671  1.00 80.46      AAAA O
ATOM   2519  C    ASP   262      58.121  35.706  51.529  1.00 56.88      AAAA C
ATOM   2520  O    ASP   262      57.851  36.918  51.510  1.00 52.48      AAAA O
ATOM   2521  N    SER   263      57.259  34.849  52.118  1.00 53.43      AAAA N
ATOM   2523  CA   SER   263      56.047  35.352  52.734  1.00 52.84      AAAA C
ATOM   2524  CB   SER   263      55.020  34.245  52.885  1.00 46.60      AAAA C
ATOM   2525  OG   SER   263      55.149  33.348  51.791  1.00 66.80      AAAA O
ATOM   2527  C    SER   263      56.310  35.965  54.117  1.00 49.52      AAAA C
ATOM   2528  O    SER   263      57.396  35.737  54.709  1.00 42.33      AAAA O
ATOM   2529  N    GLU   264      55.320  36.783  54.540  1.00 38.93      AAAA N
ATOM   2531  CA   GLU   264      55.362  37.222  55.921  1.00 36.70      AAAA C
ATOM   2532  CB   GLU   264      54.359  38.337  56.208  1.00 43.71      AAAA C
ATOM   2533  CG   GLU   264      54.575  39.482  55.218  1.00 37.74      AAAA C
ATOM   2534  CD   GLU   264      55.374  40.632  55.793  1.00 34.36      AAAA C
ATOM   2535  OE1  GLU   264      55.493  40.600  57.034  1.00 41.55      AAAA O
ATOM   2536  OE2  GLU   264      55.832  41.576  55.146  1.00 39.60      AAAA O
ATOM   2537  C    GLU   264      55.098  36.056  56.827  1.00 35.84      AAAA C
ATOM   2538  O    GLU   264      54.368  35.151  56.355  1.00 39.60      AAAA O
ATOM   2539  N    GLY   265      55.801  35.938  57.962  1.00 35.64      AAAA N
ATOM   2541  CA   GLY   265      55.671  34.690  58.727  1.00 40.30      AAAA C
ATOM   2542  C    GLY   265      54.622  34.716  59.829  1.00 39.51      AAAA C
ATOM   2543  O    GLY   265      53.951  35.699  60.135  1.00 37.20      AAAA O
ATOM   2544  N    PHE   266      54.537  33.569  60.516  1.00 35.75      AAAA N
ATOM   2546  CA   PHE   266      53.637  33.434  61.625  1.00 33.70      AAAA C
ATOM   2547  CB   PHE   266      53.924  32.155  62.386  1.00 28.20      AAAA C
ATOM   2548  CG   PHE   266      53.356  30.958  61.671  1.00 37.07      AAAA C
ATOM   2549  CD1  PHE   266      53.760  30.618  60.377  1.00 34.72      AAAA C
ATOM   2550  CD2  PHE   266      52.383  30.185  62.313  1.00 25.65      AAAA C
ATOM   2551  CE1  PHE   266      53.225  29.506  59.760  1.00 37.72      AAAA C
ATOM   2552  CE2  PHE   266      51.879  29.094  61.672  1.00 24.63      AAAA C
ATOM   2553  CZ   PHE   266      52.260  28.708  60.402  1.00 23.58      AAAA C
ATOM   2554  C    PHE   266      53.571  34.567  62.608  1.00 35.82      AAAA C
ATOM   2555  O    PHE   266      54.446  35.372  62.879  1.00 39.23      AAAA O
ATOM   2556  N    VAL   267      52.360  34.763  63.161  1.00 37.10      AAAA N
ATOM   2558  CA   VAL   267      52.118  35.812  64.113  1.00 36.09      AAAA C
ATOM   2559  CB   VAL   267      51.315  36.974  63.567  1.00 39.01      AAAA C
ATOM   2560  CG1  VAL   267      51.626  37.600  62.230  1.00 31.10      AAAA C
ATOM   2561  CG2  VAL   267      49.890  36.400  63.570  1.00 36.88      AAAA C
ATOM   2562  C    VAL   267      51.506  35.260  65.400  1.00 33.55      AAAA C
ATOM   2563  O    VAL   267      51.202  34.098  65.515  1.00 32.41      AAAA O
ATOM   2564  N    ILE   268      51.539  36.088  66.477  1.00 35.88      AAAA N
ATOM   2566  CA   ILE   268      50.867  35.573  67.681  1.00 39.79      AAAA C
ATOM   2567  CB   ILE   268      51.791  35.232  68.849  1.00 31.17      AAAA C
ATOM   2568  CG2  ILE   268      50.922  35.253  70.150  1.00 32.66      AAAA C
ATOM   2569  CG1  ILE   268      52.403  33.866  68.724  1.00 23.56      AAAA C
```

Figure 1A-26

```
ATOM   2570  CD1 ILE   268      53.421  33.546  69.806  1.00 25.93      AAAA C
ATOM   2571  C   ILE   268      49.806  36.608  68.060  1.00 42.44      AAAA C
ATOM   2572  O   ILE   268      50.116  37.767  68.327  1.00 39.99      AAAA O
ATOM   2573  N   HIS   269      48.528  36.292  67.864  1.00 44.26      AAAA N
ATOM   2575  CA  HIS   269      47.491  37.320  68.173  1.00 44.28      AAAA C
ATOM   2576  CB  HIS   269      46.885  37.876  66.901  1.00 45.48      AAAA C
ATOM   2577  CG  HIS   269      45.915  38.986  67.079  1.00 54.33      AAAA C
ATOM   2578  CD2 HIS   269      44.551  39.014  67.096  1.00 46.61      AAAA C
ATOM   2579  ND1 HIS   269      46.356  40.280  67.307  1.00 51.86      AAAA N
ATOM   2581  CE1 HIS   269      45.282  41.057  67.437  1.00 55.17      AAAA C
ATOM   2582  NE2 HIS   269      44.175  40.324  67.309  1.00 46.97      AAAA N
ATOM   2584  C   HIS   269      46.423  36.740  69.074  1.00 45.54      AAAA C
ATOM   2585  O   HIS   269      46.076  35.552  69.027  1.00 42.94      AAAA O
ATOM   2586  N   ASP   270      45.952  37.526  70.059  1.00 49.82      AAAA N
ATOM   2588  CA  ASP   270      44.948  37.025  71.001  1.00 48.03      AAAA C
ATOM   2589  CB  ASP   270      43.573  37.014  70.338  1.00 63.63      AAAA C
ATOM   2590  CG  ASP   270      42.919  38.393  70.294  1.00 80.82      AAAA C
ATOM   2591  OD1 ASP   270      41.737  38.379  69.835  1.00 90.92      AAAA O
ATOM   2592  OD2 ASP   270      43.407  39.494  70.652  1.00 86.49      AAAA O
ATOM   2593  C   ASP   270      45.226  35.667  71.594  1.00 44.66      AAAA C
ATOM   2594  O   ASP   270      44.357  34.782  71.576  1.00 45.54      AAAA O
ATOM   2595  N   GLY   271      46.477  35.379  71.924  1.00 41.63      AAAA N
ATOM   2597  CA  GLY   271      46.839  34.117  72.506  1.00 37.20      AAAA C
ATOM   2598  C   GLY   271      46.818  32.998  71.537  1.00 39.15      AAAA C
ATOM   2599  O   GLY   271      46.775  31.865  72.039  1.00 46.56      AAAA O
ATOM   2600  N   GLU   272      47.015  33.292  70.251  1.00 41.49      AAAA N
ATOM   2602  CA  GLU   272      47.108  32.092  69.371  1.00 43.56      AAAA C
ATOM   2603  CB  GLU   272      45.752  31.737  68.876  1.00 37.58      AAAA C
ATOM   2604  CG  GLU   272      45.778  30.600  67.839  1.00 45.30      AAAA C
ATOM   2605  CD  GLU   272      44.413  30.528  67.149  1.00 36.92      AAAA C
ATOM   2606  OE1 GLU   272      43.545  31.345  67.533  1.00 48.41      AAAA O
ATOM   2607  OE2 GLU   272      44.223  29.696  66.286  1.00 44.10      AAAA O
ATOM   2608  C   GLU   272      48.211  32.324  68.335  1.00 40.32      AAAA C
ATOM   2609  O   GLU   272      48.445  33.447  67.896  1.00 37.04      AAAA O
ATOM   2610  N   CYS   273      48.942  31.237  68.138  1.00 38.83      AAAA N
ATOM   2612  CA  CYS   273      50.046  31.187  67.188  1.00 40.27      AAAA C
ATOM   2613  C   CYS   273      49.321  30.810  65.883  1.00 42.16      AAAA C
ATOM   2614  O   CYS   273      48.713  29.712  65.831  1.00 40.86      AAAA O
ATOM   2615  CB  CYS   273      51.098  30.148  67.529  1.00 40.21      AAAA C
ATOM   2616  SG  CYS   273      52.337  29.825  66.260  1.00 39.79      AAAA S
ATOM   2617  N   MET   274      49.373  31.749  64.933  1.00 33.70      AAAA N
ATOM   2619  CA  MET   274      48.586  31.351  63.720  1.00 36.68      AAAA C
ATOM   2620  CB  MET   274      47.136  31.861  63.847  1.00 29.11      AAAA C
ATOM   2621  CG  MET   274      46.923  33.379  63.691  1.00 36.51      AAAA C
ATOM   2622  SD  MET   274      45.477  33.921  64.677  1.00 40.00      AAAA S
ATOM   2623  CE  MET   274      45.659  35.658  64.754  1.00 22.47      AAAA C
ATOM   2624  C   MET   274      49.426  31.900  62.608  1.00 39.35      AAAA C
ATOM   2625  O   MET   274      50.167  32.880  62.672  1.00 41.00      AAAA O
ATOM   2626  N   GLN   275      49.378  31.353  61.428  1.00 42.55      AAAA N
ATOM   2628  CA  GLN   275      50.041  31.834  60.232  1.00 37.69      AAAA C
ATOM   2629  CB  GLN   275      49.618  30.765  59.242  1.00 34.01      AAAA C
ATOM   2630  CG  GLN   275      49.329  31.274  57.864  1.00 56.40      AAAA C
ATOM   2631  CD  GLN   275      49.275  30.190  56.812  1.00 66.46      AAAA C
ATOM   2632  OE1 GLN   275      49.941  29.151  56.910  1.00 67.24      AAAA O
ATOM   2633  NE2 GLN   275      48.451  30.436  55.799  1.00 78.29      AAAA N
ATOM   2636  C   GLN   275      49.721  33.195  59.720  1.00 35.41      AAAA C
ATOM   2637  O   GLN   275      50.526  33.831  59.064  1.00 35.95      AAAA O
ATOM   2638  N   GLU   276      48.566  33.754  60.056  1.00 41.70      AAAA N
ATOM   2640  CA  GLU   276      48.222  35.080  59.571  1.00 43.96      AAAA C
ATOM   2641  CB  GLU   276      47.387  34.884  58.245  1.00 42.40      AAAA C
ATOM   2642  CG  GLU   276      47.154  36.269  57.650  1.00 53.84      AAAA C
ATOM   2643  CD  GLU   276      48.359  37.198  57.460  1.00 61.37      AAAA C
ATOM   2644  OE1 GLU   276      49.356  36.595  56.943  1.00 67.32      AAAA O
ATOM   2645  OE2 GLU   276      48.242  38.411  57.811  1.00 45.10      AAAA O
ATOM   2646  C   GLU   276      47.444  35.935  60.540  1.00 39.74      AAAA C
ATOM   2647  O   GLU   276      46.760  35.449  61.444  1.00 45.06      AAAA O
ATOM   2648  N   CYS   277      47.495  37.235  60.500  1.00 38.69      AAAA N
ATOM   2650  CA  CYS   277      46.718  38.089  61.332  1.00 46.11      AAAA C
ATOM   2651  C   CYS   277      45.205  37.938  60.994  1.00 52.70      AAAA C
ATOM   2652  O   CYS   277      44.760  37.511  59.936  1.00 49.43      AAAA O
ATOM   2653  CB  CYS   277      47.039  39.537  61.111  1.00 45.56      AAAA C
ATOM   2654  SG  CYS   277      48.629  40.083  61.645  1.00 52.86      AAAA S
ATOM   2655  N   PRO   278      44.380  38.261  61.993  1.00 54.63      AAAA N
ATOM   2656  CD  PRO   278      44.824  38.778  63.311  1.00 57.20      AAAA C
ATOM   2657  CA  PRO   278      42.946  38.185  61.899  1.00 55.82      AAAA C
ATOM   2658  CB  PRO   278      42.445  38.635  63.267  1.00 55.61      AAAA C
ATOM   2659  CG  PRO   278      43.605  38.670  64.153  1.00 55.58      AAAA C
ATOM   2660  C   PRO   278      42.487  39.116  60.781  1.00 52.55      AAAA C
```

Figure 1A-27

```
ATOM   2661  O    PRO  278      43.083  40.195  60.631  1.00 48.76      AAAA O
ATOM   2662  N    SER  279      41.370  38.845  60.143  1.00 49.35      AAAA N
ATOM   2664  CA   SER  279      40.815  39.720  59.140  1.00 52.03      AAAA C
ATOM   2665  CB   SER  279      39.280  39.572  58.975  1.00 47.62      AAAA C
ATOM   2666  OG   SER  279      39.320  38.778  57.785  1.00 68.16      AAAA O
ATOM   2668  C    SER  279      41.003  41.209  59.173  1.00 55.40      AAAA C
ATOM   2669  O    SER  279      41.225  41.740  58.059  1.00 55.40      AAAA O
ATOM   2670  N    GLY  280      40.775  41.962  60.247  1.00 55.32      AAAA N
ATOM   2672  CA   GLY  280      40.968  43.406  59.868  1.00 48.58      AAAA C
ATOM   2673  C    GLY  280      42.248  43.890  60.479  1.00 55.98      AAAA C
ATOM   2674  O    GLY  280      42.249  45.097  60.772  1.00 56.00      AAAA O
ATOM   2675  N    PHE  281      43.213  42.983  60.742  1.00 55.42      AAAA N
ATOM   2677  CA   PHE  281      44.506  43.411  61.262  1.00 52.94      AAAA C
ATOM   2678  CB   PHE  281      44.938  42.644  62.523  1.00 61.20      AAAA C
ATOM   2679  CG   PHE  281      43.958  42.792  63.637  1.00 53.66      AAAA C
ATOM   2680  CD1  PHE  281      44.142  43.702  64.630  1.00 60.47      AAAA C
ATOM   2681  CD2  PHE  281      42.839  41.992  63.712  1.00 60.98      AAAA C
ATOM   2682  CE1  PHE  281      43.272  43.901  65.678  1.00 64.71      AAAA C
ATOM   2683  CE2  PHE  281      41.931  42.162  64.756  1.00 63.18      AAAA C
ATOM   2684  CZ   PHE  281      42.141  43.115  65.744  1.00 58.88      AAAA C
ATOM   2685  C    PHE  281      45.630  43.217  60.240  1.00 48.00      AAAA C
ATOM   2686  O    PHE  281      45.738  42.395  59.327  1.00 38.84      AAAA O
ATOM   2687  N    ILE  282      46.670  43.990  60.557  1.00 49.55      AAAA N
ATOM   2689  CA   ILE  282      47.907  43.984  59.748  1.00 45.00      AAAA C
ATOM   2690  CB   ILE  282      47.945  45.188  58.799  1.00 30.25      AAAA C
ATOM   2691  CG2  ILE  282      48.041  46.494  59.507  1.00 24.60      AAAA C
ATOM   2692  CG1  ILE  282      49.092  45.022  57.795  1.00 38.71      AAAA C
ATOM   2693  CD1  ILE  282      49.194  46.043  56.669  1.00 33.38      AAAA C
ATOM   2694  C    ILE  282      49.081  43.889  60.673  1.00 44.30      AAAA C
ATOM   2695  O    ILE  282      49.078  44.447  61.759  1.00 48.49      AAAA O
ATOM   2696  N    ARG  283      50.126  43.153  60.298  1.00 48.68      AAAA N
ATOM   2698  CA   ARG  283      51.396  43.094  61.048  1.00 39.30      AAAA C
ATOM   2699  CB   ARG  283      52.300  42.200  60.286  1.00 41.10      AAAA C
ATOM   2700  CG   ARG  283      52.295  40.696  60.515  1.00 29.19      AAAA C
ATOM   2701  CD   ARG  283      53.078  39.986  59.451  1.00 29.85      AAAA C
ATOM   2702  NE   ARG  283      52.823  38.545  59.404  1.00 29.39      AAAA N
ATOM   2704  CZ   ARG  283      51.862  38.024  58.646  1.00 37.61      AAAA C
ATOM   2705  NH1  ARG  283      51.065  38.846  57.944  1.00 31.41      AAAA N
ATOM   2708  NH2  ARG  283      51.651  36.722  58.596  1.00 31.97      AAAA N
ATOM   2711  C    ARG  283      51.945  44.498  61.190  1.00 42.27      AAAA C
ATOM   2712  O    ARG  283      51.931  45.228  60.173  1.00 43.42      AAAA O
ATOM   2713  N    ASN  284      52.362  44.886  62.422  1.00 39.49      AAAA N
ATOM   2715  CA   ASN  284      52.733  46.311  62.574  1.00 42.07      AAAA C
ATOM   2721  C    ASN  284      54.078  46.656  61.929  1.00 41.64      AAAA C
ATOM   2722  O    ASN  284      54.431  47.798  61.742  1.00 39.01      AAAA O
ATOM   2716  CB   ASN  284      52.734  46.760  64.032  1.00 37.33      AAAA C
ATOM   2717  CG   ASN  284      53.917  46.028  64.611  1.00 50.21      AAAA C
ATOM   2718  OD1  ASN  284      54.609  45.104  64.192  1.00 44.30      AAAA O
ATOM   2719  ND2  ASN  284      54.323  46.432  65.842  1.00 42.46      AAAA N
ATOM   2723  N    GLY  285      54.931  45.699  61.562  1.00 40.10      AAAA N
ATOM   2725  CA   GLY  285      55.971  45.815  60.593  1.00 26.91      AAAA C
ATOM   2726  C    GLY  285      56.091  44.468  59.848  1.00 33.12      AAAA C
ATOM   2727  O    GLY  285      55.584  43.331  60.187  1.00 29.51      AAAA O
ATOM   2728  N    SER  286      56.915  44.619  58.766  1.00 26.53      AAAA N
ATOM   2730  CA   SER  286      57.109  43.385  57.975  1.00 32.67      AAAA C
ATOM   2731  CB   SER  286      57.944  43.681  56.757  1.00 33.19      AAAA C
ATOM   2732  OG   SER  286      58.283  42.480  56.014  1.00 31.95      AAAA O
ATOM   2734  C    SER  286      57.750  42.310  58.836  1.00 34.57      AAAA C
ATOM   2735  O    SER  286      58.700  42.495  59.607  1.00 44.29      AAAA O
ATOM   2736  N    GLN  287      57.227  41.148  58.940  1.00 34.45      AAAA N
ATOM   2738  CA   GLN  287      57.738  40.005  59.634  1.00 35.25      AAAA C
ATOM   2739  CB   GLN  287      59.139  39.610  59.083  1.00 27.97      AAAA C
ATOM   2740  CG   GLN  287      59.037  39.234  57.664  1.00 26.61      AAAA C
ATOM   2741  CD   GLN  287      58.539  37.963  57.130  1.00 21.25      AAAA C
ATOM   2742  OE1  GLN  287      58.192  37.023  57.845  1.00 28.18      AAAA O
ATOM   2743  NE2  GLN  287      58.492  37.838  55.782  1.00 27.55      AAAA N
ATOM   2746  C    GLN  287      57.773  40.286  61.111  1.00 30.25      AAAA C
ATOM   2747  O    GLN  287      58.163  39.415  61.908  1.00 32.78      AAAA O
ATOM   2748  N    SER  288      57.021  41.217  61.624  1.00 32.49      AAAA N
ATOM   2750  CA   SER  288      56.696  41.322  63.043  1.00 28.98      AAAA C
ATOM   2751  CB   SER  288      56.024  42.675  63.313  1.00 35.79      AAAA C
ATOM   2752  OG   SER  288      55.639  42.612  64.701  1.00 36.61      AAAA O
ATOM   2754  C    SER  288      55.665  40.285  63.442  1.00 28.96      AAAA C
ATOM   2755  O    SER  288      54.993  39.776  62.553  1.00 31.16      AAAA O
ATOM   2756  N    MET  289      55.774  39.720  64.621  1.00 32.51      AAAA N
ATOM   2758  CA   MET  289      54.875  38.697  65.105  1.00 34.53      AAAA C
ATOM   2759  CB   MET  289      55.507  37.823  66.153  1.00 30.31      AAAA C
ATOM   2760  CG   MET  289      56.571  36.872  65.680  1.00 40.50      AAAA C
```

Figure 1A-28

```
ATOM   2761  SD  MET 289      56.977  35.623  66.881  1.00 31.65      AAAA S
ATOM   2762  CE  MET 289      55.745  34.315  66.508  1.00 30.47      AAAA C
ATOM   2763  C   MET 289      53.557  39.286  65.703  1.00 35.55      AAAA C
ATOM   2764  O   MET 289      52.630  38.512  66.014  1.00 38.37      AAAA O
ATOM   2765  N   TYR 290      53.380  40.565  65.742  1.00 29.54      AAAA N
ATOM   2767  CA  TYR 290      52.363  41.358  66.297  1.00 38.81      AAAA C
ATOM   2768  CB  TYR 290      52.947  42.589  67.042  1.00 36.72      AAAA C
ATOM   2769  CG  TYR 290      53.570  42.184  68.351  1.00 41.94      AAAA C
ATOM   2770  CD1 TYR 290      54.932  41.780  68.350  1.00 37.79      AAAA C
ATOM   2771  CE1 TYR 290      55.548  41.368  69.503  1.00 32.60      AAAA C
ATOM   2772  CD2 TYR 290      52.887  42.157  69.570  1.00 39.93      AAAA C
ATOM   2773  CE2 TYR 290      53.501  41.750  70.748  1.00 36.16      AAAA C
ATOM   2774  CZ  TYR 290      54.822  41.355  70.693  1.00 38.85      AAAA C
ATOM   2775  OH  TYR 290      55.581  40.923  71.751  1.00 43.41      AAAA O
ATOM   2776  C   TYR 290      51.361  41.955  65.270  1.00 45.54      AAAA C
ATOM   2778  O   TYR 290      51.733  42.520  64.227  1.00 47.10      AAAA O
ATOM   2779  N   CYS 291      50.071  41.698  65.537  1.00 44.68      AAAA N
ATOM   2781  CA  CYS 291      49.017  42.205  64.685  1.00 47.20      AAAA C
ATOM   2782  C   CYS 291      48.295  43.434  65.194  1.00 46.06      AAAA C
ATOM   2783  O   CYS 291      47.892  43.550  66.343  1.00 49.45      AAAA O
ATOM   2784  CB  CYS 291      47.973  41.103  64.483  1.00 43.44      AAAA C
ATOM   2785  SG  CYS 291      48.766  39.715  63.683  1.00 45.49      AAAA S
ATOM   2786  N   ILE 292      48.136  44.453  64.365  1.00 46.82      AAAA N
ATOM   2788  CA  ILE 292      47.399  45.651  64.755  1.00 50.64      AAAA C
ATOM   2789  CB  ILE 292      48.267  46.932  64.779  1.00 39.19      AAAA C
ATOM   2790  CG2 ILE 292      49.291  46.885  65.861  1.00 44.39      AAAA C
ATOM   2791  CG1 ILE 292      48.920  47.095  63.402  1.00 44.25      AAAA C
ATOM   2792  CD1 ILE 292      49.234  48.568  63.108  1.00 32.80      AAAA C
ATOM   2793  C   ILE 292      46.240  46.003  63.806  1.00 50.01      AAAA C
ATOM   2794  O   ILE 292      46.165  45.526  62.670  1.00 46.64      AAAA O
ATOM   2795  N   PRO 293      45.150  46.507  64.385  1.00 51.86      AAAA N
ATOM   2796  CD  PRO 293      45.009  46.804  65.839  1.00 51.05      AAAA C
ATOM   2797  CA  PRO 293      43.958  46.930  63.675  1.00 51.40      AAAA C
ATOM   2798  CB  PRO 293      43.170  47.784  64.681  1.00 49.00      AAAA C
ATOM   2799  CG  PRO 293      43.533  47.112  65.951  1.00 53.73      AAAA C
ATOM   2800  C   PRO 293      44.253  47.870  62.525  1.00 51.68      AAAA C
ATOM   2801  O   PRO 293      45.053  48.788  62.737  1.00 51.92      AAAA O
ATOM   2802  N   CYS 294      43.607  47.621  61.408  1.00 50.66      AAAA N
ATOM   2804  CA  CYS 294      43.811  48.464  60.254  1.00 57.90      AAAA C
ATOM   2805  C   CYS 294      43.219  49.848  60.345  1.00 59.59      AAAA C
ATOM   2806  O   CYS 294      43.744  50.814  59.785  1.00 60.87      AAAA O
ATOM   2807  CB  CYS 294      43.229  47.686  59.046  1.00 57.59      AAAA C
ATOM   2808  SG  CYS 294      44.408  46.460  58.563  1.00 51.12      AAAA S
ATOM   2809  N   ALA 295      42.009  50.031  60.854  1.00 65.87      AAAA N
ATOM   2811  CA  ALA 295      41.391  51.386  60.804  1.00 71.19      AAAA C
ATOM   2812  CB  ALA 295      42.311  52.459  61.393  1.00 63.82      AAAA C
ATOM   2813  C   ALA 295      40.971  51.770  59.370  1.00 69.17      AAAA C
ATOM   2814  O   ALA 295      41.421  52.717  58.762  1.00 64.70      AAAA O
ATOM   2815  N   GLY 296      40.153  50.920  58.775  1.00 71.30      AAAA N
ATOM   2817  CA  GLY 296      39.640  51.049  57.416  1.00 72.66      AAAA C
ATOM   2818  C   GLY 296      39.895  49.686  56.769  1.00 74.20      AAAA C
ATOM   2819  O   GLY 296      40.408  48.819  57.490  1.00 75.04      AAAA O
ATOM   2820  N   PRO 297      39.561  49.540  55.497  1.00 71.88      AAAA N
ATOM   2821  CD  PRO 297      38.928  50.561  54.637  1.00 72.15      AAAA C
ATOM   2822  CA  PRO 297      39.958  48.344  54.777  1.00 68.23      AAAA C
ATOM   2823  CB  PRO 297      39.488  48.603  53.369  1.00 72.57      AAAA C
ATOM   2824  CG  PRO 297      38.470  49.687  53.490  1.00 74.04      AAAA C
ATOM   2825  C   PRO 297      41.480  48.306  54.860  1.00 65.78      AAAA C
ATOM   2826  O   PRO 297      42.147  49.323  54.997  1.00 62.72      AAAA O
ATOM   2827  N   CYS 298      42.039  47.135  55.073  1.00 63.85      AAAA N
ATOM   2829  CA  CYS 298      43.464  46.953  55.248  1.00 54.47      AAAA C
ATOM   2830  C   CYS 298      44.109  47.303  53.908  1.00 54.56      AAAA C
ATOM   2831  O   CYS 298      43.621  47.030  52.820  1.00 54.83      AAAA O
ATOM   2832  CB  CYS 298      43.665  45.544  55.669  1.00 47.65      AAAA C
ATOM   2833  SG  CYS 298      43.501  45.115  57.371  1.00 46.12      AAAA S
ATOM   2834  N   PRO 299      45.310  47.876  53.967  1.00 49.83      AAAA N
ATOM   2835  CD  PRO 299      46.087  48.168  55.194  1.00 48.14      AAAA C
ATOM   2836  CA  PRO 299      46.055  48.212  52.787  1.00 43.67      AAAA C
ATOM   2837  CB  PRO 299      47.267  48.965  53.281  1.00 44.08      AAAA C
ATOM   2838  CG  PRO 299      47.454  48.361  54.628  1.00 51.38      AAAA C
ATOM   2839  C   PRO 299      46.341  46.969  52.010  1.00 38.86      AAAA C
ATOM   2840  O   PRO 299      46.372  45.874  52.546  1.00 42.85      AAAA O
ATOM   2841  N   LYS 300      46.310  47.073  50.712  1.00 38.30      AAAA N
ATOM   2843  CA  LYS 300      46.484  45.958  49.812  1.00 42.62      AAAA C
ATOM   2844  CB  LYS 300      45.176  45.226  49.595  1.00 34.28      AAAA C
ATOM   2845  CG  LYS 300      45.346  43.901  48.920  1.00 41.45      AAAA C
ATOM   2846  CD  LYS 300      44.013  43.413  48.378  1.00 48.31      AAAA C
ATOM   2847  CE  LYS 300      44.388  42.027  47.787  1.00 48.57      AAAA C
```

Figure 1A-29

```
ATOM   2848  NZ   LYS  300     43.662  42.031  46.478  1.00 63.70      AAAA N
ATOM   2852  C    LYS  300     46.964  46.479  48.432  1.00 48.72      AAAA C
ATOM   2853  O    LYS  300     46.413  47.383  47.776  1.00 46.09      AAAA O
ATOM   2854  N    VAL  301     48.150  45.984  48.054  1.00 48.15      AAAA N
ATOM   2856  CA   VAL  301     48.802  46.462  46.871  1.00 44.52      AAAA C
ATOM   2857  CB   VAL  301     50.292  46.729  47.074  1.00 51.52      AAAA C
ATOM   2858  CG1  VAL  301     51.008  47.200  45.796  1.00 43.07      AAAA C
ATOM   2859  CG2  VAL  301     50.495  47.794  48.141  1.00 49.50      AAAA C
ATOM   2860  C    VAL  301     48.526  45.410  45.837  1.00 44.59      AAAA C
ATOM   2861  O    VAL  301     48.913  44.291  46.060  1.00 43.70      AAAA O
ATOM   2862  N    CYS  302     47.910  45.816  44.718  1.00 47.98      AAAA N
ATOM   2864  CA   CYS  302     47.645  44.735  43.739  1.00 55.19      AAAA C
ATOM   2865  C    CYS  302     48.594  44.968  42.583  1.00 57.64      AAAA C
ATOM   2866  O    CYS  302     48.852  46.152  42.343  1.00 60.23      AAAA O
ATOM   2867  CB   CYS  302     46.186  44.630  43.330  1.00 68.30      AAAA C
ATOM   2868  SG   CYS  302     45.070  44.360  44.751  1.00 70.31      AAAA S
ATOM   2869  N    GLU  303     49.183  43.921  42.075  1.00 58.15      AAAA N
ATOM   2871  CA   GLU  303     50.174  43.932  41.034  1.00 62.85      AAAA C
ATOM   2872  CB   GLU  303     51.603  44.006  41.595  1.00 67.85      AAAA C
ATOM   2873  CG   GLU  303     51.760  43.487  43.014  0.01 67.46      AAAA C
ATOM   2874  CD   GLU  303     51.989  41.992  43.097  0.01 67.94      AAAA C
ATOM   2875  OE1  GLU  303     53.011  41.514  42.561  0.01 67.67      AAAA O
ATOM   2876  OE2  GLU  303     51.147  41.290  43.697  0.01 67.65      AAAA O
ATOM   2877  C    GLU  303     50.096  42.662  40.194  1.00 64.12      AAAA C
ATOM   2878  O    GLU  303     50.162  41.562  40.708  1.00 65.08      AAAA O
ATOM   2879  N    GLU  304     49.867  42.794  38.904  1.00 67.37      AAAA N
ATOM   2881  CA   GLU  304     49.672  41.583  38.094  1.00 74.63      AAAA C
ATOM   2882  CB   GLU  304     48.285  41.596  37.458  1.00 71.71      AAAA C
ATOM   2883  CG   GLU  304     47.339  42.663  38.031  1.00 84.54      AAAA C
ATOM   2884  CD   GLU  304     45.930  42.152  38.185  1.00 87.56      AAAA C
ATOM   2885  OE1  GLU  304     45.438  41.571  37.179  1.00 89.13      AAAA O
ATOM   2886  OE2  GLU  304     45.249  42.269  39.233  1.00 93.19      AAAA O
ATOM   2887  C    GLU  304     50.866  41.307  37.190  1.00 76.10      AAAA C
ATOM   2888  O    GLU  304     51.911  41.962  37.217  1.00 74.78      AAAA O
ATOM   2889  N    GLU  305     50.899  40.126  36.568  1.00 77.31      AAAA N
ATOM   2891  CA   GLU  305     51.932  39.656  35.674  1.00 75.90      AAAA C
ATOM   2892  CB   GLU  305     51.467  38.380  34.970  1.00 79.95      AAAA C
ATOM   2893  CG   GLU  305     52.307  37.937  33.807  1.00 87.28      AAAA C
ATOM   2894  CD   GLU  305     51.758  36.891  32.886  0.01 83.39      AAAA C
ATOM   2895  OE1  GLU  305     50.762  36.234  33.252  0.01 83.66      AAAA O
ATOM   2896  OE2  GLU  305     52.310  36.700  31.780  0.01 83.73      AAAA O
ATOM   2897  C    GLU  305     52.276  40.737  34.666  1.00 75.97      AAAA C
ATOM   2898  O    GLU  305     53.381  41.268  34.613  1.00 76.54      AAAA O
ATOM   2899  N    LYS  306     51.291  41.181  33.888  1.00 78.22      AAAA N
ATOM   2901  CA   LYS  306     51.479  42.328  33.004  1.00 75.99      AAAA C
ATOM   2902  CB   LYS  306     50.467  42.253  31.855  1.00 79.78      AAAA C
ATOM   2903  CG   LYS  306     51.208  42.227  30.527  1.00 94.52      AAAA C
ATOM   2904  CD   LYS  306     50.313  42.191  29.314  1.00 92.78      AAAA C
ATOM   2905  CE   LYS  306     50.740  43.227  28.261  1.00 97.10      AAAA C
ATOM   2906  NZ   LYS  306     50.938  44.554  28.929  1.00 84.87      AAAA N
ATOM   2910  C    LYS  306     51.381  43.669  33.703  1.00 73.85      AAAA C
ATOM   2911  O    LYS  306     50.703  43.862  34.718  1.00 76.08      AAAA O
ATOM   2912  N    LYS  307     52.000  44.700  33.180  1.00 71.15      AAAA N
ATOM   2914  CA   LYS  307     51.934  46.053  33.692  1.00 69.45      AAAA C
ATOM   2915  CB   LYS  307     53.022  46.903  33.008  1.00 79.64      AAAA C
ATOM   2916  CG   LYS  307     54.419  46.837  33.564  1.00 78.88      AAAA C
ATOM   2917  CD   LYS  307     55.257  48.084  33.374  1.00 85.84      AAAA C
ATOM   2918  CE   LYS  307     55.708  48.215  31.924  1.00 97.07      AAAA C
ATOM   2919  NZ   LYS  307     54.649  48.840  31.067  1.00 97.80      AAAA N
ATOM   2923  C    LYS  307     50.562  46.716  33.525  1.00 67.97      AAAA C
ATOM   2924  O    LYS  307     50.010  47.369  34.431  1.00 64.46      AAAA O
ATOM   2925  N    THR  308     49.979  46.661  32.323  1.00 65.84      AAAA N
ATOM   2927  CA   THR  308     48.709  47.319  32.091  1.00 64.56      AAAA C
ATOM   2928  CB   THR  308     48.714  47.977  30.711  1.00 59.91      AAAA C
ATOM   2929  OG1  THR  308     49.834  48.843  30.577  1.00 61.97      AAAA O
ATOM   2931  CG2  THR  308     47.392  48.742  30.561  1.00 63.64      AAAA C
ATOM   2932  C    THR  308     47.514  46.379  32.234  1.00 61.82      AAAA C
ATOM   2933  O    THR  308     47.412  45.415  31.477  1.00 62.05      AAAA O
ATOM   2934  N    LYS  309     46.675  46.719  33.211  1.00 55.66      AAAA N
ATOM   2936  CA   LYS  309     45.456  45.926  33.445  1.00 54.67      AAAA C
ATOM   2937  CB   LYS  309     45.043  45.880  34.904  1.00 56.82      AAAA C
ATOM   2938  CG   LYS  309     43.601  45.541  35.223  1.00 57.50      AAAA C
ATOM   2939  CD   LYS  309     43.390  44.039  35.086  1.00 59.50      AAAA C
ATOM   2940  CE   LYS  309     42.703  43.448  36.324  1.00 57.31      AAAA C
ATOM   2941  NZ   LYS  309     42.758  41.954  36.236  1.00 57.22      AAAA N
ATOM   2945  C    LYS  309     44.391  46.570  32.548  1.00 51.21      AAAA C
ATOM   2946  O    LYS  309     44.074  47.763  32.680  1.00 47.23      AAAA O
ATOM   2947  N    THR  310     43.895  45.772  31.610  1.00 47.67      AAAA N
```

Figure 1A-30

```
ATOM   2949  CA   THR   310      42.862  46.328  30.733  1.00 51.89           AAAA C
ATOM   2950  CB   THR   310      43.161  46.015  29.266  1.00 54.81           AAAA C
ATOM   2951  OG1  THR   310      41.909  45.710  28.635  1.00 66.29           AAAA O
ATOM   2953  CG2  THR   310      44.032  44.791  29.139  1.00 55.18           AAAA C
ATOM   2954  C    THR   310      41.468  45.841  31.117  1.00 51.15           AAAA C
ATOM   2955  O    THR   310      41.162  44.680  30.991  1.00 49.27           AAAA O
ATOM   2956  N    ILE   311      40.684  46.706  31.732  1.00 50.18           AAAA N
ATOM   2958  CA   ILE   311      39.363  46.453  32.276  1.00 48.67           AAAA C
ATOM   2959  CB   ILE   311      39.120  47.396  33.462  1.00 49.27           AAAA C
ATOM   2960  CG2  ILE   311      37.655  47.596  33.799  1.00 50.72           AAAA C
ATOM   2961  CG1  ILE   311      39.896  46.930  34.699  1.00 41.34           AAAA C
ATOM   2962  CD1  ILE   311      39.847  48.073  35.739  1.00 52.22           AAAA C
ATOM   2963  C    ILE   311      38.334  46.729  31.186  1.00 45.37           AAAA C
ATOM   2964  O    ILE   311      38.132  47.875  30.758  1.00 37.14           AAAA O
ATOM   2965  N    ASP   312      37.871  45.678  30.524  1.00 50.10           AAAA N
ATOM   2967  CA   ASP   312      36.991  45.842  29.377  1.00 56.35           AAAA C
ATOM   2968  CB   ASP   312      37.546  45.152  28.128  1.00 59.45           AAAA C
ATOM   2969  CG   ASP   312      37.761  43.671  28.382  1.00 65.64           AAAA C
ATOM   2970  OD1  ASP   312      38.525  43.034  27.636  1.00 72.60           AAAA O
ATOM   2971  OD2  ASP   312      37.154  43.176  29.348  1.00 66.86           AAAA O
ATOM   2972  C    ASP   312      35.589  45.337  29.693  1.00 59.39           AAAA C
ATOM   2973  O    ASP   312      34.729  45.007  28.867  1.00 61.00           AAAA O
ATOM   2974  N    SER   313      35.278  45.290  30.976  1.00 61.17           AAAA N
ATOM   2976  CA   SER   313      34.053  44.683  31.459  1.00 55.73           AAAA C
ATOM   2977  CB   SER   313      34.121  43.201  31.083  1.00 48.22           AAAA C
ATOM   2978  OG   SER   313      34.373  42.514  32.282  1.00 57.89           AAAA O
ATOM   2980  C    SER   313      33.998  44.818  32.941  1.00 57.87           AAAA C
ATOM   2981  O    SER   313      34.802  45.506  33.537  1.00 66.47           AAAA O
ATOM   2982  N    VAL   314      33.001  44.205  33.545  1.00 64.35           AAAA N
ATOM   2984  CA   VAL   314      32.849  44.305  35.016  1.00 64.39           AAAA C
ATOM   2985  CB   VAL   314      31.360  44.340  35.343  1.00 69.57           AAAA C
ATOM   2986  CG1  VAL   314      31.024  43.693  36.681  1.00 65.60           AAAA C
ATOM   2987  CG2  VAL   314      30.927  45.823  35.319  1.00 65.27           AAAA C
ATOM   2988  C    VAL   314      33.492  43.088  35.638  1.00 62.65           AAAA C
ATOM   2989  O    VAL   314      34.029  43.141  36.704  1.00 63.92           AAAA O
ATOM   2990  N    THR   315      33.468  42.011  34.878  1.00 61.82           AAAA N
ATOM   2992  CA   THR   315      34.029  40.752  35.284  1.00 63.44           AAAA C
ATOM   2993  CB   THR   315      33.618  39.628  34.314  1.00 65.54           AAAA C
ATOM   2994  OG1  THR   315      32.403  40.004  33.634  1.00 74.05           AAAA O
ATOM   2996  CG2  THR   315      33.339  38.366  35.104  1.00 64.86           AAAA C
ATOM   2997  C    THR   315      35.541  40.871  35.323  1.00 65.62           AAAA C
ATOM   2998  O    THR   315      36.217  40.339  36.206  1.00 66.41           AAAA O
ATOM   2999  N    SER   316      36.071  41.593  34.332  1.00 63.28           AAAA N
ATOM   3001  CA   SER   316      37.500  41.793  34.215  1.00 58.72           AAAA C
ATOM   3002  CB   SER   316      37.785  42.537  32.900  1.00 52.20           AAAA C
ATOM   3003  OG   SER   316      37.298  43.859  32.933  1.00 48.04           AAAA O
ATOM   3005  C    SER   316      38.077  42.573  35.387  1.00 58.91           AAAA C
ATOM   3006  O    SER   316      39.293  42.522  35.520  1.00 59.86           AAAA O
ATOM   3007  N    ALA   317      37.310  43.362  36.111  1.00 55.86           AAAA N
ATOM   3009  CA   ALA   317      37.750  44.184  37.191  1.00 57.17           AAAA C
ATOM   3010  CB   ALA   317      36.833  45.409  37.269  1.00 54.23           AAAA C
ATOM   3011  C    ALA   317      37.689  43.487  38.538  1.00 62.05           AAAA C
ATOM   3012  O    ALA   317      37.702  44.128  39.599  1.00 60.30           AAAA O
ATOM   3013  N    GLN   318      37.361  42.205  38.523  1.00 67.91           AAAA N
ATOM   3015  CA   GLN   318      37.185  41.380  39.713  1.00 70.72           AAAA C
ATOM   3016  CB   GLN   318      36.857  39.956  39.293  1.00 74.48           AAAA C
ATOM   3017  CG   GLN   318      36.624  38.947  40.383  1.00 89.82           AAAA C
ATOM   3018  CD   GLN   318      35.265  39.080  41.048  1.00 92.69           AAAA C
ATOM   3019  OE1  GLN   318      34.256  38.807  40.391  1.00 98.57           AAAA O
ATOM   3020  NE2  GLN   318      35.356  39.509  42.308  1.00 92.51           AAAA N
ATOM   3023  C    GLN   318      38.380  41.413  40.653  1.00 72.63           AAAA C
ATOM   3024  O    GLN   318      38.294  41.855  41.804  1.00 68.92           AAAA O
ATOM   3025  N    MET   319      39.562  41.062  40.153  1.00 75.18           AAAA N
ATOM   3027  CA   MET   319      40.846  41.175  40.826  1.00 71.85           AAAA C
ATOM   3028  CB   MET   319      41.950  40.960  39.772  1.00 82.00           AAAA C
ATOM   3029  CG   MET   319      41.740  39.644  39.050  1.00 91.16           AAAA C
ATOM   3030  SD   MET   319      43.123  38.482  39.185  1.00106.72           AAAA S
ATOM   3031  CE   MET   319      42.486  37.105  38.231  1.00 97.56           AAAA C
ATOM   3032  C    MET   319      41.118  42.509  41.471  1.00 67.68           AAAA C
ATOM   3033  O    MET   319      41.597  42.541  42.612  1.00 69.73           AAAA O
ATOM   3034  N    LEU   320      40.740  43.639  40.887  1.00 62.95           AAAA N
ATOM   3036  CA   LEU   320      40.907  44.938  41.531  1.00 62.31           AAAA C
ATOM   3037  CB   LEU   320      40.440  46.085  40.623  1.00 54.93           AAAA C
ATOM   3038  CG   LEU   320      41.091  46.163  39.238  1.00 53.48           AAAA C
ATOM   3039  CD1  LEU   320      41.005  47.552  38.692  1.00 51.31           AAAA C
ATOM   3040  CD2  LEU   320      42.557  45.709  39.403  1.00 58.43           AAAA C
ATOM   3041  C    LEU   320      40.209  45.008  42.881  1.00 60.30           AAAA C
ATOM   3042  O    LEU   320      40.344  45.969  43.661  1.00 58.72           AAAA O
```

Figure 1A-31

```
ATOM   3043  N   GLN   321      39.267  44.106  43.112  1.00 59.62      AAAA N
ATOM   3045  CA  GLN   321      38.482  44.128  44.343  1.00 63.50      AAAA C
ATOM   3046  CB  GLN   321      37.373  43.089  44.250  1.00 62.52      AAAA C
ATOM   3047  CG  GLN   321      36.611  42.854  45.522  1.00 56.83      AAAA C
ATOM   3048  CD  GLN   321      35.337  42.064  45.291  1.00 68.77      AAAA C
ATOM   3049  OE1 GLN   321      35.362  40.969  44.718  1.00 70.37      AAAA O
ATOM   3050  NE2 GLN   321      34.218  42.632  45.764  1.00 63.77      AAAA N
ATOM   3053  C   GLN   321      39.367  44.030  45.594  1.00 60.97      AAAA C
ATOM   3054  O   GLN   321      40.262  43.196  45.782  1.00 57.29      AAAA O
ATOM   3055  N   GLY   322      39.092  44.928  46.546  1.00 57.62      AAAA N
ATOM   3057  CA  GLY   322      39.855  44.928  47.790  1.00 60.63      AAAA C
ATOM   3058  C   GLY   322      41.126  45.773  47.812  1.00 61.78      AAAA C
ATOM   3059  O   GLY   322      41.584  46.198  48.889  1.00 60.16      AAAA O
ATOM   3060  N   CYS   323      41.719  46.124  46.676  1.00 60.03      AAAA N
ATOM   3062  CA  CYS   323      42.938  46.845  46.528  1.00 54.20      AAAA C
ATOM   3063  C   CYS   323      42.924  48.307  46.910  1.00 53.48      AAAA C
ATOM   3064  O   CYS   323      42.105  49.148  46.503  1.00 56.43      AAAA O
ATOM   3065  CB  CYS   323      43.458  46.822  45.086  1.00 53.33      AAAA C
ATOM   3066  SG  CYS   323      43.325  45.222  44.248  1.00 66.22      AAAA S
ATOM   3067  N   THR   324      43.994  48.718  47.580  1.00 49.83      AAAA N
ATOM   3069  CA  THR   324      44.164  50.161  47.811  1.00 52.29      AAAA C
ATOM   3070  CB  THR   324      44.623  50.324  49.264  1.00 52.84      AAAA C
ATOM   3071  OG1 THR   324      45.245  49.087  49.634  1.00 59.82      AAAA O
ATOM   3073  CG2 THR   324      43.432  50.517  50.193  1.00 60.00      AAAA C
ATOM   3074  C   THR   324      45.154  50.802  46.844  1.00 48.91      AAAA C
ATOM   3075  O   THR   324      45.277  52.016  46.710  1.00 46.90      AAAA O
ATOM   3076  N   ILE   325      46.021  49.963  46.254  1.00 46.87      AAAA N
ATOM   3078  CA  ILE   325      47.114  50.511  45.445  1.00 45.10      AAAA C
ATOM   3079  CB  ILE   325      48.473  50.577  46.183  1.00 43.60      AAAA C
ATOM   3080  CG2 ILE   325      49.586  50.905  45.163  1.00 47.47      AAAA C
ATOM   3081  CG1 ILE   325      48.394  51.623  47.294  1.00 34.03      AAAA C
ATOM   3082  CD1 ILE   325      49.595  52.010  48.028  1.00 41.94      AAAA C
ATOM   3083  C   ILE   325      47.265  49.642  44.229  1.00 42.88      AAAA C
ATOM   3084  O   ILE   325      47.406  48.429  44.469  1.00 42.99      AAAA O
ATOM   3085  N   PHE   326      47.170  50.238  43.042  1.00 41.19      AAAA N
ATOM   3087  CA  PHE   326      47.312  49.334  41.880  1.00 42.88      AAAA C
ATOM   3088  CB  PHE   326      46.166  49.437  40.877  1.00 39.15      AAAA C
ATOM   3089  CG  PHE   326      46.403  48.474  39.738  1.00 38.03      AAAA C
ATOM   3090  CD1 PHE   326      46.186  47.125  39.951  1.00 39.68      AAAA C
ATOM   3091  CD2 PHE   326      46.917  48.892  38.525  1.00 37.31      AAAA C
ATOM   3092  CE1 PHE   326      46.447  46.139  39.023  1.00 36.52      AAAA C
ATOM   3093  CE2 PHE   326      47.136  47.919  37.551  1.00 45.74      AAAA C
ATOM   3094  CZ  PHE   326      46.924  46.570  37.787  1.00 39.92      AAAA C
ATOM   3095  C   PHE   326      48.682  49.673  41.280  1.00 48.78      AAAA C
ATOM   3096  O   PHE   326      49.024  50.826  40.966  1.00 51.39      AAAA O
ATOM   3097  N   LYS   327      49.623  48.751  41.379  1.00 50.22      AAAA N
ATOM   3099  CA  LYS   327      50.964  48.963  40.831  1.00 51.49      AAAA C
ATOM   3100  CB  LYS   327      52.050  48.091  41.519  1.00 58.64      AAAA C
ATOM   3101  CG  LYS   327      53.254  48.897  41.981  1.00 59.15      AAAA C
ATOM   3102  CD  LYS   327      54.528  48.257  41.617  1.00 63.49      AAAA C
ATOM   3103  CE  LYS   327      55.400  48.951  40.592  1.00 68.12      AAAA C
ATOM   3104  NZ  LYS   327      56.260  47.889  39.938  1.00 71.97      AAAA N
ATOM   3108  C   LYS   327      50.895  48.464  39.391  1.00 45.70      AAAA C
ATOM   3109  O   LYS   327      50.901  47.245  39.127  1.00 49.55      AAAA O
ATOM   3110  N   GLY   328      50.760  49.397  38.502  1.00 39.68      AAAA N
ATOM   3112  CA  GLY   328      50.647  49.038  37.080  1.00 39.44      AAAA C
ATOM   3113  C   GLY   328      49.845  50.161  36.427  1.00 39.49      AAAA C
ATOM   3114  O   GLY   328      49.858  51.307  36.881  1.00 31.92      AAAA O
ATOM   3115  N   ASN   329      49.286  49.813  35.289  1.00 41.47      AAAA N
ATOM   3117  CA  ASN   329      48.467  50.750  34.543  1.00 45.72      AAAA C
ATOM   3118  CB  ASN   329      49.185  50.942  33.211  1.00 42.50      AAAA C
ATOM   3119  CG  ASN   329      50.624  51.426  33.357  1.00 42.26      AAAA C
ATOM   3120  OD1 ASN   329      50.954  52.331  34.156  1.00 34.77      AAAA O
ATOM   3121  ND2 ASN   329      51.425  50.769  32.530  1.00 30.62      AAAA N
ATOM   3124  C   ASN   329      47.038  50.207  34.357  1.00 50.37      AAAA C
ATOM   3125  O   ASN   329      46.736  49.015  34.119  1.00 50.17      AAAA O
ATOM   3126  N   LEU   330      46.090  51.143  34.413  1.00 47.13      AAAA N
ATOM   3128  CA  LEU   330      44.691  50.860  34.151  1.00 42.53      AAAA C
ATOM   3129  CB  LEU   330      43.751  51.530  35.153  1.00 42.84      AAAA C
ATOM   3130  CG  LEU   330      43.768  50.995  36.598  1.00 38.65      AAAA C
ATOM   3131  CD1 LEU   330      42.864  51.924  37.417  1.00 38.12      AAAA C
ATOM   3132  CD2 LEU   330      43.283  49.565  36.669  1.00 38.74      AAAA C
ATOM   3133  C   LEU   330      44.352  51.377  32.758  1.00 39.10      AAAA C
ATOM   3134  O   LEU   330      44.509  52.545  32.460  1.00 40.71      AAAA O
ATOM   3135  N   LEU   331      43.933  50.516  31.904  1.00 36.10      AAAA N
ATOM   3137  CA  LEU   331      43.367  50.869  30.625  1.00 43.10      AAAA C
ATOM   3138  CB  LEU   331      43.958  49.894  29.585  1.00 42.29      AAAA C
ATOM   3139  CG  LEU   331      43.301  49.960  28.221  1.00 40.89      AAAA C
```

Figure 1A-32

```
ATOM   3140  CD1 LEU   331      43.501  51.319  27.627  1.00 46.64      AAAA C
ATOM   3141  CD2 LEU   331      43.844  48.834  27.367  1.00 48.76      AAAA C
ATOM   3142  C   LEU   331      41.872  50.568  30.705  1.00 41.12      AAAA C
ATOM   3143  O   LEU   331      41.562  49.365  30.779  1.00 40.08      AAAA O
ATOM   3144  N   ILE   332      41.029  51.566  30.862  1.00 41.13      AAAA N
ATOM   3146  CA  ILE   332      39.606  51.241  31.044  1.00 36.90      AAAA C
ATOM   3147  CB  ILE   332      38.885  52.085  32.076  1.00 34.77      AAAA C
ATOM   3148  CG2 ILE   332      37.413  51.612  32.195  1.00 34.66      AAAA C
ATOM   3149  CG1 ILE   332      39.550  51.895  33.452  1.00 33.64      AAAA C
ATOM   3150  CD1 ILE   332      39.479  53.152  34.337  1.00 48.21      AAAA C
ATOM   3151  C   ILE   332      38.959  51.367  29.688  1.00 34.03      AAAA C
ATOM   3152  O   ILE   332      38.867  52.489  29.200  1.00 35.89      AAAA O
ATOM   3153  N   ASN   333      38.569  50.273  29.094  1.00 35.25      AAAA N
ATOM   3155  CA  ASN   333      38.014  50.283  27.737  1.00 40.34      AAAA C
ATOM   3156  CB  ASN   333      38.960  49.499  26.797  1.00 50.50      AAAA C
ATOM   3157  CG  ASN   333      38.668  49.493  25.310  1.00 59.29      AAAA C
ATOM   3158  OD1 ASN   333      37.845  48.711  24.784  1.00 64.54      AAAA O
ATOM   3159  ND2 ASN   333      39.290  50.350  24.467  1.00 45.83      AAAA N
ATOM   3162  C   ASN   333      36.666  49.581  27.755  1.00 47.63      AAAA C
ATOM   3163  O   ASN   333      36.462  48.409  27.398  1.00 44.40      AAAA O
ATOM   3164  N   ILE   334      35.644  50.213  28.315  1.00 54.13      AAAA N
ATOM   3166  CA  ILE   334      34.332  49.537  28.460  1.00 59.07      AAAA C
ATOM   3167  CB  ILE   334      33.788  49.826  29.876  1.00 61.98      AAAA C
ATOM   3168  CG2 ILE   334      32.362  49.355  30.047  1.00 54.04      AAAA C
ATOM   3169  CG1 ILE   334      34.737  49.224  30.915  1.00 60.43      AAAA C
ATOM   3170  CD1 ILE   334      34.346  49.687  32.317  1.00 68.57      AAAA C
ATOM   3171  C   ILE   334      33.271  50.032  27.476  1.00 59.45      AAAA C
ATOM   3172  O   ILE   334      32.726  51.136  27.635  1.00 56.22      AAAA O
ATOM   3173  N   ARG   335      32.919  49.181  26.550  1.00 59.69      AAAA N
ATOM   3175  CA  ARG   335      31.910  49.567  25.573  1.00 73.93      AAAA C
ATOM   3176  CB  ARG   335      32.262  48.903  24.240  1.00 74.44      AAAA C
ATOM   3177  CG  ARG   335      33.729  48.932  23.918  1.00 82.97      AAAA C
ATOM   3178  CD  ARG   335      34.102  49.289  22.500  1.00 86.49      AAAA C
ATOM   3179  NE  ARG   335      34.361  48.040  21.777  1.00 89.83      AAAA N
ATOM   3181  CZ  ARG   335      34.011  47.838  20.496  1.00 93.67      AAAA C
ATOM   3182  NH1 ARG   335      33.409  48.852  19.843  1.00 87.24      AAAA N
ATOM   3185  NH2 ARG   335      34.256  46.674  19.877  1.00 75.31      AAAA N
ATOM   3188  C   ARG   335      30.492  49.233  26.021  1.00 81.52      AAAA C
ATOM   3189  O   ARG   335      29.664  50.115  26.239  1.00 84.11      AAAA O
ATOM   3190  N   ALA   336      30.208  47.953  26.234  1.00 87.51      AAAA N
ATOM   3192  CA  ALA   336      28.878  47.484  26.601  1.00 92.40      AAAA C
ATOM   3193  CB  ALA   336      28.835  45.980  26.633  1.00 94.03      AAAA C
ATOM   3194  C   ALA   336      28.479  48.058  27.953  1.00 96.61      AAAA C
ATOM   3195  O   ALA   336      29.316  48.019  28.855  1.00 96.96      AAAA O
ATOM   3196  N   GLY   337      27.298  48.685  28.039  1.00 99.74      AAAA N
ATOM   3198  CA  GLY   337      26.986  49.385  29.272  1.00103.11      AAAA C
ATOM   3199  C   GLY   337      25.568  49.303  29.763  1.00105.51      AAAA C
ATOM   3200  O   GLY   337      24.801  50.267  29.596  1.00106.64      AAAA O
ATOM   3201  N   ASN   338      25.243  48.146  30.346  1.00105.41      AAAA N
ATOM   3203  CA  ASN   338      23.886  48.017  30.908  1.00106.92      AAAA C
ATOM   3204  CB  ASN   338      23.714  46.689  31.624  1.00109.14      AAAA C
ATOM   3205  CG  ASN   338      24.403  45.544  30.928  1.00112.30      AAAA C
ATOM   3206  OD1 ASN   338      25.598  45.595  30.625  1.00117.94      AAAA O
ATOM   3207  ND2 ASN   338      23.604  44.508  30.683  1.00113.72      AAAA N
ATOM   3210  C   ASN   338      23.790  49.160  31.931  1.00105.84      AAAA C
ATOM   3211  O   ASN   338      23.544  50.345  31.739  1.00103.97      AAAA O
ATOM   3212  N   ASN   339      24.290  48.762  33.099  1.00105.47      AAAA N
ATOM   3214  CA  ASN   339      24.529  49.740  34.159  1.00107.10      AAAA C
ATOM   3215  CB  ASN   339      23.252  49.915  34.945  1.00109.15      AAAA C
ATOM   3216  CG  ASN   339      22.777  51.351  35.003  0.01107.52      AAAA C
ATOM   3217  OD1 ASN   339      22.715  51.931  36.088  0.01107.49      AAAA O
ATOM   3218  ND2 ASN   339      22.441  51.932  33.859  0.01107.46      AAAA N
ATOM   3221  C   ASN   339      25.697  49.237  35.007  1.00106.33      AAAA C
ATOM   3222  O   ASN   339      25.520  48.390  35.886  1.00108.82      AAAA O
ATOM   3223  N   ILE   340      26.897  49.527  34.510  1.00101.36      AAAA N
ATOM   3225  CA  ILE   340      28.136  49.101  35.138  1.00 97.43      AAAA C
ATOM   3226  CB  ILE   340      29.040  48.354  34.151  1.00 93.63      AAAA C
ATOM   3227  CG2 ILE   340      28.194  47.252  33.489  1.00 99.38      AAAA C
ATOM   3228  CG1 ILE   340      29.726  49.158  33.070  1.00 85.50      AAAA C
ATOM   3229  CD1 ILE   340      28.897  49.634  31.915  1.00 92.53      AAAA C
ATOM   3230  C   ILE   340      28.783  50.357  35.706  1.00 95.32      AAAA C
ATOM   3231  O   ILE   340      29.472  51.099  34.997  1.00 97.86      AAAA O
ATOM   3232  N   ALA   341      28.409  50.739  36.915  1.00 89.89      AAAA N
ATOM   3234  CA  ALA   341      28.892  52.008  37.450  1.00 88.45      AAAA C
ATOM   3235  CB  ALA   341      28.068  53.201  37.006  1.00 84.56      AAAA C
ATOM   3236  C   ALA   341      28.786  51.968  38.970  1.00 85.37      AAAA C
ATOM   3237  O   ALA   341      28.910  52.935  39.690  1.00 86.09      AAAA O
ATOM   3238  N   SER   342      28.204  50.877  39.386  1.00 84.24      AAAA N
```

Figure 1A-33

```
ATOM   3240  CA   SER  342      27.910  50.601  40.780  1.00 82.05       AAAA C
ATOM   3241  CB   SER  342      26.426  50.667  41.112  1.00 85.51       AAAA C
ATOM   3242  OG   SER  342      26.145  51.271  42.361  1.00 86.02       AAAA O
ATOM   3244  C    SER  342      28.487  49.196  40.965  1.00 76.62       AAAA C
ATOM   3245  O    SER  342      29.119  48.966  41.964  1.00 71.76       AAAA O
ATOM   3246  N    GLU  343      28.373  48.409  39.905  1.00 76.23       AAAA N
ATOM   3248  CA   GLU  343      29.001  47.109  39.820  1.00 74.59       AAAA C
ATOM   3249  CB   GLU  343      28.595  46.300  38.616  1.00 78.62       AAAA C
ATOM   3250  CG   GLU  343      27.118  46.105  38.316  1.00 85.33       AAAA C
ATOM   3251  CD   GLU  343      26.898  45.121  37.169  1.00 92.76       AAAA C
ATOM   3252  OE1  GLU  343      27.209  43.911  37.310  1.00 96.41       AAAA O
ATOM   3253  OE2  GLU  343      26.423  45.517  36.082  1.00 98.55       AAAA O
ATOM   3254  C    GLU  343      30.525  47.319  39.804  1.00 77.75       AAAA C
ATOM   3255  O    GLU  343      31.273  46.787  40.637  1.00 75.73       AAAA O
ATOM   3256  N    LEU  344      31.022  48.237  38.966  1.00 75.65       AAAA N
ATOM   3258  CA   LEU  344      32.415  48.596  38.839  1.00 72.36       AAAA C
ATOM   3259  CB   LEU  344      32.760  49.697  37.808  1.00 64.33       AAAA C
ATOM   3260  CG   LEU  344      32.687  49.397  36.311  1.00 50.12       AAAA C
ATOM   3261  CD1  LEU  344      33.224  50.577  35.519  1.00 57.00       AAAA C
ATOM   3262  CD2  LEU  344      33.401  48.127  35.905  1.00 51.62       AAAA C
ATOM   3263  C    LEU  344      32.963  49.130  40.174  1.00 69.74       AAAA C
ATOM   3264  O    LEU  344      34.079  48.739  40.551  1.00 69.12       AAAA O
ATOM   3265  N    GLU  345      32.166  49.959  40.822  1.00 63.10       AAAA N
ATOM   3267  CA   GLU  345      32.555  50.591  42.061  1.00 65.42       AAAA C
ATOM   3268  CB   GLU  345      31.592  51.714  42.478  1.00 55.59       AAAA C
ATOM   3269  CG   GLU  345      32.267  52.607  43.486  1.00 68.78       AAAA C
ATOM   3270  CD   GLU  345      31.324  53.374  44.376  1.00 81.31       AAAA C
ATOM   3271  OE1  GLU  345      30.614  54.320  43.976  1.00 85.60       AAAA O
ATOM   3272  OE2  GLU  345      31.237  53.078  45.595  1.00 88.79       AAAA O
ATOM   3273  C    GLU  345      32.706  49.652  43.255  1.00 63.31       AAAA C
ATOM   3274  O    GLU  345      33.501  49.913  44.134  1.00 60.06       AAAA O
ATOM   3275  N    ASN  346      32.151  48.462  43.202  1.00 62.25       AAAA N
ATOM   3277  CA   ASN  346      32.285  47.403  44.173  1.00 63.82       AAAA C
ATOM   3278  CB   ASN  346      31.024  46.498  44.095  1.00 61.66       AAAA C
ATOM   3279  CG   ASN  346      31.110  45.292  45.006  1.00 58.73       AAAA C
ATOM   3280  OD1  ASN  346      31.188  45.352  46.224  1.00 69.11       AAAA O
ATOM   3281  ND2  ASN  346      31.155  44.092  44.444  1.00 51.10       AAAA N
ATOM   3284  C    ASN  346      33.532  46.580  43.870  1.00 63.71       AAAA C
ATOM   3285  O    ASN  346      33.636  45.336  43.905  1.00 65.65       AAAA O
ATOM   3286  N    PHE  347      34.419  47.173  43.066  1.00 63.23       AAAA N
ATOM   3288  CA   PHE  347      35.540  46.411  42.506  1.00 61.39       AAAA C
ATOM   3289  CB   PHE  347      35.123  45.854  41.170  1.00 61.38       AAAA C
ATOM   3290  CG   PHE  347      34.457  44.534  41.142  1.00 65.57       AAAA C
ATOM   3291  CD1  PHE  347      33.090  44.438  40.982  1.00 75.25       AAAA C
ATOM   3292  CD2  PHE  347      35.148  43.351  41.267  1.00 77.15       AAAA C
ATOM   3293  CE1  PHE  347      32.425  43.224  40.951  1.00 75.55       AAAA C
ATOM   3294  CE2  PHE  347      34.512  42.130  41.249  1.00 72.86       AAAA C
ATOM   3295  CZ   PHE  347      33.152  42.051  41.095  1.00 72.74       AAAA C
ATOM   3296  C    PHE  347      36.712  47.375  42.440  1.00 57.70       AAAA C
ATOM   3297  O    PHE  347      37.770  46.820  42.354  1.00 59.92       AAAA O
ATOM   3298  N    MET  348      36.482  48.676  42.319  1.00 50.56       AAAA N
ATOM   3300  CA   MET  348      37.500  49.630  41.964  1.00 42.86       AAAA C
ATOM   3301  CB   MET  348      37.402  50.096  40.493  1.00 31.72       AAAA C
ATOM   3302  CG   MET  348      37.426  48.933  39.471  1.00 33.42       AAAA C
ATOM   3303  SD   MET  348      37.566  49.448  37.732  1.00 44.79       AAAA S
ATOM   3304  CE   MET  348      38.408  50.999  37.791  1.00 59.57       AAAA C
ATOM   3305  C    MET  348      37.368  50.831  42.867  1.00 45.88       AAAA C
ATOM   3306  O    MET  348      38.210  51.772  42.901  1.00 43.33       AAAA O
ATOM   3307  N    GLY  349      36.296  50.783  43.683  1.00 45.30       AAAA N
ATOM   3309  CA   GLY  349      35.998  51.965  44.504  1.00 49.19       AAAA C
ATOM   3310  C    GLY  349      36.980  52.189  45.620  1.00 52.77       AAAA C
ATOM   3311  O    GLY  349      37.033  53.299  46.156  1.00 53.43       AAAA O
ATOM   3312  N    LEU  350      37.791  51.159  45.925  1.00 56.17       AAAA N
ATOM   3314  CA   LEU  350      38.735  51.256  47.021  1.00 58.04       AAAA C
ATOM   3315  CB   LEU  350      38.873  49.949  47.834  1.00 49.00       AAAA C
ATOM   3316  CG   LEU  350      37.871  50.020  49.031  1.00 50.79       AAAA C
ATOM   3317  CD1  LEU  350      37.705  48.680  49.700  1.00 52.92       AAAA C
ATOM   3318  CD2  LEU  350      38.247  51.106  50.038  1.00 56.11       AAAA C
ATOM   3319  C    LEU  350      40.144  51.727  46.685  1.00 61.34       AAAA C
ATOM   3320  O    LEU  350      40.931  51.962  47.618  1.00 63.52       AAAA O
ATOM   3321  N    ILE  351      40.446  51.677  45.372  1.00 57.89       AAAA N
ATOM   3323  CA   ILE  351      41.729  52.088  44.873  1.00 48.69       AAAA C
ATOM   3324  CB   ILE  351      41.814  51.912  43.352  1.00 48.19       AAAA C
ATOM   3325  CG2  ILE  351      43.121  52.416  42.757  1.00 40.01       AAAA C
ATOM   3326  CG1  ILE  351      41.535  50.418  43.058  1.00 36.87       AAAA C
ATOM   3327  CD1  ILE  351      41.172  50.351  41.581  1.00 36.46       AAAA C
ATOM   3328  C    ILE  351      42.031  53.533  45.178  1.00 46.80       AAAA C
ATOM   3329  O    ILE  351      41.367  54.358  44.626  1.00 42.87       AAAA O
```

Figure 1A-34

```
ATOM   3330  N    GLU  352      43.002  53.866  46.015  1.00 50.61      AAAA N
ATOM   3332  CA   GLU  352      43.381  55.241  46.248  1.00 51.20      AAAA C
ATOM   3333  CB   GLU  352      43.907  55.353  47.678  1.00 52.12      AAAA C
ATOM   3334  CG   GLU  352      42.912  55.769  48.735  1.00 65.55      AAAA C
ATOM   3335  CD   GLU  352      43.034  54.834  49.947  1.00 71.49      AAAA C
ATOM   3336  OE1  GLU  352      43.881  55.244  50.765  1.00 66.09      AAAA O
ATOM   3337  OE2  GLU  352      42.330  53.799  50.009  1.00 76.07      AAAA O
ATOM   3338  C    GLU  352      44.502  55.751  45.314  1.00 47.43      AAAA C
ATOM   3339  O    GLU  352      44.798  56.951  45.182  1.00 40.38      AAAA O
ATOM   3340  N    VAL  353      45.342  54.838  44.852  1.00 43.54      AAAA N
ATOM   3342  CA   VAL  353      46.512  55.236  44.078  1.00 43.71      AAAA C
ATOM   3343  CB   VAL  353      47.759  55.540  44.911  1.00 45.01      AAAA C
ATOM   3344  CG1  VAL  353      47.766  55.261  46.387  1.00 30.84      AAAA C
ATOM   3345  CG2  VAL  353      48.988  54.844  44.310  1.00 42.55      AAAA C
ATOM   3346  C    VAL  353      46.828  54.233  42.957  1.00 41.41      AAAA C
ATOM   3347  O    VAL  353      46.843  53.003  43.172  1.00 39.19      AAAA O
ATOM   3348  N    VAL  354      47.074  54.855  41.816  1.00 36.31      AAAA N
ATOM   3350  CA   VAL  354      47.586  54.092  40.651  1.00 43.97      AAAA C
ATOM   3351  CB   VAL  354      46.725  54.390  39.407  1.00 40.86      AAAA C
ATOM   3352  CG1  VAL  354      47.347  53.896  38.123  1.00 36.72      AAAA C
ATOM   3353  CG2  VAL  354      45.293  53.849  39.678  1.00 35.35      AAAA C
ATOM   3354  C    VAL  354      49.043  54.510  40.388  1.00 44.56      AAAA C
ATOM   3355  O    VAL  354      49.366  55.718  40.288  1.00 43.32      AAAA O
ATOM   3356  N    THR  355      49.972  53.561  40.431  1.00 43.83      AAAA N
ATOM   3358  CA   THR  355      51.392  53.914  40.284  1.00 44.85      AAAA C
ATOM   3359  CB   THR  355      52.374  52.799  40.653  1.00 42.40      AAAA C
ATOM   3360  OG1  THR  355      52.273  51.744  39.695  1.00 45.30      AAAA O
ATOM   3362  CG2  THR  355      52.210  52.194  42.039  1.00 38.13      AAAA C
ATOM   3363  C    THR  355      51.746  54.339  38.851  1.00 43.84      AAAA C
ATOM   3364  O    THR  355      52.463  55.334  38.697  1.00 44.26      AAAA O
ATOM   3365  N    GLY  356      51.127  53.704  37.870  1.00 41.16      AAAA N
ATOM   3367  CA   GLY  356      51.358  54.073  36.470  1.00 37.81      AAAA C
ATOM   3368  C    GLY  356      50.505  55.204  35.955  1.00 38.07      AAAA C
ATOM   3369  O    GLY  356      50.364  56.261  36.615  1.00 34.65      AAAA O
ATOM   3370  N    TYR  357      49.910  55.004  34.800  1.00 38.47      AAAA N
ATOM   3372  CA   TYR  357      48.982  55.973  34.205  1.00 38.03      AAAA C
ATOM   3373  CB   TYR  357      49.557  56.343  32.805  1.00 31.44      AAAA C
ATOM   3374  CG   TYR  357      49.473  55.219  31.812  1.00 33.04      AAAA C
ATOM   3375  CD1  TYR  357      48.333  54.842  31.077  1.00 32.86      AAAA C
ATOM   3376  CE1  TYR  357      48.352  53.779  30.175  1.00 32.83      AAAA C
ATOM   3377  CD2  TYR  357      50.639  54.465  31.606  1.00 34.28      AAAA C
ATOM   3378  CE2  TYR  357      50.706  53.402  30.720  1.00 32.51      AAAA C
ATOM   3379  CZ   TYR  357      49.552  53.068  30.007  1.00 37.26      AAAA C
ATOM   3380  OH   TYR  357      49.726  51.997  29.166  1.00 35.85      AAAA O
ATOM   3382  C    TYR  357      47.582  55.368  34.150  1.00 38.55      AAAA C
ATOM   3383  O    TYR  357      47.458  54.127  34.088  1.00 36.11      AAAA O
ATOM   3384  N    VAL  358      46.593  56.216  33.814  1.00 40.98      AAAA N
ATOM   3386  CA   VAL  358      45.197  55.798  33.639  1.00 38.90      AAAA C
ATOM   3387  CB   VAL  358      44.211  56.502  34.610  1.00 49.15      AAAA C
ATOM   3388  CG1  VAL  358      42.815  55.883  34.484  1.00 33.12      AAAA C
ATOM   3389  CG2  VAL  358      44.748  56.437  36.043  1.00 29.20      AAAA C
ATOM   3390  C    VAL  358      44.760  56.194  32.234  1.00 35.64      AAAA C
ATOM   3391  O    VAL  358      44.792  57.358  31.888  1.00 34.58      AAAA O
ATOM   3392  N    LYS  359      44.387  55.188  31.461  1.00 36.00      AAAA N
ATOM   3394  CA   LYS  359      43.898  55.419  30.117  1.00 41.27      AAAA C
ATOM   3395  CB   LYS  359      44.845  54.707  29.174  1.00 37.40      AAAA C
ATOM   3396  CG   LYS  359      44.340  54.473  27.770  1.00 45.19      AAAA C
ATOM   3397  CD   LYS  359      45.040  55.317  26.750  1.00 43.40      AAAA C
ATOM   3398  CE   LYS  359      45.958  54.402  25.986  1.00 43.56      AAAA C
ATOM   3399  NZ   LYS  359      45.416  53.937  24.680  1.00 47.98      AAAA N
ATOM   3403  C    LYS  359      42.423  54.979  29.939  1.00 42.14      AAAA C
ATOM   3404  O    LYS  359      42.056  53.791  30.006  1.00 40.40      AAAA O
ATOM   3405  N    ILE  360      41.602  55.974  29.572  1.00 37.16      AAAA N
ATOM   3407  CA   ILE  360      40.164  55.742  29.334  1.00 40.02      AAAA C
ATOM   3408  CB   ILE  360      39.297  56.804  30.048  1.00 38.10      AAAA C
ATOM   3409  CG2  ILE  360      37.887  56.277  29.932  1.00 39.42      AAAA C
ATOM   3410  CG1  ILE  360      39.769  57.111  31.481  1.00 28.54      AAAA C
ATOM   3411  CD1  ILE  360      39.423  56.037  32.491  1.00 33.16      AAAA C
ATOM   3412  C    ILE  360      39.888  55.837  27.834  1.00 39.49      AAAA C
ATOM   3413  O    ILE  360      40.014  56.942  27.235  1.00 37.32      AAAA O
ATOM   3414  N    ARG  361      39.567  54.721  27.221  1.00 34.34      AAAA N
ATOM   3416  CA   ARG  361      39.472  54.782  25.744  1.00 41.24      AAAA C
ATOM   3417  CB   ARG  361      40.783  54.213  25.148  1.00 47.92      AAAA C
ATOM   3418  CG   ARG  361      40.805  54.203  23.646  1.00 50.39      AAAA C
ATOM   3419  CD   ARG  361      41.943  53.357  23.116  1.00 51.36      AAAA C
ATOM   3420  NE   ARG  361      41.473  51.974  23.263  1.00 50.97      AAAA N
ATOM   3422  CZ   ARG  361      42.297  50.962  23.490  1.00 55.78      AAAA C
ATOM   3423  NH1  ARG  361      43.612  51.074  23.616  1.00 51.62      AAAA N
```

| ATOM | 3426 | NH2 | ARG | 361 | 41.834 | 49.719 | 23.631 | 1.00 | 54.52 | AAAA | N |
| --- | --- | --- | --- | --- | --- | --- | --- | --- | --- | --- | --- |
| ATOM | 3429 | C | ARG | 361 | 38.382 | 53.866 | 25.246 | 1.00 | 42.06 | AAAA | C |
| ATOM | 3430 | O | ARG | 361 | 38.336 | 52.661 | 25.499 | 1.00 | 38.93 | AAAA | O |
| ATOM | 3431 | N | HIS | 362 | 37.514 | 54.342 | 24.373 | 1.00 | 46.19 | AAAA | N |
| ATOM | 3433 | CA | HIS | 362 | 36.372 | 53.555 | 23.885 | 1.00 | 49.34 | AAAA | C |
| ATOM | 3434 | CB | HIS | 362 | 37.000 | 52.300 | 23.266 | 1.00 | 40.94 | AAAA | C |
| ATOM | 3435 | CG | HIS | 362 | 37.849 | 52.610 | 22.084 | 1.00 | 42.78 | AAAA | C |
| ATOM | 3436 | CD2 | HIS | 362 | 38.049 | 53.765 | 21.411 | 1.00 | 48.32 | AAAA | C |
| ATOM | 3437 | ND1 | HIS | 362 | 38.628 | 51.676 | 21.469 | 1.00 | 43.59 | AAAA | N |
| ATOM | 3439 | CE1 | HIS | 362 | 39.256 | 52.247 | 20.465 | 1.00 | 46.01 | AAAA | C |
| ATOM | 3440 | NE2 | HIS | 362 | 38.923 | 53.515 | 20.408 | 1.00 | 49.22 | AAAA | N |
| ATOM | 3442 | C | HIS | 362 | 35.295 | 53.113 | 24.913 | 1.00 | 50.32 | AAAA | C |
| ATOM | 3443 | O | HIS | 362 | 34.686 | 52.030 | 24.795 | 1.00 | 41.31 | AAAA | O |
| ATOM | 3444 | N | SER | 363 | 35.222 | 53.875 | 26.013 | 1.00 | 46.96 | AAAA | N |
| ATOM | 3446 | CA | SER | 363 | 34.402 | 53.456 | 27.139 | 1.00 | 52.19 | AAAA | C |
| ATOM | 3447 | CB | SER | 363 | 35.231 | 53.837 | 28.400 | 1.00 | 53.73 | AAAA | C |
| ATOM | 3448 | OG | SER | 363 | 35.713 | 52.558 | 28.816 | 1.00 | 41.72 | AAAA | O |
| ATOM | 3450 | C | SER | 363 | 33.005 | 54.072 | 27.046 | 1.00 | 49.08 | AAAA | C |
| ATOM | 3451 | O | SER | 363 | 32.653 | 55.040 | 27.694 | 1.00 | 37.49 | AAAA | O |
| ATOM | 3452 | N | HIS | 364 | 32.243 | 53.577 | 26.058 | 1.00 | 52.25 | AAAA | N |
| ATOM | 3454 | CA | HIS | 364 | 30.954 | 54.173 | 25.717 | 1.00 | 53.66 | AAAA | C |
| ATOM | 3455 | C | HIS | 364 | 29.879 | 53.937 | 26.760 | 1.00 | 48.77 | AAAA | C |
| ATOM | 3456 | O | HIS | 364 | 29.297 | 54.899 | 27.280 | 1.00 | 51.44 | AAAA | O |
| ATOM | 3457 | CB | HIS | 364 | 30.485 | 53.699 | 24.348 | 1.00 | 49.83 | AAAA | C |
| ATOM | 3458 | CG | HIS | 364 | 31.493 | 54.182 | 23.338 | 1.00 | 51.51 | AAAA | C |
| ATOM | 3459 | ND1 | HIS | 364 | 31.870 | 55.502 | 23.156 | 1.00 | 44.83 | AAAA | N |
| ATOM | 3460 | CE1 | HIS | 364 | 32.798 | 55.533 | 22.214 | 1.00 | 28.57 | AAAA | C |
| ATOM | 3461 | CD2 | HIS | 364 | 32.194 | 53.393 | 22.472 | 1.00 | 38.62 | AAAA | C |
| ATOM | 3462 | NE2 | HIS | 364 | 32.992 | 54.274 | 21.810 | 1.00 | 41.44 | AAAA | N |
| ATOM | 3464 | N | ALA | 365 | 29.949 | 52.819 | 27.427 | 1.00 | 47.53 | AAAA | N |
| ATOM | 3466 | CA | ALA | 365 | 29.211 | 52.488 | 28.621 | 1.00 | 44.41 | AAAA | C |
| ATOM | 3467 | CB | ALA | 365 | 29.678 | 51.133 | 29.150 | 1.00 | 40.28 | AAAA | C |
| ATOM | 3468 | C | ALA | 365 | 29.318 | 53.473 | 29.768 | 1.00 | 44.70 | AAAA | C |
| ATOM | 3469 | O | ALA | 365 | 28.576 | 53.206 | 30.726 | 1.00 | 45.28 | AAAA | O |
| ATOM | 3470 | N | LEU | 366 | 30.158 | 54.517 | 29.762 | 1.00 | 40.80 | AAAA | N |
| ATOM | 3472 | CA | LEU | 366 | 30.415 | 55.243 | 30.968 | 1.00 | 42.21 | AAAA | C |
| ATOM | 3473 | CB | LEU | 366 | 31.885 | 55.241 | 31.350 | 1.00 | 43.78 | AAAA | C |
| ATOM | 3474 | CG | LEU | 366 | 32.740 | 54.037 | 31.667 | 1.00 | 51.52 | AAAA | C |
| ATOM | 3475 | CD1 | LEU | 366 | 34.192 | 54.373 | 32.043 | 1.00 | 51.77 | AAAA | C |
| ATOM | 3476 | CD2 | LEU | 366 | 32.118 | 53.305 | 32.834 | 1.00 | 51.17 | AAAA | C |
| ATOM | 3477 | C | LEU | 366 | 29.974 | 56.687 | 30.896 | 1.00 | 46.36 | AAAA | C |
| ATOM | 3478 | O | LEU | 366 | 30.305 | 57.248 | 29.849 | 1.00 | 48.40 | AAAA | O |
| ATOM | 3479 | N | VAL | 367 | 29.521 | 57.275 | 32.015 | 1.00 | 43.68 | AAAA | N |
| ATOM | 3481 | CA | VAL | 367 | 29.072 | 58.675 | 31.940 | 1.00 | 44.18 | AAAA | C |
| ATOM | 3482 | CB | VAL | 367 | 27.557 | 58.727 | 32.376 | 1.00 | 48.80 | AAAA | C |
| ATOM | 3483 | CG1 | VAL | 367 | 26.923 | 60.073 | 32.571 | 1.00 | 41.69 | AAAA | C |
| ATOM | 3484 | CG2 | VAL | 367 | 26.697 | 57.949 | 31.365 | 1.00 | 34.00 | AAAA | C |
| ATOM | 3485 | C | VAL | 367 | 29.923 | 59.518 | 32.845 | 1.00 | 44.90 | AAAA | C |
| ATOM | 3486 | O | VAL | 367 | 29.965 | 60.751 | 32.720 | 1.00 | 44.75 | AAAA | O |
| ATOM | 3487 | N | SER | 368 | 30.591 | 58.818 | 33.757 | 1.00 | 48.72 | AAAA | N |
| ATOM | 3489 | CA | SER | 368 | 31.487 | 59.465 | 34.742 | 1.00 | 52.70 | AAAA | C |
| ATOM | 3490 | CB | SER | 368 | 30.658 | 59.706 | 36.000 | 1.00 | 55.32 | AAAA | C |
| ATOM | 3491 | OG | SER | 368 | 31.300 | 60.298 | 37.091 | 1.00 | 64.86 | AAAA | O |
| ATOM | 3493 | C | SER | 368 | 32.590 | 58.497 | 35.179 | 1.00 | 52.76 | AAAA | C |
| ATOM | 3494 | O | SER | 368 | 32.352 | 57.299 | 34.976 | 1.00 | 48.99 | AAAA | O |
| ATOM | 3495 | N | LEU | 369 | 33.631 | 59.012 | 35.831 | 1.00 | 53.86 | AAAA | N |
| ATOM | 3497 | CA | LEU | 369 | 34.716 | 58.129 | 36.274 | 1.00 | 60.15 | AAAA | C |
| ATOM | 3498 | CB | LEU | 369 | 36.073 | 58.630 | 35.784 | 1.00 | 55.91 | AAAA | C |
| ATOM | 3499 | CG | LEU | 369 | 36.325 | 58.736 | 34.271 | 1.00 | 45.96 | AAAA | C |
| ATOM | 3500 | CD1 | LEU | 369 | 37.669 | 59.428 | 34.154 | 1.00 | 53.97 | AAAA | C |
| ATOM | 3501 | CD2 | LEU | 369 | 36.207 | 57.384 | 33.619 | 1.00 | 38.77 | AAAA | C |
| ATOM | 3502 | C | LEU | 369 | 34.645 | 58.036 | 37.811 | 1.00 | 62.52 | AAAA | C |
| ATOM | 3503 | O | LEU | 369 | 35.569 | 57.700 | 38.595 | 1.00 | 59.33 | AAAA | O |
| ATOM | 3504 | N | SER | 370 | 33.437 | 58.401 | 38.285 | 1.00 | 56.26 | AAAA | N |
| ATOM | 3506 | CA | SER | 370 | 33.089 | 58.431 | 39.690 | 1.00 | 53.88 | AAAA | C |
| ATOM | 3507 | CB | SER | 370 | 31.673 | 59.052 | 39.816 | 1.00 | 57.50 | AAAA | C |
| ATOM | 3508 | OG | SER | 370 | 30.771 | 58.061 | 39.261 | 1.00 | 69.12 | AAAA | O |
| ATOM | 3510 | C | SER | 370 | 33.060 | 57.085 | 40.412 | 1.00 | 47.97 | AAAA | C |
| ATOM | 3511 | O | SER | 370 | 33.228 | 56.943 | 41.596 | 1.00 | 41.93 | AAAA | O |
| ATOM | 3512 | N | PHE | 371 | 32.967 | 55.936 | 39.792 | 1.00 | 45.48 | AAAA | N |
| ATOM | 3514 | CA | PHE | 371 | 33.223 | 54.643 | 40.356 | 1.00 | 46.29 | AAAA | C |
| ATOM | 3515 | CB | PHE | 371 | 32.952 | 53.596 | 39.287 | 1.00 | 43.53 | AAAA | C |
| ATOM | 3516 | CG | PHE | 371 | 33.724 | 53.629 | 38.012 | 1.00 | 56.45 | AAAA | C |
| ATOM | 3517 | CD1 | PHE | 371 | 34.805 | 52.807 | 37.764 | 1.00 | 58.95 | AAAA | C |
| ATOM | 3518 | CD2 | PHE | 371 | 33.371 | 54.515 | 37.004 | 1.00 | 53.92 | AAAA | C |
| ATOM | 3519 | CE1 | PHE | 371 | 35.498 | 52.842 | 36.570 | 1.00 | 59.50 | AAAA | C |
| ATOM | 3520 | CE2 | PHE | 371 | 34.048 | 54.546 | 35.817 | 1.00 | 56.49 | AAAA | C |
| ATOM | 3521 | CZ | PHE | 371 | 35.119 | 53.716 | 35.579 | 1.00 | 56.39 | AAAA | C |

Figure 1A-36

```
ATOM   3522  C   PHE   371      34.654  54.467  40.895  1.00 54.84      AAAA C
ATOM   3523  O   PHE   371      35.005  53.592  41.728  1.00 52.23      AAAA O
ATOM   3524  N   LEU   372      35.633  55.305  40.510  1.00 50.17      AAAA N
ATOM   3526  CA  LEU   372      36.928  55.395  41.109  1.00 46.25      AAAA C
ATOM   3527  CB  LEU   372      38.171  55.812  40.276  1.00 44.82      AAAA C
ATOM   3528  CG  LEU   372      38.411  54.800  39.114  1.00 36.78      AAAA C
ATOM   3529  CD1 LEU   372      38.853  55.643  37.934  1.00 45.04      AAAA C
ATOM   3530  CD2 LEU   372      39.260  53.657  39.565  1.00 35.55      AAAA C
ATOM   3531  C   LEU   372      36.715  56.392  42.243  1.00 42.26      AAAA C
ATOM   3532  O   LEU   372      37.224  57.507  42.364  1.00 38.37      AAAA O
ATOM   3533  N   LYS   373      35.970  55.862  43.192  1.00 47.06      AAAA N
ATOM   3535  CA  LYS   373      35.527  56.509  44.415  1.00 50.19      AAAA C
ATOM   3536  CB  LYS   373      34.546  55.521  45.077  1.00 56.74      AAAA C
ATOM   3537  CG  LYS   373      33.645  56.162  46.119  1.00 59.64      AAAA C
ATOM   3538  CD  LYS   373      32.529  56.955  45.441  0.01 60.17      AAAA C
ATOM   3539  CE  LYS   373      31.674  57.687  46.460  0.01 60.45      AAAA C
ATOM   3540  NZ  LYS   373      31.083  58.933  45.899  0.01 60.38      AAAA N
ATOM   3544  C   LYS   373      36.646  56.863  45.366  1.00 49.72      AAAA C
ATOM   3545  O   LYS   373      36.636  57.960  45.907  1.00 42.42      AAAA O
ATOM   3546  N   ASN   374      37.657  55.986  45.513  1.00 54.43      AAAA N
ATOM   3548  CA  ASN   374      38.765  56.352  46.410  1.00 59.92      AAAA C
ATOM   3549  CB  ASN   374      39.080  55.154  47.314  1.00 63.16      AAAA C
ATOM   3550  CG  ASN   374      38.009  54.778  48.396  1.00 64.53      AAAA C
ATOM   3551  OD1 ASN   374      37.892  53.972  49.096  1.00 66.40      AAAA O
ATOM   3552  ND2 ASN   374      37.160  55.965  48.578  1.00 52.88      AAAA N
ATOM   3555  C   ASN   374      40.043  56.892  45.786  1.00 62.35      AAAA C
ATOM   3556  O   ASN   374      41.031  57.223  46.479  1.00 63.08      AAAA O
ATOM   3557  N   LEU   375      40.091  56.893  44.438  1.00 58.34      AAAA N
ATOM   3559  CA  LEU   375      41.305  57.374  43.795  1.00 54.73      AAAA C
ATOM   3560  CB  LEU   375      41.099  57.359  42.288  1.00 56.41      AAAA C
ATOM   3561  CG  LEU   375      42.396  57.422  41.459  1.00 54.12      AAAA C
ATOM   3562  CD1 LEU   375      43.135  56.112  41.689  1.00 37.88      AAAA C
ATOM   3563  CD2 LEU   375      42.030  57.796  40.041  1.00 40.97      AAAA C
ATOM   3564  C   LEU   375      41.712  58.754  44.245  1.00 52.37      AAAA C
ATOM   3565  O   LEU   375      41.151  59.777  43.877  1.00 52.11      AAAA O
ATOM   3566  N   ARG   376      42.801  58.874  44.982  1.00 55.16      AAAA N
ATOM   3568  CA  ARG   376      43.320  60.155  45.434  1.00 55.45      AAAA C
ATOM   3569  CB  ARG   376      43.706  60.222  46.928  1.00 58.68      AAAA C
ATOM   3570  CG  ARG   376      44.288  58.907  47.415  1.00 69.10      AAAA C
ATOM   3571  CD  ARG   376      44.286  58.817  48.944  1.00 81.17      AAAA C
ATOM   3572  NE  ARG   376      45.377  57.926  49.410  1.00 84.46      AAAA N
ATOM   3574  CZ  ARG   376      46.618  58.380  49.598  1.00 85.64      AAAA C
ATOM   3575  NH1 ARG   376      46.966  59.645  49.383  1.00 81.84      AAAA N
ATOM   3578  NH2 ARG   376      47.571  57.548  50.012  1.00 94.15      AAAA N
ATOM   3581  C   ARG   376      44.556  60.544  44.633  1.00 50.16      AAAA C
ATOM   3582  O   ARG   376      44.746  61.728  44.465  1.00 44.25      AAAA O
ATOM   3583  N   LEU   377      45.375  59.578  44.219  1.00 50.99      AAAA N
ATOM   3585  CA  LEU   377      46.526  59.942  43.379  1.00 49.40      AAAA C
ATOM   3586  CB  LEU   377      47.596  60.411  44.329  1.00 64.72      AAAA C
ATOM   3587  CG  LEU   377      48.806  59.577  44.667  1.00 70.76      AAAA C
ATOM   3588  CD1 LEU   377      50.031  60.157  43.954  1.00 63.32      AAAA C
ATOM   3589  CD2 LEU   377      49.010  59.696  46.179  1.00 68.60      AAAA C
ATOM   3590  C   LEU   377      47.043  59.022  42.311  1.00 46.33      AAAA C
ATOM   3591  O   LEU   377      46.868  57.788  42.286  1.00 45.17      AAAA O
ATOM   3592  N   ILE   378      47.448  59.675  41.199  1.00 45.12      AAAA N
ATOM   3594  CA  ILE   378      48.042  58.976  40.042  1.00 49.10      AAAA C
ATOM   3595  CB  ILE   378      47.342  59.303  38.724  1.00 46.36      AAAA C
ATOM   3596  CG2 ILE   378      48.115  58.696  37.574  1.00 34.36      AAAA C
ATOM   3597  CG1 ILE   378      45.871  58.862  38.829  1.00 38.59      AAAA C
ATOM   3598  CD1 ILE   378      44.999  59.515  37.765  1.00 37.18      AAAA C
ATOM   3599  C   ILE   378      49.524  59.381  40.003  1.00 49.87      AAAA C
ATOM   3600  O   ILE   378      49.801  60.595  40.040  1.00 44.72      AAAA O
ATOM   3601  N   LEU   379      50.454  58.423  40.067  1.00 49.97      AAAA N
ATOM   3603  CA  LEU   379      51.866  58.712  40.344  1.00 48.48      AAAA C
ATOM   3604  CB  LEU   379      52.575  57.531  41.054  1.00 48.44      AAAA C
ATOM   3605  CG  LEU   379      52.234  57.363  42.554  1.00 50.28      AAAA C
ATOM   3606  CD1 LEU   379      52.926  56.187  43.217  1.00 39.89      AAAA C
ATOM   3607  CD2 LEU   379      52.616  58.625  43.300  1.00 42.89      AAAA C
ATOM   3608  C   LEU   379      52.609  59.019  39.080  1.00 50.94      AAAA C
ATOM   3609  O   LEU   379      53.576  59.788  39.139  1.00 54.23      AAAA O
ATOM   3610  N   GLY   380      52.175  58.423  37.972  1.00 48.67      AAAA N
ATOM   3612  CA  GLY   380      52.831  58.715  36.702  1.00 49.94      AAAA C
ATOM   3613  C   GLY   380      54.249  58.155  36.624  1.00 52.70      AAAA C
ATOM   3614  O   GLY   380      55.026  58.657  35.803  1.00 49.94      AAAA O
ATOM   3615  N   GLU   381      54.549  57.033  37.272  1.00 52.51      AAAA N
ATOM   3617  CA  GLU   381      55.849  56.386  37.243  1.00 52.33      AAAA C
ATOM   3618  CB  GLU   381      56.055  55.310  38.323  1.00 45.22      AAAA C
ATOM   3619  CG  GLU   381      55.402  55.779  39.636  1.00 52.91      AAAA C
```

Figure 1A-37

| | | | | | | | | | | |
|---|---|---|---|---|---|---|---|---|---|---|
|ATOM|3620|CD|GLU|381|56.050|55.192|40.873|1.00|42.11|AAAA C|
|ATOM|3621|OE1|GLU|381|56.160|53.966|40.890|1.00|40.26|AAAA O|
|ATOM|3622|OE2|GLU|381|56.379|56.014|41.754|1.00|51.32|AAAA O|
|ATOM|3623|C|GLU|381|56.078|55.784|35.858|1.00|55.86|AAAA C|
|ATOM|3624|O|GLU|381|57.216|55.652|35.345|1.00|54.61|AAAA O|
|ATOM|3625|N|GLU|382|54.980|55.449|35.157|1.00|53.56|AAAA N|
|ATOM|3627|CA|GLU|382|55.091|55.018|33.766|1.00|48.15|AAAA C|
|ATOM|3628|CB|GLU|382|55.051|53.550|33.532|1.00|35.27|AAAA C|
|ATOM|3629|CG|GLU|382|54.739|53.225|32.051|1.00|49.69|AAAA C|
|ATOM|3630|CD|GLU|382|54.676|51.719|31.807|1.00|56.45|AAAA C|
|ATOM|3631|OE1|GLU|382|55.062|50.924|32.705|1.00|61.66|AAAA O|
|ATOM|3632|OE2|GLU|382|54.264|51.201|30.745|1.00|57.69|AAAA O|
|ATOM|3633|C|GLU|382|54.006|55.732|32.973|1.00|50.84|AAAA C|
|ATOM|3634|O|GLU|382|53.097|56.282|33.598|1.00|49.44|AAAA O|
|ATOM|3635|N|GLN|383|54.347|56.256|31.780|1.00|52.25|AAAA N|
|ATOM|3637|CA|GLN|383|53.498|57.153|31.016|1.00|40.15|AAAA C|
|ATOM|3638|CB|GLN|383|53.914|58.609|31.155|1.00|28.50|AAAA C|
|ATOM|3639|CG|GLN|383|54.489|58.909|32.542|1.00|31.10|AAAA C|
|ATOM|3640|CD|GLN|383|54.950|60.301|32.752|1.00|33.19|AAAA C|
|ATOM|3641|OE1|GLN|383|55.186|60.840|31.683|1.00|40.34|AAAA O|
|ATOM|3642|NE2|GLN|383|55.043|60.943|33.934|1.00|36.30|AAAA N|
|ATOM|3645|C|GLN|383|53.426|56.744|29.563|1.00|40.45|AAAA C|
|ATOM|3646|O|GLN|383|54.131|55.858|29.139|1.00|43.45|AAAA O|
|ATOM|3647|N|LEU|384|52.375|57.195|28.860|1.00|42.54|AAAA N|
|ATOM|3649|CA|LEU|384|52.257|56.889|27.443|1.00|43.24|AAAA C|
|ATOM|3650|CB|LEU|384|50.814|57.011|26.949|1.00|43.79|AAAA C|
|ATOM|3651|CG|LEU|384|49.818|56.235|27.861|1.00|41.21|AAAA C|
|ATOM|3652|CD1|LEU|384|48.611|57.095|28.221|1.00|33.99|AAAA C|
|ATOM|3653|CD2|LEU|384|49.405|54.968|27.149|1.00|33.20|AAAA C|
|ATOM|3654|C|LEU|384|53.204|57.809|26.672|1.00|40.51|AAAA C|
|ATOM|3655|O|LEU|384|53.582|58.872|27.177|1.00|29.66|AAAA O|
|ATOM|3656|N|GLU|385|53.659|57.319|25.531|1.00|45.22|AAAA N|
|ATOM|3658|CA|GLU|385|54.410|58.116|24.570|1.00|49.98|AAAA C|
|ATOM|3659|CB|GLU|385|54.424|57.475|23.174|1.00|60.50|AAAA C|
|ATOM|3660|CG|GLU|385|55.045|56.095|23.106|1.00|68.76|AAAA C|
|ATOM|3661|CD|GLU|385|54.195|54.951|23.592|1.00|72.07|AAAA C|
|ATOM|3662|OE1|GLU|385|53.150|55.213|24.244|1.00|81.88|AAAA O|
|ATOM|3663|OE2|GLU|385|54.565|53.786|23.301|1.00|73.13|AAAA O|
|ATOM|3664|C|GLU|385|53.828|59.515|24.450|1.00|47.41|AAAA C|
|ATOM|3665|O|GLU|385|52.635|59.706|24.184|1.00|54.43|AAAA O|
|ATOM|3666|N|GLY|386|54.614|60.470|24.902|1.00|43.69|AAAA N|
|ATOM|3668|CA|GLY|386|54.181|61.870|24.897|1.00|40.34|AAAA C|
|ATOM|3669|C|GLY|386|54.286|62.449|26.308|1.00|40.65|AAAA C|
|ATOM|3670|O|GLY|386|53.930|63.615|26.491|1.00|39.75|AAAA O|
|ATOM|3671|N|ASN|387|54.441|61.537|27.272|1.00|40.75|AAAA N|
|ATOM|3673|CA|ASN|387|54.479|61.912|28.675|1.00|49.18|AAAA C|
|ATOM|3674|CB|ASN|387|55.500|63.084|28.874|1.00|44.41|AAAA C|
|ATOM|3675|CG|ASN|387|56.925|62.541|28.722|1.00|61.51|AAAA C|
|ATOM|3676|OD1|ASN|387|57.199|61.313|28.677|1.00|57.85|AAAA O|
|ATOM|3677|ND2|ASN|387|58.063|63.251|28.592|1.00|61.96|AAAA N|
|ATOM|3680|C|ASN|387|53.095|62.100|29.299|1.00|48.46|AAAA C|
|ATOM|3681|O|ASN|387|52.836|62.891|30.218|1.00|48.99|AAAA O|
|ATOM|3682|N|TYR|388|52.214|61.116|29.058|1.00|46.29|AAAA N|
|ATOM|3684|CA|TYR|388|50.846|61.199|29.540|1.00|45.09|AAAA C|
|ATOM|3685|CB|TYR|388|49.823|60.957|28.399|1.00|40.70|AAAA C|
|ATOM|3686|CG|TYR|388|49.925|62.056|27.373|1.00|42.24|AAAA C|
|ATOM|3687|CD1|TYR|388|50.343|61.854|26.064|1.00|44.38|AAAA C|
|ATOM|3688|CE1|TYR|388|50.401|62.885|25.157|1.00|35.51|AAAA C|
|ATOM|3689|CD2|TYR|388|49.625|63.356|27.709|1.00|44.67|AAAA C|
|ATOM|3690|CE2|TYR|388|49.699|64.428|26.830|1.00|38.14|AAAA C|
|ATOM|3691|CZ|TYR|388|50.087|64.148|25.555|1.00|41.27|AAAA C|
|ATOM|3692|OH|TYR|388|50.151|65.181|24.604|1.00|50.18|AAAA O|
|ATOM|3694|C|TYR|388|50.563|60.288|30.714|1.00|41.88|AAAA C|
|ATOM|3695|O|TYR|388|50.727|59.092|30.511|1.00|32.99|AAAA O|
|ATOM|3696|N|SER|389|50.020|60.917|31.763|1.00|45.42|AAAA N|
|ATOM|3698|CA|SER|389|49.591|60.131|32.931|1.00|50.13|AAAA C|
|ATOM|3699|CB|SER|389|49.798|60.894|34.261|1.00|45.57|AAAA C|
|ATOM|3700|OG|SER|389|51.185|60.899|34.504|1.00|51.11|AAAA O|
|ATOM|3702|C|SER|389|48.097|59.813|32.804|1.00|48.11|AAAA C|
|ATOM|3703|O|SER|389|47.686|58.792|33.336|1.00|49.25|AAAA O|
|ATOM|3704|N|PHE|390|47.321|60.685|32.196|1.00|42.56|AAAA N|
|ATOM|3706|CA|PHE|390|45.867|60.595|32.146|1.00|40.76|AAAA C|
|ATOM|3707|CB|PHE|390|45.241|61.581|33.139|1.00|44.80|AAAA C|
|ATOM|3708|CG|PHE|390|43.764|61.358|33.328|1.00|40.53|AAAA C|
|ATOM|3709|CD1|PHE|390|43.406|60.273|34.089|1.00|40.80|AAAA C|
|ATOM|3710|CD2|PHE|390|42.768|62.157|32.748|1.00|35.59|AAAA C|
|ATOM|3711|CE1|PHE|390|42.050|59.985|34.312|1.00|47.09|AAAA C|
|ATOM|3712|CE2|PHE|390|41.454|61.824|32.965|1.00|44.50|AAAA C|

Figure 1A-38

```
ATOM   3713  CZ   PHE   390      41.063  60.745  33.739  1.00 34.54      AAAA C
ATOM   3714  C    PHE   390      45.372  60.829  30.720  1.00 38.54      AAAA C
ATOM   3715  O    PHE   390      45.542  61.918  30.126  1.00 40.29      AAAA O
ATOM   3716  N    TYR   391      44.819  59.818  30.096  1.00 33.48      AAAA N
ATOM   3718  CA   TYR   391      44.596  59.782  28.663  1.00 38.58      AAAA C
ATOM   3719  CB   TYR   391      45.579  58.871  27.972  1.00 38.95      AAAA C
ATOM   3720  CG   TYR   391      45.760  59.006  26.503  1.00 44.54      AAAA C
ATOM   3721  CD1  TYR   391      46.822  59.815  26.052  1.00 47.14      AAAA C
ATOM   3722  CE1  TYR   391      47.057  59.993  24.722  1.00 46.03      AAAA C
ATOM   3723  CD2  TYR   391      44.927  58.390  25.584  1.00 46.94      AAAA C
ATOM   3724  CE2  TYR   391      45.157  58.560  24.242  1.00 47.45      AAAA C
ATOM   3725  CZ   TYR   391      46.207  59.350  23.830  1.00 45.84      AAAA C
ATOM   3726  OH   TYR   391      46.374  59.492  22.481  1.00 44.70      AAAA O
ATOM   3728  C    TYR   391      43.194  59.232  28.349  1.00 39.74      AAAA C
ATOM   3729  O    TYR   391      42.841  58.103  28.730  1.00 38.49      AAAA O
ATOM   3730  N    VAL   392      42.417  60.158  27.779  1.00 37.07      AAAA N
ATOM   3732  CA   VAL   392      40.958  59.874  27.603  1.00 39.52      AAAA C
ATOM   3733  CB   VAL   392      40.075  60.880  28.440  1.00 41.12      AAAA C
ATOM   3734  CG1  VAL   392      38.612  60.464  28.472  1.00 37.96      AAAA C
ATOM   3735  CG2  VAL   392      40.666  61.041  29.841  1.00 33.19      AAAA C
ATOM   3736  C    VAL   392      40.531  60.092  26.182  1.00 31.08      AAAA C
ATOM   3737  O    VAL   392      40.508  61.277  25.804  1.00 34.71      AAAA O
ATOM   3738  N    LEU   393      40.299  59.113  25.383  1.00 34.62      AAAA N
ATOM   3740  CA   LEU   393      39.948  59.259  23.977  1.00 38.12      AAAA C
ATOM   3741  CB   LEU   393      41.200  59.036  23.096  1.00 42.49      AAAA C
ATOM   3742  CG   LEU   393      41.023  58.649  21.586  1.00 26.48      AAAA C
ATOM   3743  CD1  LEU   393      41.128  59.879  20.753  1.00 26.57      AAAA C
ATOM   3744  CD2  LEU   393      42.078  57.589  21.244  1.00 29.98      AAAA C
ATOM   3745  C    LEU   393      38.821  58.375  23.482  1.00 39.15      AAAA C
ATOM   3746  O    LEU   393      38.760  57.173  23.799  1.00 37.90      AAAA O
ATOM   3747  N    ASP   394      38.015  58.973  22.565  1.00 43.38      AAAA N
ATOM   3749  CA   ASP   394      36.888  58.215  21.975  1.00 44.77      AAAA C
ATOM   3750  CB   ASP   394      37.445  57.073  21.120  1.00 44.80      AAAA C
ATOM   3751  CG   ASP   394      36.466  56.477  20.156  1.00 47.14      AAAA C
ATOM   3752  OD1  ASP   394      36.750  55.577  19.333  1.00 52.81      AAAA O
ATOM   3753  OD2  ASP   394      35.311  56.948  20.180  1.00 49.27      AAAA O
ATOM   3754  C    ASP   394      35.936  57.619  23.021  1.00 43.17      AAAA C
ATOM   3755  O    ASP   394      35.831  56.385  23.212  1.00 43.51      AAAA O
ATOM   3756  N    ASN   395      35.299  58.495  23.746  1.00 39.90      AAAA N
ATOM   3758  CA   ASN   395      34.305  58.158  24.776  1.00 46.32      AAAA C
ATOM   3759  CB   ASN   395      34.804  58.512  26.212  1.00 42.96      AAAA C
ATOM   3760  CG   ASN   395      35.992  57.619  26.579  1.00 36.92      AAAA C
ATOM   3761  OD1  ASN   395      36.013  56.394  26.796  1.00 21.65      AAAA O
ATOM   3762  ND2  ASN   395      37.075  58.409  26.558  1.00 27.87      AAAA N
ATOM   3765  C    ASN   395      32.932  58.816  24.541  1.00 40.44      AAAA C
ATOM   3766  O    ASN   395      32.749  59.982  24.882  1.00 37.06      AAAA O
ATOM   3767  N    GLN   396      32.073  58.055  23.877  1.00 46.74      AAAA N
ATOM   3769  CA   GLN   396      30.771  58.582  23.421  1.00 52.93      AAAA C
ATOM   3770  CB   GLN   396      29.848  57.567  22.744  1.00 52.29      AAAA C
ATOM   3771  CG   GLN   396      30.173  57.405  21.257  1.00 46.42      AAAA C
ATOM   3772  CD   GLN   396      29.817  55.991  20.840  1.00 55.21      AAAA C
ATOM   3773  OE1  GLN   396      28.835  55.421  21.312  1.00 61.17      AAAA O
ATOM   3774  NE2  GLN   396      30.628  55.411  19.971  1.00 55.79      AAAA N
ATOM   3777  C    GLN   396      29.874  59.224  24.458  1.00 48.64      AAAA C
ATOM   3778  O    GLN   396      29.407  60.287  24.113  1.00 51.63      AAAA O
ATOM   3779  N    ASN   397      29.717  58.681  25.633  1.00 48.95      AAAA N
ATOM   3781  CA   ASN   397      28.783  59.196  26.632  1.00 51.72      AAAA C
ATOM   3782  CB   ASN   397      27.969  57.959  27.093  1.00 35.94      AAAA C
ATOM   3783  CG   ASN   397      27.231  57.430  25.860  1.00 49.09      AAAA C
ATOM   3784  OD1  ASN   397      26.591  58.304  25.229  1.00 49.32      AAAA O
ATOM   3785  ND2  ASN   397      27.258  56.175  25.431  1.00 43.31      AAAA N
ATOM   3788  C    ASN   397      29.367  59.945  27.800  1.00 52.98      AAAA C
ATOM   3789  O    ASN   397      28.586  60.344  28.627  1.00 53.33      AAAA O
ATOM   3790  N    LEU   398      30.682  59.990  28.001  1.00 55.73      AAAA N
ATOM   3792  CA   LEU   398      31.312  60.550  29.179  1.00 52.12      AAAA C
ATOM   3793  CB   LEU   398      32.827  60.388  29.148  1.00 48.47      AAAA C
ATOM   3794  CG   LEU   398      33.606  60.283  30.460  1.00 41.81      AAAA C
ATOM   3795  CD1  LEU   398      33.417  58.939  31.136  1.00 40.35      AAAA C
ATOM   3796  CD2  LEU   398      35.070  60.608  30.082  1.00 39.03      AAAA C
ATOM   3797  C    LEU   398      30.923  61.995  29.353  1.00 52.35      AAAA C
ATOM   3798  O    LEU   398      31.422  62.909  28.681  1.00 49.91      AAAA O
ATOM   3799  N    GLN   399      30.241  62.225  30.469  1.00 58.76      AAAA N
ATOM   3801  CA   GLN   399      29.688  63.558  30.796  1.00 60.03      AAAA C
ATOM   3802  CB   GLN   399      28.236  63.331  31.262  1.00 59.55      AAAA C
ATOM   3803  CG   GLN   399      27.235  63.962  30.316  1.00 73.07      AAAA C
ATOM   3804  CD   GLN   399      25.944  63.146  30.340  1.00 78.39      AAAA C
ATOM   3805  OE1  GLN   399      25.097  63.455  31.194  1.00 71.79      AAAA O
ATOM   3806  NE2  GLN   399      25.856  62.158  29.440  1.00 69.88      AAAA N
```

Figure 1A-39

```
ATOM   3809  C   GLN  399      30.490  64.252  31.888  1.00 54.49      AAAA C
ATOM   3810  O   GLN  399      30.528  65.477  32.068  1.00 51.96      AAAA O
ATOM   3811  N   GLN  400      31.058  63.389  32.734  1.00 50.44      AAAA N
ATOM   3813  CA  GLN  400      31.938  63.948  33.756  1.00 53.83      AAAA C
ATOM   3814  CB  GLN  400      31.215  64.314  35.049  1.00 54.97      AAAA C
ATOM   3815  CG  GLN  400      30.717  63.150  35.887  1.00 58.99      AAAA C
ATOM   3816  CD  GLN  400      30.678  63.430  37.389  1.00 65.82      AAAA C
ATOM   3817  OE1 GLN  400      30.906  64.502  37.962  1.00 68.10      AAAA O
ATOM   3818  NE2 GLN  400      30.341  62.444  38.222  1.00 55.35      AAAA N
ATOM   3821  C   GLN  400      33.113  63.008  34.052  1.00 52.08      AAAA C
ATOM   3822  O   GLN  400      33.107  61.783  33.942  1.00 51.90      AAAA O
ATOM   3823  N   LEU  401      34.073  63.580  34.751  1.00 49.58      AAAA N
ATOM   3825  CA  LEU  401      35.175  62.844  35.334  1.00 49.57      AAAA C
ATOM   3826  CB  LEU  401      36.378  63.803  35.260  1.00 47.94      AAAA C
ATOM   3827  CG  LEU  401      36.638  64.237  33.772  1.00 46.61      AAAA C
ATOM   3828  CD1 LEU  401      37.658  65.326  33.677  1.00 39.09      AAAA C
ATOM   3829  CD2 LEU  401      36.919  63.069  32.860  1.00 40.72      AAAA C
ATOM   3830  C   LEU  401      34.866  62.357  36.734  1.00 51.23      AAAA C
ATOM   3831  O   LEU  401      34.258  61.299  36.892  1.00 49.06      AAAA O
ATOM   3832  N   TRP  402      35.297  63.140  37.690  1.00 54.58      AAAA N
ATOM   3834  CA  TRP  402      34.975  63.090  39.097  1.00 59.76      AAAA C
ATOM   3835  CB  TRP  402      36.279  62.953  39.933  1.00 59.56      AAAA C
ATOM   3836  CG  TRP  402      36.971  61.624  39.737  1.00 58.17      AAAA C
ATOM   3837  CD2 TRP  402      37.981  61.243  38.784  1.00 53.18      AAAA C
ATOM   3838  CE2 TRP  402      38.286  59.897  39.002  1.00 56.61      AAAA C
ATOM   3839  CE3 TRP  402      38.643  61.917  37.764  1.00 43.25      AAAA C
ATOM   3840  CD1 TRP  402      36.719  60.517  40.459  1.00 53.50      AAAA C
ATOM   3841  NE1 TRP  402      37.488  59.467  40.032  1.00 57.66      AAAA N
ATOM   3843  CZ2 TRP  402      39.212  59.160  38.249  1.00 51.44      AAAA C
ATOM   3844  CZ3 TRP  402      39.546  61.199  37.026  1.00 53.69      AAAA C
ATOM   3845  CH2 TRP  402      39.820  59.857  37.263  1.00 50.75      AAAA C
ATOM   3846  C   TRP  402      34.223  64.389  39.429  1.00 64.09      AAAA C
ATOM   3847  O   TRP  402      34.408  65.449  38.808  1.00 61.98      AAAA O
ATOM   3848  N   ASP  403      33.503  64.418  40.551  1.00 68.85      AAAA N
ATOM   3850  CA  ASP  403      32.947  65.668  41.068  1.00 67.83      AAAA C
ATOM   3851  CB  ASP  403      31.918  65.343  42.151  1.00 72.19      AAAA C
ATOM   3852  CG  ASP  403      30.853  66.417  42.306  1.00 73.08      AAAA C
ATOM   3853  OD1 ASP  403      31.177  67.625  42.297  1.00 71.67      AAAA O
ATOM   3854  OD2 ASP  403      29.693  65.979  42.454  1.00 75.08      AAAA O
ATOM   3855  C   ASP  403      34.005  66.607  41.607  1.00 66.63      AAAA C
ATOM   3856  O   ASP  403      34.245  66.672  42.811  1.00 67.18      AAAA O
ATOM   3857  N   TRP  404      34.449  67.588  40.846  1.00 69.29      AAAA N
ATOM   3859  CA  TRP  404      35.412  68.588  41.291  1.00 77.11      AAAA C
ATOM   3860  CB  TRP  404      35.859  69.269  40.063  1.00 79.10      AAAA C
ATOM   3861  CG  TRP  404      36.504  68.509  39.047  1.00 82.59      AAAA C
ATOM   3862  CD2 TRP  404      37.294  67.346  39.322  1.00 84.82      AAAA C
ATOM   3863  CE2 TRP  404      37.686  66.813  38.081  1.00 84.56      AAAA C
ATOM   3864  CE3 TRP  404      37.703  66.710  40.506  1.00 80.95      AAAA C
ATOM   3865  CD1 TRP  404      36.460  68.622  37.694  1.00 83.37      AAAA C
ATOM   3866  NE1 TRP  404      37.165  67.617  37.111  1.00 80.33      AAAA N
ATOM   3868  CZ2 TRP  404      38.477  65.662  37.982  1.00 85.91      AAAA C
ATOM   3869  CZ3 TRP  404      38.471  65.573  40.392  1.00 86.36      AAAA C
ATOM   3870  CH2 TRP  404      38.860  65.051  39.133  1.00 85.05      AAAA C
ATOM   3871  C   TRP  404      35.034  69.517  42.420  1.00 81.60      AAAA C
ATOM   3872  O   TRP  404      35.387  70.709  42.504  1.00 84.57      AAAA O
ATOM   3873  N   ASP  405      34.281  69.063  43.393  1.00 84.45      AAAA N
ATOM   3875  CA  ASP  405      33.771  69.861  44.496  1.00 87.48      AAAA C
ATOM   3876  CB  ASP  405      32.352  70.365  44.262  1.00 88.04      AAAA C
ATOM   3877  CG  ASP  405      32.274  71.612  43.409  1.00 92.54      AAAA C
ATOM   3878  OD1 ASP  405      33.306  72.285  43.207  1.00 94.82      AAAA O
ATOM   3879  OD2 ASP  405      31.130  71.854  42.955  1.00 95.26      AAAA O
ATOM   3880  C   ASP  405      33.730  68.906  45.693  1.00 87.80      AAAA C
ATOM   3881  O   ASP  405      34.245  69.224  46.743  1.00 92.18      AAAA O
ATOM   3882  N   ALA  406      33.239  67.709  45.460  1.00 84.46      AAAA N
ATOM   3884  CA  ALA  406      33.176  66.671  46.451  1.00 82.87      AAAA C
ATOM   3885  CB  ALA  406      31.943  65.805  46.133  1.00 76.32      AAAA C
ATOM   3886  C   ALA  406      34.445  65.840  46.459  1.00 85.77      AAAA C
ATOM   3887  O   ALA  406      34.470  64.823  47.185  1.00 89.38      AAAA O
ATOM   3888  N   ARG  407      35.433  66.073  45.577  1.00 83.74      AAAA N
ATOM   3890  CA  ARG  407      36.541  65.151  45.400  1.00 79.60      AAAA C
ATOM   3891  CB  ARG  407      36.165  64.140  44.297  1.00 77.84      AAAA C
ATOM   3892  CG  ARG  407      35.457  62.950  44.921  1.00 81.91      AAAA C
ATOM   3893  CD  ARG  407      35.362  61.688  44.113  1.00 86.97      AAAA C
ATOM   3894  NE  ARG  407      36.281  60.660  44.607  1.00 86.94      AAAA N
ATOM   3896  CZ  ARG  407      37.564  60.583  44.279  1.00 92.14      AAAA C
ATOM   3897  NH1 ARG  407      38.169  61.441  43.469  1.00 97.06      AAAA N
ATOM   3900  NH2 ARG  407      38.309  59.616  44.770  1.00 96.33      AAAA N
ATOM   3903  C   ARG  407      37.880  65.749  45.048  1.00 76.72      AAAA C
```

Figure 1A-40

| | | | | | | | | | | | |
|---|---|---|---|---|---|---|---|---|---|---|---|
| ATOM | 3904 | O | ARG | 407 | 37.989 | 66.774 | 44.410 | 1.00 | 77.47 | AAAA | O |
| ATOM | 3905 | N | ASN | 408 | 38.958 | 65.081 | 45.453 | 1.00 | 75.75 | AAAA | N |
| ATOM | 3907 | CA | ASN | 408 | 40.311 | 65.556 | 45.173 | 1.00 | 73.79 | AAAA | C |
| ATOM | 3908 | CB | ASN | 408 | 40.938 | 66.240 | 46.388 | 1.00 | 74.46 | AAAA | C |
| ATOM | 3909 | CG | ASN | 408 | 41.986 | 67.242 | 45.947 | 1.00 | 82.51 | AAAA | C |
| ATOM | 3910 | OD1 | ASN | 408 | 41.813 | 68.429 | 46.240 | 1.00 | 90.33 | AAAA | O |
| ATOM | 3911 | ND2 | ASN | 408 | 43.028 | 66.821 | 45.253 | 1.00 | 84.46 | AAAA | N |
| ATOM | 3914 | C | ASN | 408 | 41.257 | 64.468 | 44.654 | 1.00 | 65.97 | AAAA | C |
| ATOM | 3915 | O | ASN | 408 | 41.251 | 63.374 | 45.151 | 1.00 | 63.82 | AAAA | O |
| ATOM | 3916 | N | LEU | 409 | 42.041 | 64.793 | 43.650 | 1.00 | 61.41 | AAAA | N |
| ATOM | 3918 | CA | LEU | 409 | 42.896 | 63.872 | 42.947 | 1.00 | 60.90 | AAAA | C |
| ATOM | 3919 | CB | LEU | 409 | 42.153 | 63.250 | 41.768 | 1.00 | 62.98 | AAAA | C |
| ATOM | 3920 | CG | LEU | 409 | 42.992 | 62.553 | 40.704 | 1.00 | 59.77 | AAAA | C |
| ATOM | 3921 | CD1 | LEU | 409 | 43.488 | 61.205 | 41.197 | 1.00 | 54.06 | AAAA | C |
| ATOM | 3922 | CD2 | LEU | 409 | 42.094 | 62.445 | 39.486 | 1.00 | 55.74 | AAAA | C |
| ATOM | 3923 | C | LEU | 409 | 44.151 | 64.599 | 42.485 | 1.00 | 61.19 | AAAA | C |
| ATOM | 3924 | O | LEU | 409 | 44.141 | 65.809 | 42.370 | 1.00 | 60.64 | AAAA | O |
| ATOM | 3925 | N | THR | 410 | 45.281 | 63.903 | 42.424 | 1.00 | 63.74 | AAAA | N |
| ATOM | 3927 | CA | THR | 410 | 46.588 | 64.462 | 42.131 | 1.00 | 60.44 | AAAA | C |
| ATOM | 3928 | CB | THR | 410 | 47.454 | 64.676 | 43.385 | 1.00 | 67.08 | AAAA | C |
| ATOM | 3929 | OG1 | THR | 410 | 46.870 | 65.746 | 44.157 | 1.00 | 74.29 | AAAA | O |
| ATOM | 3931 | CG2 | THR | 410 | 48.909 | 65.103 | 43.162 | 1.00 | 48.56 | AAAA | C |
| ATOM | 3932 | C | THR | 410 | 47.426 | 63.565 | 41.218 | 1.00 | 56.62 | AAAA | C |
| ATOM | 3933 | O | THR | 410 | 47.382 | 62.354 | 41.317 | 1.00 | 54.99 | AAAA | O |
| ATOM | 3934 | N | ILE | 411 | 48.077 | 64.245 | 40.288 | 1.00 | 53.97 | AAAA | N |
| ATOM | 3936 | CA | ILE | 411 | 48.897 | 63.562 | 39.291 | 1.00 | 53.29 | AAAA | C |
| ATOM | 3937 | CB | ILE | 411 | 48.409 | 63.854 | 37.864 | 1.00 | 49.81 | AAAA | C |
| ATOM | 3938 | CG2 | ILE | 411 | 49.216 | 63.128 | 36.806 | 1.00 | 30.86 | AAAA | C |
| ATOM | 3939 | CG1 | ILE | 411 | 46.911 | 63.489 | 37.729 | 1.00 | 40.83 | AAAA | C |
| ATOM | 3940 | CD1 | ILE | 411 | 46.322 | 63.547 | 36.338 | 1.00 | 38.51 | AAAA | C |
| ATOM | 3941 | C | ILE | 411 | 50.319 | 64.018 | 39.568 | 1.00 | 55.38 | AAAA | C |
| ATOM | 3942 | O | ILE | 411 | 50.656 | 65.179 | 39.291 | 1.00 | 57.59 | AAAA | O |
| ATOM | 3943 | N | SER | 412 | 51.073 | 63.182 | 40.270 | 1.00 | 54.26 | AAAA | N |
| ATOM | 3945 | CA | SER | 412 | 52.434 | 63.502 | 40.689 | 1.00 | 54.46 | AAAA | C |
| ATOM | 3946 | CB | SER | 412 | 53.071 | 62.210 | 41.248 | 1.00 | 55.78 | AAAA | C |
| ATOM | 3947 | OG | SER | 412 | 53.756 | 62.536 | 42.434 | 1.00 | 67.12 | AAAA | O |
| ATOM | 3949 | C | SER | 412 | 53.326 | 63.910 | 39.523 | 1.00 | 55.52 | AAAA | C |
| ATOM | 3950 | O | SER | 412 | 54.081 | 64.876 | 39.527 | 1.00 | 55.04 | AAAA | O |
| ATOM | 3951 | N | ALA | 413 | 53.254 | 63.124 | 38.438 | 1.00 | 50.12 | AAAA | N |
| ATOM | 3953 | CA | ALA | 413 | 54.064 | 63.402 | 37.281 | 1.00 | 50.01 | AAAA | C |
| ATOM | 3954 | CB | ALA | 413 | 55.334 | 62.520 | 37.365 | 1.00 | 34.96 | AAAA | C |
| ATOM | 3955 | C | ALA | 413 | 53.301 | 63.078 | 35.994 | 1.00 | 48.71 | AAAA | C |
| ATOM | 3956 | O | ALA | 413 | 52.495 | 62.168 | 35.998 | 1.00 | 48.81 | AAAA | O |
| ATOM | 3957 | N | GLY | 414 | 53.675 | 63.690 | 34.895 | 1.00 | 47.92 | AAAA | N |
| ATOM | 3959 | CA | GLY | 414 | 53.057 | 63.454 | 33.607 | 1.00 | 51.75 | AAAA | C |
| ATOM | 3960 | C | GLY | 414 | 52.017 | 64.524 | 33.294 | 1.00 | 52.77 | AAAA | C |
| ATOM | 3961 | O | GLY | 414 | 51.684 | 65.370 | 34.114 | 1.00 | 53.23 | AAAA | O |
| ATOM | 3962 | N | LYS | 415 | 51.385 | 64.406 | 32.138 | 1.00 | 56.31 | AAAA | N |
| ATOM | 3964 | CA | LYS | 415 | 50.289 | 65.317 | 31.759 | 1.00 | 52.49 | AAAA | C |
| ATOM | 3965 | CB | LYS | 415 | 50.884 | 66.358 | 30.833 | 1.00 | 50.94 | AAAA | C |
| ATOM | 3966 | CG | LYS | 415 | 51.198 | 65.855 | 29.429 | 1.00 | 54.39 | AAAA | C |
| ATOM | 3967 | CD | LYS | 415 | 52.288 | 66.691 | 28.765 | 1.00 | 53.96 | AAAA | C |
| ATOM | 3968 | CE | LYS | 415 | 52.785 | 66.151 | 27.441 | 1.00 | 56.01 | AAAA | C |
| ATOM | 3969 | NZ | LYS | 415 | 52.426 | 67.032 | 26.284 | 1.00 | 66.36 | AAAA | N |
| ATOM | 3973 | C | LYS | 415 | 49.110 | 64.576 | 31.155 | 1.00 | 50.04 | AAAA | C |
| ATOM | 3974 | O | LYS | 415 | 49.077 | 63.337 | 31.036 | 1.00 | 49.77 | AAAA | O |
| ATOM | 3975 | N | MET | 416 | 48.091 | 65.353 | 30.771 | 1.00 | 48.34 | AAAA | N |
| ATOM | 3977 | CA | MET | 416 | 46.890 | 64.734 | 30.186 | 1.00 | 46.77 | AAAA | C |
| ATOM | 3978 | CB | MET | 416 | 45.629 | 65.186 | 30.949 | 1.00 | 42.79 | AAAA | C |
| ATOM | 3979 | CG | MET | 416 | 45.836 | 65.880 | 32.273 | 1.00 | 40.91 | AAAA | C |
| ATOM | 3980 | SD | MET | 416 | 44.511 | 65.636 | 33.517 | 1.00 | 56.20 | AAAA | S |
| ATOM | 3981 | CE | MET | 416 | 44.002 | 67.366 | 33.690 | 1.00 | 35.94 | AAAA | C |
| ATOM | 3982 | C | MET | 416 | 46.623 | 65.064 | 28.728 | 1.00 | 40.40 | AAAA | C |
| ATOM | 3983 | O | MET | 416 | 46.963 | 66.137 | 28.247 | 1.00 | 34.84 | AAAA | O |
| ATOM | 3984 | N | TYR | 417 | 45.893 | 64.169 | 28.104 | 1.00 | 38.49 | AAAA | N |
| ATOM | 3986 | CA | TYR | 417 | 45.355 | 64.387 | 26.765 | 1.00 | 39.50 | AAAA | C |
| ATOM | 3987 | CB | TYR | 417 | 46.156 | 63.471 | 25.831 | 1.00 | 32.02 | AAAA | C |
| ATOM | 3988 | CG | TYR | 417 | 45.583 | 63.430 | 24.428 | 1.00 | 39.48 | AAAA | C |
| ATOM | 3989 | CD1 | TYR | 417 | 45.730 | 64.501 | 23.511 | 1.00 | 39.29 | AAAA | C |
| ATOM | 3990 | CE1 | TYR | 417 | 45.196 | 64.429 | 22.253 | 1.00 | 34.56 | AAAA | C |
| ATOM | 3991 | CD2 | TYR | 417 | 44.884 | 62.321 | 24.005 | 1.00 | 36.81 | AAAA | C |
| ATOM | 3992 | CE2 | TYR | 417 | 44.379 | 62.241 | 22.722 | 1.00 | 38.80 | AAAA | C |
| ATOM | 3993 | CZ | TYR | 417 | 44.535 | 63.292 | 21.872 | 1.00 | 44.20 | AAAA | C |
| ATOM | 3994 | OH | TYR | 417 | 44.053 | 63.361 | 20.552 | 1.00 | 58.10 | AAAA | O |
| ATOM | 3996 | C | TYR | 417 | 43.853 | 64.065 | 26.698 | 1.00 | 44.18 | AAAA | C |
| ATOM | 3997 | O | TYR | 417 | 43.376 | 62.974 | 27.135 | 1.00 | 42.19 | AAAA | O |
| ATOM | 3998 | N | PHE | 418 | 43.068 | 64.971 | 26.100 | 1.00 | 45.84 | AAAA | N |
| ATOM | 4000 | CA | PHE | 418 | 41.644 | 64.701 | 25.910 | 1.00 | 45.87 | AAAA | C |

Figure 1A-41

```
ATOM   4001  CB   PHE  418      40.772  65.657  26.730  1.00 47.19        AAAA C
ATOM   4002  CG   PHE  418      40.675  65.264  28.177  1.00 43.44        AAAA C
ATOM   4003  CD1  PHE  418      41.552  65.685  29.132  1.00 38.43        AAAA C
ATOM   4004  CD2  PHE  418      39.638  64.417  28.544  1.00 51.21        AAAA C
ATOM   4005  CE1  PHE  418      41.402  65.291  30.440  1.00 46.44        AAAA C
ATOM   4006  CE2  PHE  418      39.486  64.023  29.845  1.00 46.63        AAAA C
ATOM   4007  CZ   PHE  418      40.358  64.454  30.801  1.00 44.68        AAAA C
ATOM   4008  C    PHE  418      41.251  64.730  24.440  1.00 44.64        AAAA C
ATOM   4009  O    PHE  418      41.375  65.762  23.812  1.00 47.60        AAAA O
ATOM   4010  N    ALA  419      40.554  63.713  23.936  1.00 43.06        AAAA N
ATOM   4012  CA   ALA  419      40.015  63.793  22.607  1.00 39.21        AAAA C
ATOM   4013  CB   ALA  419      41.090  63.562  21.555  1.00 30.88        AAAA C
ATOM   4014  C    ALA  419      38.837  62.846  22.366  1.00 41.77        AAAA C
ATOM   4015  O    ALA  419      38.871  61.628  22.557  1.00 36.08        AAAA O
ATOM   4016  N    PHE  420      37.829  63.398  21.618  1.00 40.41        AAAA N
ATOM   4018  CA   PHE  420      36.742  62.621  21.070  1.00 40.03        AAAA C
ATOM   4019  CB   PHE  420      37.157  61.430  20.180  1.00 45.54        AAAA C
ATOM   4020  CG   PHE  420      37.832  61.909  18.912  1.00 54.18        AAAA C
ATOM   4021  CD1  PHE  420      39.221  61.987  18.751  1.00 49.23        AAAA C
ATOM   4022  CD2  PHE  420      37.006  62.345  17.871  1.00 47.65        AAAA C
ATOM   4023  CE1  PHE  420      39.783  62.496  17.567  1.00 46.00        AAAA C
ATOM   4024  CE2  PHE  420      37.572  62.833  16.725  1.00 51.10        AAAA C
ATOM   4025  CZ   PHE  420      38.964  62.928  16.549  1.00 44.01        AAAA C
ATOM   4026  C    PHE  420      35.762  62.146  22.126  1.00 41.65        AAAA C
ATOM   4027  O    PHE  420      35.352  60.991  22.215  1.00 38.35        AAAA O
ATOM   4028  N    ASN  421      35.459  63.024  23.049  1.00 45.35        AAAA N
ATOM   4030  CA   ASN  421      34.477  62.960  24.112  1.00 46.86        AAAA C
ATOM   4031  CB   ASN  421      35.183  63.276  25.449  1.00 43.60        AAAA C
ATOM   4032  CG   ASN  421      36.407  62.401  25.654  1.00 47.90        AAAA C
ATOM   4033  OD1  ASN  421      36.426  61.147  25.714  1.00 44.83        AAAA O
ATOM   4034  ND2  ASN  421      37.541  63.101  25.732  1.00 37.46        AAAA N
ATOM   4037  C    ASN  421      33.432  64.069  23.835  1.00 47.83        AAAA C
ATOM   4038  O    ASN  421      33.617  65.233  24.237  1.00 38.85        AAAA O
ATOM   4039  N    PRO  422      32.453  63.777  22.968  1.00 47.86        AAAA N
ATOM   4040  CD   PRO  422      32.213  62.423  22.372  1.00 44.11        AAAA C
ATOM   4041  CA   PRO  422      31.463  64.776  22.605  1.00 47.85        AAAA C
ATOM   4042  CB   PRO  422      30.731  64.084  21.446  1.00 44.86        AAAA C
ATOM   4043  CG   PRO  422      30.947  62.623  21.606  1.00 43.01        AAAA C
ATOM   4044  C    PRO  422      30.577  65.284  23.735  1.00 51.16        AAAA C
ATOM   4045  O    PRO  422      30.223  66.486  23.744  1.00 48.54        AAAA O
ATOM   4046  N    LYS  423      30.320  64.487  24.774  1.00 52.90        AAAA N
ATOM   4048  CA   LYS  423      29.431  64.908  25.865  1.00 58.82        AAAA C
ATOM   4049  CB   LYS  423      28.556  63.721  26.360  1.00 52.93        AAAA C
ATOM   4050  CG   LYS  423      28.209  62.810  25.196  1.00 70.55        AAAA C
ATOM   4051  CD   LYS  423      26.743  62.448  24.996  1.00 73.79        AAAA C
ATOM   4052  CE   LYS  423      26.030  63.374  24.021  1.00 77.06        AAAA C
ATOM   4053  NZ   LYS  423      25.949  64.748  24.614  1.00 64.99        AAAA N
ATOM   4057  C    LYS  423      30.158  65.482  27.071  1.00 57.43        AAAA C
ATOM   4058  O    LYS  423      29.582  65.482  28.152  1.00 55.22        AAAA O
ATOM   4059  N    LEU  424      31.425  65.859  26.862  1.00 55.95        AAAA N
ATOM   4061  CA   LEU  424      32.261  66.162  28.017  1.00 57.07        AAAA C
ATOM   4062  CB   LEU  424      33.463  65.250  28.237  1.00 49.16        AAAA C
ATOM   4063  CG   LEU  424      34.390  65.748  29.370  1.00 68.27        AAAA C
ATOM   4064  CD1  LEU  424      33.821  65.362  30.734  1.00 60.66        AAAA C
ATOM   4065  CD2  LEU  424      35.825  65.276  29.123  1.00 60.35        AAAA C
ATOM   4066  C    LEU  424      32.709  67.585  27.878  1.00 56.29        AAAA C
ATOM   4067  O    LEU  424      33.696  67.861  27.201  1.00 59.98        AAAA O
ATOM   4068  N    CYS  425      31.995  68.488  28.492  1.00 58.76        AAAA N
ATOM   4070  CA   CYS  425      32.342  69.916  28.406  1.00 60.39        AAAA C
ATOM   4071  C    CYS  425      33.771  70.119  28.810  1.00 62.59        AAAA C
ATOM   4072  O    CYS  425      34.288  69.665  29.831  1.00 64.45        AAAA O
ATOM   4073  CB   CYS  425      31.249  70.644  29.214  1.00 68.23        AAAA C
ATOM   4074  SG   CYS  425      29.916  71.303  28.086  1.00 81.03        AAAA S
ATOM   4075  N    VAL  426      34.529  70.953  28.102  1.00 65.31        AAAA N
ATOM   4077  CA   VAL  426      35.943  71.149  28.358  1.00 65.49        AAAA C
ATOM   4078  CB   VAL  426      36.644  72.022  27.310  1.00 66.62        AAAA C
ATOM   4079  CG1  VAL  426      36.715  71.413  25.925  1.00 62.49        AAAA C
ATOM   4080  CG2  VAL  426      35.962  73.365  27.239  1.00 60.92        AAAA C
ATOM   4081  C    VAL  426      36.105  71.711  29.757  1.00 65.99        AAAA C
ATOM   4082  O    VAL  426      37.180  71.724  30.388  1.00 64.51        AAAA O
ATOM   4083  N    SER  427      35.090  72.361  30.267  1.00 67.67        AAAA N
ATOM   4085  CA   SER  427      35.091  72.927  31.599  1.00 66.85        AAAA C
ATOM   4086  CB   SER  427      33.685  73.499  31.864  1.00 61.16        AAAA C
ATOM   4087  OG   SER  427      34.088  74.860  32.098  1.00 67.05        AAAA O
ATOM   4089  C    SER  427      35.515  71.972  32.701  1.00 64.24        AAAA C
ATOM   4090  O    SER  427      36.332  72.328  33.573  1.00 63.66        AAAA O
ATOM   4091  N    GLU  428      34.965  70.771  32.618  1.00 58.75        AAAA N
ATOM   4093  CA   GLU  428      35.384  69.753  33.585  1.00 63.39        AAAA C
```

Figure 1A-42

```
ATOM   4094  CB   GLU  428     34.594  68.485  33.240  1.00 68.67      AAAA C
ATOM   4095  CG   GLU  428     33.115  68.560  33.537  1.00 66.59      AAAA C
ATOM   4096  CD   GLU  428     32.785  68.560  35.023  1.00 72.33      AAAA C
ATOM   4097  OE1  GLU  428     32.729  67.522  35.722  1.00 81.62      AAAA O
ATOM   4098  OE2  GLU  428     32.581  69.688  35.517  1.00 70.97      AAAA O
ATOM   4099  C    GLU  428     36.870  69.485  33.429  1.00 61.63      AAAA C
ATOM   4100  O    GLU  428     37.671  69.696  34.307  1.00 62.03      AAAA O
ATOM   4101  N    ILE  429     37.265  69.262  32.165  1.00 61.26      AAAA N
ATOM   4103  CA   ILE  429     38.631  69.038  31.789  1.00 61.09      AAAA C
ATOM   4104  CB   ILE  429     38.759  68.933  30.263  1.00 59.32      AAAA C
ATOM   4105  CG2  ILE  429     40.257  68.915  29.895  1.00 45.93      AAAA C
ATOM   4106  CG1  ILE  429     37.968  67.719  29.794  1.00 57.66      AAAA C
ATOM   4107  CD1  ILE  429     38.038  67.555  28.285  1.00 53.48      AAAA C
ATOM   4108  C    ILE  429     39.498  70.166  32.323  1.00 61.90      AAAA C
ATOM   4109  O    ILE  429     40.592  70.017  32.867  1.00 61.28      AAAA O
ATOM   4110  N    TYR  430     38.987  71.384  32.200  1.00 65.34      AAAA N
ATOM   4112  CA   TYR  430     39.729  72.543  32.719  1.00 68.10      AAAA C
ATOM   4113  CB   TYR  430     39.180  73.822  32.099  1.00 71.02      AAAA C
ATOM   4114  CG   TYR  430     39.538  74.006  30.639  1.00 75.98      AAAA C
ATOM   4115  CD1  TYR  430     38.653  73.821  29.599  1.00 77.60      AAAA C
ATOM   4116  CE1  TYR  430     38.953  73.977  28.270  1.00 75.72      AAAA C
ATOM   4117  CD2  TYR  430     40.810  74.401  30.260  1.00 75.95      AAAA C
ATOM   4118  CE2  TYR  430     41.155  74.575  28.937  1.00 74.81      AAAA C
ATOM   4119  CZ   TYR  430     40.221  74.359  27.952  1.00 78.51      AAAA C
ATOM   4120  OH   TYR  430     40.564  74.542  26.616  1.00 85.40      AAAA O
ATOM   4122  C    TYR  430     39.779  72.634  34.241  1.00 63.72      AAAA C
ATOM   4123  O    TYR  430     40.654  73.321  34.758  1.00 58.26      AAAA O
ATOM   4124  N    ARG  431     38.819  72.017  34.907  1.00 65.53      AAAA N
ATOM   4126  CA   ARG  431     38.747  72.043  36.356  1.00 68.15      AAAA C
ATOM   4127  CB   ARG  431     37.348  71.748  36.898  1.00 73.32      AAAA C
ATOM   4128  CG   ARG  431     37.345  71.815  38.430  1.00 82.99      AAAA C
ATOM   4129  CD   ARG  431     37.270  73.279  38.860  1.00 88.39      AAAA C
ATOM   4130  NE   ARG  431     37.698  73.472  40.258  1.00 92.48      AAAA N
ATOM   4132  CZ   ARG  431     36.835  73.258  41.259  1.00 94.93      AAAA C
ATOM   4133  NH1  ARG  431     35.610  72.872  40.872  1.00 87.40      AAAA N
ATOM   4136  NH2  ARG  431     37.021  73.371  42.567  1.00 95.17      AAAA N
ATOM   4139  C    ARG  431     39.718  70.986  36.877  1.00 67.75      AAAA C
ATOM   4140  O    ARG  431     40.637  71.292  37.629  1.00 66.74      AAAA O
ATOM   4141  N    MET  432     39.541  69.791  36.305  1.00 63.87      AAAA N
ATOM   4143  CA   MET  432     40.437  68.703  36.652  1.00 64.40      AAAA C
ATOM   4144  CB   MET  432     40.237  67.522  35.718  1.00 54.25      AAAA C
ATOM   4145  CG   MET  432     41.254  66.426  35.971  1.00 40.18      AAAA C
ATOM   4146  SD   MET  432     40.829  64.925  35.112  1.00 52.21      AAAA S
ATOM   4147  CE   MET  432     41.582  63.681  36.137  1.00 54.89      AAAA C
ATOM   4148  C    MET  432     41.891  69.170  36.626  1.00 64.65      AAAA C
ATOM   4149  O    MET  432     42.530  68.992  37.653  1.00 65.88      AAAA O
ATOM   4150  N    GLU  433     42.331  69.811  35.556  1.00 65.78      AAAA N
ATOM   4152  CA   GLU  433     43.622  70.469  35.510  1.00 69.16      AAAA C
ATOM   4153  CB   GLU  433     43.704  71.506  34.401  1.00 69.58      AAAA C
ATOM   4154  CG   GLU  433     44.121  70.967  33.048  1.00 76.91      AAAA C
ATOM   4155  CD   GLU  433     44.623  72.149  32.242  1.00 82.02      AAAA C
ATOM   4156  OE1  GLU  433     44.718  73.224  32.874  1.00 86.82      AAAA O
ATOM   4157  OE2  GLU  433     44.905  72.050  31.042  1.00 88.26      AAAA O
ATOM   4158  C    GLU  433     44.016  71.219  36.781  1.00 71.29      AAAA C
ATOM   4159  O    GLU  433     45.133  71.083  37.294  1.00 74.29      AAAA O
ATOM   4160  N    GLU  434     43.178  72.120  37.280  1.00 72.93      AAAA N
ATOM   4162  CA   GLU  434     43.505  72.873  38.485  1.00 72.88      AAAA C
ATOM   4163  CB   GLU  434     42.458  73.916  38.840  1.00 81.36      AAAA C
ATOM   4164  CG   GLU  434     41.191  73.956  38.032  1.00 83.34      AAAA C
ATOM   4165  CD   GLU  434     40.181  75.004  38.432  1.00 97.32      AAAA C
ATOM   4166  OE1  GLU  434     39.521  74.928  39.505  1.00 97.34      AAAA O
ATOM   4167  OE2  GLU  434     40.080  75.941  37.583  1.00 99.95      AAAA O
ATOM   4168  C    GLU  434     43.675  71.886  39.632  1.00 71.46      AAAA C
ATOM   4169  O    GLU  434     44.728  71.858  40.251  1.00 78.49      AAAA O
ATOM   4170  N    VAL  435     42.670  71.095  39.926  1.00 66.34      AAAA N
ATOM   4172  CA   VAL  435     42.711  70.129  41.001  1.00 62.49      AAAA C
ATOM   4173  CB   VAL  435     41.451  69.217  40.972  1.00 60.38      AAAA C
ATOM   4174  CG1  VAL  435     41.547  68.214  42.104  1.00 52.32      AAAA C
ATOM   4175  CG2  VAL  435     40.203  70.073  41.029  1.00 50.79      AAAA C
ATOM   4176  C    VAL  435     43.939  69.253  41.018  1.00 60.74      AAAA C
ATOM   4177  O    VAL  435     44.607  69.165  42.034  1.00 62.37      AAAA O
ATOM   4178  N    THR  436     44.282  68.506  39.988  1.00 60.67      AAAA N
ATOM   4180  CA   THR  436     45.335  67.516  39.936  1.00 56.36      AAAA C
ATOM   4181  CB   THR  436     45.199  66.565  38.736  1.00 50.92      AAAA C
ATOM   4182  OG1  THR  436     44.913  67.283  37.503  1.00 47.03      AAAA O
ATOM   4184  CG2  THR  436     44.108  65.526  38.901  1.00 54.38      AAAA C
ATOM   4185  C    THR  436     46.701  68.184  39.930  1.00 60.55      AAAA C
ATOM   4186  O    THR  436     47.714  67.490  40.024  1.00 60.61      AAAA O
```

Figure 1A-43

| | | | | | | | | | | |
|---|---|---|---|---|---|---|---|---|---|---|
| ATOM | 4187 | N | GLY | 437 | 46.836 | 69.496 | 39.835 | 1.00 | 60.65 | AAAA N |
| ATOM | 4189 | CA | GLY | 437 | 48.102 | 70.164 | 39.749 | 1.00 | 59.47 | AAAA C |
| ATOM | 4190 | C | GLY | 437 | 48.800 | 69.864 | 38.424 | 1.00 | 64.78 | AAAA C |
| ATOM | 4191 | O | GLY | 437 | 49.983 | 70.254 | 38.245 | 1.00 | 62.70 | AAAA O |
| ATOM | 4192 | N | THR | 438 | 48.112 | 69.387 | 37.380 | 1.00 | 63.79 | AAAA N |
| ATOM | 4194 | CA | THR | 438 | 48.731 | 69.169 | 36.076 | 1.00 | 65.09 | AAAA C |
| ATOM | 4195 | CB | THR | 438 | 47.967 | 68.027 | 35.411 | 1.00 | 66.87 | AAAA C |
| ATOM | 4196 | OG1 | THR | 438 | 46.600 | 68.385 | 35.731 | 1.00 | 62.22 | AAAA O |
| ATOM | 4198 | CG2 | THR | 438 | 48.208 | 66.659 | 36.019 | 1.00 | 68.74 | AAAA C |
| ATOM | 4199 | C | THR | 438 | 48.590 | 70.415 | 35.220 | 1.00 | 66.14 | AAAA C |
| ATOM | 4200 | O | THR | 438 | 49.003 | 70.543 | 34.070 | 1.00 | 68.05 | AAAA O |
| ATOM | 4201 | N | LYS | 439 | 48.089 | 71.481 | 35.822 | 1.00 | 67.37 | AAAA N |
| ATOM | 4203 | CA | LYS | 439 | 47.927 | 72.757 | 35.154 | 1.00 | 71.08 | AAAA C |
| ATOM | 4204 | CB | LYS | 439 | 47.114 | 73.708 | 36.034 | 1.00 | 69.23 | AAAA C |
| ATOM | 4205 | CG | LYS | 439 | 46.677 | 74.938 | 35.265 | 1.00 | 77.26 | AAAA C |
| ATOM | 4206 | CD | LYS | 439 | 45.832 | 75.942 | 36.014 | 1.00 | 81.65 | AAAA C |
| ATOM | 4207 | CE | LYS | 439 | 44.385 | 75.475 | 36.182 | 1.00 | 87.39 | AAAA C |
| ATOM | 4208 | NZ | LYS | 439 | 43.667 | 76.431 | 37.100 | 1.00 | 93.85 | AAAA N |
| ATOM | 4212 | C | LYS | 439 | 49.249 | 73.396 | 34.752 | 1.00 | 73.01 | AAAA C |
| ATOM | 4213 | O | LYS | 439 | 49.996 | 73.986 | 35.541 | 1.00 | 74.60 | AAAA O |
| ATOM | 4214 | N | GLY | 440 | 49.517 | 73.453 | 33.441 | 1.00 | 73.33 | AAAA N |
| ATOM | 4216 | CA | GLY | 440 | 50.733 | 74.167 | 33.014 | 1.00 | 71.39 | AAAA C |
| ATOM | 4217 | C | GLY | 440 | 51.716 | 73.204 | 32.389 | 1.00 | 71.20 | AAAA C |
| ATOM | 4218 | O | GLY | 440 | 52.684 | 73.650 | 31.822 | 1.00 | 72.70 | AAAA O |
| ATOM | 4219 | N | ARG | 441 | 51.445 | 71.908 | 32.436 | 1.00 | 72.99 | AAAA N |
| ATOM | 4221 | CA | ARG | 441 | 52.343 | 70.945 | 31.831 | 1.00 | 74.12 | AAAA C |
| ATOM | 4222 | CB | ARG | 441 | 52.617 | 69.740 | 32.716 | 1.00 | 69.44 | AAAA C |
| ATOM | 4223 | CG | ARG | 441 | 51.847 | 69.695 | 34.003 | 1.00 | 63.34 | AAAA C |
| ATOM | 4224 | CD | ARG | 441 | 52.060 | 68.314 | 34.595 | 1.00 | 67.64 | AAAA C |
| ATOM | 4225 | NE | ARG | 441 | 52.244 | 68.395 | 36.030 | 1.00 | 61.00 | AAAA N |
| ATOM | 4227 | CZ | ARG | 441 | 52.326 | 67.357 | 36.831 | 1.00 | 59.21 | AAAA C |
| ATOM | 4228 | NH1 | ARG | 441 | 52.258 | 66.117 | 36.395 | 1.00 | 60.57 | AAAA N |
| ATOM | 4231 | NH2 | ARG | 441 | 52.468 | 67.596 | 38.128 | 1.00 | 72.94 | AAAA N |
| ATOM | 4234 | C | ARG | 441 | 51.760 | 70.446 | 30.511 | 1.00 | 73.50 | AAAA C |
| ATOM | 4235 | O | ARG | 441 | 52.195 | 69.424 | 30.012 | 1.00 | 74.73 | AAAA O |
| ATOM | 4236 | N | GLN | 442 | 50.732 | 71.114 | 30.043 | 1.00 | 74.69 | AAAA N |
| ATOM | 4238 | CA | GLN | 442 | 49.959 | 70.646 | 28.914 | 1.00 | 75.13 | AAAA C |
| ATOM | 4239 | CB | GLN | 442 | 48.457 | 70.875 | 29.126 | 1.00 | 68.73 | AAAA C |
| ATOM | 4240 | CG | GLN | 442 | 47.669 | 69.576 | 29.195 | 1.00 | 71.20 | AAAA C |
| ATOM | 4241 | CD | GLN | 442 | 47.623 | 69.028 | 30.607 | 1.00 | 70.98 | AAAA C |
| ATOM | 4242 | OE1 | GLN | 442 | 47.714 | 67.822 | 30.868 | 1.00 | 78.66 | AAAA O |
| ATOM | 4243 | NE2 | GLN | 442 | 47.477 | 69.907 | 31.584 | 1.00 | 66.86 | AAAA N |
| ATOM | 4246 | C | GLN | 442 | 50.326 | 71.359 | 27.627 | 1.00 | 77.69 | AAAA C |
| ATOM | 4247 | O | GLN | 442 | 50.227 | 72.569 | 27.530 | 1.00 | 75.57 | AAAA O |
| ATOM | 4248 | N | ALA | 443 | 50.474 | 70.554 | 26.575 | 1.00 | 81.54 | AAAA N |
| ATOM | 4250 | CA | ALA | 443 | 50.643 | 71.148 | 25.236 | 1.00 | 82.95 | AAAA C |
| ATOM | 4251 | CB | ALA | 443 | 51.104 | 70.118 | 24.220 | 1.00 | 81.69 | AAAA C |
| ATOM | 4252 | C | ALA | 443 | 49.259 | 71.706 | 24.952 | 1.00 | 83.73 | AAAA C |
| ATOM | 4253 | O | ALA | 443 | 48.398 | 71.744 | 25.830 | 1.00 | 83.87 | AAAA O |
| ATOM | 4254 | N | LYS | 444 | 48.914 | 72.052 | 23.713 | 1.00 | 86.20 | AAAA N |
| ATOM | 4256 | CA | LYS | 444 | 47.559 | 72.524 | 23.482 | 1.00 | 85.88 | AAAA C |
| ATOM | 4257 | CB | LYS | 444 | 47.426 | 73.997 | 23.128 | 1.00 | 83.99 | AAAA C |
| ATOM | 4258 | CG | LYS | 444 | 46.673 | 74.734 | 24.241 | 1.00 | 93.60 | AAAA C |
| ATOM | 4259 | CD | LYS | 444 | 45.883 | 73.841 | 25.186 | 1.00 | 95.14 | AAAA C |
| ATOM | 4260 | CE | LYS | 444 | 46.390 | 73.786 | 26.614 | 1.00 | 97.04 | AAAA C |
| ATOM | 4261 | NZ | LYS | 444 | 45.368 | 73.090 | 27.473 | 1.00 | 97.22 | AAAA N |
| ATOM | 4265 | C | LYS | 444 | 46.659 | 71.779 | 22.508 | 1.00 | 84.20 | AAAA C |
| ATOM | 4266 | O | LYS | 444 | 45.428 | 71.901 | 22.635 | 1.00 | 85.63 | AAAA O |
| ATOM | 4267 | N | GLY | 445 | 47.214 | 70.734 | 21.916 | 1.00 | 78.85 | AAAA N |
| ATOM | 4269 | CA | GLY | 445 | 46.368 | 69.786 | 21.208 | 1.00 | 75.06 | AAAA C |
| ATOM | 4270 | C | GLY | 445 | 45.803 | 68.844 | 22.260 | 1.00 | 72.30 | AAAA C |
| ATOM | 4271 | O | GLY | 445 | 44.963 | 67.993 | 21.940 | 1.00 | 74.90 | AAAA O |
| ATOM | 4272 | N | ASP | 446 | 46.300 | 68.981 | 23.492 | 1.00 | 67.97 | AAAA N |
| ATOM | 4274 | CA | ASP | 446 | 45.914 | 68.174 | 24.642 | 1.00 | 62.81 | AAAA C |
| ATOM | 4275 | CB | ASP | 446 | 46.754 | 68.552 | 25.873 | 1.00 | 55.24 | AAAA C |
| ATOM | 4276 | CG | ASP | 446 | 48.213 | 68.169 | 25.801 | 1.00 | 54.07 | AAAA C |
| ATOM | 4277 | OD1 | ASP | 446 | 48.693 | 67.385 | 24.946 | 1.00 | 45.08 | AAAA O |
| ATOM | 4278 | OD2 | ASP | 446 | 49.091 | 68.595 | 26.593 | 1.00 | 50.12 | AAAA O |
| ATOM | 4279 | C | ASP | 446 | 44.438 | 68.274 | 25.016 | 1.00 | 58.07 | AAAA C |
| ATOM | 4280 | O | ASP | 446 | 43.610 | 67.369 | 25.127 | 1.00 | 55.59 | AAAA O |
| ATOM | 4281 | N | ILE | 447 | 44.043 | 69.527 | 25.226 | 1.00 | 54.13 | AAAA N |
| ATOM | 4283 | CA | ILE | 447 | 42.652 | 69.822 | 25.510 | 1.00 | 54.09 | AAAA C |
| ATOM | 4284 | CB | ILE | 447 | 42.505 | 70.502 | 26.877 | 1.00 | 48.92 | AAAA C |
| ATOM | 4285 | CG2 | ILE | 447 | 41.030 | 70.663 | 27.182 | 1.00 | 41.02 | AAAA C |
| ATOM | 4286 | CG1 | ILE | 447 | 43.211 | 69.621 | 27.932 | 1.00 | 52.36 | AAAA C |
| ATOM | 4287 | CD1 | ILE | 447 | 43.468 | 70.329 | 29.237 | 1.00 | 48.47 | AAAA C |
| ATOM | 4288 | C | ILE | 447 | 42.027 | 70.591 | 24.364 | 1.00 | 53.06 | AAAA C |
| ATOM | 4289 | O | ILE | 447 | 41.718 | 71.772 | 24.423 | 1.00 | 56.08 | AAAA O |

Figure 1A-44

```
ATOM   4290  N    ASN  448     41.625  69.915  23.307  1.00 53.17      AAAA N
ATOM   4292  CA   ASN  448     41.013  70.642  22.202  1.00 54.61      AAAA C
ATOM   4293  CB   ASN  448     41.283  69.982  20.863  1.00 49.17      AAAA C
ATOM   4294  CG   ASN  448     40.415  68.786  20.577  1.00 49.40      AAAA C
ATOM   4295  OD1  ASN  448     39.287  68.977  20.113  1.00 52.34      AAAA O
ATOM   4296  ND2  ASN  448     40.990  67.622  20.871  1.00 52.49      AAAA N
ATOM   4299  C    ASN  448     39.518  70.824  22.402  1.00 56.44      AAAA C
ATOM   4300  O    ASN  448     38.816  69.974  22.939  1.00 55.83      AAAA O
ATOM   4301  N    THR  449     39.071  71.917  21.764  1.00 58.52      AAAA N
ATOM   4303  CA   THR  449     37.682  72.351  21.901  1.00 58.62      AAAA C
ATOM   4304  CB   THR  449     37.497  73.845  22.169  1.00 55.90      AAAA C
ATOM   4305  OG1  THR  449     37.913  74.485  20.943  1.00 68.89      AAAA O
ATOM   4307  CG2  THR  449     38.354  74.352  23.310  1.00 59.06      AAAA C
ATOM   4308  C    THR  449     36.920  72.053  20.628  1.00 56.82      AAAA C
ATOM   4309  O    THR  449     35.750  72.381  20.473  1.00 60.87      AAAA O
ATOM   4310  N    ARG  450     37.539  71.304  19.757  1.00 55.76      AAAA N
ATOM   4312  CA   ARG  450     36.887  70.935  18.507  1.00 54.66      AAAA C
ATOM   4313  CB   ARG  450     37.845  71.179  17.377  1.00 48.33      AAAA C
ATOM   4314  CG   ARG  450     38.385  69.975  16.645  1.00 54.81      AAAA C
ATOM   4315  CD   ARG  450     39.487  70.561  15.696  1.00 44.92      AAAA C
ATOM   4316  NE   ARG  450     40.706  70.719  16.488  1.00 52.49      AAAA N
ATOM   4318  CZ   ARG  450     41.544  69.757  16.882  1.00 39.08      AAAA C
ATOM   4319  NH1  ARG  450     41.176  68.572  16.466  1.00 41.07      AAAA N
ATOM   4322  NH2  ARG  450     42.601  70.001  17.610  1.00 45.18      AAAA N
ATOM   4325  C    ARG  450     36.267  69.553  18.557  1.00 56.82      AAAA C
ATOM   4326  O    ARG  450     35.186  69.303  17.992  1.00 58.15      AAAA O
ATOM   4327  N    ASN  451     36.800  68.583  19.324  1.00 56.66      AAAA N
ATOM   4329  CA   ASN  451     36.107  67.311  19.434  1.00 50.27      AAAA C
ATOM   4330  CB   ASN  451     36.725  66.127  18.760  1.00 48.54      AAAA C
ATOM   4331  CG   ASN  451     38.243  66.143  18.764  1.00 60.51      AAAA C
ATOM   4332  OD1  ASN  451     38.779  66.279  19.855  1.00 53.45      AAAA O
ATOM   4333  ND2  ASN  451     38.707  65.976  17.506  1.00 54.88      AAAA N
ATOM   4336  C    ASN  451     35.849  66.854  20.869  1.00 52.97      AAAA C
ATOM   4337  O    ASN  451     35.330  65.750  21.096  1.00 49.71      AAAA O
ATOM   4338  N    ASN  452     36.126  67.668  21.851  1.00 51.98      AAAA N
ATOM   4340  CA   ASN  452     35.769  67.485  23.229  1.00 55.88      AAAA C
ATOM   4341  CB   ASN  452     36.947  67.873  24.136  1.00 54.62      AAAA C
ATOM   4342  CG   ASN  452     37.936  66.736  24.285  1.00 60.96      AAAA C
ATOM   4343  OD1  ASN  452     37.646  65.633  24.735  1.00 51.30      AAAA O
ATOM   4344  ND2  ASN  452     39.153  67.098  23.855  1.00 56.75      AAAA N
ATOM   4347  C    ASN  452     34.603  68.385  23.688  1.00 58.11      AAAA C
ATOM   4348  O    ASN  452     34.785  69.629  23.657  1.00 55.07      AAAA O
ATOM   4349  N    GLY  453     33.444  67.813  23.985  1.00 55.08      AAAA N
ATOM   4351  CA   GLY  453     32.313  68.658  24.296  1.00 59.47      AAAA C
ATOM   4352  C    GLY  453     31.500  69.269  23.174  1.00 64.95      AAAA C
ATOM   4353  O    GLY  453     30.302  69.603  23.276  1.00 65.71      AAAA O
ATOM   4354  N    GLU  454     31.910  69.109  21.910  1.00 67.44      AAAA N
ATOM   4356  CA   GLU  454     31.266  69.543  20.690  1.00 63.63      AAAA C
ATOM   4357  CB   GLU  454     31.739  68.818  19.401  1.00 53.71      AAAA C
ATOM   4358  CG   GLU  454     32.348  67.430  19.738  1.00 49.50      AAAA C
ATOM   4359  CD   GLU  454     32.368  66.620  18.454  1.00 54.61      AAAA C
ATOM   4360  OE1  GLU  454     31.368  66.637  17.702  0.01 54.10      AAAA O
ATOM   4361  OE2  GLU  454     33.417  66.003  18.160  0.01 54.17      AAAA O
ATOM   4362  C    GLU  454     29.762  69.301  20.767  1.00 65.41      AAAA C
ATOM   4363  O    GLU  454     29.022  70.089  20.169  1.00 67.86      AAAA O
ATOM   4364  N    ARG  455     29.288  68.187  21.333  1.00 66.45      AAAA N
ATOM   4366  CA   ARG  455     27.843  67.997  21.371  1.00 69.33      AAAA C
ATOM   4367  CB   ARG  455     27.448  66.733  20.652  1.00 73.38      AAAA C
ATOM   4368  CG   ARG  455     28.467  65.912  19.924  1.00 74.27      AAAA C
ATOM   4369  CD   ARG  455     27.775  64.740  19.240  1.00 79.54      AAAA C
ATOM   4370  NE   ARG  455     27.301  63.638  20.052  1.00 86.31      AAAA N
ATOM   4372  CZ   ARG  455     27.802  62.412  20.189  1.00 88.60      AAAA C
ATOM   4373  NH1  ARG  455     28.890  61.997  19.538  1.00 84.51      AAAA N
ATOM   4376  NH2  ARG  455     27.225  61.523  21.003  1.00 87.36      AAAA N
ATOM   4379  C    ARG  455     27.213  67.934  22.756  1.00 67.35      AAAA C
ATOM   4380  O    ARG  455     26.423  67.025  22.961  1.00 66.26      AAAA O
ATOM   4381  N    ALA  456     27.499  68.879  23.623  1.00 66.52      AAAA N
ATOM   4383  CA   ALA  456     26.947  68.906  24.964  1.00 72.01      AAAA C
ATOM   4384  CB   ALA  456     27.832  68.147  25.939  1.00 61.84      AAAA C
ATOM   4385  C    ALA  456     26.802  70.370  25.371  1.00 75.25      AAAA C
ATOM   4386  O    ALA  456     27.706  71.219  25.202  1.00 81.30      AAAA O
ATOM   4387  N    SER  457     25.653  70.720  25.939  0.50 71.91      AAAA N
ATOM   4389  CA   SER  457     25.431  72.095  26.358  0.50 69.64      AAAA C
ATOM   4390  CB   SER  457     23.991  72.247  26.836  0.50 73.30      AAAA C
ATOM   4391  OG   SER  457     23.422  73.294  26.060  0.50 73.31      AAAA O
ATOM   4393  C    SER  457     26.418  72.510  27.437  0.50 69.27      AAAA C
ATOM   4394  O    SER  457     26.458  71.957  28.530  0.50 67.32      AAAA O
ATOM   4395  N    CYS  458     27.197  73.531  27.117  0.50 70.44      AAAA N
```

Figure 1A-45

```
ATOM   4397  CA   CYS   458      28.287   73.960   27.972  0.50 72.57      AAAA C
ATOM   4398  C    CYS   458      27.949   75.205   28.757  0.50 72.54      AAAA C
ATOM   4399  O    CYS   458      27.065   75.128   29.606  0.50 76.63      AAAA O
ATOM   4400  CB   CYS   458      29.527   74.171   27.089  0.50 75.38      AAAA C
ATOM   4401  SG   CYS   458      30.844   73.032   27.490  0.50 72.18      AAAA S
ATOM   4402  N    ALA   459      28.607   76.306   28.441  0.50 70.13      AAAA N
ATOM   4404  CA   ALA   459      28.445   77.572   29.116  0.50 70.05      AAAA C
ATOM   4405  CB   ALA   459      27.046   78.149   28.996  0.50 70.57      AAAA C
ATOM   4406  C    ALA   459      28.826   77.461   30.601  0.50 70.13      AAAA C
ATOM   4407  O    ALA   459      29.080   78.556   31.154  0.50 69.96      AAAA O
ATOM   4407  OT   ALA   459      28.855   76.301   31.054  0.50 68.22      AAAA O
ATOM   4522  C1   NAG   461      59.581    7.102   61.119  1.00 88.13      AAAA C
ATOM   4524  C2   NAG   461      59.964    7.338   59.697  1.00 91.94      AAAA C
ATOM   4526  N2   NAG   461      58.738    7.699   58.920  1.00 92.72      AAAA N
ATOM   4528  C7   NAG   461      58.400    9.020   58.999  1.00 96.97      AAAA C
ATOM   4529  O7   NAG   461      58.879    9.774   59.726  1.00 98.62      AAAA O
ATOM   4530  C8   NAG   461      57.323    9.390   58.043  1.00100.60      AAAA C
ATOM   4534  C3   NAG   461      60.725    6.225   59.085  1.00 94.77      AAAA C
ATOM   4536  O3   NAG   461      61.417    6.725   57.930  1.00 98.51      AAAA O
ATOM   4538  C4   NAG   461      61.873    5.869   60.064  1.00 96.01      AAAA C
ATOM   4540  O4   NAG   461      62.661    4.821   59.484  1.00 99.20      AAAA O
ATOM   4542  C5   NAG   461      61.359    5.529   61.474  1.00 95.13      AAAA C
ATOM   4545  C6   NAG   461      62.465    5.321   62.495  1.00 93.66      AAAA C
ATOM   4548  O6   NAG   461      62.745    6.364   63.354  1.00 92.13      AAAA O
ATOM   4544  O5   NAG   461      60.625    6.648   61.949  1.00 91.92      AAAA O
ATOM   4550  C1   NAG   463      33.054   15.249   72.938  1.00 43.58      AAAA C
ATOM   4552  C2   NAG   463      31.644   15.282   73.412  1.00 43.62      AAAA C
ATOM   4554  N2   NAG   463      30.709   14.527   72.541  1.00 42.16      AAAA N
ATOM   4556  C7   NAG   463      29.912   13.584   73.099  1.00 40.84      AAAA C
ATOM   4557  O7   NAG   463      29.928   13.406   74.222  1.00 40.10      AAAA O
ATOM   4558  C8   NAG   463      28.975   12.694   72.394  1.00 35.47      AAAA C
ATOM   4562  C3   NAG   463      31.150   16.675   73.448  1.00 45.40      AAAA C
ATOM   4564  O3   NAG   463      29.979   16.555   74.196  1.00 45.99      AAAA O
ATOM   4566  C4   NAG   463      32.117   17.617   74.171  1.00 50.36      AAAA C
ATOM   4568  O4   NAG   463      31.596   18.919   73.891  1.00 53.97      AAAA O
ATOM   4569  C5   NAG   463      33.589   17.477   73.725  1.00 48.50      AAAA C
ATOM   4572  C6   NAG   463      34.490   17.996   74.742  1.00 48.34      AAAA C
ATOM   4575  O6   NAG   463      34.906   18.739   75.671  1.00 57.11      AAAA O
ATOM   4571  O5   NAG   463      33.942   16.120   73.583  1.00 48.58      AAAA O
ATOM   4576  C1   FUC   464      34.544   19.954   76.083  1.00 81.45      AAAA C
ATOM   4578  C2   FUC   464      35.179   21.173   75.463  1.00 86.35      AAAA C
ATOM   4579  O2   FUC   464      35.153   21.169   74.021  1.00 92.94      AAAA O
ATOM   4582  C3   FUC   464      34.252   22.284   75.945  1.00 86.79      AAAA C
ATOM   4584  O3   FUC   464      34.691   23.613   75.596  1.00 87.83      AAAA O
ATOM   4586  C4   FUC   464      33.871   22.274   77.412  1.00 86.67      AAAA C
ATOM   4588  O4   FUC   464      34.598   23.297   78.115  1.00 87.06      AAAA O
ATOM   4590  C5   FUC   464      33.921   20.894   78.040  1.00 85.85      AAAA C
ATOM   4593  C6   FUC   464      34.279   20.768   79.512  1.00 83.37      AAAA C
ATOM   4592  O5   FUC   464      35.042   20.150   77.425  1.00 82.43      AAAA O
ATOM   4597  C1   NAG   465      31.575   19.813   74.940  1.00 64.68      AAAA C
ATOM   4599  C2   NAG   465      31.267   21.207   74.437  1.00 69.57      AAAA C
ATOM   4601  N2   NAG   465      32.480   21.642   73.690  1.00 71.25      AAAA N
ATOM   4603  C7   NAG   465      32.401   21.953   72.381  1.00 73.86      AAAA C
ATOM   4604  O7   NAG   465      31.373   21.835   71.881  1.00 74.80      AAAA O
ATOM   4605  C8   NAG   465      33.679   22.401   71.787  1.00 76.00      AAAA C
ATOM   4609  C3   NAG   465      31.050   22.214   75.546  1.00 72.71      AAAA C
ATOM   4611  O3   NAG   465      30.713   23.517   75.108  1.00 71.03      AAAA O
ATOM   4613  C4   NAG   465      30.035   21.654   76.560  1.00 75.71      AAAA C
ATOM   4615  O4   NAG   465      29.993   22.409   77.793  1.00 76.79      AAAA O
ATOM   4617  C5   NAG   465      30.498   20.238   76.977  1.00 75.45      AAAA C
ATOM   4620  C6   NAG   465      29.461   19.647   77.930  1.00 75.64      AAAA C
ATOM   4623  O6   NAG   465      28.385   19.238   77.142  1.00 76.25      AAAA O
ATOM   4619  O5   NAG   465      30.514   19.425   75.807  1.00 71.44      AAAA O
ATOM   4625  C1   NAG   467      49.927   11.058   87.926  1.00 96.51      AAAA C
ATOM   4627  C2   NAG   467      50.538   11.751   89.100  1.00 99.92      AAAA C
ATOM   4629  N2   NAG   467      49.662   12.898   89.458  1.00101.79      AAAA N
ATOM   4631  C7   NAG   467      49.299   13.021   90.759  1.00103.63      AAAA C
ATOM   4632  O7   NAG   467      49.541   12.267   91.586  1.00105.48      AAAA O
ATOM   4633  C8   NAG   467      48.526   14.239   91.102  1.00105.02      AAAA C
ATOM   4637  C3   NAG   467      51.967   12.134   88.802  1.00101.03      AAAA C
ATOM   4639  O3   NAG   467      52.535   12.761   89.949  1.00100.89      AAAA O
ATOM   4641  C4   NAG   467      52.643   10.771   88.506  1.00101.15      AAAA C
ATOM   4643  O4   NAG   467      54.067   10.834   88.441  1.00101.35      AAAA O
ATOM   4645  C5   NAG   467      52.039   10.160   87.218  1.00100.16      AAAA C
ATOM   4648  C6   NAG   467      52.746    8.852   86.934  1.00 99.75      AAAA C
ATOM   4651  O6   NAG   467      52.088    7.704   87.302  1.00101.54      AAAA O
ATOM   4647  O5   NAG   467      50.671    9.918   87.503  1.00 98.59      AAAA O
ATOM   4653  C1   NAG   469      55.375   46.143   66.863  1.00 48.45      AAAA C
```

Figure 1A-46

| ATOM | 4655 | C2 | NAG | 469 | 56.601 | 46.993 | 66.861 | 1.00 | 50.42 | AAAA | C |
| ATOM | 4657 | N2 | NAG | 469 | 57.106 | 47.015 | 65.451 | 1.00 | 51.50 | AAAA | N |
| ATOM | 4659 | C7 | NAG | 469 | 57.235 | 48.143 | 64.746 | 1.00 | 48.88 | AAAA | C |
| ATOM | 4660 | O7 | NAG | 469 | 56.849 | 49.101 | 65.234 | 1.00 | 55.62 | AAAA | O |
| ATOM | 4661 | C8 | NAG | 469 | 57.838 | 48.134 | 63.394 | 1.00 | 43.70 | AAAA | C |
| ATOM | 4665 | C3 | NAG | 469 | 57.608 | 46.491 | 67.844 | 1.00 | 49.62 | AAAA | C |
| ATOM | 4667 | O3 | NAG | 469 | 58.640 | 47.461 | 68.031 | 1.00 | 47.76 | AAAA | O |
| ATOM | 4669 | C4 | NAG | 469 | 56.843 | 46.263 | 69.172 | 1.00 | 48.47 | AAAA | C |
| ATOM | 4671 | O4 | NAG | 469 | 57.826 | 45.800 | 70.134 | 1.00 | 50.06 | AAAA | O |
| ATOM | 4672 | C5 | NAG | 469 | 55.847 | 45.130 | 68.959 | 1.00 | 50.81 | AAAA | C |
| ATOM | 4675 | C6 | NAG | 469 | 55.190 | 44.720 | 70.239 | 1.00 | 53.92 | AAAA | C |
| ATOM | 4678 | O6 | NAG | 469 | 54.829 | 45.551 | 71.193 | 1.00 | 56.25 | AAAA | O |
| ATOM | 4674 | O5 | NAG | 469 | 54.914 | 45.599 | 68.043 | 1.00 | 55.45 | AAAA | O |
| ATOM | 4679 | C1 | FUC | 470 | 53.830 | 46.395 | 71.203 | 1.00 | 61.17 | AAAA | C |
| ATOM | 4681 | C2 | FUC | 470 | 53.642 | 47.121 | 72.534 | 1.00 | 59.23 | AAAA | C |
| ATOM | 4682 | O2 | FUC | 470 | 54.861 | 46.876 | 73.241 | 1.00 | 55.14 | AAAA | O |
| ATOM | 4685 | C3 | FUC | 470 | 53.421 | 48.429 | 71.757 | 1.00 | 58.39 | AAAA | C |
| ATOM | 4687 | O3 | FUC | 470 | 53.381 | 49.515 | 72.637 | 1.00 | 56.30 | AAAA | O |
| ATOM | 4689 | C4 | FUC | 470 | 52.245 | 48.255 | 70.809 | 1.00 | 61.24 | AAAA | C |
| ATOM | 4691 | O4 | FUC | 470 | 51.061 | 47.904 | 71.544 | 1.00 | 63.74 | AAAA | O |
| ATOM | 4693 | C5 | FUC | 470 | 52.455 | 47.086 | 69.828 | 1.00 | 62.20 | AAAA | C |
| ATOM | 4696 | C6 | FUC | 470 | 51.462 | 46.723 | 68.784 | 1.00 | 59.15 | AAAA | C |
| ATOM | 4695 | O5 | FUC | 470 | 52.567 | 45.889 | 70.781 | 1.00 | 64.68 | AAAA | O |
| ATOM | 4700 | C1 | NAG | 471 | 58.034 | 46.760 | 71.149 | 1.00 | 37.00 | AAAA | C |
| ATOM | 4702 | C2 | NAG | 471 | 58.977 | 46.225 | 72.186 | 1.00 | 40.30 | AAAA | C |
| ATOM | 4704 | N2 | NAG | 471 | 58.958 | 44.787 | 72.509 | 1.00 | 36.82 | AAAA | N |
| ATOM | 4706 | C7 | NAG | 471 | 57.856 | 44.183 | 72.903 | 1.00 | 44.21 | AAAA | C |
| ATOM | 4707 | O7 | NAG | 471 | 56.892 | 44.744 | 72.885 | 1.00 | 51.50 | AAAA | O |
| ATOM | 4708 | C8 | NAG | 471 | 58.202 | 42.814 | 73.323 | 1.00 | 46.02 | AAAA | C |
| ATOM | 4712 | C3 | NAG | 471 | 58.901 | 47.250 | 73.291 | 1.00 | 34.50 | AAAA | C |
| ATOM | 4714 | O3 | NAG | 471 | 59.698 | 46.917 | 74.385 | 1.00 | 35.84 | AAAA | O |
| ATOM | 4716 | C4 | NAG | 471 | 59.645 | 48.488 | 72.694 | 1.00 | 38.52 | AAAA | C |
| ATOM | 4718 | O4 | NAG | 471 | 59.754 | 49.464 | 73.694 | 1.00 | 37.44 | AAAA | O |
| ATOM | 4719 | C5 | NAG | 471 | 59.056 | 48.958 | 71.332 | 1.00 | 36.94 | AAAA | C |
| ATOM | 4722 | C6 | NAG | 471 | 60.116 | 49.692 | 70.525 | 1.00 | 36.14 | AAAA | C |
| ATOM | 4725 | O6 | NAG | 471 | 61.106 | 50.390 | 71.080 | 1.00 | 43.49 | AAAA | O |
| ATOM | 4721 | O5 | NAG | 471 | 58.853 | 47.785 | 70.530 | 1.00 | 34.98 | AAAA | O |
| ATOM | 4727 | C1 | MAN | 472 | 61.035 | 49.984 | 73.959 | 1.00 | 53.37 | AAAA | C |
| ATOM | 4729 | C2 | MAN | 472 | 60.920 | 51.497 | 74.260 | 1.00 | 56.72 | AAAA | C |
| ATOM | 4730 | O2 | MAN | 472 | 59.924 | 51.584 | 75.272 | 1.00 | 62.11 | AAAA | O |
| ATOM | 4733 | C3 | MAN | 472 | 62.216 | 52.031 | 74.840 | 1.00 | 60.70 | AAAA | C |
| ATOM | 4735 | O3 | MAN | 472 | 62.028 | 53.337 | 75.383 | 1.00 | 60.70 | AAAA | O |
| ATOM | 4736 | C4 | MAN | 472 | 62.787 | 51.161 | 75.932 | 1.00 | 55.46 | AAAA | C |
| ATOM | 4738 | O4 | MAN | 472 | 64.085 | 51.595 | 76.171 | 1.00 | 57.16 | AAAA | O |
| ATOM | 4740 | C5 | MAN | 472 | 62.797 | 49.685 | 75.511 | 1.00 | 52.10 | AAAA | C |
| ATOM | 4743 | C6 | MAN | 472 | 63.458 | 48.905 | 76.595 | 1.00 | 50.32 | AAAA | C |
| ATOM | 4746 | O6 | MAN | 472 | 62.990 | 48.969 | 77.885 | 1.00 | 51.02 | AAAA | O |
| ATOM | 4742 | O5 | MAN | 472 | 61.443 | 49.407 | 75.200 | 1.00 | 53.33 | AAAA | O |
| ATOM | 4748 | C1 | MAN | 473 | 62.594 | 54.401 | 74.672 | 1.00 | 72.61 | AAAA | C |
| ATOM | 4750 | C2 | MAN | 473 | 62.417 | 55.679 | 75.569 | 1.00 | 75.28 | AAAA | C |
| ATOM | 4751 | O2 | MAN | 473 | 63.378 | 56.709 | 75.348 | 1.00 | 74.98 | AAAA | O |
| ATOM | 4754 | C3 | MAN | 473 | 60.977 | 56.163 | 75.493 | 1.00 | 78.65 | AAAA | C |
| ATOM | 4756 | O3 | MAN | 473 | 60.841 | 57.447 | 76.148 | 1.00 | 79.16 | AAAA | O |
| ATOM | 4758 | C4 | MAN | 473 | 60.344 | 56.204 | 74.114 | 1.00 | 78.70 | AAAA | C |
| ATOM | 4760 | O4 | MAN | 473 | 58.983 | 56.571 | 74.178 | 1.00 | 78.93 | AAAA | O |
| ATOM | 4762 | C5 | MAN | 473 | 60.499 | 54.802 | 73.474 | 1.00 | 76.89 | AAAA | C |
| ATOM | 4765 | C6 | MAN | 473 | 59.968 | 54.490 | 72.091 | 1.00 | 74.73 | AAAA | C |
| ATOM | 4768 | O6 | MAN | 473 | 60.239 | 55.469 | 71.138 | 1.00 | 71.38 | AAAA | O |
| ATOM | 4764 | O5 | MAN | 473 | 61.916 | 54.562 | 73.463 | 1.00 | 74.97 | AAAA | O |
| ATOM | 4408 | CB | ALA | 479 | 42.462 | 74.494 | 16.374 | 1.00 | 82.09 | BBBB | C |
| ATOM | 4409 | C | ALA | 479 | 40.017 | 74.702 | 17.001 | 1.00 | 91.42 | BBBB | C |
| ATOM | 4410 | O | ALA | 479 | 40.393 | 75.108 | 18.103 | 1.00 | 96.11 | BBBB | O |
| ATOM | 4413 | N | ALA | 479 | 40.696 | 74.461 | 14.624 | 1.00 | 88.43 | BBBB | N |
| ATOM | 4415 | CA | ALA | 479 | 41.033 | 74.108 | 16.033 | 1.00 | 88.85 | BBBB | C |
| ATOM | 4416 | N | ALA | 480 | 38.749 | 74.752 | 16.610 | 1.00 | 92.12 | BBBB | N |
| ATOM | 4418 | CA | ALA | 480 | 37.684 | 75.264 | 17.467 | 1.00 | 91.28 | BBBB | C |
| ATOM | 4419 | CB | ALA | 480 | 37.925 | 76.731 | 17.769 | 1.00 | 86.84 | BBBB | C |
| ATOM | 4420 | C | ALA | 480 | 36.306 | 75.030 | 16.849 | 1.00 | 91.39 | BBBB | C |
| ATOM | 4421 | O | ALA | 480 | 35.413 | 74.647 | 17.610 | 1.00 | 93.79 | BBBB | O |
| ATOM | 4422 | N | GLN | 481 | 36.135 | 75.304 | 15.564 | 0.01 | 89.69 | BBBB | N |
| ATOM | 4424 | CA | GLN | 481 | 34.832 | 75.164 | 14.915 | 1.00 | 87.19 | BBBB | C |
| ATOM | 4425 | CB | GLN | 481 | 34.471 | 76.492 | 14.224 | 0.01 | 92.74 | BBBB | C |
| ATOM | 4426 | CG | GLN | 481 | 34.277 | 77.627 | 15.220 | 1.00 | 99.93 | BBBB | C |
| ATOM | 4427 | CD | GLN | 481 | 34.067 | 79.003 | 14.626 | 1.00 | 103.59 | BBBB | C |
| ATOM | 4428 | OE1 | GLN | 481 | 35.011 | 79.777 | 14.381 | 1.00 | 103.27 | BBBB | O |
| ATOM | 4429 | NE2 | GLN | 481 | 32.792 | 79.328 | 14.398 | 1.00 | 108.00 | BBBB | N |
| ATOM | 4432 | C | GLN | 481 | 34.755 | 73.947 | 14.005 | 1.00 | 85.31 | BBBB | C |
| ATOM | 4433 | O | GLN | 481 | 33.736 | 73.508 | 13.456 | 1.00 | 83.41 | BBBB | O |

Figure 1A-47

```
ATOM   4434  N    LYS  482      35.849  73.188  13.908  1.00 82.85      BBBB N
ATOM   4436  CA   LYS  482      35.982  71.990  13.089  1.00 73.49      BBBB C
ATOM   4437  CB   LYS  482      37.377  71.930  12.480  1.00 73.13      BBBB C
ATOM   4438  CG   LYS  482      38.287  73.128  12.494  1.00 76.33      BBBB C
ATOM   4439  CD   LYS  482      39.413  72.968  11.471  1.00 80.62      BBBB C
ATOM   4440  CE   LYS  482      39.985  74.310  11.027  0.01 76.66      BBBB C
ATOM   4441  NZ   LYS  482      41.252  74.136  10.262  0.01 76.20      BBBB N
ATOM   4445  C    LYS  482      35.779  70.701  13.872  1.00 67.70      BBBB C
ATOM   4446  O    LYS  482      35.879  70.744  15.092  1.00 69.99      BBBB O
ATOM   4447  N    LEU  483      35.530  69.585  13.199  1.00 61.47      BBBB N
ATOM   4449  CA   LEU  483      35.193  68.356  13.896  1.00 59.03      BBBB C
ATOM   4450  CB   LEU  483      34.256  67.529  13.039  1.00 55.20      BBBB C
ATOM   4451  CG   LEU  483      32.779  67.860  12.875  1.00 61.94      BBBB C
ATOM   4452  CD1  LEU  483      32.405  69.154  13.595  1.00 44.78      BBBB C
ATOM   4453  CD2  LEU  483      32.433  67.707  11.385  1.00 44.63      BBBB C
ATOM   4454  C    LEU  483      36.421  67.509  14.229  1.00 59.73      BBBB C
ATOM   4455  O    LEU  483      36.465  66.709  15.165  1.00 57.22      BBBB O
ATOM   4456  N    ILE  484      37.345  67.543  13.262  1.00 56.21      BBBB N
ATOM   4458  CA   ILE  484      38.597  66.822  13.367  1.00 52.58      BBBB C
ATOM   4459  CB   ILE  484      38.480  65.390  12.870  1.00 50.27      BBBB C
ATOM   4460  CG2  ILE  484      37.769  65.319  11.524  1.00 44.85      BBBB C
ATOM   4461  CG1  ILE  484      39.870  64.766  12.756  1.00 39.78      BBBB C
ATOM   4462  CD1  ILE  484      39.888  63.291  12.404  1.00 30.43      BBBB C
ATOM   4463  C    ILE  484      39.623  67.645  12.608  1.00 53.49      BBBB C
ATOM   4464  O    ILE  484      39.158  68.568  11.942  1.00 48.33      BBBB O
ATOM   4465  N    SER  485      40.911  67.499  12.887  1.00 50.86      BBBB N
ATOM   4467  CA   SER  485      41.898  68.335  12.209  1.00 49.78      BBBB C
ATOM   4468  CB   SER  485      41.969  69.753  12.747  1.00 46.06      BBBB C
ATOM   4469  OG   SER  485      43.190  70.035  13.376  1.00 63.03      BBBB O
ATOM   4471  C    SER  485      43.294  67.711  12.240  1.00 50.57      BBBB C
ATOM   4472  O    SER  485      43.510  66.601  12.740  1.00 46.55      BBBB O
ATOM   4473  N    GLU  486      44.246  68.389  11.604  1.00 52.16      BBBB N
ATOM   4475  CA   GLU  486      45.624  67.874  11.509  1.00 59.12      BBBB C
ATOM   4476  CB   GLU  486      46.547  68.683  10.598  1.00 59.71      BBBB C
ATOM   4477  CG   GLU  486      46.221  70.162  10.568  1.00 76.75      BBBB C
ATOM   4478  CD   GLU  486      47.370  71.045  10.983  1.00 80.53      BBBB C
ATOM   4479  OE1  GLU  486      48.315  70.404  11.472  1.00 91.67      BBBB O
ATOM   4480  OE2  GLU  486      47.480  72.289  10.897  1.00 86.00      BBBB O
ATOM   4481  C    GLU  486      46.272  67.773  12.896  1.00 56.50      BBBB C
ATOM   4482  O    GLU  486      46.768  66.747  13.326  1.00 49.83      BBBB O
ATOM   4483  N    GLU  487      45.955  68.738  13.732  1.00 58.37      BBBB N
ATOM   4485  CA   GLU  487      46.129  68.736  15.169  1.00 59.36      BBBB C
ATOM   4486  CB   GLU  487      45.303  69.887  15.729  1.00 61.32      BBBB C
ATOM   4487  CG   GLU  487      45.645  70.232  17.159  1.00 79.21      BBBB C
ATOM   4488  CD   GLU  487      46.397  71.545  17.177  1.00 86.09      BBBB C
ATOM   4489  OE1  GLU  487      45.768  72.610  17.320  1.00 92.00      BBBB O
ATOM   4490  OE2  GLU  487      47.637  71.452  17.026  1.00 96.51      BBBB O
ATOM   4491  C    GLU  487      45.735  67.436  15.841  1.00 58.84      BBBB C
ATOM   4492  O    GLU  487      46.421  67.018  16.761  1.00 61.93      BBBB O
ATOM   4493  N    ASP  488      44.748  66.661  15.474  1.00 56.50      BBBB N
ATOM   4495  CA   ASP  488      44.446  65.347  15.932  1.00 55.61      BBBB C
ATOM   4496  CB   ASP  488      42.947  64.977  15.699  1.00 51.22      BBBB C
ATOM   4497  CG   ASP  488      42.047  66.008  16.267  1.00 45.27      BBBB C
ATOM   4498  OD1  ASP  488      42.114  66.563  17.387  1.00 56.45      BBBB O
ATOM   4499  OD2  ASP  488      41.154  66.399  15.492  1.00 55.11      BBBB O
ATOM   4500  C    ASP  488      45.206  64.211  15.238  1.00 58.91      BBBB C
ATOM   4501  O    ASP  488      44.967  63.042  15.634  1.00 57.00      BBBB O
ATOM   4502  N    LEU  489      45.933  64.513  14.163  1.00 57.39      BBBB N
ATOM   4504  CA   LEU  489      46.659  63.426  13.528  1.00 64.03      BBBB C
ATOM   4505  CB   LEU  489      46.722  63.677  12.024  1.00 62.69      BBBB C
ATOM   4506  CG   LEU  489      45.746  62.788  11.226  1.00 53.71      BBBB C
ATOM   4507  CD1  LEU  489      44.324  63.243  11.514  1.00 51.88      BBBB C
ATOM   4508  CD2  LEU  489      46.072  62.967   9.766  1.00 55.20      BBBB C
ATOM   4509  C    LEU  489      48.017  63.355  14.210  1.00 68.12      BBBB C
ATOM   4510  O    LEU  489      48.860  62.560  13.838  1.00 71.57      BBBB O
ATOM   4511  N    ASN  490      48.306  64.318  15.063  1.00 68.24      BBBB N
ATOM   4513  CA   ASN  490      49.497  64.424  15.855  1.00 75.04      BBBB C
ATOM   4514  CB   ASN  490      49.734  65.910  16.187  1.00 84.46      BBBB C
ATOM   4515  CG   ASN  490      51.191  66.105  16.589  1.00 98.83      BBBB C
ATOM   4516  OD1  ASN  490      52.082  65.342  16.178  1.00 97.25      BBBB O
ATOM   4517  ND2  ASN  490      51.459  67.128  17.407  1.00100.47      BBBB N
ATOM   4520  C    ASN  490      49.350  63.610  17.139  1.00 80.30      BBBB C
ATOM   4521  O    ASN  490      49.891  62.484  17.264  1.00 80.97      BBBB O
ATOM   4521  OT   ASN  490      48.510  64.012  18.001  1.00 89.51      BBBB O
ATOM   4770  S    SUL  493      37.234  -7.808  65.465  1.00108.87      DDDD S
ATOM   4771  O1   SUL  493      38.452  -7.921  66.345  1.00112.65      DDDD O
ATOM   4772  O2   SUL  493      37.611  -7.873  64.020  1.00110.21      DDDD O
ATOM   4773  O3   SUL  493      36.533  -6.555  65.856  1.00109.93      DDDD O
```

Figure 1A-48

```
ATOM   4774  O4  SUL   493     36.333   -8.978  65.639  1.00107.58      DDDD O
ATOM   4775  S   SUL   494     56.567   19.753  66.302  1.00109.81      DDDD S
ATOM   4776  O1  SUL   494     56.597   19.128  67.659  1.00107.98      DDDD O
ATOM   4777  O2  SUL   494     57.964   20.027  65.795  1.00112.59      DDDD O
ATOM   4778  O3  SUL   494     55.749   21.006  66.267  1.00111.35      DDDD O
ATOM   4779  O4  SUL   494     55.886   18.792  65.379  1.00109.86      DDDD O
ATOM   4780  S   SUL   495     34.533   11.240  75.722  1.00114.67      DDDD S
ATOM   4781  O1  SUL   495     35.274   12.213  76.595  1.00111.38      DDDD O
ATOM   4782  O2  SUL   495     35.476   10.329  74.974  1.00113.60      DDDD O
ATOM   4783  O3  SUL   495     33.552   11.860  74.748  1.00112.77      DDDD O
ATOM   4784  O4  SUL   495     33.773   10.278  76.604  1.00113.18      DDDD O
ATOM   4785  S   SUL   496     35.466   24.844  59.093  1.00 50.73      DDDD S
ATOM   4786  O1  SUL   496     35.613   24.843  60.607  1.00 62.59      DDDD O
ATOM   4787  O2  SUL   496     36.002   23.581  58.571  1.00 48.59      DDDD O
ATOM   4788  O3  SUL   496     35.880   26.084  58.455  1.00 56.74      DDDD O
ATOM   4789  O4  SUL   496     33.958   24.953  59.034  1.00 59.34      DDDD O
ATOM   4790  S   SUL   497     47.653   -2.303  70.199  1.00 68.98      DDDD S
ATOM   4791  O1  SUL   497     47.849   -1.058  70.996  1.00 68.52      DDDD O
ATOM   4792  O2  SUL   497     48.594   -2.509  69.072  1.00 70.94      DDDD O
ATOM   4793  O3  SUL   497     46.187   -2.393  69.810  1.00 73.47      DDDD O
ATOM   4794  O4  SUL   497     47.799   -3.446  71.129  1.00 71.33      DDDD O
ATOM   4795  S   SUL   498     56.527   35.758  75.513  1.00 71.48      DDDD S
ATOM   4796  O1  SUL   498     55.870   35.013  76.621  1.00 72.97      DDDD O
ATOM   4797  O2  SUL   498     57.759   34.996  75.167  1.00 69.11      DDDD O
ATOM   4798  O3  SUL   498     56.619   37.237  75.785  1.00 72.45      DDDD O
ATOM   4799  O4  SUL   498     55.623   35.809  74.330  1.00 72.74      DDDD O
ATOM   4800  S   SUL   499     40.639   27.365  69.499  1.00 74.04      DDDD S
ATOM   4801  O1  SUL   499     40.218   26.039  70.045  1.00 76.00      DDDD O
ATOM   4802  O2  SUL   499     42.089   27.608  69.835  1.00 75.15      DDDD O
ATOM   4803  O3  SUL   499     39.823   28.467  70.098  1.00 77.27      DDDD O
ATOM   4804  O4  SUL   499     40.424   27.245  68.018  1.00 75.70      DDDD O
ATOM   4805  S   SUL   500     44.996   53.228  20.568  1.00 83.89      DDDD S
ATOM   4806  O1  SUL   500     45.080   54.400  21.461  1.00 84.79      DDDD O
ATOM   4807  O2  SUL   500     46.109   52.266  20.827  1.00 90.38      DDDD O
ATOM   4808  O3  SUL   500     45.032   53.674  19.135  1.00 92.23      DDDD O
ATOM   4809  O4  SUL   500     43.762   52.396  20.723  1.00 91.61      DDDD O
ATOM   4810  OW  WAT   501     29.970    6.904  77.713  1.00 34.84      DDDD O
ATOM   4813  OW  WAT   502     42.522   18.998  78.232  1.00 55.27      DDDD O
ATOM   4816  OW  WAT   503     37.561   21.003  67.518  1.00 41.63      DDDD O
ATOM   4819  OW  WAT   504     50.446    5.721  63.485  1.00 57.37      DDDD O
ATOM   4822  OW  WAT   505     56.668   24.854  72.729  1.00 57.34      DDDD O
ATOM   4825  OW  WAT   506     50.605   57.695  22.727  1.00 54.26      DDDD O
ATOM   4828  OW  WAT   507     55.123   37.781  61.204  1.00 43.71      DDDD O
ATOM   4831  OW  WAT   508     17.414   -9.070  74.793  1.00 48.79      DDDD O
ATOM   4834  OW  WAT   509     44.263   20.885  63.811  1.00 28.64      DDDD O
ATOM   4837  OW  WAT   510     45.085   19.708  84.433  1.00 49.09      DDDD O
ATOM   4840  OW  WAT   511     33.537    1.927  71.115  1.00 60.39      DDDD O
ATOM   4843  OW  WAT   512     19.279    4.902  75.254  1.00 55.23      DDDD O
ATOM   4846  OW  WAT   513     11.502   -0.835  68.996  1.00 57.51      DDDD O
ATOM   4849  OW  WAT   514     24.591   17.207  56.665  1.00 56.36      DDDD O
ATOM   4852  OW  WAT   515     56.947   34.914  62.552  1.00 36.47      DDDD O
ATOM   4855  OW  WAT   516     58.092   39.983  66.234  1.00 30.34      DDDD O
ATOM   4858  OW  WAT   517     48.308   40.726  56.768  1.00 81.69      DDDD O
ATOM   4861  OW  WAT   518     25.776    2.355  85.630  1.00 66.34      DDDD O
ATOM   4864  OW  WAT   519     30.644   68.108  30.765  1.00 82.28      DDDD O
ATOM   4867  OW  WAT   520     38.739   54.257  43.611  1.00 43.41      DDDD O
ATOM   4870  OW  WAT   521     22.886    4.470  64.871  1.00 48.71      DDDD O
ATOM   4873  OW  WAT   522     30.938   50.249  19.364  1.00 54.00      DDDD O
ATOM   4876  OW  WAT   523     32.413    9.061  42.441  1.00 44.45      DDDD O
ATOM   4879  OW  WAT   524     41.019   42.560  55.653  1.00 43.40      DDDD O
ATOM   4882  OW  WAT   525     54.268   51.393  37.513  1.00 55.10      DDDD O
ATOM   4885  OW  WAT   526     37.130   13.599  81.397  1.00 46.49      DDDD O
ATOM   4888  OW  WAT   527     42.585   10.244  84.472  1.00 35.95      DDDD O
ATOM   4891  OW  WAT   528     43.661   61.633  18.450  1.00 41.05      DDDD O
ATOM   4894  OW  WAT   529     27.980   19.862  53.348  1.00 54.59      DDDD O
ATOM   4897  OW  WAT   530     59.527   38.520  64.116  1.00 37.96      DDDD O
ATOM   4900  OW  WAT   531     22.451    1.046  57.437  1.00 59.31      DDDD O
ATOM   4903  OW  WAT   532     30.380   16.123  70.205  1.00 40.39      DDDD O
ATOM   4906  OW  WAT   533     46.835   27.888  65.854  1.00 52.34      DDDD O
ATOM   4909  OW  WAT   534     39.446   49.001  45.379  1.00 46.05      DDDD O
ATOM   4912  OW  WAT   535     46.992   51.272  50.722  1.00 52.62      DDDD O
ATOM   4915  OW  WAT   536     44.263   18.776  73.017  1.00 40.61      DDDD O
ATOM   4918  OW  WAT   537     33.670   58.861  20.848  1.00 51.56      DDDD O
ATOM   4921  OW  WAT   538     52.469   21.639  73.804  1.00 61.98      DDDD O
ATOM   4924  OW  WAT   539     49.985   44.871  37.324  1.00 45.45      DDDD O
ATOM   4927  OW  WAT   540     24.074   -1.791  60.077  1.00 40.40      DDDD O
ATOM   4930  OW  WAT   541     35.207    0.714  79.039  1.00 51.34      DDDD O
ATOM   4933  OW  WAT   542     31.231   -1.176  62.362  1.00 48.33      DDDD O
```

Figure 1A-49

```
ATOM   4936  OW   WAT   543    41.726  -5.156  55.290  1.00 60.67       DDDD O
ATOM   4939  OW   WAT   544    48.564  37.335  72.612  1.00 71.69       DDDD O
ATOM   4942  OW   WAT   545    49.501  40.030  67.582  1.00 44.88       DDDD O
ATOM   4945  OW   WAT   546    54.851   7.987  60.018  1.00 49.91       DDDD O
ATOM   4948  OW   WAT   547    30.459 -14.058  70.554  1.00 84.42       DDDD O
ATOM   4951  OW   WAT   548    57.310  32.779  60.848  1.00 50.77       DDDD O
END
```

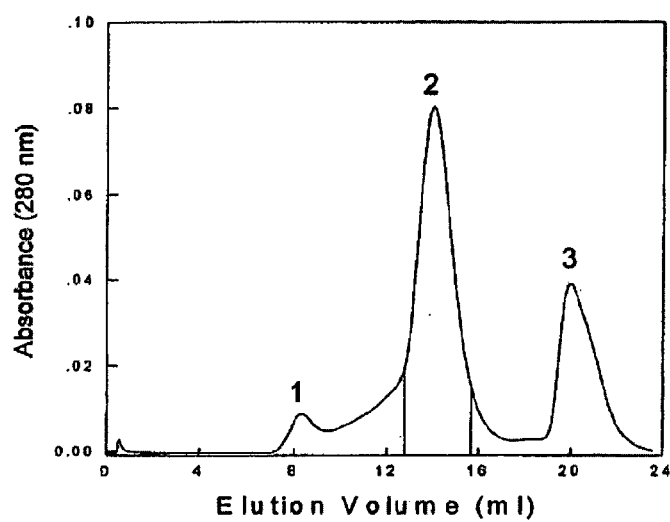 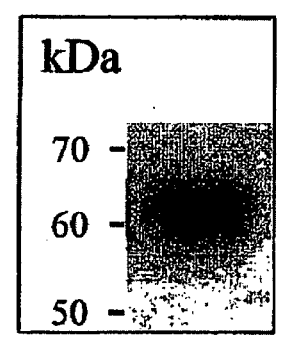
Figure 3a                    Figure 3b

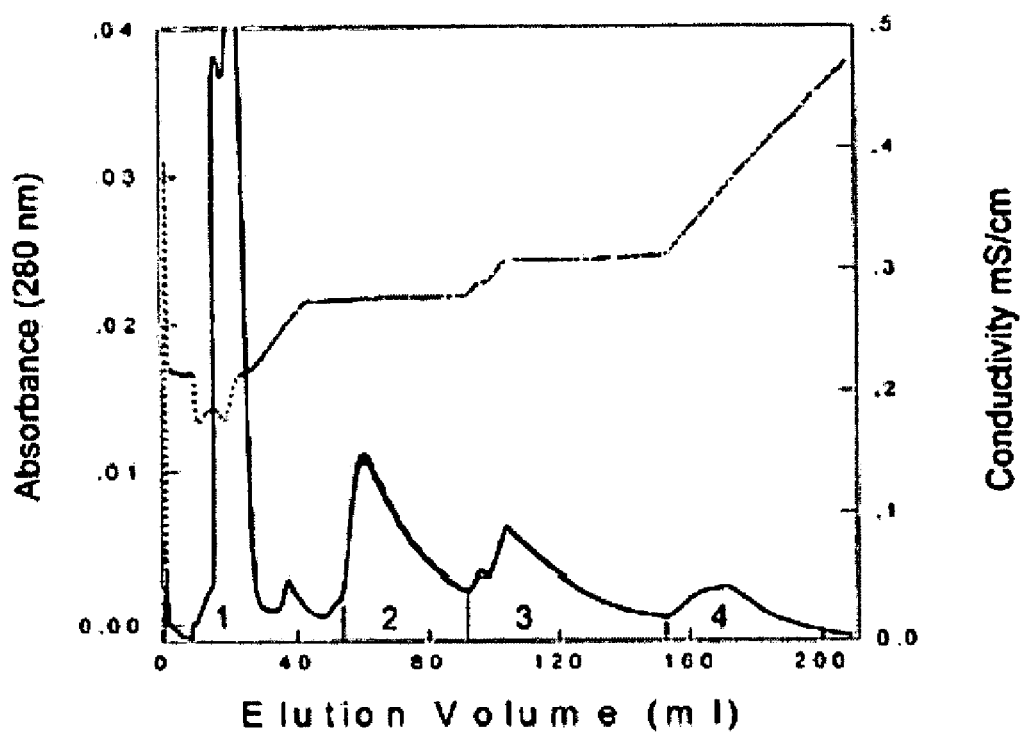
Figure 4a
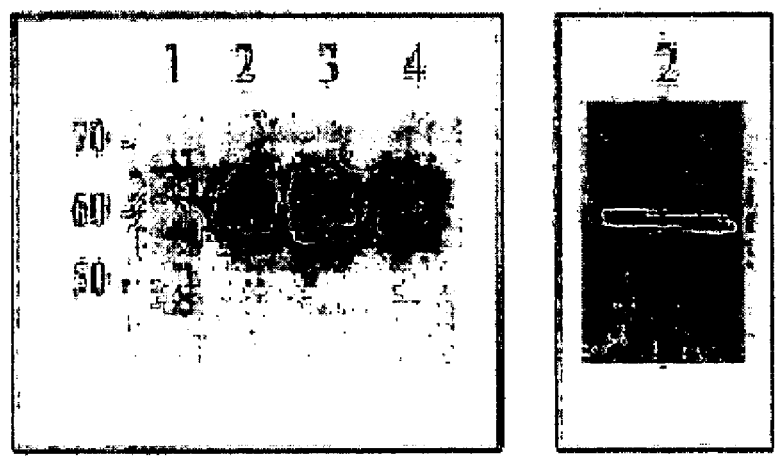
Figure 4b       Figure 4c

Figure 6

Sequence Alignment of hIGF-1R, hIR and hIRR ectodomains.

Derived by use of the PileUp program in the software package of the Genetics Computer Group, 575 Science Drive, Madison, Wisconsin, USA.

```
Symbol Comparison table: GenRunData:PileUpPep.Cmp  CompCheCk: 1254

GapWeight: 3.0
          GapLengthWeight: 0.1

Name: Higf1r         Len:   972   CheCk: 1781   Weight:  1.00
Name: Hir            Len:   972   CheCk: 2986   Weight:  1.00
Name: Hirr           Len:   972   CheCk: 9819   Weight:  1.00

*                      *
Higf1r  .....EICGP GIDIRNDYQQ LKRLENCTVI EGYLHILLIS K..AEDYRSY  43
   Hir  HLYPGEVC.P GMDIRNNLTR LHELENCSVI EGHLQILLMF KTRPEDFRDL  49
  Hirr  ....MNVC.P SLDIRSEVAE LRQLENCSVV EGHLQILLMF TATGEDFRGL  45

Higf1r  RFPKLTVITE YLLLFRVAGL ESLGDLFPNL TVIRGWKLFY NYALVIFEMT  93
   Hir  SFPKLIMITD YLLLFRVYGL ESLKDLFPNL TVIRGSRLFF NYALVIFEMV  99
  Hirr  SFPRLTQVTD YLLLFRVYGL ESLRDLFPNL AVIRGTRLFL GYALVIFEMP  95

*
Higf1r  NLKDIGLYNL RNITRGAIRI EKNADLCYLS TVDWSLILDA VSNNYIVGNK 143
   Hir  HLKELGLYNL MNITRGSVRI EKNNELCYLA TIDWSRILDS VEDNYIVLNK 149
  Hirr  HLRDVALPAL GAVLRGAVRV EKNQELCHLS TIDWGLLQPA PGANHIVGNK 145

*   *           *                *      *    *    *
Higf1r  PPK.ECGDLC PGTMEEKPM. CEKTTINNEY NYRCWTTNRC QKMCPSTCGK 191
   Hir  DDNEECGDIC PGTAKGKTN. CPATVINGQF VERCWTHSHC QKVCPTICKS 198
  Hirr  LG.EECADVC PGVLGAAGEP CAKTTFSGHT DYRCWTSSHC QRVCPCPHG. 193

*    **    *    *          *   *        *    *
Higf1r  RACTENNECC HPECLGSCSA PDNDTACVAC RHYYYAGVCV PACPPNTYRF 241
   Hir  HGCTAEGLCC HSECLGNCSQ PDDPTKCVAC RNFYLDGRCV ETCPPPYYHF 248
  Hirr  MACTARGECC HTECLGGCSQ PEDPRACVAC RHLYFQGACL WACPPGTYQY 243

*         *        *--------*        *    *
Higf1r  EGWRCVDRDF CANILSAES. ...SDSEGFV IHDGECMQEC PSGFIRNGSQ 287
   Hir  QDWRCVNFSF CQDLHHKCKN SRRQGCHQYV IHNNKCIPEC PSGYTMNSSN 298
  Hirr  ESWRCVTAER CASLHSVPG. ....RASTFG IHQGSCLAQC PSGFTRNSS. 287

*  *      *   *                         *
Higf1r  SMYCIPCEGP CPKVCEEEKK TKTIDSVTSA QMLQGCTIFK GNLLINIRRG 337
   Hir  .LLCTPCLGP CPKVCHLLEG EKTIDSVTSA QELRGCTVIN GSLIINIRGG 347
  Hirr  SIFCHKCEGL CPKECKV..G TKTIDSIQAA QDLVGCTHVE GSLILNLRQG 335

Higf1r  NNIASELENF MGLIEVVTGY VKIRHSHALV SLSFLKNLRL ILGEEQLEGN 387
   Hir  NNLAAELEAN LGLIEEISGY LKIRRSYALV SLSFFRKLRL IRGETLEIGN 397
  Hirr  YNLEPQLQHS LGLVETITGF LKIKHSFALV SLGFFKNLKL IRGDAMVDGN 385

*
Higf1r  YSFYVLDNQN LQQLWDWDHR NLTIKAGKMY FAFNPKLCVS EIYRMEEVTG 437
   Hir  YSFYALDNQN LRQLWDWSKH NLTITQGKLF FHYNPKLCLS EIHKMEEVSG 447
  Hirr  YTLYVLDNQN LQQLGSWVAA GLTIPVGKIY FAFNPRLCLE HIYRLEEVTG 435
```

Figure 9

```
                         *     !End of 1-462 fragment
Higflr  TKGRQSKGDI NTRNNGERAS CESDV  LHFTS TTTSKNRIII TWHRYRPPDY  487
   Hir  TKGRQERNDI ALKTNGDQAS CENEL  LKFSY IRTSFDKILL RWEPYWPPDF  497
  Hirr  TRGRQNKAEI NPRTNGDRAA CQTRT  LRFVS NVTEADRILL RWERYEPLEA  485
*
Higflr  RDLISFTVYY KEAPFKNVTE YDGQDACGSN SWNMVDVDLP .....PNKDV    532
   Hir  RDLLGFMLFY KEAPYQNVTE FDGQDACGSN SWTVVDIDPP LRSNDPKSQN    547
  Hirr  RDLLSFIVYY KESPFQNATE HVGPDACGTQ SWNLLDVELP L.....SRTQ    530

Higflr  EPGILLHGLK PWTQYAVYVK AVTLTMVEND HIRGAKSEIL YIRTNASVPS    582
   Hir  HPGWLMRGLK PWTQYAIFVK TL.VTFSDER RTYGAKSDII YVQTDATNPS    596
  Hirr  EPGVTLASLK PWTQYAVFVR AITLTTEEDS PHQGAQSPIV YLRTLPAAPT    580

Higflr  IPLDVLSASN SSSQLIVKWN PPSLPNGNLS YYIVRWQRQP QDGYLYRHNY    632
   Hir  VPLDPISVSN SSSQIILKWK PPSDPNGNIT HYLVFWERQA EDSELFELDY    646
  Hirr  VPQDVISTSN SSSHLLVRWK PPTQRNGNLT YYLVLWQRLA EDGDLYLNDY    630

*                            *    ** **     *
Higflr  CSKD.KIPIR KYADGTIDIE EVTENPKTEV CGGEKGPCCA C...PKTEAE    678
   Hir  CLKGLKLPSR TWS.PPFESE DSQKHNQSE. YEDSAGECCS C...PKTDSQ    691
  Hirr  CHRGLRLPTS N.NDPRFDGE DGDPEAEME. .....SDCCP CQHPPPGQVL    673

α------->< ------β
Higflr  KQAEKEEAEY RKVFENFLHN SIFVPRPERK RRDVMQVANT TMSSRSRNTT    728
   Hir  ILKELEESSF RKTFEDYLHN VVFVPRPSRK RRSLGDVGNV TVAVP...TV    738
  Hirr  PPLEAQEASF QKKFENFLHN AITIPISPWK VTSINKSPQR D.SGRHRRAA    722
                                                            *
Higflr  AA..DTYNIT DPEELETEYP FFESRVDNKE RTVISNLRPF TLYRIDIHSC  776
   Hir  AAFPNTSSTS VPTSPEEHRP F..EKVVNKE SLVISGLRHF TGYRIELQAC  786
  Hirr  GPLRLGGNSS DFEIQEDKVP ........RE RAVLSGLRHF TEYRIDIHAC  764

*
Higflr  NHEAEKLGCS ASNFVFARTM PAEGADDIPG PVTWEPRPEN SIFLKWPEPE  826
   Hir  NQDTPEERCS VAAYVSARTM PEAKADDIVG PVTHEIFENN VVHLMWQEPK  836
  Hirr  NHAAHTVGCS AATFVFARTM PHREADGIPG KVAWEASSKN SVLLRWLEPP  814

*                 *
Higflr  NPNGLILMYE IKYGS.QVED QRECVSRQEY RKYGGAKLNR LNPGNYTARI  875
   Hir  EPNGLIVLYE VSYRRYGDEE LHLCVSRKHF ALERGCRLRG LSPGNYSVRI  886
  Hirr  DPNGLILKYE IKYRRLGEEA TVLCVSRLRY AKFGGVHLAL LPPGNYSARV  864

Higflr  QATSLSGNGS WTDPVFFYVQ AKTGYENFIH L                     906
   Hir  RATSLAGNGS WTEPTYFYVT DYLDVPSNIA K                     917
  Hirr  RATSLAGNGS WTDSVAFYIL GPEEEDAGGL H                     895
```

Figure 9-A

| Schematic interpretations of EM images | | | |
|---|---|---|---|
| Sample | Projection along y axis | z axis | x axis |
| hIR |  |  | |
| hIR/ 83-7 |  | |  |
| hIR/ 83-14 |  |  | |
| hIR/ 18-44/83-14 |  |  | |
| hIR/ 83-7/18-44 |  | | |
| hIR/ 83-7/83-14 |  | | |

METHOD OF DESIGNING AGONISTS AND ANTAGONISTS TO IGF RECEPTOR

FIELD OF THE INVENTION

This invention relates to the field of receptor structure and receptor/ligand interactions. In particular it relates to the field of rising receptor structure to predict the structure of related receptors and to the use of the determined structures and predicted structures to select and screen for agonists and antagonists of the polypeptide ligands.

BACKGROUND OF THE INVENTION

Insulin is the peptide hormone that regulates glucose uptake and metabolism. The two types of diabetes mellitus are associated either with an inability to produce insulin because of destruction of the pancreatic islet cells (Homo-Delarche, F. & Boitard, C., 1996, Immunol. Today 10: 456–460) or with poor glucose metabolism resulting from either insulin resistance at the target tissues, or from inadequate insulin secretion by the islets or faulty liver function (Taylor, S. I., et al., 1994, Diabetes, 43: 735–740).

Insulin-like growth factors-1 and 2 (IGF-1 and 2) are structurally related to insulin, but are more important in tissue growth and development than in metabolism. They are primarily produced in the liver in response to growth hormone, but are also produced in most other tissues, where they function as paracrine/autocrine regulators. The IGFs are strong mitogens, and are involved in numerous physiological states and certain cancers (Baserga, R., 1996, TibTech 14: 150–152).

Epidermal growth factor (EGF) is a small polypeptide cytokine that is unrelated to the insulin/IGF family. It stimulates marked proliferation of epithelial tissues, and is a member of a larger family of structurally-related cytokines, such as transforming growth factor $\alpha$, amphiregulin, betacellulin, heparin-binding EGF and some viral gene products. Abnormal EGF family signalling is a characteristic of certain cancers (Soler, C. & Carpenter, G., 1994 In Nicola, N. (ed)"Guidebook to Cytokines and Their receptors", Oxford Univ. Press, Oxford, pp 194–197; Walker, F. & Burgess, A. W., 1994, In Nicola, N. (ed) "Guidebook to Cytokines and Their receptors", Oxford Univ. Press, Oxford, pp 198–201).

Each of these growth factors mediates its biological actions through binding to the corresponding receptor. The IR, IGF-1R and the insulin receptor-related receptor (IRR), for which the ligand is not known, are closely related to each other, and are referred to as the insulin receptor subfamily. A large body of information is now available concerning the primary structure of these insulin receptor subfamily members (Ebina, Y., et al., 1985 Cell 40: 747–758. Ullrich, A., et al., 1985, Nature 313: 756–761; Ullrich, A. et al., 1986, EMBO J 5: 2503–2512; Shier, P. & Watt, V. M., 1989, J. Biol. Chem. 264: 14605–14608) and the identification of some of their functional domains (for reviews see De Meyts, P. 1994, Diabetologia 37: 135–148; Lee, J. & Pilch, P. F. 1994 Amer. J. Physiol. 266: C319–C334; Schaffer, L. 1994, Eur. J. Biochem. 221: 1127–1132). IGF-1R, IR and IRR are members of the tyrosine kinase receptor superfamily and are closely related to the epidermal growth factor receptor (EGFR) subfamily, with which they share significant sequence identity in the extracellular region as well as in the cytoplasmic kinase domains (Ullrich, A. et al., 1984 Nature 309: 418–425; Ward, C. W. et al., 1995 Proteins: Structure Function & Genetics 22: 141–153). Both the insulin and EGF receptor subfamilies have a similar arrangement of two homologous domains (L1 and L2) separated by a cys-rich region of approximately 160 amino acids containing 22–24 cys residues (Bajaj, M., et al., 1987 Biochim. Biophys. Acta 916: 220–226; Ward, C. W. et al., 1995 Proteins: Structure Function & Genetics 22: 141–153). The C-terminal portion of the IGF-1R ectodomain (residues 463 to 906) is comprised of four domains: a connecting domain, two fibronectin type 3 (Fn3) repeats, and an insert domain (O'Bryan, J. P., et al., 1991 Mol Cell Biol 11: 5016–5031). The C-terminal portion of the EGFR ectodomain (residues 477–621) consists solely of a second cys-rich region containing 20 cys residues (Ullrich, A. et al., 1984, Nature 309: 418–425).

Little is known about the secondary, tertiary and quaternary structure of the ectodomains of these receptor subfamilies. Unlike the members of the EGFR subfamily which are transmembrane monomers which dimerise on binding ligand, the IR subfamily members are homodimers, held together by disulphide bonds. The extracellular region of the IR/IGF-1R/IRR monomers contains an $\alpha$-chain (~703 to 735 amino acid residues) and 192–196 residues of the $\beta$-chain. There is a ~23 residue transmembrane segment, followed by the cytoplasmic portion (354 to 408 amino acids), which contains the catalytic tyrosine kinase domain flanked by juxtamembrane and C-tail regulatory regions and is responsible for mediating all receptor-specific functions (White, M. F. & Kahn, C. R. 1994 J. Biol. Chem. 269: 1–4). Chemical analyses of the receptor suggest that the $\alpha$-chains are linked to the $\beta$-chains via a single disulphide bond, with the IR dimer being formed by at least two $\alpha$—$\alpha$ disulphide linkages (Finn, F. M., et al., 1990, Proc. Natl. Acad. Sci. 87: 419–423; Chiacchia, K. B., 1991, Biochem. Biophys. Res. Commun. 176, 1178–1182: Schaffer, L. & Ljungqvist, L., 1992, Biochem. Biophys. Res. Comm. 189: 650–653; Sparrow, L. G., et al., 1997, J. Biol. Chem. 47: 29460–29467).

Although the three-dimensional (3D) structures of the ligands EGF, TGF-alpha (Hommel, U., et al., 1992, J. Mol. Biol. 227:271–282), insulin (Dodson, E. J., et al., 1983, Biopolymers 22:281–291), IGF-1 (Sato, A., et al., 1993, Int J Peptide Protein Res 41:433–440) and IGF-2 (Torres, A. M., et al., 1995, J. Mol. Biol. 248:385–401) are known, and numerous analytical and functional studies of ligand binding to EGFR (Soler, C. & Carpenter, G., 1994 In Nicola (ed) "Guidebook to Cytokines and Their receptors", Oxford Univ. Press, Oxford, pp 194–197), IGF-1R and IR (see De Meyts, P., 1994 Diabetologia, 37:135–148) have been carried out, the mechanisms of ligand binding and subsequent transmembrane signalling have not been resolved.

Ligand-induced, receptor-mediated phosphorylation is the signalling mechanism by which most cytokines, polypeptide hormones and membrane-anchored ligands exert their biological effects. The primary kinase may be part of the intracellular portion of the transmembrane receptor protein, as in the tyrosine kinase receptors (for review see Yarden, Y., et al., 1988, Ann. Rev. Biochem. 57:443–478) or the Ser/Thr kinase receptors (Alevizopoulos, A. & Mermod, N., 1997, BioEssays, 19:581–591) or may be non-covalently associated with the cytoplasmic tail of the transmembrane protein(s) making up the receptor complex, as in the case of the haemopoietic growth factor receptors (Stahl, N., et al., 1995, Science 267:1349–1353). The end result is the same, ligand binding leads to receptor dimerization or oligomerization or a conformational change in pre-existing receptor dimers or oligomers, resulting in activation by transphosphorylation, of the covalently attached or non-covalently associated protein kinase domains (Hunter, T., 1995, Cell, 80:225–236).

Many oncogenes have been shown to be homologous to growth factors, growth factor receptors or molecules in the signal transduction pathways (Baserga, R., 1994 Cell, 79:927–930; Hunter, T., 1997 Cell, 88:333–346). One of the best examples is v-Erb (related to the EGFR). Since overexpression of a number of growth factor receptors results in ligand-dependent transformation, an alternate strategy for oncogenes is to regulate the expression of growth factor receptors or their ligands or to directly bind to the receptors to stimulate the same effect (Baserga, R., 1994 Cell, 79:927–930). Examples are v-Src, which activates IGF-1 R intracellularly; c-Myb, which transforms cells by enhancing the expression of IGF1R; and SV40 T antigen which interacts with the IGF-1R and enhances the secretion of IGF-1 (see Baserga, R., 1994 Cell, 79:927–930 for review). Cells in which the IGF-R has been disrupted or deleted cannot be transformed by SV40 T antigen. If oncogenes activate growth factors and their receptors, then tumour suppressor genes should have the opposite effect. One good example of this is the Wilm's tumour suppressor gene, WT1, which suppresses the expression of IGF-1R (Drummond, J. A., et al., 1992, Science, 257:275–277). Cells that are driven to proliferate by oncogenes undergo massive apoptosis when growth factor receptors are ablated, since, unlike normal cells, they appear unable to withdraw from the cell-cycle and enter into the $G_0$ phase (Baserga, R., 1994 Cell, 79:927–930).

The insulin-like growth factor-1 receptor (IGF-1R) is one of several growth-factor receptors that regulate the proliferation of mammalian cells. However, its ubiquitousness and certain unique aspects of its function make IGF-1R an ideal target for specific therapeutic interventions against abnormal growth, with very little effect on normal cells (see Baserga, R., 1996 TIBTECH, 14:150–152). The receptor is activated by IGF1, IGF2 and insulin, and plays a major role in cellular proliferation in at least three ways: it is essential for optimal growth of cells in vitro and in vivo; several cell types require IGF-1R to maintain the transformed state; and activated IGF-1R has a protective effect against apoptotic cell death (Baserga, R., 1996 TIBTECH, 14:150–152). These properties alone make it an ideal target for therapeutic interventions. Transgenic experiments have shown that IGF-1R is not an absolute requirement for cell growth, but is essential for the establishment of the transformed state (Baserga, R., 1994 Cell, 79: 927–930). In several cases (human glioblastoma, human melanoma; human breast carcinoma; human lung carcinoma; human ovarian carcinoma; human rhabdomyosarcoma: mouse melanoma, mouse leukaemia; rat glioblastoma; rat rhabdomyosarcoma; hamster mesothelioma) the transformed phenotype can be reversed by decreasing the expression of IGF-1R using antisense to IGF-1R (Baserga, R., 1996 TIBTECH 14:150–152); or by interfering with its function by antibodies to IGF-1R (human breast carcinoma; human rhabdomyosarcoma) or by dominant negatives of IGF-1R (rat glioblastoma; Baserga, R., 1996 TIBTECH 14:150–152).

Three effects are observed when the function of IGF-1R is impaired: tumour cells undergo massive apoptosis which results in inhibition of tumourogenesis; surviving tumour cells are eliminated by a specific immune response; and such a host response can cause a regression of an established wild-type tumour (Resnicoff, M., et al., 1995, Cancer Res. 54:2218–2222). These effects, plus the fact that interference with IGF-R function has a limited effect on normal cells (partial inhibition of growth without apoptosis) makes IGF-1R a unique target for therapeutic interventions (Baserga, R., 1996 TIBTECH 14:150–152). In addition IGF-1R is downstream of many other growth factor receptors, which makes it an even more generalised target. The implication of these findings is that if the number of IGF-1Rs on cells can be decreased or their function antagonised, then tumours cease to grow and can be removed immunologically. These studies establish that IGF-1R antagonists will be extremely important therapeutically.

Many cancer cells have constitutively active EGFR (Sandgreen, E. P., et al., 1990, Cell, 61:1121–135; Karnes, W. E. J., et al., 1992, Gastroenterology, 102:474–485) or other EGFR family members (Hines, N. E., 1993, Semin. Cancer Biol. 4:19–26). Elevated levels of activated EGFR occur in bladder, breast, lung and brain tumours (Harris, A. L., et al., 1989, In Furth & Greaves (eds) The Molecular Diagnostics of human cancer. Cold Spring Harbor Lab. Press, CSH, NY, pp 353–357). Antibodies to EGFR can inhibit ligand activation of EGFR (Sato, J. D., et al., 1983 Mol. Biol. Med. 1:511–529) and the growth of many epithelial cell lines (Aboud-Pirak E., et al., 1988, J. Natl Cancer Inst. 85:1327–1331). Patients receiving repeated doses of a humanised chimeric anti-EGFR monoclonal antibody showed signs of disease stabilization. The large doses required and the cost of production of humanised monoclonal antibody is likely to limit the application of this type of therapy. These findings indicate that the development of EGF antagonists will be attractive anticancer agents.

SUMMARY OF THE INVENTION

The present inventors have now obtained 3D structural information concerning the insulin-like growth factor receptor (IGF-1R). This information can be used to predict the structure of related members of the insulin receptor family and provides a rational basis for the development of ligands for specific therapeutic applications.

Accordingly, in a first aspect the present invention provides a method of designing a compound able to bind to a molecule of the insulin receptor family and to modulate an activity mediated by the molecule, including the step of assessing the stereochemical complementarity between the compound and the receptor site of the molecule, wherein the receptor site includes:

(a) amino acids 1 to 462 of the receptor for IGF-1, having the atomic coordinates substantially as shown in FIG. 1;

(b) a subset of said amino acids, or;

(c) amino acids present in the amino acid sequence of a member of the insulin receptor family, which form an equivalent three-dimensional structure to that of the receptor molecule as depicted in FIG. 1.

The phrase "insulin receptor family" encompasses, for example, IGF-1R, IR and IRR. In general, insulin receptor family members show similar domain arrangements and share significant sequence identity (preferably at least 40% identity).

By "stereochemical complementarity" we mean that the biologically active substance or a portion thereof correlates, in the manner of the classic "lock-and-key" visualisation of ligand-receptor interaction, with the groove in the receptor site.

In a preferred embodiment of this aspect of the invention, the compound is selected or modified from a known compound identified from a database.

In a further preferred embodiment, the compound is designed so as to complement the structure of the receptor molecule as depicted in FIG. 1.

In a further preferred embodiment, the compound has structural regions able to make close contact with amino acid residues at the surface of the receptor site lining the groove, as depicted in FIG. 2.

In a further preferred embodiment, the compound has a stereochemistry such that it can interact with both the L1 and L2 domains of the receptor site.

In a further preferred embodiment, the compound has a stereochemistry such that it can interact with the L1 domain of a first monomer of the receptor homodimer, and with the L2 domain of the other monomer of the receptor homodimer.

In a further preferred embodiment, the interaction of the compound with the receptor site alters the position of at least one of the L1, L2 or cysteine-rich domains of the receptor molecule relative to the position of at least one of the other of said domains. Preferably, the compound interacts with the β sheet of the L1 domain of the receptor molecule, thereby causing an alteration in the position of the L1 domain relative to the position of the cysteine-rich domain or of the L2 domain. Alternatively, the compound interacts with the receptor site in the region of the interface between the L1 domain an the cysteine-rich domain of the receptor molecule, thereby causing the L1 domain and the cysteine-rich domain to move away from each other. In another preferred embodiment, the compound interacts with the hinge region between the L2 domain and the cysteine-rich domain of the receptor molecule, thereby causing an alteration in the positions of the L2 domain and the cysteine-rich domain relative to each other.

In a further preferred embodiment, the stereochemical complementarity between the compound and the receptor site is such that the compound has a $K_b$ for the receptor side of less than $10^{-6}$M, more preferably is less than $10^{-8}$M.

In a further preferred embodiment or the first aspect of the present invention, the compound has the ability to increase an activity mediated by the receptor molecule.

In a further preferred embodiment, the compound has the ability to decrease an activity mediated by the receptor molecule. Preferably, the stereochemical interaction between the compound and the receptor site is adapted to prevent the binding of a natural ligand of the receptor molecule to the receptor site. It is preferred that the compound has a $K_1$ of less than $10^{-6}$M, more preferably less than $10^{-8}$M and more preferably less than $10^{-9}$M.

In a further preferred embodiment of the first aspect of the present invention, the receptor is the IGF-1R, or the insulin receptor.

In a second aspect, the present invention provides a computer-assisted method for identifying potential compounds able to bind to a molecule of the insulin receptor family and to modulate an activity mediated by the molecule, using a programmed computer including a processor, an input device, and an output device, including the steps of:
 (a) inputting into the programmed computer, through the input device, data comprising the atomic coordinates of the IGF-1R molecule as shown in FIG. 1, or a subset thereof;
 (b) generating, using computer methods, a set of atomic coordinates of a structure that possesses stereochemical complementarity to the atomic coordinates of the IGF-1R site as shown in FIG. 1, or a subset thereof, thereby generating a criteria data set;
 (c) comparing, using the processor, the criteria data set to a computer database of chemical structures;
 (d) selecting from the database, using computer methods, chemical structures which are structurally similar to a portion of said criteria data set; and
 (e) outputting, to the output device, the selected chemical structures which are similar to a portion of the criteria data set.

In a preferred embodiment of the second aspect, the programmed computer includes a data storage system which includes the database of chemical structures.

In a preferred embodiment of the second aspect, the method is used to identify potential compounds which have the ability to decrease an activity mediated by the receptor.

In another preferred embodiment, the computer-assisted method further includes the step of selecting one or more chemical structures from step (e) which interact with the receptor site of the molecule in a manner which prevents the binding of natural ligands to the receptor site.

In another preferred embodiment, the computer-assisted method further includes the step of obtaining a compound with a chemical structure selected in steps (d) and (e), and testing the compound for the ability to decrease an activity mediated by the receptor.

In a further preferred embodiment, the computer-assisted method is used to identify potential compounds which have the ability to increase an activity mediated by the receptor molecule.

In another preferred embodiment, the computer-assisted method further includes the step of obtaining a molecule with a chemical structure selected in steps (d) and (e), and testing the compound for the ability to increase an activity mediated by the receptor.

In a further preferred embodiment of the second aspect of the present invention, the receptor is the IGF-1R, or the insulin receptor.

In a third aspect, the present invention provides a method of screening of a putative compound having the ability to modulate the activity of a receptor of the insulin receptor family, including the steps of identifying a putative compound by a method according to the first or second aspects, and testing the compound for the ability to increase or decrease an activity mediated by the receptor.

In a preferred embodiment of the third aspect, the test is carried out in vitro.

In a further preferred embodiment of the third aspect, the test is a high throughput assay.

In a preferred embodiment of the third aspect, the test is carried out in vivo.

BRIEF DESCRIPTION OF THE DRAWINGS

FIG. 1. IGF-1R residues 1–462, in terms of atomic coordinates refined to a resolution of 2.6 Å (average accuracy ≈0.3 Å). The coordinates are in relation to a Cartesian system of orthogonal axes.

FIG. 2. Depiction of the residues lining the groove of the IGF-1R receptor fragment 1–462.

FIG. 3. Gel filtration chromatography of affinity-purified IGF-1R/462 protein. The protein was purified on a Superdex S200 column (Pharmacia) fitted to a BioLogic L.C. system (Biorad), equilibrated and eluted at 0.8 ml/min with 40 mM Tris/150 mM NaCl/0.02% NaN3 adjusted to pH 8.0. (a) Protein eluting in peak 1 contained aggregated IGF-1R/462 protein, peak 2 contained monomeric protein and peak 3 contained the c-myc undecapeptide used for elution from the Mab 9E10 immunoaffinity column. (b) Non-reduced SDS-PAGE of fraction 2 from IGF-1R/462 obtained following Superdex S200 (FIG. 1a). Standard proteins are indicated.

FIGS. 4(a), 4(b) and 4(c). Ion exchange chromatography of affinity-purified, truncated IGF-1R ectodomain. A mixture of gradient and isocratic elution chromatography was performed on a Resource Q column (Pharmacia) fitted to a BioLogic System (Biorad), using 20 mM Tris/pH 8.0 as buffer A and the same buffer containing 1M NaCl as buffer B. Protein solution in TBSA was diluted at least 1:2 with water and loaded onto the column at 2 ml/min. Elution was monitored by absorbance (280 nM) AND CONDUCTIVITY (mS/cm). Target protein gel (pH 3–7; Novex Australian Pty Ltd) of fraction 2. The pI was estimated at 5.1 from standard proteins (now shown).

FIG. 6. Amino acid sequence of IGF-IR and related proteins (SEQ ID NO. 1, SEQ ID No. 2, SEQ ID NO. 3, SEQ ID NO. 4, SEQ ID NO. 5, and SEQ ID NO. 6). a, L1 and L2 domains of human IGF-1R are shown based on a sequence alignment for the two proteins and a structural alignment for the L1 and L2 domains. Positions showing conservation physico-chemical properties of amino acids are boxed, residues used in the structural alignment are shown in Times Italic and residues which form the Trp 176 pocket are in Times Bold. Secondary structure elements for L1 (above the sequences) and L2 (below) are indicated as cylinders for helices and arrows for B-strands. Strands are shaded (pale, medium and dark grey) according to the B-sheet to which they belong. Disulfide bonds are also indicated. b, Cys-rich domains of human IGF-1R, IR and EGFR (domains 2 and 4) are aligned based on sequence and structural considerations. Secondary structural elements and disulfide bonds are indicated above the sequences. The dashed bond is only present in IR. Different types of disulfide bonded modules are labeled below the sequences as open, filled or broken lines. Boxed residues show conservation of physico-chemical properties and structurally conserved residues for modules 4–7 are shown in Times Italic. Residues from EGFR which do not conform to the pattern are in lowercase with probable disulfide bonding indicated below and the conserved Trp 176 and the semi-conserved Gln 182 are in Times Bold.

FIG. 9. Sequence alignment of hIGF-1R (SEQ ID NO.11), Hir (SEQ ID NO. 12), and hIRR (SEQ ID NO. 13) ectodomains, derived by use of the PileUp program in the software package of Genetics Computer Group, 575 Science Drive, Madison, Wis., USA. for assignment of homologous 3D structures see FIG. 6.

DETAILED DESCRIPTION OF THE INVENTION

Figure 5:
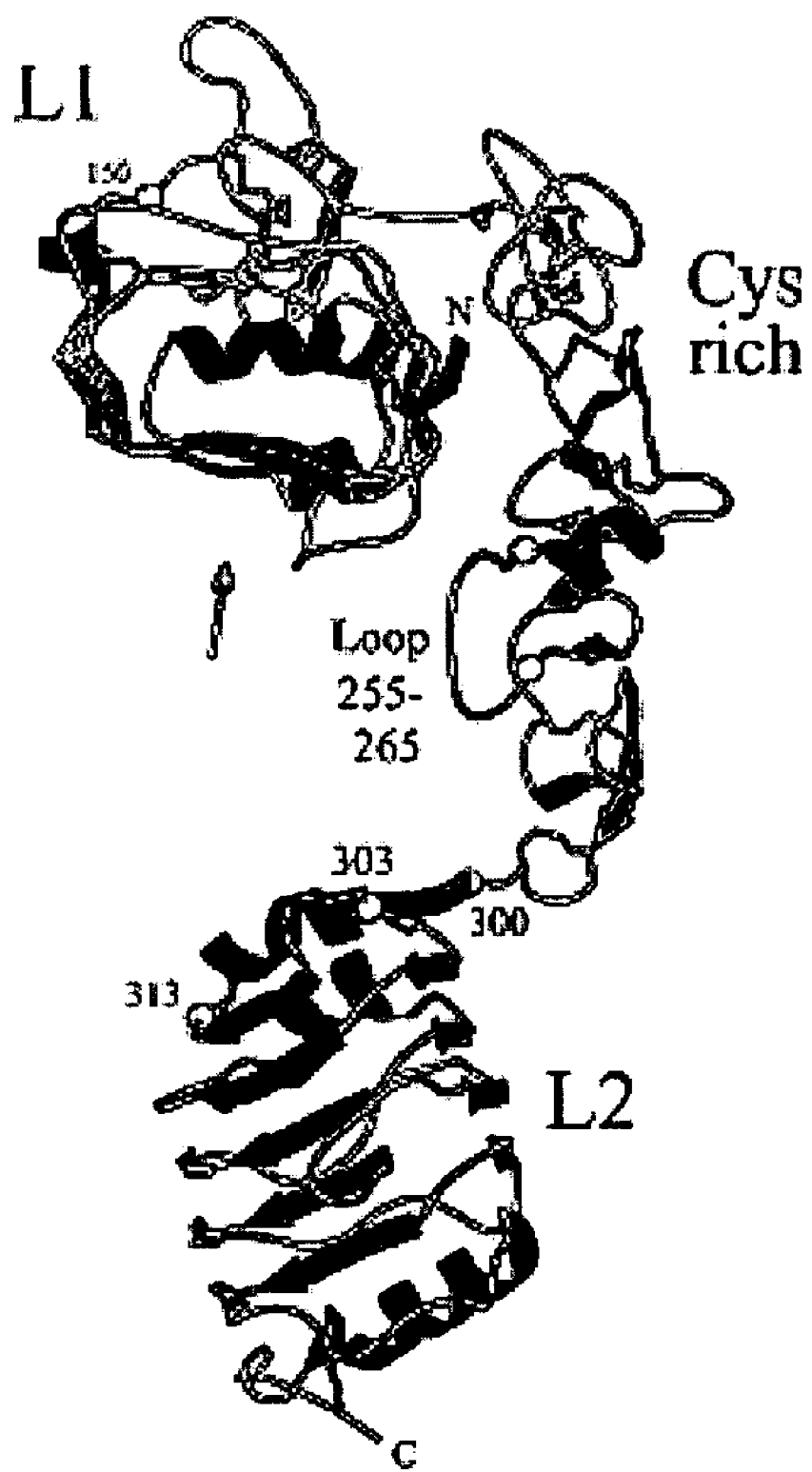
FIG. 5. Polypeptide fold for residues 1–462 of IGF-1R. The L1 domain is at the top, viewed from the N-terminal end and L2 is at the bottom. The space at the centre is of sufficient size to accommodate IGF-1. Helices are indicated by curled ribbon and b-strands by arrows. Cysteine side chains are drawn as ball-and-stick with lines showing disulfide bonds. The arrow points in the direction of view for L1 in FIG. 7.

We describe herein the expression, purification, and crystallization of a recombinant truncated IGF-1R fragment (residues 1–462) containing the L1-cysteine-rich-L2 region of the ectodomain. The selected truncation position is just downstream of the exon 6/exon 7 junction (Abbott. A. M., et al., 1992. J Biol. Chem., 267:10759–10763), and occurs at a position where the sequences of the IR and EGFR families diverge markedly (Ward, C. W., et al., 1995, Proteins: Struct., Funct., Genet. 22:141–153; Lax, I., et al., 1988, Molec. Cellul. Biol. 8:1970–1978) suggesting it represents a domain boundary. To limit the effects of glycosylation, the IGF-1R fragment was expressed in Lec8 cells, a glycosylation mutant of Chinese hamster ovary (CHO) cells, whose defined glycosylation defect produces N-linked oligosaccharides truncated at N-acetyl glucosamine residues distal to mannose residues (Stanley, P. 1989, Molec. Cellul. Biol. 9:377–383). Such an approach has facilitated glycoprotein crystallization (Davis, S. J., et al., 1993. Protein Eng. 6:229–232; Liu, J., et al., 1996, J. Biol. Chem. 271:33639–33646).

The IGF-1R construct described herein includes a c-myc peptide tag (Hoogenboom, H. R., et al., 1991, Nucleic Acids Res. 19:4133–4137) that is recognised by the Mab 9E10 (Evan, G. I., et al., 1985, Mol. Cell. Biol. 5:3610–3616) enabling the expressed product to be purified by peptide elution from an antibody affinity column followed by gel filtration over Superdex S200. The purified proteins crystallized under a sparse matrix screen (Jancarik, J. & Kim, S.-H., 1991, J. Appl. Cryst. 24:409–411) but the crystals were of variable quality, with the best diffracting to 3.0–3.5 Å. Isocratic gradient elution by anion-exchange chromatography yielded protein that was less heterogenous and gave crystals of sufficient quality to determine the structure of the first three domains of the human IGF-1R.

The IGF-1R fragment consisted of residues 1–462 of IGF-1R linked via an enterokinase-cleavable pentapeptide sequence to an eleven residue c-myc peptide tag at the C-terminal end. The fragment was expressed in Lec8 cells by continuous media perfusion in a bioreactor using porous carrier disks. It was secreted into the culture medium and purified by peptide elution from an anti-c-myc antibody column followed by Superdex S200 gel filtration. The receptor fragment bound two anti-IGF-1R monoclonal antibodies, 24–31 and 24–60, which recognize conformationial epitopes, but could not be shown to bind IGF-1 or IGF-2. Crystals of variable quality were grown as rhombic prisms in 1.7 M ammonium sulfate at pH 7.5 with the best diffracting to 3.0–3.5 Å. Further purification by isocratic elution on an anion-exchange column gave protein which produced better quality crystals, diffracting to 2.6 Å, that were suitable for X-ray structure determination.

The structure of this fragment (IGF-1R residues 1–462: L1-cys rich-L2 domains) has been determined to 2.6 Å resolution by X-ray diffraction. The L domains each adopt a compact shape consisting of a single stranded right-handed β-helix. The cys-rich region is composed of eight disulphide-bonded modules, seven of which form a rod-shaped domain with modules associated in a novel manner. At the centre of this reasonably extended structure is a space, bounded by all three domains, and of sufficient size to accommodate a ligand molecule. Functional studies on IGF-1R and other members of the insulin receptor family show that the regions primarily responsible for hormone-binding map to this central site. Thus this structure gives a first view of how members of the insulin receptor family might interact with their ligands.

Another group has reported the crystallization of a related receptor, the EGFR, in a complex with its ligand EGF (Weber, W. et al., 1994, J Chromat. 679:181–189). However, difficulties were encountered with these crystals which diffracted to only 6 Å, insufficient for the determination of an atomic resolution structure of this complex (Weber, W., et al., 1994, J Chromat 679:181–189) or the generation of accurate models of structurally related receptor domains such as IGF-1R and IR by homology modelling.

The present inventors have developed 3D structural information about cytokine receptors in order to enable a more accurate understanding of how the binding of ligand leads to signal transduction. Such information provides a rational basis for the development of ligands for specific therapeutic applications, something that heretofore could not have been predicted de novo from available sequence data.

The precise mechanisms underlying the binding of agonists and antagonists to the IGF-1R site are not fully clarified. However, the binding of ligands to the receptor site, preferably with an affinity in the order of $10^{-8}M$ or higher, is understood to arise from enhanced stereochemical complementarity relative to naturally occurring IGF-1 ligands.

Figure 2:
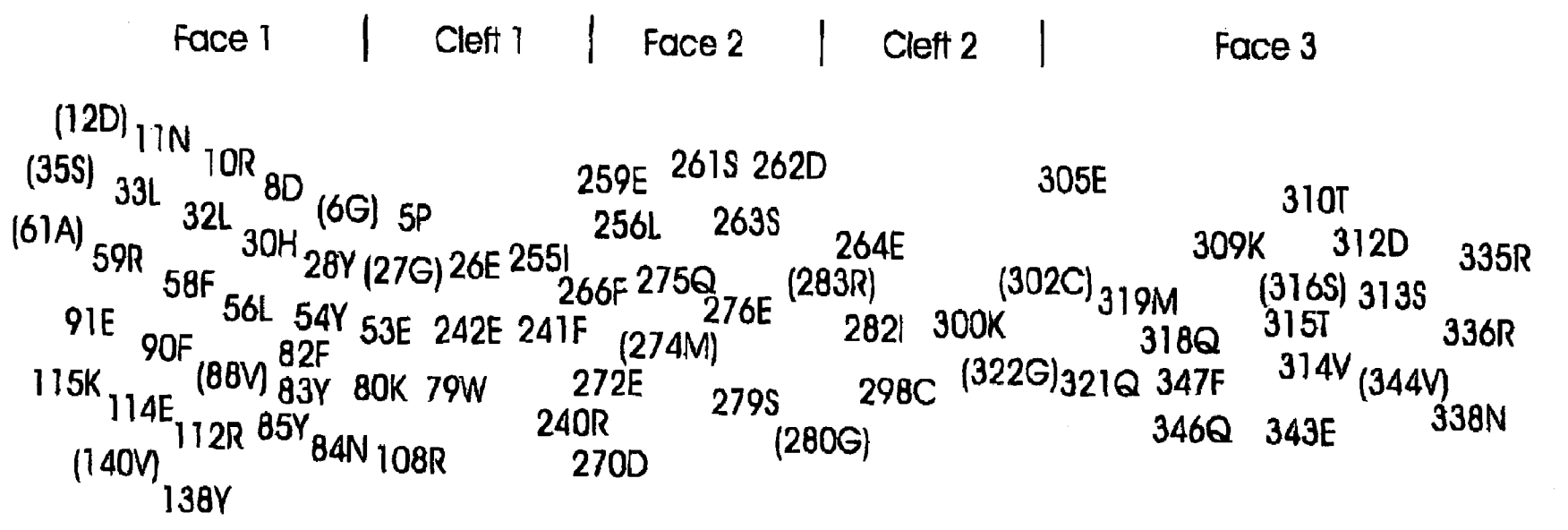

Such stereochemical complementarity, pursuant to the present invention, is characteristic of a molecule that matches intra-site surface residues lining the groove of the receptor site as eneumerated by the coordinates set out in FIG. 1. The residues lining the groove are depicted in FIG. 2. By "match" we mean that the identified portions interact with the surface residues, for example, via hydrogen bonding or by enthalpy-reducing Van der Waals interactions which promote desolvation of the biologically active substance within the site, in such a way that retention of the biologically active substance within the groove is favoured energetically.

Substances which are complemetary to the shape of the receptor site characterised by amino acids positioned at atomic coordinates set out in FIG. 1 may be able to bind to the receptor site and, when the binding is sufficiently strong, substantially prohibit binding of the naturally occurring ligands to the site.

It will be appreciated that it is not necessary that the complementarity between ligands and the receptor site extend over all residues lining the groove in order to inhibit binding of the natural ligand. Accordingly, agonists or antagonists which bind to a portion of the residues lining the groove are encompassed by the present invention.

In general, the design of a molecule possessing stereochemical complementarity can be accomplished by means of techniques that optimize, either chemically or geometrically, the "fit" between a molecule and a target receptor. Known techniques of this sort are reviewed by Sheridan and Venkataraghavan, Acc. Chem Res. 1987 20 322; Goodford, J. Med. Chem. 1984 27 557; Beddell, Chem. Soc. Reviews 1985, 279; Hol, Angew. Chem. 1986 25 767 and Verlinde C. L. M. J & Hol, W. G. J. Structure 1994, 2, 577, the respective contents of which are hereby incorporated by reference. See also Blundell et al., Nature 1987 326 347 (drug development based on information regarding receptor structure).

Thus, there are two preferred approaches to designing a molecule, according to the present invention, that complements the shape of IGF-1R or a related receptor molecule. By the geometric approach, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule, as ligand). The second preferred approach entails an assessment of the interaction of respective chemical groups ("probes") with the active site at sample positions within and around the site, resulting in an array of energy values from which three-dimensional contour surfaces at selected energy levels can be generated.

The geometric approach is illustrated by Kuntz et al., J. Mol. Biol. 1982 161 269, the contents of which are hereby incorporated by reference, whose algorithm for ligand design is implemented in a commercial software package distributed by the Regents of the University of California and further described in a document, provided by the distributor, which is entitled "Overview of the DOCK Package, Version 1.0,", the contents of which are hereby incorporated by reference. Pursuant to the Kuntz algorithm, the shape of the cavity represented by the IGF-R1 site is defined as a series of overlapping spheres of different radii. One or more extant data bases of crystallographic data, such as the Cambridge Structural Database System maintained by Cambridge University (University Chemical Laboratory, Lensfield Road, Cambridge CB2 1EW, U.K.) and the Protein Data Bank maintained by Brookhaven National Laboratory (Chemistry Dept. Upton, N.Y. 11973, U.S.A.), is then searched for molecules which approximate the shape thus defined.

Molecules identified in this way, on the basis of geometric parameters, can then be modified to satisfy criteria associated with chemical complementarity, such as hydrogen bonding, ionic interactions and Van der Waals interactions.

The chemical-probe approach to ligand design is described, for example, by Goodford, J. Med. Chem. 1985 28 849, the contents of which are hereby incorporated by reference, and is implemented in several commercial software packages, such as GRID (product of Molecular Discovery Ltd., West Way House, Elms Parade, Oxford OX2 9LL, U.K.). Pursuant to this approach, the chemical prerequisites for a site-complementing molecule are identified at the outset, by probing the active site (as represented via the atomic coordinates shown in FIG. 1) with different chemical probes, e.g., water, a methyl group, an amine nitrogen, a carboxyl oxygen, and a hydroxyl. Favored sites for interaction between the active site and each probe are thus determined, and from the resulting three-dimensional pattern of such sites a putative complementary molecule can be generated.

The chemical-probe approach is especially useful in defining variants of a molecule known to bind the target receptor. Accordingly, crystallographic analysis of IGF-1 bound to the receptor site is expected to provide useful information regarding the interaction between the archetype ligand and the active site of interest.

Programs suitable for searching three-dimensional databases to identify molecules bearing a desired pharmacophore include: MACCS-3D and ISIS/3D (Molecular Design Ltd., San Leandro, Calif.), ChemDBS-3D (Chemical Design Ltd., Oxford, U.K.), and Sybyl/3 DB Unity (Tripos Associates, St. Louis, Mo.).

Programs suitable for pharmacophore selection and design include: DISCO (Abbott Laboratories, Abbott Park, Ill.), Catalyst (Bio-CAD Corp., Mountain View, Calif.), and ChemDBS-3D (Chemical Design Ltd., Oxford, U.K.).

Databases of chemical structures are available from a number of sources including Cambridge Crystallographic Data Centre (Cambridge, U.K.) and Chemical Abstracts Service (Columbus, Ohio).

De novo design programs include Ludi (Biosym Technologies Inc., San Diego, Calif.), Sybyl (Tripos Associates) and Aladdin (Daylight Chemical Information Systems, Irvine, Calif.).

Those skilled in the art will recognize that the design of a mimetic may require slight structural alteration or adjustment of a chemical structure designed or identified using the methods of the invention.

The invention may be implemented in hardware or software, or a combination of both. However, preferably, the invention is implemented in computer programs executing on programmable computers each comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object-oriented programming language to communicate with a computer system. However, the programs can be implemented in assembly or machine language, if desired. In any case, the language may be compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Compounds designed according to the methods of the present invention may be assessed by a number of in vitro and in vivo assays of hormone function. For example, the identification of IGF-1R antagonists of may be undertaken using a solid-phase receptor binding assay. Potential antagonists may be screened for their ability to inhibit the binding of europium-labelled IGF ligands to soluble, recombinant IGF-1R in a microplate-based format. Europium is a lanthanide fluorophore, the presence of which can be measured using time-resolved fluorometry. The sensitivity of this assay matches that achieved by radioisotopes, measurement is rapid and is performed in a microplate format to allow high-sample throughput, and the approach is gaining wide acceptance as the method of choice in the development of screens for receptor agonists/antagonists (see Apell et. al. J. Biomolec. Screening 3:19–27, 1998: Inglese et. al. Biochemistry 37:2372–2377, 1998).

Binding affinity and inhibitor potency may be measured for candidate inhibitors using biosensor technology.

The IGF-1R antagonists may be tested for their ability to modulate receptor activity using a cell-based assay incorporating a stably transfected, IGF-1-responsive reporter gene [Souriau, C., Fort, P., Roux, P., Hartley, O., LeFranc, M-P. and Weill, M., 1997, Nucleic Acids Res. 25, 1585–1590]. An IGF-1-responsive, luciferase reporter gene has been assembled and transfected in 293 cells. The assay addresses the ability of IGF-1 to activate the reporter gene in the presence of novel ligands. It offers a rapid (results within 6–8 hours of hormone exposure), high-throughput (assay can be conducted in a 96-well format for automated counting) analysis using an extremely sensitive detection system (chemiluminescence). Once candidate compounds have been identified, their ability to antagonise signal transduction via the IGF-1R can be assessed using a number of routine in vitro cellular assays such as inhibition of IGF-1-mediated cell proliferation, induction of apoptosis in the presence of IGF-1 and the ablation of IGF-1-driven anchorage-independent cell growth in soft agar [D'Ambrosio, C., Ferber, A., Resnicoff, M. and Baserga, R., 1996, Cancer Res. 56, 4013–4020]. Such assays may be conducted on the P6 cell line, a cell line highly responsive to IGF as a result of the constitutive overexpression of the IGF-1R (45–50.000 receptors/cell, [Pietrzkowski, Z., Sell, C., Lammers, R., Ullrich, A. and Baserga, R., 1992, Cell Growth. Diff. 3, 199–205]). Ultimately, the efficacy of any antagonist as a tumour therapeutic may be tested in vivo in animals bearing tumour isografts and xenografts as described [Resnicoff. M. Burgaud, J-L., Rotman, H. L., Abraham, D. and Baserga, R., 1995, Cancer Res. 55, 3739–3741; Resnicoff, M., Sell, C., Rubini, M., Coppola, D., Ambrose, D., Baserga, R. and Rubin, R., 1994 Cancer Res. 54: 2218–2222].

Tumour growth inhibition assays may be designed around a nude mouse xenograft model using a range of cell lines. The effects of the receptor antagonists and inhibitors may be tested on the growth of subcutaneous tumours.

A further use of the structure of the IGF-1R fragment described here is in facilitating structure determination of a related protein, such as a larger fragment of this receptor, another member of the insulin receptor family or a member of the EGF receptor family. This new structure may be either of the protein alone, or in complex with its ligand. For crystallographic analysis this is achieved using the method of molecular replacement (Brunger, Meth. Enzym. 1997 276 558–580, Navaza and Saludjian, ibid. 581–594, Tong and Rossmann, ibid. 594–611, Bentley, ibid. 611–619) in a program such as XPLOR. In this procedure diffraction data is collected from a crystalline protein of unknown structure. A transform of these data (Patterson function) is compared with a Patterson function calculated from a known structure. Firstly, the one Patterson function is rotated on the other to determine the correct orientation of the unknown molecule in the crystal. The translation function is then calculated to determine the location of the molecule with respect to the crystal axes. Once the molecule has been correctly positioned in the unit cell initial phases for the experimental data may be calculated. These phases are necessary for calculation of an electron density map from which structural differences may be observed and for refinement of the structure. Due to limitations in the method the search molecule must be structurally related to that which is to be determined. However it is sufficient for only part of the unknown structure (e.g. <50%) to be similar to the search molecule. Thus the three dimensional structure of IGF-1R residues 1–462 may be used to solve structures consisting of related receptors, enabling a program of drug design as outlined above.

In summary, the general principles of receptor-based drug design can be applied by persons skilled in the art, using the crystallographic results presented above, to produce ligands of IGF-1R or other related receptors, having sufficient stereochemical complementarity to exhibit high affinity binding to the receptor site.

The present invention is further described below with reference to the following, non-limiting examples.

EXAMPLE 1

Expression, Purification and Crystallization of the IGF-1R Fragment.

Several factors hamper macromolecular crystallization including sample selection, purity, stability, solubility (McPherson, A., et al., 1995, Structure 3:759–768); Gilliland, G. L. & Ladner, J. E., 1996, Curr. Opin. Struct. Biol. 6:595–603), and the nature and extent of glycosylation (Davis, S. J., et al., 1993, Protein Eng. 6:229–232). Initial attempts to obtain structural data from soluble IGF-1R ectodomain (residues 1–906) protein, expressed in Lec8 cells (Stanley, P. 1989, Molec. Cellul. Biol. 9:377–383) and purified by affinity chromatography, produced large, well-formed crystals (1.0 mm×0.2 mm×0.2 mm) which gave no discernible X-ray diffraction pattern (unpublished data). Similar difficulties have been encountered with crystals of the structurally-related epidermal growth factor receptor (EGFR) ectodomain, which diffracted to only 6 Å, insufficient for the determination of an atomic resolution structure (Weber, W. et al., 1994, J Chromat 679:181–189). This prompted us to search for a fragment of IGF-1R that was more amenable to X-ray crystallographic studies.

The fragment expressed (residues 1–462) comprises the L1-cysteine-rich-L2 region of the ectodomain. The selected truncation position at Val462 is four residues downstream of the exon 6/exon 7 junction (Abbott, A. M., et al., 1992, J Biol. Chem. 267:10759–10763) and occurs at a position where the sequences of the IR and the structurally related EGFR families diverge markedly (Lax. I., et al., 1988, Molec Cell Biol. 8:1970–1978: Ward, C. W., et al., 1995, Proteins: Struct., Funct., Genet. 22:141–153), suggesting that it represents a domain boundary. The expression strategy included use of the pEE14 vector (Bebbington, C. R. & Hentschel, C. C. G., 1987, In: Glover, D. M., ed. DNA Cloning. Academic Press, San Diego. Vol 3, p 163) in glycosidase-defective Lec8 cells (Stanley, P., 1989, Molec. Cellul. Biol. 9:377–383), which produce N-linked oligosaccharides lacking the terminal galactose and N-acetylneuraminic acid residues (Davis, S. J., et al., 1993, Protein Eng. 6:229–232: Liu, T. et al., 1996, J Biol Chem 271: 33639–33646). The construct contained a C-terminal c-myc affinity tag (Hoogenboom, H. R., et al., 1991, Nucl Acids Res. 19:4133–4137), which facilitated immunoaffinity purification by specific peptide elution and avoided aggressive purification conditions. These procedures yielded protein which readily crystallized after a further gel filtration purification step. This provided a general protocol to enhance crystallisation prospects for labile multidomain glycoproteins.

The structure of this fragment is of considerable interest, since it contains the major determinants governing insulin and IGF-1 binding specificity (Gustafson, T. A. & Rutter, W. J., 1990, J. Biol. Chem. 265:18663–18667; Andersen, A. S., et al., 1990, Biochemistry, 29:7363–7366; Schumacher, R., et al., 1991, J. Biol. Chem. 266:19288–19295: Schumacher, R. et al., 1993, J. Biol. Chem. 268:1087–1094: Schaffer, L., et al., 1993, J. Biol. Chem. 268:3044–3047; Williams, P. F., et al., 1995, J. Biol. Chem. 270:3012–3016), and is very similar to an IGF-1R fragment (residues 1–486) reported to act as a strong dominant negative for several growth functions and which induces apoptosis of tumour cells in vivo (D'Ambrosio, C., et al., 1996, Cancer Res. 56:4013–4020).

The expression plasmid pEE14/IGF-1R/462 was constructed by inserting the olignucleotide cassette (SEQ ID NO. 14 and SEQ ID NO. 15):

```
    AatII
5'  GACGTC GACGAT GACGATAAG GAACAAAAACTCATC
    D  V   D D   D D K     E Q K L I
              (EK cleavage)     (c-myc tail)
    S E E D L N (Stop)
    TCAGAAGAGGATCTGAAT TAGAATTC GACGTC 3'
                       EcoRI    AatII
``` encoding an enterokinase cleavage site, c-myc epitope tag (Hoogenboom, H. R., et al., 1991, Nucleic acids Res. 19:4133–4137) and stop codon into the AatII site (within codon 462) of Igf-1r cDNA in the mammalian expression vector pECE (Ebina, Y., et al., 1985, Cell, 40:747–758; kindly supplied by W. J. Rutter, UCSF, USA), and introducing the DNA comprising the 5' 1521 bp of the cDNA (Ulrich, A., et al., 1986, EMBO J. 5:2503–2512) ligated to the oligonucleotide cassette into the EcoRI site of the mammalian plasmid expression vector pEE14 (Bebbington, C. R. & Hentschel, C. C. G., 1987, In: Glover, D. M., ed. DNA Cloning. Academic Press, San Diego. Vol 3, p 163; Celltech Ltd., UK). Plasmid pEE14/IGF-1R/462 was transfected into Lec8 mutant CHO cells (Stanley, P. 1989, Molec. Cellul. Biol. 9:377–383) obtained from the American Tissue Culture Collection (CRL: 1737), using Lipofectin (Gibco-BRL). Cell lines were maintained after transfection in glutamine-free medium (Glasgow modification of Eagle's medium (GMEM; ICN Biomedicals, Australia) and 10% dialysed FCS (Sigma, Australia) containing 25 μm methionine sulphoximine (MSX; Sigma, Australia) as described (Bebbington, C. R. & Hentschel, C. C. G., 1987, In: Glover, D. M., ed. DNA Cloning. Academic Press, San Diego. Vol 3, p 163). Transfectants were screened for protein expression by Western blotting and sandwich enzyme-linked immunosorbent assay (ELISA) (Cosgrove, L., et al., 1995 using monoclonal antibody (Mab) 9E10 (Evan et al., 1985) as the capture antibody, and either biotinylated anti-IGF-1R Mab 24–60 or 24–31 for detection (Soos et al., 1992; gifts from Ken Siddle, University of Cambridge, UK). Large-scale cultivation of selected clones expressing IGF-1R/462 was carried out in a Celligen Plus bioreactor (New Brunswick Scientific, USA) containing 70 g Fibra-Cel Disks (Sterilin, UK) as carriers in a 1.25 L working volume. Continuous perfusion culture using GMEM medium supplemented with non-essential amino acids, nucleosides, 25 μM MSX and 10% FCS was maintained for 1 to 2 weeks followed by the more enriched DMEM/F12 without glutamine, with the same supplementation for the next 4–5 weeks. The fermentation production run was carried out three times under similar conditions, and resulted in an estimated overall yield of 50 mg of receptor protein from 430 L of harvested medium. Cell growth was poor during the initial stages of the fermentation when GMEM medium was employed, but improved dramatically following the switch to the more enriched medium. Target protein productivity was essentially constant during the period form ~100 to 700 h of the 760 h fermentation, as measured by ELISA using Mab 9E10 as capture antibody and bitinylated Mab 24–31 as the developing antibody.

Soluble IGF-1R/462 protein was recovered from harvested fermentation medium by affinity chromatography on columns prepared by coupling Mab 9E10 to divinyl sulphone-activated agarose beads (Mini Leak; Kem En Tec. Denmark) as recommended by the manufacturer. Mini-Leak Low and Medium affinity columns with antibody loadings of 1.5–4.5 mg/ml of hydrated matrix were obtained, with the loading range of 2.5–3 mg/ml giving optimal performance (data not shown). Mab 9E10 was produced by growing hybridoma cells (American Tissue Culture Collection) in serum-free medium in the Celligen Plus bioreactor and recovering the secreted antibody (4 g) using protein A glass beads (Prosep-A, Bioprocessing Limited, USA). Harvested culture medium containing IGF-1R/462 protein was adjusted to pH 8.0 with Tris-HCl (Sigma), made 0.02% (w/v) in sodium azide and passed at 3–5 ml/min over 50 ml Mab 9E10 antibody columns at 4° C. Bound protein was recovered by recycling a solution of 2–10 mg of the undecamer c-myc peptide EQKLISEEDLN (Hoogenboom et al., 1991) in 20 ml of Tris-buffered saline containing 0.02% sodium azide (TBSA). Between 65% and 75% of the product was recovered from the medium as estimated by ELISA, with a further 15–25% being recovered by a second pass over the columns. Peptide recirculation (~10 times) through the column eluted bound protein more efficiently than a single, slower elution. Residual bound protein was eluted with sodium citrate buffer at pH 3.0 into 1 M Tris HCl pH 8.0 to neutralize the eluant, and columns were re-equilibrated with TBSA.

Gel filtration over Superdex S200 (Pharmacia, Sweden), of affinity-purified material showed a dominant protein peak at ~63 kDa, together with a smaller quantity of aggregated protein (FIG. 3a). The peak protein migrated primarily as two closely spaced bands on reduced, sodium dodecyl sulfate polyacrylamide gel electrophoresis (SDS-PAGE; FIG. 3b), reacted positively in the ELISA with both Mab 24–60 and Mab 24–31, and gave a single sequence corresponding to the N-terminal 14 residues of IGF-1R. No binding of IGF-1 or IGF-2 could be detected in the solid plate binding assay (Cosgrove et al., 1995, Protein Express Purif. 6:789–798). The IGF-1R/462 fragment was further purified by ion-exchange chromatography on Resource Q (Pharmacia, Sweden). Using shallow salt gradients, protein enriched in the slowest migrating SDS-PAGE band was obtained (data not shown), which formed relatively large, well-formed crystals (see below). Isoelectric focussing showed the presence of one major and two minor isoforms. Protein purified on Resource Q with an isocratic elution step of 0.14 M NaCl in 20 nM TrisCl at pH 8.0 (fraction 2, FIG. 4) showed less heterogeneity on isoelectric focussing (FIG. 4 inset) and SDS-PAGE (data not shown), and produced crystals of sufficient quality for structure determination (see below).

Crystals were grown by the hanging drop vapour diffusion method using purified protein concentrated in Centricon 10 concentrators (Amicon Inc, USA) to 5–10 mg/ml in 10–20 mM Tris-HCl pH 8.0 and 0.02% (w/v) sodium azide, or 100 mM ammonium sulfate and 0.02% (w/v) sodium azide. Crystallization conditions were initially identified using the factorial screen (Jancarik, J. & Kim, S.-H., 1991, J Appl Cryst 24:409–411) and then optimised. Crystals were examined on an M18XHF rotating anode generator (Siemens, Germany) equipped with Franks mirrors (MSC, USA) and RAXIS IIC and IV image plate detectors (Rigaku, Japan).

From the initial crystallization screen of this protein, crystals of about 0.1 mm in size grew in one week. Upon refining conditions, crystals of up to 0.6×0.4×0.4 mm could be grown from a solution of 1.7–2.0 M ammonium sulfate, 0.1 M HEPES pH 7.5. The crystals varied considerably in shape and diffraction quality, growing predominantly as rhombic prisms with a length to width ratio of up to 5:1, but sometimes as rhombic bipyramids, the latter form being favoured when using material which had been eluted from the Mab 9E10 column at pH 3.0. Each crystal showed a minor imperfection in the form of very faint lines from the centre to the vertices. Protein from dissolved crystals did not appear to be different from the protein stock solution when run on an isoelectric focusing gel. Upon X-ray examination, the crystals diffracted to 3.0–4.0 Å and were found to belong to the space group $P2_12_12_1$, with a=76.8 Å, b=99.0 Å, c=119.6 Å. In the diffraction pattern, the crystal variability noted above was manifest as a large (1–2°) and anisotropic mosaic spread, with concomitant variation in resolution. To improve the quality of the crystals, they were grown in the presence of various additives or were recrystallized. These methods failed to substantially improve the crystal quality although bigger crystals were obtained by recrystallization. The variability in crystal quality appeared to be due to protein heterogeneity as demonstrated by the observation that more highly purified protein, eluted isocratically from the Resource Q column and showing one major band on isoelectric focusing (FIG. 4 inset), produced crystals of sufficient quality for structure determination. These crystals diffracted to 2.6 Å resolution with cell dimensions, a=77.0 Å, b=99.5 Å, c=120.1 Å and mosaic spread of 0.5°. Heavy metal derivatives of the IGF-1 R/462 crystals have been obtained and are leading to the determination of an atomic resolution structure of this fragment, which contains the L1, cysteine-rich and L2 domains of human IGF-1R.

EXAMPLE 2

Structure of the IGF-1R/1-462

Crystals were cryo-cooled to −170° C. in a mother liquor containing 20% glycerol, 2.2 M ammonium sulfate and 100 mM Tris at pH 8.0. Native and derivative diffraction data were recorded on Rigaku RAXIS IIc or IV area detectors using copper Kα radiation from a Siemens rotating anode generator with Yale/MSC mirroroptics. The space group was $P2_12_12_1$ with a=77.39 Å, b=99.72 Å, and c=120.29 Å. Data were reduced using DENZO and SCALEPACK (Otwinowski, Z. & Minor, W., 1996. Mode. Meth. Enzym. 276: 307–326). Diffraction was notably anisotropic for all crystals examined.

Phasing by multiple isomorphous replacement (MIR) was performed with PROTEIN (Steigeman, W. Dissertation (Technical Univ. Munich, 1974) using anomalous scattering for both UO2 and PIP derivatives. Statistics for data collection and phasing are given in Table 1. In the initial MIR map regions of protein and solvent could clearly be seen, but the path of the polypeptide was by no means obvious. That map was subject to solvent flattening and histogram matching in DM (Cowtan, K., 1994, Joint CCP4 and ESF-EACBM newslett. Protein Crystallogr. 31:34–38). The structure was traced and rebuilt using O (Jones, T. A., et al., 1991, Acta Crystallogr. A47:110–119) and refined with X-PLOR 3.851 (Brunger, A. T., 1996, X-PLOR Reference Manual 3.851, Yale Univ., New Haven, Conn.). After 5 rounds of rebuilding and energy minimisation the R-factor dropped to 0.279 and Rfree=0.359 for data 7–2.6 Å resolution. The current model contains 458 amino acids and 3 N-linked carbohydrates but no solvent molecules. For residues with B(Ca)>70, Å atomic positions are less reliable (37–42, 155–159, 305, 336–341, 404–406, 453–458). There is weak electron density for residues 459–461, but the c-myc tail appears completely disordered.

The 1-462 fragment consists of the N-terminal three domains of IGF-1R (L1, cys-rich, L2), and contains regions of the molecule which dictate ligand specificity (17–23). The molecule adopts a reasonably extended structure (approximately 40×48×10$^5$ Å) with domain 2 (cys-rich region) making contact along the length of domain 1 (L1) but very little contact with the third domain (L2) (see FIG. 5). This leaves a space at the centre of the molecule of approximately 24 Å×24 Å×24 Å which is bounded on three sides by the three domains of the molecule. The space is of sufficient size to accommodate the ligand, IGF-1.

domain (14, 15), the pocket motif can be found in both L domains and the Trp is conserved in both cys-rich regions (FIG. 6*b*).

The repetitive nature of the β-helix is reflected in the sequence and the first five turns were correctly identified by Bajaj, M., et al. (1987, Biochim. Biophys. Acta 916:220–226), the conserved Gly residues being found in turns making one bottom edge of the domain. However, their conclusions about the fold were incorrect. The "helix-like" repeat is actually a pair of bends at the top edge of the domain. In their Motif V, the Gly is not in a bend but is followed by the insertion of a conserved loop of 7–8 residues (see FIG. 6*a*). Glycine is structurally important in the Gly bends as mutation of these residues compromises folding of the receptor [van der Vorm, E. R., et al., 1992, J. Biol. Chem. 267, 66–71; Wertheimer, E. et al. 1994, J. Biol. Chem. 269, 7587–7592].

Comparison of the L domains with other right-handed β-helix structures such as pectate lyase (Yoder, M. D., et al.,

TABLE 1

Summary of Crystallographic data

| Data set[a] | Resol. (Å) | Mean I/s | $R_{merge}$[b] | Completeness (multiplicity) | No. of sites | $R_{cullis}$[c] | Phasing power[d] | FOM[e] |
|---|---|---|---|---|---|---|---|---|
| Native | 2.6 | 18.7 | 0.064 | 0.996 (4.1) | | | | 0.47/0.71 |
| PIP | 3.0 | 15.8 | 0.060 | 0.982 (2.2) | 3 | 0.66 | 1.71 | |
| UO2Ac2 | 4.5 | 7.5 | 0.095 | 0.989 (2.3) | 2 | 0.82 | 1.17 | |

| Refinement resolution (Å) | No of refl. (free) | No. of Atoms | $R_{cryst}$[f] | $R_{free}$[f] | Bonds[g] (Å) | Angles[g] (Å) |
|---|---|---|---|---|---|---|
| 7.0–2.6 | 24270 (2693) | 3903 | 0.237 | 0.304 | 0.017 | 0.048 |

[a]PIP, Di-μ-iodobis(ethylenediamine)diplatinum dinitrate; UO$_2$Ac$_2$, Uranyl acetate.
[b]$R_{merge} = \Sigma_h\Sigma_j|I_{h,j}-I_h|/\Sigma_h\Sigma_j\ I_h$, where $I_{h,j}$ is an intensity measurement j and $I_h$ is the mean intensity for that reflection h.
[c]$R_{cullis} = \Sigma_h||F_{PH}-F_P| - |F_{Hcalc}||/\Sigma_h|F_{PH}|-|F_P||$, where $F_{PH}$, $F_P$ and $F_{Hcalc}$ are, respectively, derivative, native and heavy atom structure factors for centric reflections h.
[d]Phasing power = $\Sigma_h|F_{Hcalc}|/\Sigma_h\epsilon$, where $F_{Hcalc}$ is defined above and $\epsilon$ is the lack of closure.
[e]FOM(figure of merit) = $<\cos(\Delta\alpha_h)>$, where $\Delta\alpha_h$ is the error in the phase angle for reflection h. Values are given before and after density modification at 3.0 and 2.8 Å resolution, respectively.
[f]$R_{cryst}$ and $R_{free}$ are defined in Brunger, A. T. XPLOR reference manual 3.851 (Yale Univ., New Haven, CT, 1996)
[g]r.m.s. deviation from ideal bond and angle-related (1–3) distances.

The L Domains

Figure 6:
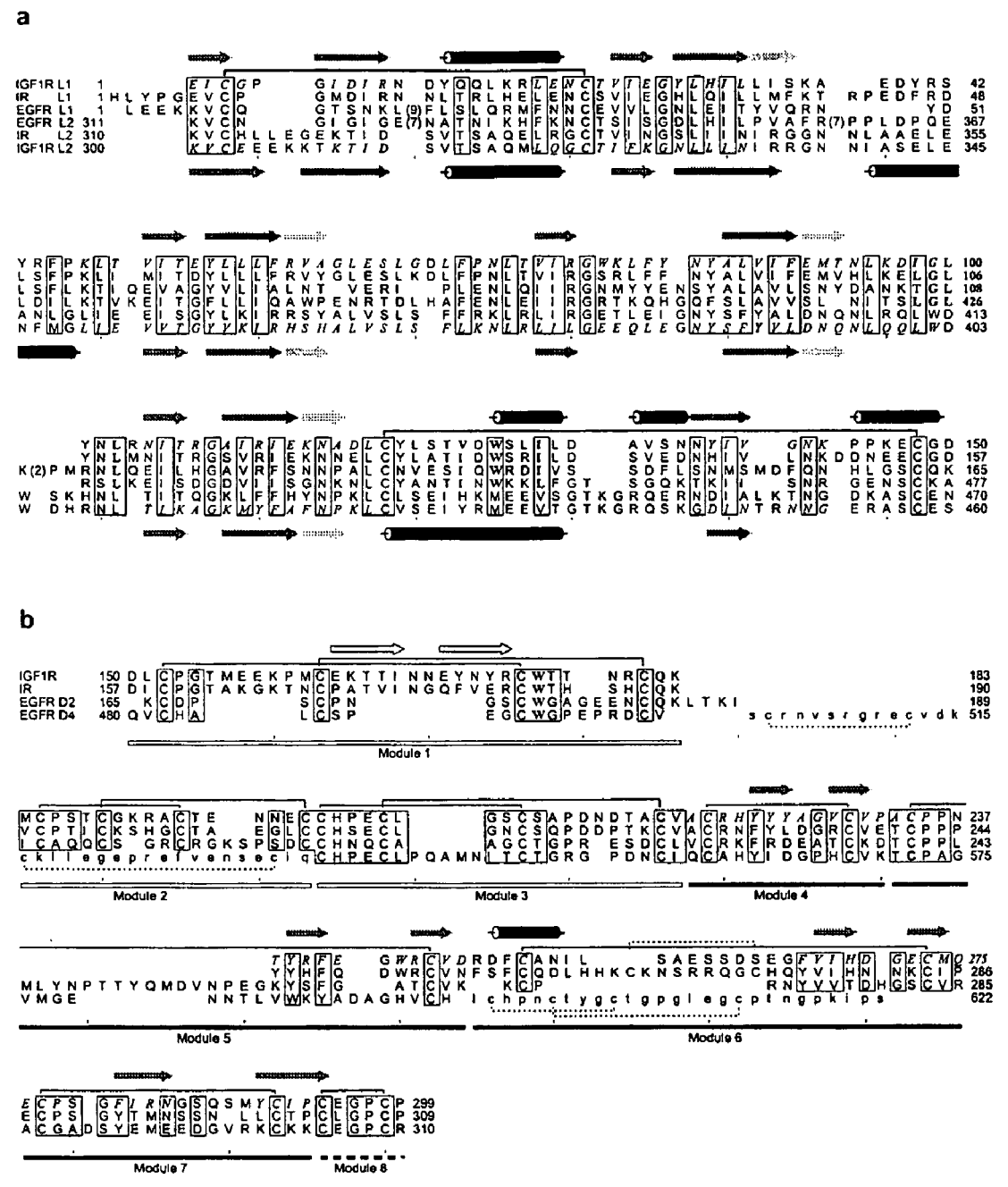
Figure 7:
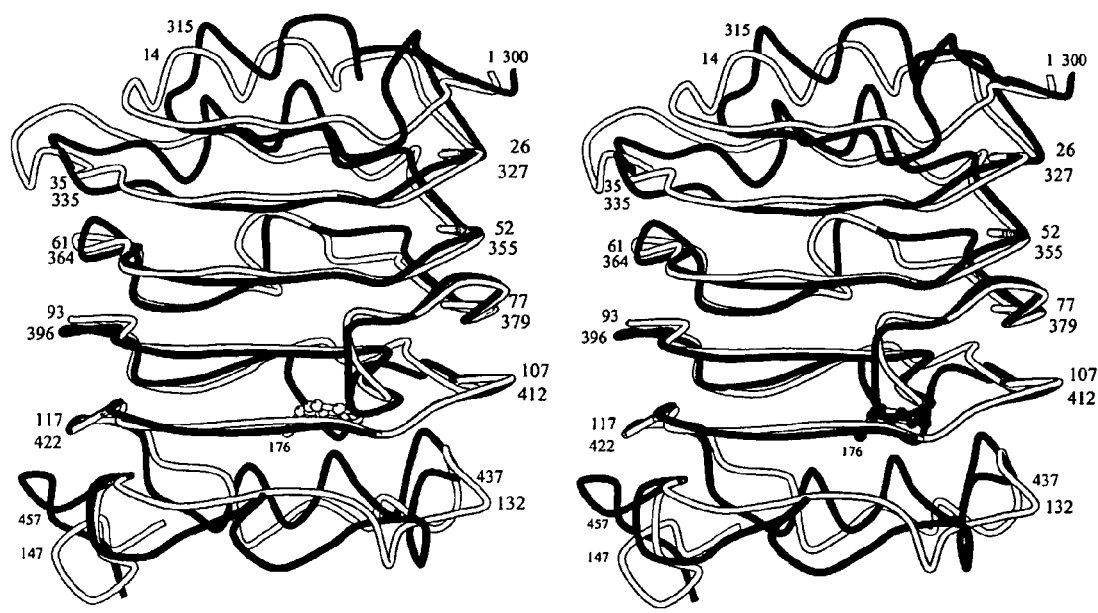
FIG. 7. Stereo view of a superposition of the L1 (white) and L2 (black) domains. Residues numbers above are for L1 and below for L2. The side chain of Trp 176 which protrudes into the core of L1 is drawn as ball-and-stick.
Figure 8:
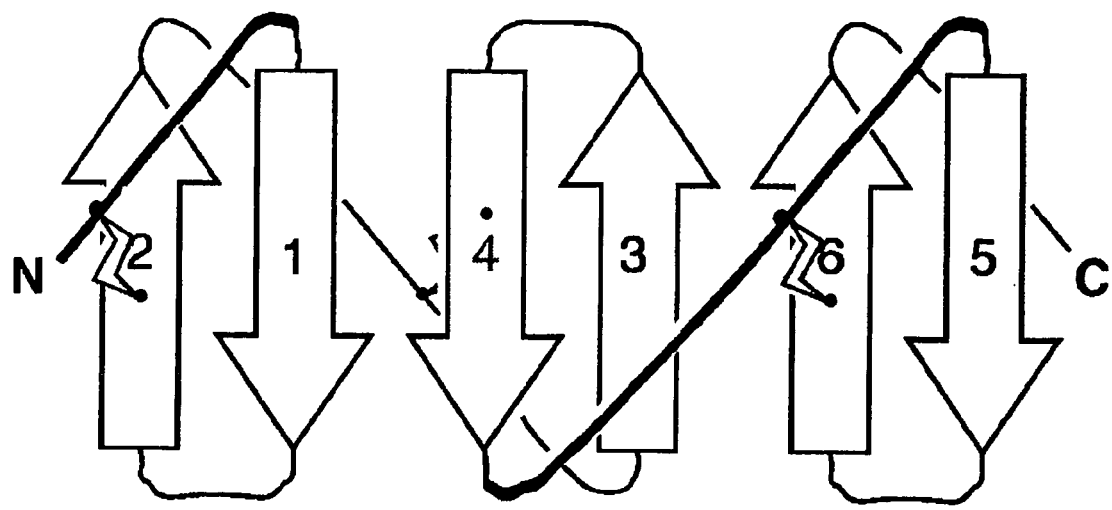
FIG. 8. Schematic diagram showing the association of three β-finger motifs. β-strands are drawn as arrows and disulfide bonds as zigzags.

Each of the L domains (residues 1–150 and 300–460) adopts a compact shape (24×32×37 Å) consisting of a single-stranded right handed β-helix and capped on the ends by short α-helices and disulfide bonds. The body of the domain looks like a loaf of bread, with the base formed from a flat six-stranded β-sheet, 5 residues long and the sides being β-sheets three residues long (FIGS. 5 & 6). The top is irregular, but in places is similar for the two domains. The two domains are superposable with an rms deviation in Cα positions of 1.6 Å for 109 atoms (FIG. 7). Although this fold is reminiscent of other β-helix proteins it is much simpler and smaller with very few elaborations, and thus it represents a new superfamily of domains. One notable difference between the two domains is that the indole ring of Trp 176 from the cys-rich region (FIG. 6*b*) is inserted into the hydrophobic core of L1, and the C-terminal helix is only vestigial (FIG. 8). For the insulin receptor family the sequence motif of residues which form the Trp pocket in L1 does not occur in L2 (FIG. 6*a*). However in the EGF receptor, which has an additional cys-rich region after the L2

1993, Structure, 1:241–251–1507) and the p 22 tailspike protein (Steinbacher, S., et al., 1997, J. Mol. Biol. 267: 865–880) shows some striking similarities as well as differences. In all cases the ends of the domain are capped by α-helices, but the L domains also have a disulphide bond at each end to hold the termini. The others β-helix domains are considerably longer and have significant twist to their sheets, while the L domains have flat sheets. Although the sizes of the helix repeats are similar (here 24–25 residues vs 22–23 for pectate lyase) the cross-sections are quite different. The L domains have a rectangular cross-section, while pectate lyase and p22 tailspike protein are V-shaped, and have many, and sometimes quite large, insertions (Yoder, M. D., et al., 1993, Structure, 1:241–251–1507; Steinbacher, S., et al., 1997, J. Mol. Biol. 267:865–880). In the hydrophobic core a common feature is the stacking of aliphatic residues from successive turns of the β-helix, and near the C-terminus of each L domain there is also a short Asn ladder, reminiscent of the long Asn ladder observed in pectate lyase (Yoder, M. D., et al., 1993, Structure 1:241–251–1507). On the opposite side of the L domains the Gly bend, as well as the two bends and sheet preceding it, have no counterpart in the other β-helix domains. Thus although the L domains are built on similar principles to the other β-helix domains they constitute a separate superfamily.

The cys-Rich Domain

The cys-rich domain is composed of eight disulfide-bonded modules (FIG. 6b), the first of which sits at the end of L1, while the remainder make a curved rod running diagonally across L1 and reaching to L2 (FIG. 5). The strands in modules 2–7 run roughly perpendicular to the axis of the rod in a manner more akin to laminin (Stetefeld, J., et al., 1996, J. Mol. Biol. 257:644–657) than to TNF receptor (Banner, D. W., et al., 1993, Cell, 73:431–445), but the modular arrangement of the cys-rich domain is different to those of other cys-rich proteins for which structures are known. The first 3 modules of IGF-1R have a common core, containing a pair of disulfide bonds, but show considerable variation in the loops (FIG. 6b). The connectivity of these modules is the same as in the first half of EGF (Cys 1-3 and 2-4), but their structures do not appear to be closely related to any member of the EGF family. Modules 4 to 7 have a different motif, a β-finger, and best match residues 2152–2168 of fibrillin (Dowling, A. K., et al., 1996. Cell, 85:597–605). Each is composed of three polypeptide strands, the first and third being disulfide bonded and the latter two forming a β-ribbon. The β-ribbon of each β-finger module lines up antiparallel to form a tightly twisted 8-stranded β-sheet (FIGS. 5 and 8). Module 6 deviates from the common pattern, with the first segment being replaced by an α-helix followed by a large loop that is likely to have a role in ligand binding (see below). As module 5 is most similar to module 7 it is possible that the four modules arose from serial gene duplications. The final module is a disulfide-linked bend of five residues.

The fact that the two major types of cys-rich modules occur separately implies that these are the minimal building blocks of cys-rich domains found in many proteins. Although it can be as short as 16 residues, the motif of modules 4–7 is clearly distinct, and capable of forming a regular extended structure. Thus cys-rich domains such as these can be considered as being made of repeat units each composed of a small number of modules.

Hormone Binding

Attempts have been made to locate the IGF-1 (and insulin) binding site by examining natural (Taylor, S. I., 1992, Diabetes, 41:1473–1490) and site-directed mutants (Williams, P. F., et al., 1995, J. Biol. Chem. 270:3012–3016; Mynarcik, D. C. et al., 1996, J. Biol. Chem. 271:2439–2442; Mynarcik, D. C., et al., 1997, J. Biol. Chem. 272:2077–2081), chimeric receptors (Andersen, A. S., et al., 1990, Biochemistry 29:7363–7366. Gustafson, T. A., & Rutter, W. J., 1990, J. Biol. Chem. 265:18663–18667; Schäffer. L., et al., 1993. J. Biol. Chem. 268:3044–3047; Schumacher, R., 1993, J. Biol. Chem. 268:1087–1094: Kjeldsen, T., et al., 1991, Proc. Natl. Acad. Sci. USA, 88:4404–4408) and by crosslinking studies (Wedekind, F., et al., 1989, Biol. Chem Hoppe-Seyler, 370:251–258; Fabry, M., 1992, J. Biol. Chem. 267:8950–8956; Waugh, S. M., et al., 1989, Biochemistry, 28:3448–3458; Kurose, T., et al., 1994), J. Biol. Chem. 269:29190–29197–34). IGF-R/1R chimeras not only show which regions of the receptors account for ligand specificity, but also provide an efficient means of identifying some parts of the hormone binding site. Paradoxically, regions controlling specificity are not the same for insulin and IGF-1. Replacing the first 68 residues of IGF-1R with those of IR confers insulin-binding ability on the chimeric IGF-1R (Kjeldsen, T., et al., 1991, Proc. Natl. Acad. Sci. USA, 88:4404–4408), and replacing residues 198–300 in the cys-rich region of IR with the corresponding residues 191–290 of IGF-1R allows the chimeric receptor to bind IGF-1 (Schäffer. L. et al., 1993, J. Biol. Chem. 268:3044–3047). Thus a receptor can be constructed which binds both IGF-1 and insulin with near native affinity. From the structure it is clear that if the hormone bound in the central space it could contact both these regions.

From analysis of a series of chimeras examined by Gustafson, T. A., & Rutter, W. J. (J. Biol. Chem. 265: 18663–18667, 1990), the specificity determinant in the cys-rich region can be limited further to residues 223–274. This region corresponds to modules 4–6, and includes a large and somewhat mobile loop (residues 255–263, mean B[Cα atoms]=57 Å2) which extends into the central space (see FIG. 5). In IR this loop is four residues bigger, and is stabilised by an additional disulfide bond (Schäffer, L. & Hansen. P. H., 1996, Exp. Clin. Endocrinol. Diabetes, 104: Suppl. 2, 89). The larger loop of IR may serve to exclude IGF-1 from the hormone binding site while allowing the smaller insulin molecule to bind. It is interesting to note that mosquito IR homologue, which has a loop two residues larger than the mammalian IRs, also appears to bind insulin but not IGF-1 (Graf, R. et al., 1997, Insect Molec. Biol. 6:151–163). Analysis of the structure indicates that the insulin/IGF-1 specificity is controlled by residues in this loop (amino acids 253–272 in IGF-1R; amino acids 260–283 in IR).

As chimeras only address residues which differ between the two receptors, a more precise analysis of the site can be obtained from single site mutants. In particular, from an alanine-replacement study, four regions of L1 important for insulin binding were identified (Williams, P. F., et al., 1995, J. Biol. Chem. 270:3012–3016). The first three are at similar positions on successive turns of the β-helix and the fourth lies on the conserved bulge on the large β-sheet. Thus there is a footprint for insulin binding to the L1 domain which lies on the first half of the large β-sheet facing into the central space. Residues further along the sheet which are conserved in IGF-1R could also be important. The conservative substitution of leucine for methionine at residue 119 of IR (113 of IGF-1R) causes a mild form of leprechaunism [Hone, J. et al., 1994, J. Med. Genet. 31, 715–716]. This residue is buried, and the mutation could perturb neighbouring residues to affect insulin binding.

The axis of the L2 domain is perpendicular to that of the L1 domain, and the N-terminal end of its α-helix is presented to the hormone-binding site. On this face of the L2 domain the only mutation studied so far is the naturally occurring IR mutant, S323L, which gives rise to Rabson-Mendehall syndrome and severe insulin resistance (Roach, P. 1994, Diabetes 43:1096–1102). As this mutant only affects insulin binding and not cell-surface expression, residue 323 of IR (residue 313 of IGF-1R) is probably at or near the binding site. Structurally this residue lies in the middle of a region (residues 309–318 of IGF-1R) which is conserved in both IR and IGF-1R, and the surrounding region, 332–345 (of IGF-1R), is also quite well conserved in the these receptors (FIG. 6a). Therefore this region is quite likely to form part of the hormone-binding site, but would not have been detected by chimeras. It is interesting to note that in this region IRR is not as well conserved as the other two receptors (Shier, P. & Watt. V. M., 1989, J. Biol. Chem. 264:4605–14608).

The distance from this putative hormone-binding region on L2 to that found on L1 is about 30 Å (FIG. 5). Thus L1 and L2 appear too far apart to bind IGF-1 or insulin.

However, in the crystal structure there is a deep cleft between part of the cys-rich domain (residue 262) and L2 (residue 305), and this cleft is occupied by a loop from a neighbouring molecule. Thus it seems probable that the position of the L2 domain in the receptor structure or the hormone-receptor complex adopts a different position with respect to the cys-rich domain than that found in the crystal. The movement required to bring L2 sufficiently close to L1 is small, namely a rotation of approximately 25° about residue 298.

A number of IR mutants have been identified which constitutively activate the receptor, and the majority of these are found in the a chain. Curiously all a chain mutants involve changes to or from proline or the deletion of an amino acid, implying that they cause local structural rearrangements. The mutation R86N is similar to wild type, but R86P reduces cell-surface expression and insulin binding while constitutively activating autophosphorylation [Grønskov, K. et al., 1993, Biochem. Biophys. Res. Commun. 192, 905–911]. The proline mutation probably disturbs residues preceding 87 which lie in the interface between the L1 and cys-rich domains, but it could also affect insulin binding. In the cys-rich domain residues 233, 281, 244 and 247 of IR are not conserved in IGF-1R (FIG. 6b), yet L233P [Klinkhamer, M. P. et al., 1989, EMBO J. 8, 2503–2507], deletion of N281 [Debois-Mouthon, C. et al. 1996, J. Clin. Endochronol. Metab. 81, 719–727] or the triple mutant P243R, P244R and H247D [Rafaeloff, R. et al., 1989, J. Biol. Chem. 264, 15900–15904] cause constitutive kinase activation. Due to their locations each of these three mutants appears likely to compromise the folding of a β-finger domain and, in turn, the structural integrity of the rod-like cys-rich domain. The structural ramifications of these mutations could be significant for the whole receptor ectodomain, as disturbing the L1/cys-rich interface or distorting the rod-like domain could affect the relative position of L1 and the cys-rich domain in this context.

L1 has been further implicated, as deletion of K121 on the opposite side of L1 from the cys-rich domain was also found to cause autophosphorylation (Jospe, N. et al., 1994, J. Clin. Endochronol. Metab. 79, 1294–13021. By contrast this mutation does not affect insulin binding. Thus a possible mechanism emerges for insulin binding and signal transduction. When insulin binds between L1 and L2 it modifies the relative position of L1 and the cys-rich domain in the receptor, perhaps by hinge motion between L2 and the cys-rich domain like that suggested above, and the structural rearrangement is transmitted across the plasma membrane. In the absence of insulin the same signal can be initiated by mutations in the cys-rich region or at the L1/cys-rich interface, but at the expense on insulin binding. The signal can also be initiated more directly by mutations on the opposite side of L1 which affect the interaction of L1 with other parts of the ectodomain, possibly the other half of the receptor dimer.

Ligand Studies

Although there is no structural information about an IGF-1/IGF-1R complex a number of studies have probed the nature of this interaction. Results from cross-linking experiments with IGF-1 and insulin and their cognate receptors are consistent with the hormone binding site proposed above. For example B29 of insulin can be cross-linked to the cys-rich region (residues 205–316 ((Yip, C. C., et al., 1988, Biochim. Biophys. Res. Commun. 157:321–329) or the L1 domain (Wedekind, F., et al., 1989, Biol. Chem Hoppe-Seyler, 370:251–258). However, these two regions are reasonably well separated, and those studies may indicate that B29 is mobile. Other studies unfortunately do not map the site any more precisely.

Analogues and site-directed mutants of IGF-1 and IGF-2 have been more fruitful. IGF-1 and IGF-2 contain two extra regions relative to insulin, the C region between B and A and a D peptide at the C-terminus. For IGF-1, replacement of the C region by a four Gly linker reduced affinity for IGF-1R by a factor of 40 but increased affinity for IR 5-fold (Bayne, M. L., et al., 1988, J. Biol. Chem. 264:11004–11008). Changes in affinity are consistent with the deletion in IGF-1 complementing differences in the cys-rich regions of IGF-1R and IR noted above. Mutation of residues either side of the C region (residue 24 for IGF-1[Cascieri, M. A., et al., 1988, Biochemistry 27:3229– 3233], residues 27,43 for IGF-2, [Sakano, K., et al., 1991. J. Biol. Chem. 266:20626–20635]) also has deleterious effects on the affinity of the hormone for IGF-1R, as has truncation of the nearby D peptide in IGF-2 (Roth, B. V., et al., 1991, Biochem. Biophys. Res. Commun. 181:907–914).

Insulin has been extensively mutated. Binding studies [summarised in Kristensen, C. et al., 1997, J. Biol. Chem. 272, 12978–12983] indicate that insulin may bind its receptor via a hydrophobic patch (residues A2, A3, A19, B8, B11, B12, B15 and possibly B23 & B24). However this patch is normally buried, and requires the removal of the B chain's C-terminus from the observed position. Assuming IGF-1, IGF-2 and insulin bind their receptors in the same orientation, these data suggest an approximate orientation for the hormone when bound to the receptor.

One notable feature of IGF-1 and IGF-2 is the large number of charged residues and their uneven distribution over the surface. Basic residues are predominantly found in the C region and, in solution, this region is not well ordered in either IGF-1 or -2 (Sato, A., et al., 1993, Int J Peptide Protein Res. 41:433–440; Torres, A. M., et al., 1995, J. Mol. Biol. 248:385–401). In contrast the binding site of the receptor has a sizable patch of acidic residues in the corner where the cys-rich domain departs from L1. Other acidic residues which are specific to this receptor are found along the inside face of the cys-rich domain and the loop (residues 255–263) extending from module 6. Thus it is possible that electrostatic interactions play an important part in IGF-1 binding, with the C region binding to the acidic patch of the cys-rich region near L1 and the acidic patch on the other side of the hormone directed towards a small patch of basic residues (residues 307–310) on the N-terminal end of L2.

Although the structure of this fragment gives significant information about the nature of the hormone binding site, residues outside this region have also been shown to affect binding of ligand. A number of studies have implicated residues 704–715 of IR (Mynarcik, D. C. et al., 1996, J. Biol. Chem. 271, 2439–2442; Kurose, T. et al., 1994, J. Biol. Chem. 269:29190–29197). These residues could contact insulin on one of the sides left open in the current structure. Using insulin labelled at the B1 residue, Fabry, M., et al., (1992, J. Biol. Chem. 267:8950–8956) cross-linked insulin to the fragment 390–488, part of which is not near the site as described. The explanation for this could be either the region 390–488 reaches back to the hormone binding site, or this region could contact another hormone bound to the other half of the receptor. Further structural information is needed to establish how these other regions contact the hormone and to elucidate how binding of the hormone is communicated to the kinase inside the cell.

The structure of the L1-cys-rich-L2 domains of IGF-1R presented here represents the first structural information for the extracellular portion of a member of the insulin receptor family. The L domains display a novel fold which is common to the EGF receptor family, and the modular architecture of the cys-rich domain implies that smaller building blocks should be used to describe the composition of cysteine-rich domains. This fragment contains the major specificity determinants of receptors of this class for their ligands. It has an elongated structure with a space in the middle which could accommodate the ligand. The three sides of this site correspond to regions which have been implicated in hormone binding. Although other sites are present in the receptor ectodomain which interact with the ligand, this structure gives us an initial view of how the insulin, IGF-1 and IGF-2 might interact with their cell surface receptors to control their metabolic and mitogenic effects.

Such information will provide valuable insight into the structure of the corresponding domains of the IR and insulin receptor-related receptor as well as members of the related EGFR family (Bajaj, M., et al., 1987, Biochim Biophys Acta 916:220–226; Ward, C. W. et al., 1995. Proteins: Struct Funct Genet 22:141–153).

EXAMPLE 3

Prediction of 3D Structure of the Corresponding Domains of IRR and IR Based on Structure of IGF-R Fragment.

The sequence identities between the different members of the insulin receptor family are sufficient to allow accurate sequence alignments to facilitate 3D structure predictions by homology modelling. The alignments of the ectodomains of human IGF-1R, IR, and IRR are shown in FIG. 9.

EXAMPLE 4

Single-Molecule Imaging of Human Insulin Receptor Ectodomain and its Fab Complexes Cloning and Expression of hIR −11 Ectodomain Protein A full length clone of the human IR exon −11 form (hIR −11) was prepared by exchanging an Aat II fragment, nucleotides 1195 to 2987, of the exon +11 clone (plasmid pET; Ellis et al., 1986; gift from Dr W. J. Rutter, UCSF) of hIR (Ebina et al., 1985, Cell 40, 747–758) with the equivalent Aat II fragment from a plasmid (pHIR/P12-1. ATCC 57493) encoding part of the extracellular domain and the entire cytoplasmic domain of hIR −11 (Ullrich et al., 1985, Nature 313, 756–761). The ectodomain fragment of hIR −11 (2901 bp, coding for the 27 residue signal sequence and residues His 1-Asn914) was produced by SalI and SspI digestion and inserted into the mammalian expression vector pEE6.HCMV-GS (Celltech Limited. Slough, Berkshire, UK) into which a stop codon linker had been inserted, as described previously (Cosgrove et al., 1995, Protein Expression and Purification 6, 789–798) for the hIR exon +11 ectodomain.

The resulting recombinant plasmid pHIR II (2 μg) was transfected into glycosylation-deficient Chinese hamster ovary (Lec 8) cells (Stanley, 1989, Molec. Cellul. Biol. 9, 377–383) with Lipofectin (Gibco-BRL). After transfection, the cells were maintained in glutamine-free medium GMEM (ICN Biomedicals, Australia) as described previously (Bebbington & Hentschel, 1987, In DNA Cloning (Glover, D., ectodomain.), Vol III, Academic Press, san Diego; Cosgrove et al., 1995, Protein Expression and Purification 6, 789–798). Expressing cell lines were selected for growth in GMEM with 25 μM methionine sulphoximine (MSX, Sigma). Transfectants were screened for protein expression using sandwich ELISA with anti-IR monoclonal antibodies 83-7 and 83-14. Metabolic labelling of cells, immunoprecipitations, insulin binding assays and Scatchard analyses were performed as described previously for the exon +11 form of hIR ectodomain (Cosgrove et al., 1995, Protein Expression and Purification 6, 789–798).

hIR −11 Ectodomain Production and Purification

The selected clone (inoculum of 1.28×108 cells) was grown in a spinner flask packed with 10 g of Fibra-cel disc carriers (Sterilin, U.K.) in 500 ml of GMEM medium containing 10% fetal calf serum (FCS) and 25 μM MSX. Selection pressure was maintained for the duration of the culture.

Ectodomain was recovered from harvested medium by affinity chromatography on immobilized insulin, and further purified by gel filtration chromatography on Superdex S200 (Pharmacia; 1×40 cm) in Tris-buffered saline containing 0.02% sodium azide (TBSA) as described previously (Cosgrove et al., 1995, Protein Expression and Purification 6, 789–798). Solutions of purified hIR −11 ectodomain were stored at 4° C. prior to use.

Production of Fab Fragments and their Complexes with Ectodomain

Purification of Mabs 83-7, 83-14 and 18-44 from ascites fluid by affinity chromatography using Protein A-Sepharose, and the production of Fabs, were based on the methodologies described in Coligan et al., 1993, Current Protocols in Immunology, Vol 1, pp 2.7.1–2.8.9, Greene Publishing Associates & Wiley—Interscience, John Wiley and Sons. Fab was produced from monoclonal antibody by mercuripapain digestion for 1–4 h, followed by gel filtration on Superdex S200. Products were monitored by reducing and non-reducing SDS-PAGE. For 83-7 Mab, an IgG Type 1 monoclonal antibody, the bivalent (Fab)2' isolated by this method was reduced to monovalent Fab 83-7 by mild reduction with mM L-cysteine.HCl in 100 mM Tris pH 8.0 (Coligan et al., 1993, Current Protocols in Immunology, Vol 1, pp 2.7.1–2.8.9, Greene Publishing Associates & Wiley—Interscience, John Wiley and Sons).

Complexes of Fab with hIR −11 ectodomain were produced by mixing ~2.5 to 3.5 molar excess of Fab with hIR −11 ectodomain at ambient temperature in TBSA at pH 8.0. After 1–3 h, the complex was separated from unbound Fab by gel filtration over a Superdex S200 column in the same buffer.

Electron Microscopy

Uncomplexed hIR −11 ectodomain and the Fab complexes described above were diluted in phosphate-buffered saline (PBS) to concentrations of the order of 0.01–0.03 mg/ml. Prior to dilution, 10% glutaraldehyde (Fluka) was added to the PBS to achieve a final concentration of 1% glutaraldehyde. Droplets of ~3 ml of this solution were applied to thin carbon film on 700-mesh gold grids after glow-discharging in nitrogen for 30 s. After 1 min. the excess protein solution was drawn off and followed by application and withdrawal of 4–5 droplets of negative stain [2% uranyl acetate (Agar), 2% uranyl formate (K and K), 2% potassium phosphotungstate (Probing and Structure) adjusted to pH 6.0 with KOH, or 2% methylamine tungstate (Agar) adjusted to pH 6.8 with NH4OH]. In the case of both uranyl acetate and uranyl formate staining, an intermediate wash with 2 or 3 droplets of PBS was included prior to application of the stain. The grids were air-dried and then examined at 60 kV accelerating voltage in a JEOL 100B transmission electron microscope at a magnification of 100,000×. It was found that there was a typical thickness of negative stain in which Fabs were most easily seen. Hence areas for photography had to be chosen from particular zones of the grid. Electron micrographs were recorded on Kodak SO-163 film and developed in undiluted Kodak D19 developer. The electron-optical magnification was calibrated under identical imaging conditions by recording single-molecule images of the antigen-antibody complex of influenza virus neuraminidase heads and NC10 MFab (Tulloch et al., 1986, *J. Mol. Biol.* 190. 215–225: Malby et al., 1994, *Structure*, 2, 733–746).

Image Processing

Electron micrographs showing particles in a limited number of identifiable projections were chosen for digitisation. Micrographs were digitised oil a Perkin-Elmer model 1010 GMS PDS flatbed scanning microdensitometer with a scanning aperture (square) size of 20 mm and stepping increment of 20 mm corresponding to a distance of 0.2 nm on the specimen. Particles were selected from the digitised micrograph using the interactive windowing facility of the SPIDER image processing system (Frank et al., 1996, *J. Struct. Biol.* 116, 190–199). Particles were scaled to an optical density range of 0.0–2.0 and aligned by the PSPC reference-free alignment algorithm (Marco et al., 1996, *Ultramicroscopy*, 66, 5–10). Averages were then calculated over a subset of correctly aligned particles chosen interactively as being representative of a single view of the particle. The final average image presented here is derived from a library of 94 images.

Biochemical Characterization of Expressed hIR −11 Ectodomain

The recombinant protein examined corresponded to the the first 914 residues of the 917 residue ectodomain of the exon −11 form of the human insulin receptor (Ullrich et al., 1986, *Nature* 313, 756–761). Expressed protein was shown, by SDS-PAGE and autoradiography of immunoprecipitated product from metabolically labelled cells, to exist as a homodimeric complex of ~270–320 kDa apparent mass, which dissociated under reducing conditions into monomeric $\alpha$ and $\beta'$ subunits of respective apparent mass ~120 kDa and ~35 kDa (data not shown).

Figure 10:
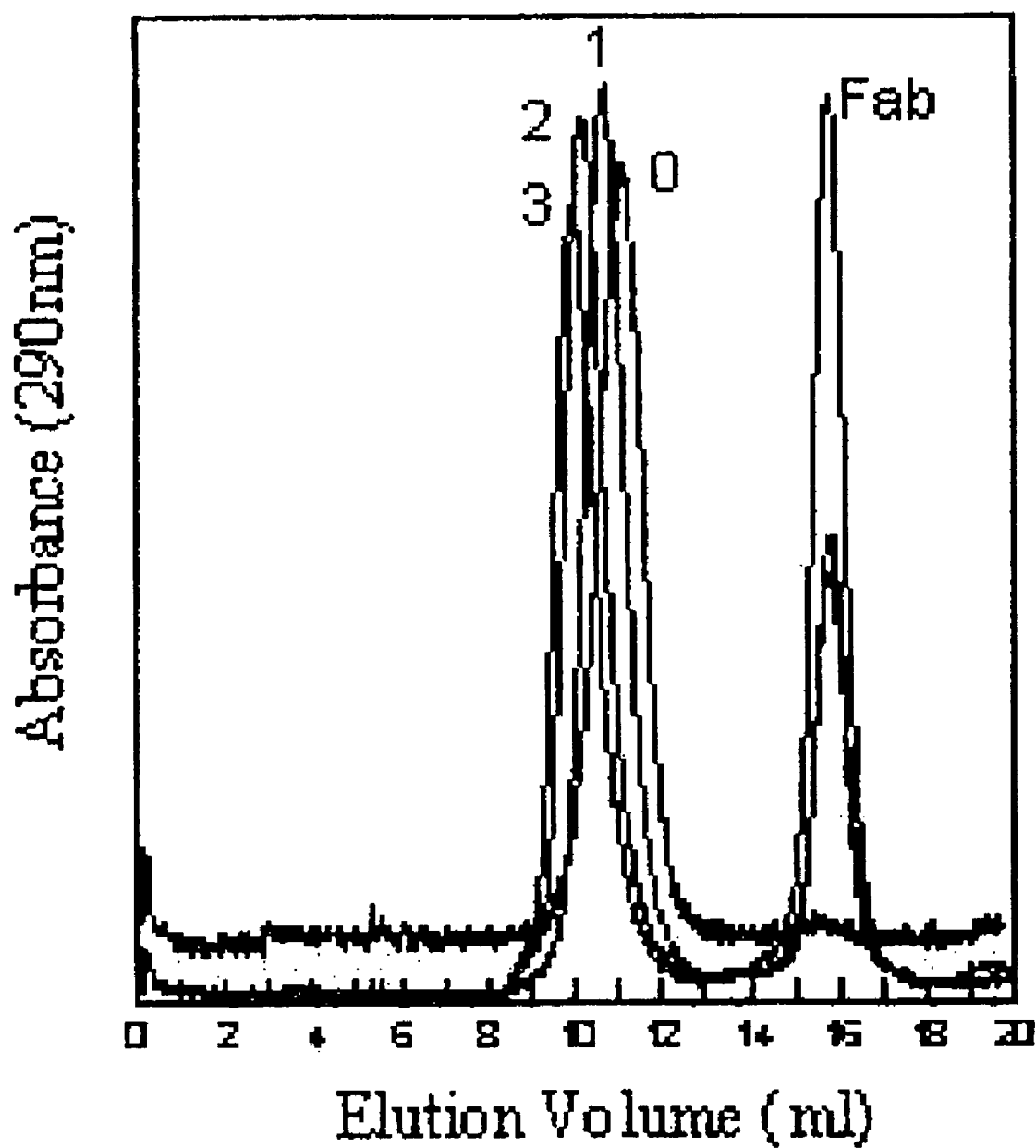
FIG. 10 Gel filtration chromatography of insulin receptor ectodomain and MFab complexes. hIR −11 ectodomain dimer (5–20 mg) was complexed with MFab derivatives (15–25 mg each) of the anti-hIR antibodies 18-44, 83-7 and 83-14 (Soos et al., 1986). Flution profiles were generated from samples loaded on to a Superdex S200 column (Pharmacia), connected to a BioLogic chromatography system (Biorad) and monitored at 280 nm. The column was eluted at 0.8 ml/min with 40 mM Tris/150 mM sodium chloride/ 0.02% sodium azide buffer adjusted to pH 8.0: Profile 0, hIR −11 ectodomain, Profile 1, ectodomain mixed with MFab 18-44; Profile 2, ectodomain mixed with MFab 18-44 and MFab 83-14; Profile 3, ectodomain mixed with MFab 18-44, MFab 83-14 and MFab 83-7. The apparent mass of each complex was determined from a plot of the following standard proteins: thyroglobulin (660 kDa), ferritin (440 kDa), bovine gamma globulin (158 kDa), bovine serum albumin (67 kDa), chicken ovalbumin (44 kDa) and equine myoglobin (17 kDa).

Purified hIR −11 ectodomain, expressed in Lec8 cells and purified by affinity chromatography on an insulin affinity column, eluted as a symmetrical peak on a Superdex S200 gel filtration column (FIG. 10). The protein eluted with an apparent mass of ~400 kDa, calculated from a standard curve generated by the elution positions of standard proteins (not shown). As expected for protein expressed in Lec 8 cells, whose glycosylation defect produces truncated oligosaccharides (Stanley, 1989. *Molec. Cellul. Biol.* 9, 377–383), this value is less than the apparent mass (450–500 kDa) reported for hIR +11 ectodomain expressed in wild-type CHO-K1 cells (Johnson et al., 1988, *Proc. Natl. Acad. Sci USA* 85, 7516–7520; Cosgrove et al.,. 1995, *Protein Expression and Purification* 6, 789–798).

Radioassay of insulin binding to purified ectodomain gave linear Scatchard plots and Kd values of 1.5–1.8×10-9 M, similar to the values of 2.4–5.0×10-9 M reported for the hIR −11 ectodomain (Andersen et al., 1990, *Biochemistry* 29, 7363-7366; Markussen et al., 1991, *J. Biol. Chem.* 266, 18814–18818; Schaffer, 1994, *Eur. J. Biochem.* 221, 1127–1132) and the values of ~1.0–5.0×10-9 M reported for the hIR +11 ectodomain (Schaefer et al., 1992, *J. Biol. Chem.* 267, 23393–23402; Whittaker et al., 1994, *Molec. Endocrinol.* 8, 1521–1527; Cosgrove et al., 1995, *Protein Expression and Purification* 6, 789–798).

Expression of hIGF-1R Ectodomain

Cloning, expression and purification of this protein used elements common to those described for hIR −11 ectodomain (Cosgrove et al., 1995, *Protein Expression and Purification* 6, 789–798), and resulted in purified product that was recognised by receptor-specific Mabs 17–69, 24–31 and 24–60 (Soos et al., 1992, *J. Biol. Chem.* 267, 12955–63) and was composed of $\alpha$ and $\beta'$ subunits of mass similar to those of hIR ectodomain.

Preparation of hIR −11 Ectodomain/MFab Complexes

A complex of hIR −11 ectodomain and Fab from antibody 83-14 eluted as a symmetrical peak of 460–500 kDa (FIG. 10), as did complexes generated from a mixture of hIR −11 ectodomain with Fab from antibody 18-44 and a mixture of hIR −11 ectodomain with Fab 83-7 (not shown). A co-complex of ectodomain with Fabs from antibodies 18-44 and 83-14 eluted at ~620 kDa, as did a co-complex with MFabs 83-14/83-7 and another with MFabs 83-7/18-44 (not shown). A complex of hIR −11 ectodomain with all three MFab derivatives, 18-44, 83-7 and 83-14, eluted at an apparent mass of ~710 kDa (FIG. 10).

Electron Microscopy

Imaging of hIR −11 and hIGF-1R Ectodomains

Figure 11:
FIG. 11 Schematic representations of electron microscopy images of the hIR ectodomain dimer.
Figure 11:
Figure 11:
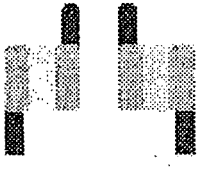
Figure 11:
Figure 11:
Figure 11:
Figure 11:
Figure 11:
Figure 11:
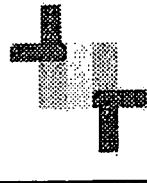
Figure 11:

Single-molecule imaging of uncomplexed dimeric hIR −11 ectodomain was carried out under a variety of negative staining conditions, which emphasised different aspects of the structure of the molecular envelope. Images obtained by this investigation are depicted in FIG. 11.

The least aggressive or penetrative stain was potassium phosphotungstate (KPT), which revealed consistent globular particles with very little internal structure other than a suggestion of a division into two parallel bars. Staining with methylamine tungstate also revealed the parallel bar images.

Further investigation using progressively more penetrative, but also potentially more disruptive, stains confirmed the observations above. Staining with uranyl acetate and uranyl formate showed the separation of the parallel bars most clearly, but uranyl acetate showed evidence of disrupting the structure of the particles, i.e. a decrease in the consistency of the particle shape and a tendency for particles to look unravelled or denatured despite having been subjected to chemical cross-linking prior to staining. In areas of thicker stain, parallel bars predominated, whereas in more thinly stained regions, U-shaped particles could be identified, sometimes outnumbering the parallel-bar structures (see FIG. 11).

Imaging of hIR −11 Ectodomain Complexed with 83-7 MFab

This complex was particularly noteworthy for the consistency of the form of the particles, especially under the gentler staining conditions afforded by stains such as KPT and methylamine tungstate. The particles were interpreted as having been restricted in the views they presented, after air-drying on the carbon support film, by the almost diametrically opposite binding of the two Fab arms to the antigen to form a highly elongated complex structure. Under these conditions three distinct views could be recognised (see FIG. 11). Two views (interpreted as top-down/bottom-up) show the Fab arms displaced clockwise or anti-clockwise as extensions of the parallel plates with two-fold symmetry. The third view shows an image with the two Fab arms in line roughly through the centre of the receptor on its opposite sides, interpreted as a side projection of binding half-way up the plates.

The use of aggressive uranyl stains operating at lower pHs revealed internal structure of the molecular envelope at the expense of consistency of the particle morphology. For example, staining with uranyl acetate or uranyl formate showed that parallel bars can be seen in particles in which the Fab arms are displaced either clockwise or anticlockwise but not where the intermediate central or axial position of the two Fab arms is presented in projection. These observations show 83-7 MFab binding roughly half-way up the side-edge of each hIR –11 ectodomain plate. The epitope recognised by Mab 83-7 has been mapped to the cys-rich region, residues 191–297, by analysis of chimeric receptors (Zhang and Roth, 1991, *Proc. Natl. Acad. Sci. USA* 88, 9858–9862).

Imaging of hIR –11 Ectodomain Complexed with Either 83-14 MFab or 18-44 MFab

Complexes were formed with Fabs from the most insulin-mimetic antibody Mab 83-14. Projections showing the Fab arms bound to and extending out from near the base of the U-shaped particles were identified. A second field of particles showed objects composed of two parallel bars as observed for the undecorated ectodomain, with Fab arms projecting obliquely from diametrically opposite extremities (see FIG. 11). Similar but less definitive images were also seen when MFab 18-44 was bound to hIR –11 ectodomain. The epitope for Mab 83-14 is between residues 469–592 (Prigent et al., 1990) in the connecting domain. This domain contains one of the disulphide bonds (Cys524—Cys524) between the two monomers in the IR dimer (Schaffer and Ljungqvist, 1992, *Biochem. Biophys. Res. Commun.* 189, 650–653). The epitope for Mab 18-44 is a linear epitope, residues 765–770 (Prigent et al., 1990, *J. Biol. Chem.* 265, 9970–9977) in the β-chain, near the end of the insert domain (O'Bryan et al., 1991, *Mol. Cell. Biol.* 11, 5016–5031). The insert domain contains the second disulphide bond connecting the two monomers in the IR dimer (Sparrow et al., 1997, *J. Biol. Chem.*, 272, 29460–29467).

Imaging of hIR –11 Ectodomain Co-Complexed with Two Different MFabs Per Monomer

The double complex of hIR –11 ectodomain with MFabs 83-7 and 18-44 was stained with 2% KPT at pH 6.0, and revealed the molecular envelopes. The particle appears complex in shape, and can assume a number of different orientations on the carbon support film, giving rise to a number of different projections in the micrograph. The predominant view is of an asymmetric X-shape (some examples circled). It shows the 83-7 MFab arms bound at opposite ends of the parallel bars with the two 18-44 MFabs appearing as shorter projections extending out from either side of each ectodomain.

Images of the double complex of hIR –11 ectodomain with 83-7 and 83-14 MFabs gave X-shaped images similar to those seen with the 83-7/18-44 double complex. In contrast the double complex of hIR –11 ectodomain with 18-44 and 83-14 MFabs did not present the characteristic asymmetric X-shapes described above. Instead, the molecular envelope appeared to be elongated in many views, with only an occasional X-shaped projection. While a detailed interpretation of these images would be premature, it is clear that MFabs 18-44 and 83-14, two of the more potent insulin mimetic antibodies (Prigent et al., 1990, *J. Biol. Chem.* 265, 9970–9977), can bind simultaneously to the receptor.

Imaging of hIR –11 Ectodomain Co-Complexed with Three Different MFabs Per Monomer A field of particles from a micrograph of hIR –11 ectodomain were complexed simultaneously with MFabs 83-7, 83-14 and 18-44. In the thicker stain regions the molecular envelope was X-shaped, and looked very similar to that of the double complexes of hIR –11 ectodomain with either 83-7 and 18-44 or 83-7 and 83-14. However, in the more thinly stained regions particles of greater complexity were visible, and it was possible occasionally to identify that there are in fact more than four MFabs bound to the ectodomain dimer.

The single-molecule imaging of hIR –11 ectodomain presented here suggests a molecular envelope for this dimeric species significantly different from that of any previously published study. However, an unequivocal determination of the molecular envelope even from the present study is not entirely straightforward. A major complicating factor here has been the relative fragility of the expressed ectodomain when exposed to the rigors of electron microscope preparation by negative staining. For example, staining with potassium phosphotungstate (KPT, pH 6.0–7.0) frequently suggested a denaturation of the dimeric molecules, but when appropriate conditions were satisfied, good seemingly interpretable molecular envelope images were achieved; staining with methylamine tungstate (pH ~7.0) supported the best KPT molecular envelope images, but had the suggestion of a swelling of the molecular structure at neutral pH; and the acid-pH stains of uranyl acetate (pH ~4.2) and uranyl formate (pH ~3.0), with their ability to penetrate the ectodomain structure, appeared to illuminate not so much the molecular envelope as the zones of high projected protein density within the dimer.

An amalgam of impressions from these various staining regimens has led to the following interpretation of single-molecule images of these undecorated, or naked, dimers: the predominant dimeric molecular image encountered here has been that of "parallel bars" of projected protein density. This view is so predominant, indeed, that it suggests there is either a single preferred orientation of the molecules on the glow-discharged carbon support film, or that this impression of parallel bars of density may represent a mixture of superficially similar structure projections, with the subtleties of these different projections being masked by the relatively coarse resolution of this single-molecule direct imaging. The impression of parallel bars of projected protein density is particularly predominant in regions of thicker negative stain. A second view of the molecular envelope, appreciably less well represented in regions of thicker stain but predominant in regions of thin staining, is that of 'open' U's, or V's. These two views of hIR –11 ectodomain were supported by the single-molecule imaging of hIGF-1R ectodomain under comparable conditions of negative staining.

If the assumption is made that these two recognisable projected views, that of parallel bars and of open U's/V's, are different views of the same dimeric molecule, an assumption strongly supported by the MFab complex imaging, a coarse model of the molecular envelope can be rationalized. The model structure is roughly that of a cube, composed of two almost-parallel plates of high protein density, separated by a deep cleft of low protein main-chain and side-chain density able to be penetrated by stain, and connected by intermediate stain-excluding density near what is assumed here to be their base (that is, nearest the membrane-anchoring region). The width of the low-density cleft appears to be of the order of 30–35 Å, sufficient to accommodate the binding of the insulin molecule of diameter ca.

30 Å, although we have no electron microscopical evidence to support insulin-binding in this cleft at this stage.

It has been established through imaging of bound 83-7 MFab that there is a dimeric two-fold axis normal to the membrane surface between these plates of density. Occasionally, dimer images display a relative displacement of the bars of density, interpreted here as a limited capacity for a shearing of the interconnecting zone between the two plates along their horizontal axis parallel to the membrane; other images show bars skewed from parallel, implying a limited capacity for the plates to rotate independently around the two-fold axis, again via this interconnecting zone. These two observations each suggest a relatively flexible connectivity between the dimer plates in the membrane-proximal region of intermediate protein density, which could possibly contribute to the transmembrane signalling process.

The approximate overall measured dimensions of the ectodomain dimer are 110×90×120 Å, calibrated against the dimensions of imaged influenza neuraminidase heads, known from the solved X-ray structure (Varghese et al., 1983, Nature 303, 35–40). It can be noted that there is a compatibility here between the molecular weights and molecular dimensions of these two molecular species: the compact tetrameric influenza neuramimidase heads of Mr ~200 kDa occupy a volume almost 100×100×60 Å; the more open dimeric insulin receptor ectodomains of similar Mr ~240 kDa imaged here occupy a volume approximately 110×90×120 Å, roughly twice that of the neuramimidase heads, accommodating the slightly higher molecular weight and substantial central low-density cleft.

The low-resolution roughly cubic compact structure proposed here differs substantially from the T-shaped model proposed by Christiansen et al. (1991, Proc. Natl. Acad. Sci. U.S.A. 88, 249–252) and Tranum-Jensen et al., (1994, J. Membrane Biol. 140, 215–223) for the whole receptor and the elongated model proposed by Schaefer et al. (1992, J. Biol. Chem. 267, 23393–23402) for soluble ectodomain. Significantly, those previous studies did not provide any convincing independent electron microscopical evidence that their imaged objects were in fact insulin receptor.

In the present study, the identity of the imaged molecules as hIR −11 ectodomain has been confirmed by imaging complexes of the dimer with Fabs of the three well-established conformationial Mabs against native hIR, 83-7, 83-14 and 18-44 (Soos et al., 1986, Biochem. J. 235, 199–208; 1989, Proc. Natl Acad. Sci. USA 86, 5217–5221), bound singly and in combination. In all these instances, virtually every particle in the field of view exhibited MFab decoration through binding to conformational epitopes, establishing not only the identity of the imaged particles but also the conformational integrity of the expressed ectodomains. Furthermore, the cleanliness and uniformity of these hIR −11 ectodomain preparations, both naked and decorated, visualised here by electron microscopy demonstrate their high suitability for X-ray crystallization trials.

The known flexibility of the Fab arms exacerbates image-to-image variability beyond the limited extent already described for the undecorated dimeric ectodomains, complicating any precise interpretation of these antigen-antibody complexes. Such molecular flexibility also renders largely impractical any single-molecule computer image averaging to facilitate image interpretation, progressively more so with the higher order antigen-antibody complexes studied here.

The most readily interpretable of these images, showing least image-to-image variability, are those of 83-7 MFab bound to dimers where, fortuitously, the antigen-antibody complex is constrained in its degrees of rotational freedom on the carbon support film. Many projected images show the two Fab arms in line roughly through the centre of the antigen on its opposite sides, interpreted as a side projection of binding half-way up the plates from their membrane-proximal base. Other sub-sets of images show the two Fab arms still parallel but displaced clockwise or anticlockwise with 2-fold symmetry, each Fab approximating an extension of one of the parallel bars of antigen density, interpreted here as representing top or bottom projections along the 2-fold axis. The third projection, along the axis of the Fab arms, could not be sampled here because of the constraining geometry of this molecular complex. These observations suggest binding of 83-7 MFab roughly half-way up the side-edge of the hIR −11 ectodomain plate. This then allows an initial attempt at spatially mapping the 83-7 MFab epitope, which has been sequence-mapped to residues 191–297 in the cys-rich region of the insulin receptor (Zhang and Roth, 1991. Proc. Natl. Acad. Sci. USA 88, 9858–9862). The spatial separation and relative orientations of the two binding epitopes of Mab 83-7 on the hIR −11 ectodomain dimer as indicated here appear inconsistent with the proposal that Mab 83-7 could bind intramolecularly to hIR (O'Brien et al., 1987, Biochem J. 6, 4003–4010).

Decoration of the ectodomain dimer with 83-7 MFab established that the two plates of high protein-density are arranged with 2-fold symmetry. Decoration with either 83-14 or 18-44 MFab, on the other hand, allowed sampling of the third projection of the ectodomain dimer precluded by 83-7 MFab binding. Significantly, this third view established unequivocally the U-shaped projection of the hIR −11 ectodomain dimer, something which was only able to be assumed with the undecorated ectodomain images. Further, this projection has allowed a rough spatial mapping close to the base of the U-shaped dimer for the epitopes recognised by 83-14 MFab (residues 469–592, connecting domain) and 18-44 MFab (residues 765–770, b-chain insert domain; exon 11 plus numbering, Prigent et al., 1990. J. Biol. Chem. 265, 9970–9977).

Inherent in the model structure is the implication that, with the two-fold axis aligned normal to the membrane surface, the mouth of the low-density cleft where insulin binding may occur would lie most distant from the transmembrane anchor, whilst the zone of intermediate density connecting the two high-density plates would be in close proximity to the membrane. It follows, in this model, that the L1/cys-rich/L2 domains (Bajaj et al., 1997, Biochim. Biophys. Acta 916, 220–226; Ward et al., 1995, Proteins: Struct., Funct., Genet. 22, 141–153), which comprise much of the insulin-binding region (see Mynarcik et al., 1997, J. Biol. Chen. 272, 2077–2081), most probably lie in the membrane-distal upper halves of the two plates, whilst the membrane-proximal lower halves contain the connecting domains, the fibronectin-type domains, the insert domains and the interchain disulphide bonds (Schaffer and Ljungqvist, 1992, Biochem. Biophys. Res. Commun. 189, 650–653; Sparrow et al., 1997, J. Biol. Chem., 272, 29460–29467). Such a disposition of domains is supported by the images seen with the single MFab decoration, the 83-7 MFab epitope in the cys-rich region being spatially mapped roughly half-way up the side-edge of the ectodomain plates, and the 83-14 and 18-44 MFab epitopes (connecting domain and β-chain insert domain, respectively) being mapped near the base of the plates. Our preference is for a single a-bc monomer to occupy a single plate, although the possibility of a single monomer straddling the two plates of protein density cannot be discounted.

The more complex images involving co-binding of two, and even more so of all three, MFabs to each monomer of the ectodomain dimer are not easily interpretable with respect to relative domain arrangements within the monomer at present, not least of all because of the difficulty of finding conditions of negative staining that will simultaneously maintain the integrity of the Fab binding while highlighting recognisable and reproducible details of the internal structure of the dimeric IR ectodomain.

The data presented here demonstrate the ability of single-molecule imaging to give an initial insight into the topology of multidomain structures such as the ectodomain of hIR, and the value of combining this technique with that of either single or multiple monoclonal Fab attachment per monomer as a potential means of epitope, and domain, mapping of the structure. By imaging Fab complexes of other members of the family, such as hIGF-1R ectodomain, and combining available sequence-mapped epitope information with that presented here, a more comprehensive understanding of domain arrangements within the IR family ectodomains should be forthcoming.

EXAMPLE 5

Structure-Based Design of Ligands for the IGF Receptor as Potential Inhibitors of IGF Binding The structure of IGF receptor can be considered as a filter or screen to design, or evaluate, potential ligands for the receptor. Those skilled in the art can use a number of well known methods for de novo ligand design, such as GRID, GREEN, HSITE, MCSS, HINT, BUCKETS, CLIX, LUDI, CAVEAT, SPLICE, HOOK, NEWLEAD, PRO_LIGAND, ELANA, LEGEND, GenStar, GrowMol, GROW, GEMINI, GroupBuild, SPROUT, and LEAPFROG, to generate potential agonists or antagonists for IGF-1R. In addition, the IGF-1R structure may be used as a query for database searches for potential ligands. The databases searched may be existing eg ACD, Cambridge Crystallographic, NCI, or virtual. Virtual databases, which contain very large numbers (currently up to $10^{12}$) of chemically reasonable structures, may be generated by those skilled in the art using techniques such as DBMaker, ChemSpace, TRIAD and ILIAD.

The IGFR structure contains a number of sites into which putative ligands may bind. Search strategies known to those skilled in the art may be used to identify putative ligands for these sites. Examples of two suitable search strategies are described below:

(i) Database Search

The properties of key parts of the putative site may be used as a database search query. For example, the Unity 2.x database software may be used. A flexible 3D search can be run in which a "directed tweak" algorithm is used to find low energy conformations of potential ligands which satisfy the query.

(ii) De Novo Design of Ligands

The Leapfrog algorithm as incorporated in the software package, Sybyl version 6.4.2 (Tripos Associates, St Louis), may be used to design potential ligands for IGF-1R sites. The coordinates of residues around the site may be taken from the x-ray structure, hydrogens and charges (Kollman all atom dictionary charges) added. From the size, shape and properties of the site, a number of potential ligands may be proposed. Leapfrog may be used to optimize the conformation of ligands and position on the site, to rank the likely strength of binding interactions with IGF-1R, and to suggest modifications to the structures which would have enhanced binding.

It is also possible to design ligands capable of interacting with more than one site. One way in which this may be done is by attaching flexible linkers to ligands designed for specific sites so as to join them. The linkers may be attached in such a way that they do not disrupt the binding to individual sites.

All references cited above are incorporated herein in their entirety by reference.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of identifying a compound which modulates binding of a ligand to an IGF-1 receptor comprising:
   (A) designing or screening for a compound which binds to the structure formed by amino acids 1–462 having the atomic coordinates as shown in FIG. 1, where binding of the compound to the structure is favored energetically, and
   (B) testing the compound designed or screened for in (A) for its ability to modulate binding of the ligand to the IGF-1 receptor in vivo or in vitro, thereby identifying a compound that modulates binding to the IGF-1 receptor.

2. The method according to claim 1, wherein the testing in step (B) is performed by a high-throughput assay.

3. The method according to claim 1, wherein the testing in step (B) comprises testing the compound for the ability to modulate IGF-1 receptor mediated cell proliferation.

4. The method according to claim 1 in which the compound is identified from test compounds in a database.

5. The method according to claim 1, wherein step (B) comprises testing the compound for its ability to increase signal transduction by binding to the IGF-1 receptor.

6. The method according to claim 1, wherein step (B) comprises testing the compound for its ability to decrease signal transduction by binding to the IGF-1 receptor.

7. The method according to claim 1, wherein step (B) comprises testing the compound for its ability to inhibit or prevent the binding of a ligand to the IGF-1 receptor.

8. A method of selecting a compound which binds to the IGF-1 receptor comprising:
   (A) designing or screening for a compound which binds to the structure formed by amino acids 1–462 having the atomic coordinates as shown in FIG. 1, where binding of the compound to the structure is favored energetically, and
   (B) selecting a compound designed or screened for in (A) which has an experimentally determined $K_d$ or $K_I$ of less than $10^{-6}$ M for the IGF-1 receptor, thereby selecting a compound which binds to the IGF-1 receptor.

9. The method according to claim 8, wherein the $K_d$ is less than $10^{-8}$ M.

10. The method according to claim 8, wherein the $K_I$ is less than $10^{-8}$ M.

* * * * *

UNITED STATES PATENT AND TRADEMARK OFFICE
CERTIFICATE OF CORRECTION

| | | |
|---|---|---|
| PATENT NO. | : 7,020,563 B1 | Page 1 of 1 |
| APPLICATION NO. | : 09/555275 | |
| DATED | : March 28, 2006 | |
| INVENTOR(S) | : David John Bentley et al. | |

It is certified that error appears in the above-identified patent and that said Letters Patent is hereby corrected as shown below:

TITLE PAGE,
Item "(75) Inventors:", after the data for inventor "George Oscar Lovrecz, North Balwyn (AU)", insert -- Neil Moreton McKern, Lilydale (AU) --.

Signed and Sealed this

Seventeenth Day of October, 2006

JON W. DUDAS
*Director of the United States Patent and Trademark Office*

SEQUENCE LISTING

<160> NUMBER OF SEQ ID NOS: 16

<210> SEQ ID NO 1
<211> LENGTH: 150
<212> TYPE: PRT
<213> ORGANISM: Homo sapiens

<400> SEQUENCE: 1

```
Glu Ile Cys Gly Pro Gly Ile Asp Ile Arg Asn Asp Tyr Gln Gln Leu
1               5                   10                  15

Lys Arg Leu Glu Asn Cys Thr Val Ile Glu Gly Tyr Leu His Ile Leu
            20                  25                  30

Leu Ile Ser Lys Ala Glu Asp Tyr Arg Ser Tyr Arg Phe Pro Lys Leu
        35                  40                  45

Thr Val Ile Thr Glu Tyr Leu Leu Leu Phe Arg Val Ala Gly Leu Glu
    50                  55                  60

Ser Leu Gly Asp Leu Phe Pro Asn Leu Thr Val Ile Arg Gly Trp Lys
```

-continued

```
            65                  70                  75                  80
Leu Phe Tyr Asn Tyr Ala Leu Val Ile Phe Glu Met Thr Asn Leu Lys
                    85                  90                  95

Asp Ile Gly Leu Tyr Asn Leu Arg Asn Ile Thr Arg Gly Ala Ile Arg
            100                 105                 110

Ile Glu Lys Asn Ala Asp Leu Cys Tyr Leu Ser Thr Val Asp Trp Ser
        115                 120                 125

Leu Ile Leu Asp Ala Val Ser Asn Asn Tyr Ile Val Gly Asn Lys Pro
    130                 135                 140

Pro Lys Glu Cys Gly Asp
145                 150

<210> SEQ ID NO 2
<211> LENGTH: 157
<212> TYPE: PRT
<213> ORGANISM: Homo sapiens

<400> SEQUENCE: 2

His Leu Tyr Pro Gly Glu Val Cys Pro Gly Met Asp Ile Arg Asn Asn
1               5                   10                  15

Leu Thr Arg Leu His Glu Leu Glu Asn Cys Ser Val Ile Glu Gly His
            20                  25                  30

Leu Gln Ile Leu Leu Met Phe Lys Thr Arg Pro Glu Asp Phe Arg Asp
        35                  40                  45

Leu Ser Phe Pro Lys Leu Ile Met Ile Thr Asp Tyr Leu Leu Leu Phe
    50                  55                  60

Arg Val Tyr Gly Leu Glu Ser Leu Lys Asp Leu Phe Pro Asn Leu Thr
65                  70                  75                  80

Val Ile Arg Gly Ser Arg Leu Phe Phe Asn Tyr Ala Leu Val Ile Phe
                    85                  90                  95

Glu Met Val His Leu Lys Glu Leu Gly Leu Tyr Asn Leu Met Asn Ile
            100                 105                 110

Thr Arg Gly Ser Val Arg Ile Glu Lys Asn Asn Glu Leu Cys Tyr Leu
        115                 120                 125

Ala Thr Ile Asp Trp Ser Arg Ile Leu Asp Ser Val Glu Asp Asn His
    130                 135                 140

Ile Val Leu Asn Lys Asp Asp Asn Glu Glu Cys Gly Asp
145                 150                 155

<210> SEQ ID NO 3
<211> LENGTH: 165
<212> TYPE: PRT
<213> ORGANISM: Homo sapiens
<220> FEATURE:
<221> NAME/KEY: MISC_FEATURE
<222> LOCATION: (15)..(24)
<223> OTHER INFORMATION: Protein sequence known but not provided in
      Figure 6a
<220> FEATURE:
<221> NAME/KEY: MISC_FEATURE
<222> LOCATION: (109)..(110)
<223> OTHER INFORMATION: Protein sequence known but not provided in
      Figure 6a

<400> SEQUENCE: 3

Leu Glu Glu Lys Lys Val Cys Gln Gly Thr Ser Asn Lys Leu Xaa Xaa
1               5                   10                  15

Xaa Xaa Xaa Xaa Xaa Xaa Xaa Phe Leu Ser Leu Gln Arg Met Phe Asn
            20                  25                  30
```

```
Asn Cys Glu Val Val Leu Gly Asn Leu Glu Ile Thr Tyr Val Gln Arg
            35                  40                  45

Asn Tyr Asp Leu Ser Phe Leu Lys Thr Ile Gln Glu Val Ala Gly Tyr
 50                  55                  60

Val Leu Ile Ala Leu Asn Thr Val Glu Arg Ile Pro Leu Glu Asn Leu
 65                  70                  75                  80

Gln Ile Ile Arg Gly Asn Met Tyr Tyr Glu Asn Ser Tyr Ala Leu Ala
                    85                  90                  95

Val Leu Ser Asn Tyr Asp Ala Asn Lys Thr Gly Leu Xaa Xaa Lys Pro
                100                 105                 110

Met Arg Asn Leu Gln Glu Ile Leu His Gly Ala Val Arg Phe Ser Asn
            115                 120                 125

Asn Pro Ala Leu Cys Asn Val Glu Ser Ile Gln Trp Arg Asp Ile Val
130                 135                 140

Ser Ser Asp Phe Leu Ser Asn Met Ser Met Asp Phe Gln Asn His Leu
145                 150                 155                 160

Gly Ser Cys Gln Lys
                165

<210> SEQ ID NO 4
<211> LENGTH: 167
<212> TYPE: PRT
<213> ORGANISM: Homo sapiens
<220> FEATURE:
<221> NAME/KEY: MISC_FEATURE
<222> LOCATION: (11)..(17)
<223> OTHER INFORMATION: Protein sequence known but not provided in
      Figure 6a
<220> FEATURE:
<221> NAME/KEY: MISC_FEATURE
<222> LOCATION: (44)..(50)
<223> OTHER INFORMATION: Protein sequence known but not provided in
      Figure 6a

<400> SEQUENCE: 4

Lys Val Cys Asn Gly Ile Gly Ile Gly Glu Xaa Xaa Xaa Xaa Xaa Xaa
 1                5                  10                  15

Xaa Asn Ala Thr Asn Ile Lys His Phe Lys Asn Cys Thr Ser Ile Ser
                 20                  25                  30

Gly Asp Leu His Ile Leu Pro Val Ala Phe Arg Xaa Xaa Xaa Xaa Xaa
                 35                  40                  45

Xaa Xaa Pro Pro Leu Asp Pro Gln Glu Leu Asp Ile Leu Lys Thr Val
 50                  55                  60

Lys Glu Ile Thr Gly Phe Leu Leu Ile Gln Ala Trp Pro Glu Asn Arg
 65                  70                  75                  80

Thr Asp Leu His Ala Phe Glu Asn Leu Glu Ile Ile Arg Gly Arg Thr
                 85                  90                  95

Lys Gln His Gly Gln Phe Ser Leu Ala Val Val Ser Leu Asn Ile Thr
                100                 105                 110

Ser Leu Gly Leu Arg Ser Leu Lys Glu Ile Ser Asp Gly Asp Val Ile
            115                 120                 125

Ile Ser Gly Asn Lys Asn Leu Cys Tyr Ala Asn Thr Ile Asn Trp Lys
130                 135                 140

Lys Leu Phe Gly Thr Ser Gly Gln Lys Thr Lys Ile Ile Ser Asn Arg
145                 150                 155                 160

Gly Glu Asn Ser Cys Lys Ala
                165
```

<210> SEQ ID NO 5
<211> LENGTH: 161
<212> TYPE: PRT
<213> ORGANISM: Homo sapiens

<400> SEQUENCE: 5

```
Lys Val Cys His Leu Glu Gly Glu Lys Thr Ile Asp Ser Val Thr
1               5                   10                  15

Ser Ala Gln Glu Leu Arg Gly Cys Thr Val Ile Asn Gly Ser Leu Ile
            20                  25                  30

Ile Asn Ile Arg Gly Gly Asn Asn Leu Ala Ala Glu Leu Glu Ala Asn
            35                  40                  45

Leu Gly Leu Ile Glu Glu Ile Ser Gly Tyr Leu Lys Ile Arg Arg Ser
    50                  55                  60

Tyr Ala Leu Val Ser Leu Ser Phe Phe Arg Lys Leu Arg Leu Ile Arg
65                  70                  75                  80

Gly Glu Thr Leu Glu Ile Gly Asn Tyr Ser Phe Tyr Ala Leu Asp Asn
                85                  90                  95

Gln Asn Leu Arg Gln Leu Trp Asp Trp Ser Lys His Asn Leu Thr Ile
            100                 105                 110

Thr Gln Gly Lys Leu Phe Phe His Tyr Asn Pro Lys Leu Cys Leu Ser
            115                 120                 125

Glu Ile His Lys Met Glu Glu Val Ser Gly Thr Lys Gly Arg Gln Glu
        130                 135                 140

Arg Asn Asp Ile Ala Leu Lys Thr Asn Gly Asp Lys Ala Ser Cys Glu
145                 150                 155                 160

Asn
```

<210> SEQ ID NO 6
<211> LENGTH: 161
<212> TYPE: PRT
<213> ORGANISM: Homo sapiens

<400> SEQUENCE: 6

```
Lys Val Cys Glu Glu Lys Lys Thr Lys Thr Ile Asp Ser Val Thr
1               5                   10                  15

Ser Ala Gln Met Leu Gln Gly Cys Thr Ile Phe Lys Gly Asn Leu Leu
            20                  25                  30

Ile Asn Ile Arg Arg Gly Asn Asn Ile Ala Ser Glu Leu Glu Asn Phe
            35                  40                  45

Met Gly Leu Ile Glu Val Val Thr Gly Tyr Val Lys Ile Arg His Ser
    50                  55                  60

His Ala Leu Val Ser Leu Ser Phe Leu Lys Asn Leu Arg Leu Ile Leu
65                  70                  75                  80

Gly Glu Glu Gln Leu Glu Gly Asn Tyr Ser Phe Tyr Val Leu Asp Asn
                85                  90                  95

Gln Asn Leu Gln Gln Leu Trp Asp Trp Asp His Arg Asn Leu Thr Ile
            100                 105                 110

Lys Ala Gly Lys Met Tyr Phe Ala Phe Asn Pro Lys Leu Cys Val Ser
            115                 120                 125

Glu Ile Tyr Arg Met Glu Glu Val Thr Gly Thr Lys Gly Arg Gln Ser
        130                 135                 140

Lys Gly Asp Ile Asn Thr Arg Asn Asn Gly Glu Arg Ala Ser Cys Glu
145                 150                 155                 160

Ser
```

```
<210> SEQ ID NO 7
<211> LENGTH: 150
<212> TYPE: PRT
<213> ORGANISM: Homo sapiens

<400> SEQUENCE: 7

Asp Leu Cys Pro Gly Thr Met Glu Glu Lys Pro Met Cys Glu Lys Thr
1               5                   10                  15

Thr Ile Asn Asn Glu Tyr Asn Tyr Arg Cys Trp Thr Thr Asn Arg Cys
                20                  25                  30

Gln Lys Met Cys Pro Ser Thr Cys Gly Lys Arg Ala Cys Thr Glu Asn
            35                  40                  45

Asn Glu Cys Cys His Pro Glu Cys Leu Gly Ser Cys Ser Ala Pro Asp
        50                  55                  60

Asn Asp Thr Ala Cys Val Ala Cys Arg His Tyr Tyr Tyr Ala Gly Val
65                  70                  75                  80

Cys Val Pro Ala Cys Pro Pro Asn Thr Tyr Arg Phe Glu Gly Trp Arg
                85                  90                  95

Cys Val Asp Arg Asp Phe Cys Ala Asn Ile Leu Ser Ala Glu Ser Ser
                100                 105                 110

Asp Ser Glu Gly Phe Val Ile His Asp Gly Glu Cys Met Gln Glu Cys
            115                 120                 125

Pro Ser Gly Phe Ile Arg Asn Gly Ser Gln Ser Met Tyr Cys Ile Pro
        130                 135                 140

Cys Glu Gly Pro Cys Pro
145                 150

<210> SEQ ID NO 8
<211> LENGTH: 153
<212> TYPE: PRT
<213> ORGANISM: Homo sapiens

<400> SEQUENCE: 8

Asp Ile Cys Pro Gly Thr Ala Lys Gly Lys Thr Asn Cys Pro Ala Thr
1               5                   10                  15

Val Ile Asn Gly Gln Phe Val Glu Arg Cys Trp Thr His Ser His Cys
                20                  25                  30

Gln Lys Val Cys Pro Thr Ile Cys Lys Ser His Gly Cys Thr Ala Glu
            35                  40                  45

Gly Leu Cys Cys His Ser Glu Cys Leu Gly Asn Cys Ser Gln Pro Asp
        50                  55                  60

Asp Pro Thr Lys Cys Val Ala Cys Arg Asn Phe Tyr Leu Asp Gly Arg
65                  70                  75                  80

Cys Val Glu Thr Cys Pro Pro Tyr Tyr His Phe Gln Asp Trp Arg
                85                  90                  95

Cys Val Asn Phe Ser Phe Cys Gln Asp Leu His His Lys Cys Lys Asn
                100                 105                 110

Ser Arg Arg Gln Gly Cys His Gln Tyr Val Ile His Asn Asn Lys Cys
            115                 120                 125

Ile Pro Glu Cys Pro Ser Gly Tyr Thr Met Asn Ser Ser Asn Leu Leu
        130                 135                 140

Cys Thr Pro Cys Leu Gly Pro Cys Pro
145                 150

<210> SEQ ID NO 9
<211> LENGTH: 146
```

```
<212> TYPE: PRT
<213> ORGANISM: Homo sapiens

<400> SEQUENCE: 9

Lys Cys Asp Pro Ser Cys Pro Asn Gly Ser Cys Trp Gly Ala Gly Glu
1               5                   10                  15

Glu Asn Cys Gln Lys Leu Thr Lys Ile Ile Cys Ala Gln Gln Cys Ser
            20                  25                  30

Gly Arg Cys Arg Gly Lys Ser Pro Ser Asp Cys Cys His Asn Gln Cys
        35                  40                  45

Ala Ala Gly Cys Thr Gly Pro Arg Glu Ser Asp Cys Leu Val Cys Arg
    50                  55                  60

Lys Phe Arg Asp Glu Ala Thr Cys Lys Asp Thr Cys Pro Pro Leu Met
65                  70                  75                  80

Leu Tyr Asn Pro Thr Thr Tyr Gln Met Asp Val Asn Pro Glu Gly Lys
                85                  90                  95

Tyr Ser Phe Gly Ala Thr Cys Val Lys Lys Cys Pro Arg Asn Tyr Val
            100                 105                 110

Val Thr Asp His Gly Ser Cys Val Arg Ala Cys Gly Ala Asp Ser Tyr
        115                 120                 125

Glu Met Glu Glu Asp Gly Val Arg Lys Cys Lys Lys Cys Glu Gly Pro
    130                 135                 140

Cys Arg
145

<210> SEQ ID NO 10
<211> LENGTH: 142
<212> TYPE: PRT
<213> ORGANISM: Homo sapiens

<400> SEQUENCE: 10

Gln Val Cys His Ala Leu Cys Ser Pro Glu Gly Cys Trp Gly Pro Glu
1               5                   10                  15

Pro Arg Asp Cys Val Ser Cys Arg Asn Val Ser Arg Gly Arg Glu Cys
            20                  25                  30

Val Asp Lys Cys Lys Leu Leu Glu Gly Glu Pro Arg Glu Phe Val Glu
        35                  40                  45

Asn Ser Glu Cys Ile Gln Cys His Pro Glu Cys Leu Pro Gln Ala Met
    50                  55                  60

Asn Ile Thr Cys Thr Gly Arg Gly Pro Asp Asn Cys Ile Gln Cys Ala
65                  70                  75                  80

His Tyr Ile Asp Gly Pro His Cys Val Lys Thr Cys Pro Ala Gly Val
                85                  90                  95

Met Gly Glu Asn Asn Thr Leu Val Trp Lys Tyr Ala Asp Ala Gly His
            100                 105                 110

Val Cys His Leu Cys His Pro Asn Cys Thr Tyr Gly Cys Thr Gly Pro
        115                 120                 125

Gly Leu Glu Gly Cys Pro Thr Asn Gly Pro Lys Ile Pro Ser
    130                 135                 140

<210> SEQ ID NO 11
<211> LENGTH: 906
<212> TYPE: PRT
<213> ORGANISM: Homo sapiens

<400> SEQUENCE: 11

Glu Ile Cys Gly Pro Gly Ile Asp Ile Arg Asn Asp Tyr Gln Gln Leu
```

-continued

```
1               5               10              15
Lys Arg Leu Glu Asn Cys Thr Val Ile Glu Gly Tyr Leu His Ile Leu
                20              25              30
Leu Ile Ser Lys Ala Glu Asp Tyr Arg Ser Tyr Arg Phe Pro Lys Leu
                35              40              45
Thr Val Ile Thr Glu Tyr Leu Leu Phe Arg Val Ala Gly Leu Glu
                50              55              60
Ser Leu Gly Asp Leu Phe Pro Asn Leu Thr Val Ile Arg Gly Trp Lys
65              70              75              80
Leu Phe Tyr Asn Tyr Ala Leu Val Ile Phe Glu Met Thr Asn Leu Lys
                85              90              95
Asp Ile Gly Leu Tyr Asn Leu Arg Asn Ile Thr Arg Gly Ala Ile Arg
                100             105             110
Ile Glu Lys Asn Ala Asp Leu Cys Tyr Leu Ser Thr Val Asp Trp Ser
                115             120             125
Leu Ile Leu Asp Ala Val Ser Asn Asn Tyr Ile Val Gly Asn Lys Pro
                130             135             140
Pro Lys Glu Cys Gly Asp Leu Cys Pro Gly Thr Met Glu Glu Lys Pro
145             150             155             160
Met Cys Glu Lys Thr Thr Ile Asn Asn Glu Tyr Asn Tyr Arg Cys Trp
                165             170             175
Thr Thr Asn Arg Cys Gln Lys Met Cys Pro Ser Thr Cys Gly Lys Arg
                180             185             190
Ala Cys Thr Glu Asn Asn Glu Cys Cys His Pro Glu Cys Leu Gly Ser
                195             200             205
Cys Ser Ala Pro Asp Asn Asp Thr Ala Cys Val Ala Cys Arg His Tyr
        210             215             220
Tyr Tyr Ala Gly Val Cys Val Pro Ala Cys Pro Pro Asn Thr Tyr Arg
225             230             235             240
Phe Glu Gly Trp Arg Cys Val Asp Arg Asp Phe Cys Ala Asn Ile Leu
                245             250             255
Ser Ala Glu Ser Ser Asp Ser Glu Gly Phe Val Ile His Asp Gly Glu
                260             265             270
Cys Met Gln Glu Cys Pro Ser Gly Phe Ile Arg Asn Gly Ser Gln Ser
                275             280             285
Met Tyr Cys Ile Pro Cys Glu Gly Pro Cys Pro Lys Val Cys Glu Glu
                290             295             300
Glu Lys Lys Thr Lys Thr Ile Asp Ser Val Thr Ser Ala Gln Met Leu
305             310             315             320
Gln Gly Cys Thr Ile Phe Lys Gly Asn Leu Leu Ile Asn Ile Arg Arg
                325             330             335
Gly Asn Asn Ile Ala Ser Glu Leu Glu Asn Phe Met Gly Leu Ile Glu
                340             345             350
Val Val Thr Gly Tyr Val Lys Ile Arg His Ser His Ala Leu Val Ser
                355             360             365
Leu Ser Phe Leu Lys Asn Leu Arg Leu Ile Leu Gly Glu Glu Gln Leu
        370             375             380
Glu Gly Asn Tyr Ser Phe Tyr Val Leu Asp Asn Gln Asn Leu Gln Gln
385             390             395             400
Leu Trp Asp Trp Asp His Arg Asn Leu Thr Ile Lys Ala Gly Lys Met
                405             410             415
Tyr Phe Ala Phe Asn Pro Lys Leu Cys Val Ser Glu Ile Tyr Arg Met
                420             425             430
```

```
Glu Glu Val Thr Gly Thr Lys Gly Arg Gln Ser Lys Gly Asp Ile Asn
        435                 440                 445

Thr Arg Asn Asn Gly Glu Arg Ala Ser Cys Glu Ser Asp Val Leu His
    450                 455                 460

Phe Thr Ser Thr Thr Thr Ser Lys Asn Arg Ile Ile Ile Thr Trp His
465                 470                 475                 480

Arg Tyr Arg Pro Pro Asp Tyr Arg Asp Leu Ile Ser Phe Thr Val Tyr
                485                 490                 495

Tyr Lys Glu Ala Pro Phe Lys Asn Val Thr Glu Tyr Asp Gly Gln Asp
            500                 505                 510

Ala Cys Gly Ser Asn Ser Trp Asn Met Val Asp Val Asp Leu Pro Pro
        515                 520                 525

Asn Lys Asp Val Glu Pro Gly Ile Leu Leu His Gly Leu Lys Pro Trp
    530                 535                 540

Thr Gln Tyr Ala Val Tyr Val Lys Ala Val Thr Leu Thr Met Val Glu
545                 550                 555                 560

Asn Asp His Ile Arg Gly Ala Lys Ser Glu Ile Leu Tyr Ile Arg Thr
                565                 570                 575

Asn Ala Ser Val Pro Ser Ile Pro Leu Asp Val Leu Ser Ala Ser Asn
            580                 585                 590

Ser Ser Ser Gln Leu Ile Val Lys Trp Asn Pro Pro Ser Leu Pro Asn
        595                 600                 605

Gly Asn Leu Ser Tyr Tyr Ile Val Arg Trp Gln Arg Gln Pro Gln Asp
    610                 615                 620

Gly Tyr Leu Tyr Arg His Asn Tyr Cys Ser Lys Asp Lys Ile Pro Ile
625                 630                 635                 640

Arg Lys Tyr Ala Asp Gly Thr Ile Asp Ile Glu Glu Val Thr Glu Asn
                645                 650                 655

Pro Lys Thr Glu Val Cys Gly Gly Glu Lys Gly Pro Cys Cys Ala Cys
            660                 665                 670

Pro Lys Thr Glu Ala Glu Lys Gln Ala Glu Lys Glu Glu Ala Glu Tyr
        675                 680                 685

Arg Lys Val Phe Glu Asn Phe Leu His Asn Ser Ile Phe Val Pro Arg
    690                 695                 700

Pro Glu Arg Lys Arg Arg Asp Val Met Gln Val Ala Asn Thr Thr Met
705                 710                 715                 720

Ser Ser Arg Ser Arg Asn Thr Thr Ala Ala Asp Thr Tyr Asn Ile Thr
                725                 730                 735

Asp Pro Glu Glu Leu Glu Thr Glu Tyr Pro Phe Phe Glu Ser Arg Val
            740                 745                 750

Asp Asn Lys Glu Arg Thr Val Ile Ser Asn Leu Arg Pro Phe Thr Leu
        755                 760                 765

Tyr Arg Ile Asp Ile His Ser Cys Asn His Glu Ala Glu Lys Leu Gly
    770                 775                 780

Cys Ser Ala Ser Asn Phe Val Phe Ala Arg Thr Met Pro Ala Glu Gly
785                 790                 795                 800

Ala Asp Asp Ile Pro Gly Pro Val Thr Trp Glu Pro Arg Pro Glu Asn
                805                 810                 815

Ser Ile Phe Leu Lys Trp Pro Glu Pro Glu Asn Pro Asn Gly Leu Ile
            820                 825                 830

Leu Met Tyr Glu Ile Lys Tyr Gly Ser Gln Val Glu Asp Gln Arg Glu
        835                 840                 845
```

-continued

```
Cys Val Ser Arg Gln Glu Tyr Arg Lys Tyr Gly Gly Ala Lys Leu Asn
850                 855                 860

Arg Leu Asn Pro Gly Asn Tyr Thr Ala Arg Ile Gln Ala Thr Ser Leu
865                 870                 875                 880

Ser Gly Asn Gly Ser Trp Thr Asp Pro Val Phe Phe Tyr Val Gln Ala
                885                 890                 895

Lys Thr Gly Tyr Glu Asn Phe Ile His Leu
            900                 905
```

<210> SEQ ID NO 12
<211> LENGTH: 916
<212> TYPE: PRT
<213> ORGANISM: Homo sapiens

<400> SEQUENCE: 12

```
His Leu Tyr Pro Gly Glu Val Cys Pro Gly Met Asp Ile Arg Asn Asn
1               5                   10                  15

Leu Thr Arg Leu His Glu Leu Glu Asn Cys Ser Val Ile Glu Gly His
            20                  25                  30

Leu Gln Ile Leu Leu Met Phe Lys Thr Arg Pro Glu Asp Phe Arg Asp
        35                  40                  45

Leu Ser Phe Pro Lys Leu Ile Met Ile Thr Asp Tyr Leu Leu Leu Phe
    50                  55                  60

Arg Val Tyr Gly Leu Glu Ser Leu Lys Asp Leu Phe Pro Asn Leu Thr
65                  70                  75                  80

Val Ile Arg Gly Ser Arg Leu Phe Phe Asn Tyr Ala Leu Val Ile Phe
                85                  90                  95

Glu Met Val His Leu Lys Glu Leu Gly Leu Tyr Asn Leu Met Asn Ile
            100                 105                 110

Thr Arg Gly Ser Val Arg Ile Glu Lys Asn Asn Glu Leu Cys Tyr Leu
        115                 120                 125

Ala Thr Ile Asp Trp Ser Arg Ile Leu Asp Ser Val Glu Asp Asn Tyr
    130                 135                 140

Ile Val Leu Asn Asp Asp Asn Glu Glu Cys Gly Asp Ile Cys Pro Gly
145                 150                 155                 160

Thr Ala Lys Gly Lys Thr Asn Cys Pro Ala Thr Val Ile Asn Gly Gln
                165                 170                 175

Phe Val Glu Arg Cys Trp Thr His Ser His Cys Gln Lys Val Cys Pro
            180                 185                 190

Thr Ile Cys Lys Ser His Gly Cys Thr Ala Glu Gly Leu Cys Cys His
        195                 200                 205

Ser Glu Cys Leu Gly Asn Cys Ser Gln Pro Asp Asp Pro Thr Lys Cys
    210                 215                 220

Val Ala Cys Arg Asn Phe Tyr Leu Asp Gly Arg Cys Val Glu Thr Cys
225                 230                 235                 240

Pro Pro Pro Tyr Tyr His Phe Gln Asp Trp Arg Cys Val Asn Phe Ser
                245                 250                 255

Phe Cys Gln Asp Leu His His Lys Cys Lys Asn Ser Arg Arg Gln Gly
            260                 265                 270

Cys His Gln Tyr Val Ile His Asn Asn Lys Cys Ile Pro Glu Cys Pro
        275                 280                 285

Ser Gly Tyr Thr Met Asn Ser Ser Asn Leu Leu Cys Thr Pro Cys Leu
    290                 295                 300

Gly Pro Cys Pro Lys Val Cys His Leu Leu Glu Gly Glu Lys Thr Ile
305                 310                 315                 320
```

-continued

Asp Ser Val Thr Ser Ala Gln Glu Leu Arg Gly Cys Thr Val Ile Asn
            325                 330                 335

Gly Ser Leu Ile Ile Asn Ile Arg Gly Gly Asn Asn Leu Ala Ala Glu
            340                 345                 350

Leu Glu Ala Asn Leu Gly Leu Ile Glu Glu Ile Ser Gly Tyr Leu Lys
            355                 360                 365

Ile Arg Arg Ser Tyr Ala Leu Val Ser Leu Ser Phe Phe Arg Lys Leu
370                 375                 380

Arg Leu Ile Arg Gly Glu Thr Leu Glu Ile Gly Asn Tyr Ser Phe Tyr
385                 390                 395                 400

Ala Leu Asp Asn Gln Asn Leu Arg Gln Leu Trp Asp Trp Ser Lys His
            405                 410                 415

Asn Leu Thr Ile Thr Gln Gly Lys Leu Phe Phe His Tyr Asn Pro Lys
            420                 425                 430

Leu Cys Leu Ser Glu Ile His Lys Met Glu Glu Val Ser Gly Thr Lys
            435                 440                 445

Gly Arg Gln Glu Arg Asn Asp Ile Ala Leu Lys Thr Asn Gly Asp Gln
    450                 455                 460

Ala Ser Cys Glu Asn Glu Leu Leu Lys Phe Ser Tyr Ile Arg Thr Ser
465                 470                 475                 480

Phe Asp Lys Ile Leu Leu Arg Trp Glu Pro Tyr Trp Pro Pro Asp Phe
            485                 490                 495

Arg Asp Leu Leu Gly Phe Met Leu Phe Tyr Lys Glu Ala Pro Tyr Gln
            500                 505                 510

Asn Val Thr Glu Phe Asp Gly Gln Asp Ala Cys Gly Ser Asn Ser Trp
            515                 520                 525

Thr Val Val Asp Ile Asp Pro Pro Leu Arg Ser Asn Asp Pro Lys Ser
            530                 535                 540

Gln Asn His Pro Gly Trp Leu Met Arg Gly Leu Lys Pro Trp Thr Gln
545                 550                 555                 560

Tyr Ala Ile Phe Val Lys Thr Leu Val Thr Phe Ser Asp Glu Arg Arg
            565                 570                 575

Thr Tyr Gly Ala Lys Ser Asp Ile Ile Tyr Val Gln Thr Asp Ala Thr
            580                 585                 590

Asn Pro Ser Val Pro Leu Asp Pro Ile Ser Val Ser Asn Ser Ser Ser
            595                 600                 605

Gln Ile Ile Leu Lys Trp Lys Pro Pro Ser Asp Pro Asn Gly Asn Ile
            610                 615                 620

Thr His Tyr Leu Val Phe Trp Glu Arg Gln Ala Glu Asp Ser Glu Leu
625                 630                 635                 640

Phe Glu Leu Asp Tyr Cys Leu Lys Gly Leu Lys Leu Pro Ser Arg Thr
            645                 650                 655

Trp Ser Pro Pro Phe Glu Ser Glu Asp Ser Gln Lys His Asn Gln Ser
            660                 665                 670

Glu Tyr Glu Asp Ser Ala Gly Glu Cys Cys Ser Cys Pro Lys Thr Asp
            675                 680                 685

Ser Gln Ile Leu Lys Glu Leu Glu Glu Ser Ser Phe Arg Lys Thr Phe
    690                 695                 700

Glu Asp Tyr Leu His Asn Val Val Phe Val Pro Arg Pro Ser Arg Lys
705                 710                 715                 720

Arg Arg Ser Leu Gly Asp Val Gly Asn Val Thr Val Ala Val Pro Thr
            725                 730                 735

```
Val Ala Ala Phe Pro Asn Thr Ser Ser Thr Ser Val Pro Thr Ser Pro
            740                 745                 750

Glu Glu His Arg Pro Phe Glu Lys Val Val Asn Lys Glu Ser Leu Val
            755                 760                 765

Ile Ser Gly Leu Arg His Phe Thr Gly Tyr Arg Ile Glu Leu Gln Ala
    770                 775                 780

Cys Asn Gln Asp Thr Pro Glu Glu Arg Cys Ser Val Ala Ala Tyr Val
785                 790                 795                 800

Ser Ala Arg Thr Met Pro Glu Ala Lys Ala Asp Asp Ile Val Gly Pro
                805                 810                 815

Val Thr His Glu Ile Phe Glu Asn Asn Val Val His Leu Met Trp Gln
            820                 825                 830

Glu Pro Lys Glu Pro Asn Gly Leu Ile Val Leu Tyr Glu Val Ser Tyr
            835                 840                 845

Arg Arg Tyr Gly Asp Glu Glu Leu His Leu Cys Val Ser Arg Lys His
    850                 855                 860

Phe Ala Leu Glu Arg Gly Cys Arg Leu Arg Gly Leu Ser Pro Gly Asn
865                 870                 875                 880

Tyr Ser Val Arg Ile Arg Ala Thr Ser Leu Ala Gly Asn Gly Ser Trp
                885                 890                 895

Thr Glu Pro Thr Tyr Phe Tyr Val Thr Asp Tyr Leu Asp Val Pro Ser
            900                 905                 910

Asn Ile Ala Lys
        915

<210> SEQ ID NO 13
<211> LENGTH: 895
<212> TYPE: PRT
<213> ORGANISM: Homo sapiens

<400> SEQUENCE: 13

Met Asn Val Cys Pro Ser Leu Asp Ile Arg Ser Glu Val Ala Glu Leu
1               5                   10                  15

Arg Gln Leu Glu Asn Cys Ser Val Val Glu Gly His Leu Gln Ile Leu
            20                  25                  30

Leu Met Phe Thr Ala Thr Gly Glu Asp Phe Arg Gly Leu Ser Phe Pro
        35                  40                  45

Arg Leu Thr Gln Val Thr Asp Tyr Leu Leu Leu Phe Arg Val Tyr Gly
    50                  55                  60

Leu Glu Ser Leu Arg Asp Leu Phe Pro Asn Leu Ala Val Ile Arg Gly
65                  70                  75                  80

Thr Arg Leu Phe Leu Gly Tyr Ala Leu Val Ile Phe Glu Met Pro His
                85                  90                  95

Leu Arg Asp Val Ala Leu Pro Ala Leu Gly Ala Val Leu Arg Gly Ala
            100                 105                 110

Val Arg Val Glu Lys Asn Gln Glu Leu Cys His Leu Ser Thr Ile Asp
            115                 120                 125

Trp Gly Leu Leu Gln Pro Ala Pro Gly Ala Asn His Ile Val Gly Asn
        130                 135                 140

Lys Leu Gly Glu Glu Cys Ala Asp Val Cys Pro Gly Val Leu Gly Ala
145                 150                 155                 160

Ala Gly Glu Pro Cys Ala Lys Thr Thr Phe Ser Gly His Thr Asp Tyr
                165                 170                 175

Arg Cys Trp Thr Ser Ser His Cys Gln Arg Val Cys Pro Cys Pro His
            180                 185                 190
```

-continued

```
Gly Met Ala Cys Thr Ala Arg Gly Glu Cys Cys His Thr Glu Cys Leu
            195                 200                 205
Gly Gly Cys Ser Gln Pro Glu Asp Pro Arg Ala Cys Val Ala Cys Arg
        210                 215                 220
His Leu Tyr Phe Gln Gly Ala Cys Leu Trp Ala Cys Pro Pro Gly Thr
225                 230                 235                 240
Tyr Gln Tyr Glu Ser Trp Arg Cys Val Thr Ala Glu Arg Cys Ala Ser
                245                 250                 255
Leu His Ser Val Pro Gly Arg Ala Ser Thr Phe Gly Ile His Gln Gly
            260                 265                 270
Ser Cys Leu Ala Gln Cys Pro Ser Gly Phe Thr Arg Asn Ser Ser Ser
        275                 280                 285
Ile Phe Cys His Lys Cys Glu Gly Leu Cys Pro Lys Glu Cys Lys Val
    290                 295                 300
Gly Thr Lys Thr Ile Asp Ser Ile Gln Ala Ala Gln Asp Leu Val Gly
305                 310                 315                 320
Cys Thr His Val Glu Gly Ser Leu Ile Leu Asn Leu Arg Gln Gly Tyr
                325                 330                 335
Asn Leu Glu Pro Gln Leu Gln His Ser Leu Gly Leu Val Glu Thr Ile
            340                 345                 350
Thr Gly Phe Leu Lys Ile Lys His Ser Phe Ala Leu Val Ser Leu Gly
        355                 360                 365
Phe Phe Lys Asn Leu Lys Leu Ile Arg Gly Asp Ala Met Val Asp Gly
    370                 375                 380
Asn Tyr Thr Leu Tyr Val Leu Asp Asn Gln Asn Leu Gln Gln Leu Gly
385                 390                 395                 400
Ser Trp Val Ala Ala Gly Leu Thr Ile Pro Val Gly Lys Ile Tyr Phe
                405                 410                 415
Ala Phe Asn Pro Arg Leu Cys Leu Glu His Ile Tyr Arg Leu Glu Glu
            420                 425                 430
Val Thr Gly Thr Arg Gly Arg Gln Asn Lys Ala Glu Ile Asn Pro Arg
        435                 440                 445
Thr Asn Gly Asp Arg Ala Ala Cys Gln Thr Arg Thr Leu Arg Phe Val
    450                 455                 460
Ser Asn Val Thr Glu Ala Asp Arg Ile Leu Leu Arg Trp Glu Arg Tyr
465                 470                 475                 480
Glu Pro Leu Glu Ala Arg Asp Leu Leu Ser Phe Ile Val Tyr Tyr Lys
                485                 490                 495
Glu Ser Pro Phe Gln Asn Ala Thr Glu His Val Gly Pro Asp Ala Cys
            500                 505                 510
Gly Thr Gln Ser Trp Asn Leu Leu Asp Val Glu Leu Pro Leu Ser Arg
        515                 520                 525
Thr Gln Glu Pro Gly Val Thr Leu Ala Ser Leu Lys Pro Trp Thr Gln
    530                 535                 540
Tyr Ala Val Phe Val Arg Ala Ile Thr Leu Thr Thr Glu Glu Asp Ser
545                 550                 555                 560
Pro His Gln Gly Ala Gln Ser Pro Ile Val Tyr Leu Arg Thr Leu Pro
                565                 570                 575
Ala Ala Pro Thr Val Pro Gln Asp Val Ile Ser Thr Ser Asn Ser Ser
            580                 585                 590
Ser His Leu Leu Val Arg Trp Lys Pro Pro Thr Gln Arg Asn Gly Asn
        595                 600                 605
```

```
Leu Thr Tyr Tyr Leu Val Leu Trp Gln Arg Leu Ala Glu Asp Gly Asp
    610                 615                 620

Leu Tyr Leu Asn Asp Tyr Cys His Arg Gly Leu Arg Leu Pro Thr Ser
625                 630                 635                 640

Asn Asn Asp Pro Arg Phe Asp Gly Glu Asp Gly Asp Pro Glu Ala Glu
                645                 650                 655

Met Glu Ser Asp Cys Cys Pro Cys Gln His Pro Pro Gly Gln Val
            660                 665                 670

Leu Pro Pro Leu Glu Ala Gln Glu Ala Ser Phe Gln Lys Lys Phe Glu
            675                 680                 685

Asn Phe Leu His Asn Ala Ile Thr Ile Pro Ile Ser Pro Trp Lys Val
690                 695                 700

Thr Ser Ile Asn Lys Ser Pro Gln Arg Asp Ser Gly Arg His Arg Arg
705                 710                 715                 720

Ala Ala Gly Pro Leu Arg Leu Gly Gly Asn Ser Ser Asp Phe Glu Ile
                725                 730                 735

Gln Glu Asp Lys Val Pro Arg Glu Arg Ala Val Leu Ser Gly Leu Arg
            740                 745                 750

His Phe Thr Glu Tyr Arg Ile Asp Ile His Ala Cys Asn His Ala Ala
        755                 760                 765

His Thr Val Gly Cys Ser Ala Ala Thr Phe Val Phe Ala Arg Thr Met
770                 775                 780

Pro His Arg Glu Ala Asp Gly Ile Pro Gly Lys Val Ala Trp Glu Ala
785                 790                 795                 800

Ser Ser Lys Asn Ser Val Leu Leu Arg Trp Leu Glu Pro Pro Asp Pro
                805                 810                 815

Asn Gly Leu Ile Leu Lys Tyr Glu Ile Lys Tyr Arg Arg Leu Gly Glu
            820                 825                 830

Glu Ala Thr Val Leu Cys Val Ser Arg Leu Arg Tyr Ala Lys Phe Gly
        835                 840                 845

Gly Val His Leu Ala Leu Leu Pro Pro Gly Asn Tyr Ser Ala Arg Val
    850                 855                 860

Arg Ala Thr Ser Leu Ala Gly Asn Gly Ser Trp Thr Asp Ser Val Ala
865                 870                 875                 880

Phe Tyr Ile Leu Gly Pro Glu Glu Glu Asp Ala Gly Gly Leu His
                885                 890                 895
```

<210> SEQ ID NO 14
<211> LENGTH: 68
<212> TYPE: DNA
<213> ORGANISM: Artificial sequence
<220> FEATURE:
<223> OTHER INFORMATION: Unknown Organism

<400> SEQUENCE: 14
gacgtcgacg atgacgataa ggaacaaaaa ctcatctcag aagaggatct gaattagaat    60
tcgacgtc    68

<210> SEQ ID NO 15
<211> LENGTH: 18
<212> TYPE: PRT
<213> ORGANISM: Homo sapiens

<400> SEQUENCE: 15

```
Asp Val Asp Asp Asp Asp Lys Glu Gln Lys Leu Ile Ser Glu Glu Asp
1               5                   10                  15
```

```
Leu Asn

<210> SEQ ID NO 16
<211> LENGTH: 11
<212> TYPE: PRT
<213> ORGANISM: Homo sapiens

<400> SEQUENCE: 16

Glu Gln Lys Leu Ile Ser Glu Glu Asp Leu Asn
1               5                   10
```